United States Patent
Cornen et al.

(10) Patent No.: US 11,447,545 B2
(45) Date of Patent: Sep. 20, 2022

(54) COMBINATION THERAPY USING ANTIBODY TO HUMAN SIGLEC-9 AND ANTIBODY TO HUMAN NKG2A FOR TREATING CANCER

(71) Applicant: INNATE PHARMA, Marseilles (FR)

(72) Inventors: Stéphanie Cornen, Marseilles (FR); Benjamin Rossi, Marseilles (FR); Nicolai Wagtmann, Concord, MA (US)

(73) Assignee: INNATE PHARMA, Marseilles (FR)

( * ) Notice: Subject to any disclaimer, the term of this patent is extended or adjusted under 35 U.S.C. 154(b) by 246 days.

(21) Appl. No.: 16/629,585

(22) PCT Filed: Jul. 9, 2018

(86) PCT No.: PCT/EP2018/068532
§ 371 (c)(1),
(2) Date: Jan. 9, 2020

(87) PCT Pub. No.: WO2019/011852
PCT Pub. Date: Jan. 17, 2019

(65) Prior Publication Data
US 2020/0369764 A1 Nov. 26, 2020

Related U.S. Application Data

(60) Provisional application No. 62/530,454, filed on Jul. 10, 2017.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61K 39/00* (2013.01); *A61P 35/00* (2018.01);
(Continued)

(58) Field of Classification Search
CPC .......... C07K 16/2803; C07K 2317/565; C07K 2317/92; A61K 39/00; A61K 2039/507; A61P 35/00
See application file for complete search history.

(56) References Cited

U.S. PATENT DOCUMENTS

| | | | |
|---|---|---|---|
| 10,329,348 B2 | 6/2019 | Andre et al. | |
| 2017/0298131 A1 | 10/2017 | Andre et al. | |
| 2017/0306014 A1 | 10/2017 | Cornen et al. | |

FOREIGN PATENT DOCUMENTS

| | | | | |
|---|---|---|---|---|
| FR | WO20016041945 | * | 3/2016 | ........... A61K 39/395 |
| WO | WO 2016/038064 | | 3/2016 | |

(Continued)

OTHER PUBLICATIONS

Ruggari et al. "Effects of anti-NKG2A antibody administration on leukemia and normal hematopoietic cells" Haematologica vol. 101 Issue 5 (p. 626-633) (Year: 2016).*
(Continued)

*Primary Examiner* — Joanne Hama
*Assistant Examiner* — Miles Joseph Delahoussaye
(74) *Attorney, Agent, or Firm* — Saliwanchik, Lloyd & Eisenschenk

(57) ABSTRACT

This invention relates to agents that bind human Siglecs having inhibitory activity in immune cells, and that neutralize the inhibitory activity of such Siglec. Such agents can be used for the treatment of cancers.

14 Claims, 16 Drawing Sheets

Specification includes a Sequence Listing.

(52) U.S. Cl.
CPC .. *A61K 2039/507* (2013.01); *C07K 2317/565* (2013.01); *C07K 2317/92* (2013.01)

(56) References Cited

FOREIGN PATENT DOCUMENTS

| | | |
|---|---|---|
| WO | WO 2016/041947 | 3/2016 |
| WO | WO 2016/062851 | 4/2016 |
| WO | WO 2017/123745 | 7/2017 |
| WO | WO 2018/027203 | 2/2018 |
| WO | WO 2019/011855 | 1/2019 |

OTHER PUBLICATIONS

Jandus, C. et al. "Interactions between Siglec-7/9 receptors and ligands influence NK celldependent tumor immunosurveillance" *The Journal of Clinical Investigation,* Apr. 2014, pp. 1810-1820, vol. 124, No. 4.

Läubli, H. et al. "Engagement of myelomonocytic Siglecs by tumor-associated ligands modulates the innate immune response to cancer" *PNAS,* Sep. 30, 2014, pp. 14211-14216, vol. 111, No. 39.

Shao, J.-Y. et al. "Siglec-7 Defines a Highly Functional Natural Killer Cell Subset and Inhibits Cell-Mediated Activities" *Scandinavian Journal of Immunology,* 2016, pp. 182-190, vol. 84, No. 3.

Ikehara, Y. et al. "Negative Regulation of T Cell Receptor Signaling by Siglec-7 (p70/AIRM) and Siglec-9" The Journal of Biological Chemistry, Oct. 8, 2004, pp. 43117-43125, vol. 279, No. 41.

Written Opinion in International Application No. PCT/EP2018/068532, dated Sep. 28, 2018, pp. 1-7.

\* cited by examiner

Blockade of Siglec-9 Fc binding on Ramos cell line

Blockade of Siglec-9 Fc binding on K562 E6 cell line mAb.C

SEQUENCE LISTING

<160> NUMBER OF SEQ ID NOS: 184

<210> SEQ ID NO 1
<211> LENGTH: 467
<212> TYPE: PRT
<213> ORGANISM: homo sapiens

<400> SEQUENCE: 1

```
Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
                20                  25                  30

Ser Val Thr Val Gln Glu Gly Met Cys Val His Val Arg Cys Ser Phe
            35                  40                  45

Ser Tyr Pro Val Asp Ser Gln Thr Asp Ser Asp Pro Val His Gly Tyr
        50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
            100                 105                 110

Ala Arg Met Ser Asp Ala Gly Arg Tyr Phe Phe Arg Met Glu Lys Gly
        115                 120                 125

Asn Ile Lys Trp Asn Tyr Lys Tyr Asp Gln Leu Ser Val Asn Val Thr
    130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
            180                 185                 190

His Pro Ser Thr Thr Arg Ser Ser Val Leu Thr Leu Ile Pro Gln Pro
        195                 200                 205

Gln His His Gly Thr Ser Leu Thr Cys Gln Val Thr Leu Pro Gly Ala
    210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
            260                 265                 270

Arg Leu Val Cys Ala Val Asp Ser Asn Pro Pro Ala Arg Leu Ser Trp
        275                 280                 285

Thr Trp Arg Ser Leu Thr Leu Tyr Pro Ser Gln Pro Ser Asn Pro Leu
    290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
            340                 345                 350

Leu Gly Ala Val Gly Gly Ala Gly Ala Thr Ala Leu Val Phe Leu Ser
        355                 360                 365
```

Phe Cys Val Ile Phe Ile Val Arg Ser Cys Arg Lys Lys Ser Ala
            370                 375                 380

Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
                405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
            435                 440                 445

Asp Leu Ser Gly Gln Glu Ala Thr Asn Asn Glu Tyr Ser Glu Ile Lys
450                 455                 460

Ile Pro Lys
465

<210> SEQ ID NO 2
<211> LENGTH: 463
<212> TYPE: PRT
<213> ORGANISM: homo sapiens

<400> SEQUENCE: 2

Met Leu Leu Leu Leu Pro Leu Leu Trp Gly Arg Glu Arg Ala Glu
1               5                   10                  15

Gly Gln Thr Ser Lys Leu Leu Thr Met Gln Ser Ser Val Thr Val Gln
                20                  25                  30

Glu Gly Leu Cys Val His Val Pro Cys Ser Phe Ser Tyr Pro Ser His
            35                  40                  45

Gly Trp Ile Tyr Pro Gly Pro Val Val His Gly Tyr Trp Phe Arg Glu
        50                  55                  60

Gly Ala Asn Thr Asp Gln Asp Ala Pro Val Ala Thr Asn Asn Pro Ala
65                  70                  75                  80

Arg Ala Val Trp Glu Glu Thr Arg Asp Arg Phe His Leu Leu Gly Asp
                85                  90                  95

Pro His Thr Lys Asn Cys Thr Leu Ser Ile Arg Asp Ala Arg Arg Ser
            100                 105                 110

Asp Ala Gly Arg Tyr Phe Phe Arg Met Glu Lys Gly Ser Ile Lys Trp
        115                 120                 125

Asn Tyr Lys His His Arg Leu Ser Val Asn Val Thr Ala Leu Thr His
130                 135                 140

Arg Pro Asn Ile Leu Ile Pro Gly Thr Leu Glu Ser Gly Cys Pro Gln
145                 150                 155                 160

Asn Leu Thr Cys Ser Val Pro Trp Ala Cys Glu Gln Gly Thr Pro Pro
                165                 170                 175

Met Ile Ser Trp Ile Gly Thr Ser Val Ser Pro Leu Asp Pro Ser Thr
            180                 185                 190

Thr Arg Ser Ser Val Leu Thr Leu Ile Pro Gln Pro Gln Asp His Gly
        195                 200                 205

Thr Ser Leu Thr Cys Gln Val Thr Phe Pro Gly Ala Ser Val Thr Thr
210                 215                 220

Asn Lys Thr Val His Leu Asn Val Ser Tyr Pro Pro Gln Asn Leu Thr
225                 230                 235                 240

Met Thr Val Phe Gln Gly Asp Gly Thr Val Ser Thr Val Leu Gly Asn
                245                 250                 255

Gly Ser Ser Leu Ser Leu Pro Glu Gly Gln Ser Leu Arg Leu Val Cys

```
                    260                 265                 270
Ala Val Asp Ala Val Asp Ser Asn Pro Pro Ala Arg Leu Ser Leu Ser
            275                 280                 285

Trp Arg Gly Leu Thr Leu Cys Pro Ser Gln Pro Ser Asn Pro Gly Val
    290                 295                 300

Leu Glu Leu Pro Trp Val His Leu Arg Asp Ala Ala Glu Phe Thr Cys
305                 310                 315                 320

Arg Ala Gln Asn Pro Leu Gly Ser Gln Gln Val Tyr Leu Asn Val Ser
                325                 330                 335

Leu Gln Ser Lys Ala Thr Ser Gly Val Thr Gln Gly Val Val Gly Gly
            340                 345                 350

Ala Gly Ala Thr Ala Leu Val Phe Leu Ser Phe Cys Val Ile Phe Val
        355                 360                 365

Val Val Arg Ser Cys Arg Lys Lys Ser Ala Arg Pro Ala Ala Gly Val
    370                 375                 380

Gly Asp Thr Gly Ile Glu Asp Ala Asn Ala Val Arg Gly Ser Ala Ser
385                 390                 395                 400

Gln Gly Pro Leu Thr Glu Pro Trp Ala Glu Asp Ser Pro Pro Asp Gln
                405                 410                 415

Pro Pro Pro Ala Ser Ala Arg Ser Ser Val Gly Glu Gly Glu Leu Gln
            420                 425                 430

Tyr Ala Ser Leu Ser Phe Gln Met Val Lys Pro Trp Asp Ser Arg Gly
        435                 440                 445

Gln Glu Ala Thr Asp Thr Glu Tyr Ser Glu Ile Lys Ile His Arg
    450                 455                 460

<210> SEQ ID NO 3
<211> LENGTH: 116
<212> TYPE: PRT
<213> ORGANISM: Mus musculus

<400> SEQUENCE: 3

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Gly Gly
            20                  25                  30

Phe Ala Trp Asn Trp Ile Arg Gln Phe Pro Gly Asn Thr Leu Glu Trp
        35                  40                  45

Met Gly Tyr Ile Gly Tyr Gly Gly Ser Thr Ser Tyr Asn Pro Ser Leu
    50                  55                  60

Asn Ser Arg Ile Ser Ile Thr Arg Asp Thr Ser Lys Asn His Phe Phe
65                  70                  75                  80

Leu Gln Phe Asn Ser Val Thr Thr Asp Asp Ser Ala Thr Tyr Tyr Cys
                85                  90                  95

Ala Arg Gly Asp Tyr Leu Phe Ala Tyr Trp Gly Gln Gly Thr Leu Val
            100                 105                 110

Thr Val Ser Ala
        115

<210> SEQ ID NO 4
<211> LENGTH: 107
<212> TYPE: PRT
<213> ORGANISM: Mus musculus

<400> SEQUENCE: 4

Asp Ile Val Met Thr Gln Ser His Lys Phe Met Ser Thr Ser Val Gly
```

```
               1               5                  10                  15
           Asp Arg Val Ser Ile Thr Cys Lys Ala Ser Gln Asp Val Asn Thr Ala
                          20                  25                  30

Val Ala Trp Tyr Gln Gln Lys Pro Gly Gln Ser Pro Lys Leu Leu Ile
                          35                  40                  45

Tyr Ser Ala Ser Tyr Arg Tyr Thr Gly Val Pro Asp Arg Phe Thr Gly
                          50                  55                  60

Ser Gly Ser Gly Thr Asp Phe Thr Phe Thr Ile Ser Ser Val Gln Ala
           65                  70                  75                  80

Glu Asp Leu Ala Val Tyr Tyr Cys Gln Gln His Tyr Ser Thr Pro Arg
                          85                  90                  95

Thr Phe Gly Gly Gly Thr Lys Leu Glu Ile Lys
                          100                 105

<210> SEQ ID NO 5
<211> LENGTH: 116
<212> TYPE: PRT
<213> ORGANISM: Mus musculus

<400> SEQUENCE: 5

Glu Val Gln Leu Gln Glu Ser Gly Pro Gly Leu Val Lys Pro Ser Gln
           1               5                  10                  15

Ser Leu Ser Leu Thr Cys Thr Val Thr Gly Tyr Ser Ile Thr Gly Gly
                          20                  25                  30

Phe Ala Trp Asn Trp Ile Arg Gln Phe Pro Gly Asn Thr Leu Glu Trp
                          35                  40                  45

Met Gly Tyr Ile Gly Tyr Gly Ser Thr Ser Tyr Asn Pro Ser Leu
                          50                  55                  60

Asn Ser Arg Ile Ser Ile Thr Arg Asp Thr Ser Lys Asn His Phe Phe
           65                  70                  75                  80

Leu Gln Phe Asn Ser Val Thr Thr Glu Asp Ser Ala Thr Tyr Tyr Cys
                          85                  90                  95

Ala Arg Gly Asp Tyr Leu Phe Ala Tyr Trp Gly Gln Gly Thr Leu Val
                          100                 105                 110

Thr Val Ser Ala
                   115

<210> SEQ ID NO 6
<211> LENGTH: 107
<212> TYPE: PRT
<213> ORGANISM: Mus musculus

<400> SEQUENCE: 6

Asp Ile Val Met Thr Gln Ser His Lys Phe Met Ser Thr Ser Val Gly
           1               5                  10                  15

Asp Arg Val Ser Ile Thr Cys Lys Ala Ser Gln Asp Val Asn Thr Ala
                          20                  25                  30

Val Ala Trp Tyr Gln Gln Lys Pro Gly Gln Ser Pro Lys Leu Leu Ile
                          35                  40                  45

Tyr Ser Ala Ser Tyr Arg Tyr Thr Gly Val Pro Asp Arg Phe Thr Gly
                          50                  55                  60

Ser Gly Ser Gly Thr Asp Phe Thr Phe Thr Ile Ser Ser Val Gln Ala
           65                  70                  75                  80

Glu Asp Leu Ala Val Tyr Tyr Cys Gln Gln His Tyr Ser Thr Pro Arg
                          85                  90                  95

Thr Phe Gly Gly Gly Thr Lys Leu Glu Ile Lys
```

-continued

<210> SEQ ID NO 7
<211> LENGTH: 116
<212> TYPE: PRT
<213> ORGANISM: Mus musculus

<400> SEQUENCE: 7

```
Glu Val Gln Leu Leu Glu Thr Gly Pro Gly Leu Val Lys Pro Ser Gln
1               5                   10                  15

Ser Leu Ser Leu Thr Cys Thr Val Thr Gly Tyr Ser Ile Thr Gly Gly
            20                  25                  30

Phe Ala Trp Asn Trp Ile Arg Gln Phe Pro Gly Asn Thr Leu Glu Trp
        35                  40                  45

Met Gly Tyr Ile Gly Tyr Gly Gly Ser Thr Ser Tyr Asn Pro Ser Leu
    50                  55                  60

Asn Ser Arg Ile Ser Ile Thr Arg Asp Thr Ser Lys Asn His Phe Phe
65                  70                  75                  80

Leu Gln Phe Asn Ser Val Thr Thr Glu Asp Ser Ala Thr Tyr Tyr Cys
                85                  90                  95

Ala Arg Gly Asp Tyr Leu Phe Ala Tyr Trp Gly Gln Gly Thr Leu Val
            100                 105                 110

Thr Val Ser Ala
        115
```

<210> SEQ ID NO 8
<211> LENGTH: 107
<212> TYPE: PRT
<213> ORGANISM: Mus musculus

<400> SEQUENCE: 8

```
Asp Ile Leu Met Thr Gln Ser Pro Ala Ser Leu Ser Ala Ser Val Gly
1               5                   10                  15

Glu Thr Val Ser Ile Thr Cys Arg Ala Ser Gly Asn Ile His Asn Tyr
            20                  25                  30

Leu Ala Trp Tyr Leu Gln Arg Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Thr Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys
            100                 105
```

<210> SEQ ID NO 9
<211> LENGTH: 121
<212> TYPE: PRT
<213> ORGANISM: Mus musculus

<400> SEQUENCE: 9

```
Asp Val Gln Leu Val Glu Ser Gly Gly Asp Leu Val Lys Pro Gly Gly
1               5                   10                  15

Ser Leu Lys Leu Ser Cys Ala Ala Ser Gly Phe Ala Phe Ser Ser Tyr
            20                  25                  30

Asp Met Ser Trp Val Arg Gln Ser Pro Glu Lys Arg Leu Glu Trp Ile
        35                  40                  45
```

Ala His Ile Gly Ser Gly Gly Asn Ile Tyr Tyr Pro Asp Thr Val
            50                  55                  60

Lys Gly Arg Phe Thr Ile Ser Arg Asp Asn Ala Lys Asn Thr Leu Tyr
 65                  70                  75                  80

Leu Gln Met Arg Ser Leu Lys Ser Glu Asp Thr Ala Met Tyr Tyr Cys
                85                  90                  95

Ala Arg Leu Ile Phe Thr Thr Gly Phe Tyr Gly Met Asp Tyr Trp Gly
                100                 105                 110

Gln Gly Thr Ser Val Thr Val Ser Ser
            115                 120

<210> SEQ ID NO 10
<211> LENGTH: 107
<212> TYPE: PRT
<213> ORGANISM: Mus musculus

<400> SEQUENCE: 10

Asp Ile Gln Met Thr Gln Thr Thr Ser Ser Leu Ser Ala Ser Leu Gly
 1               5                   10                  15

Asp Arg Val Thr Ile Ser Cys Arg Ala Ser Gln Asp Ile Ser Ser Tyr
                20                  25                  30

Leu Asn Trp Tyr Gln Gln Lys Pro Asp Gly Thr Ile Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Asp Gln
 65                  70                  75                  80

Asp Asp Ile Ala Thr Tyr Phe Cys Gln Gln Gly Asn Ala Leu Pro Trp
                85                  90                  95

Thr Phe Gly Gly Gly Thr Lys Leu Glu Ile Lys
                100                 105

<210> SEQ ID NO 11
<211> LENGTH: 116
<212> TYPE: PRT
<213> ORGANISM: Mus musculus

<400> SEQUENCE: 11

Glu Ile Gln Leu Gln Gln Ser Gly Pro Glu Leu Glu Lys Pro Gly Ala
 1               5                   10                  15

Ser Val Lys Ile Ser Cys Lys Ala Ser Gly Tyr Ser Phe Ser Asp Tyr
                20                  25                  30

Asn Met Asn Trp Val Lys Gln Ser Asn Gly Lys Ser Leu Glu Trp Ile
            35                  40                  45

Gly Asn Ile Asp Pro Tyr Tyr Gly Ala Thr Ser Tyr Asn Gln Arg Phe
 50                  55                  60

Lys Gly Lys Ala Thr Leu Thr Val Asp Lys Ser Ser Thr Ala Tyr
 65                  70                  75                  80

Met Gln Leu Lys Ser Leu Thr Ser Glu Asp Ser Ala Val Tyr Tyr Cys
                85                  90                  95

Ala Arg Gly Asp Ser Leu Phe Ala Tyr Trp Gly His Gly Thr Leu Val
                100                 105                 110

Thr Val Ser Ala
            115

<210> SEQ ID NO 12

```
<211> LENGTH: 107
<212> TYPE: PRT
<213> ORGANISM: Mus musculus

<400> SEQUENCE: 12

Asp Ile Val Met Thr Gln Ser Gln Glu Phe Met Ser Thr Ser Leu Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Leu
        35                  40                  45

Tyr Ser Ala Ser Ser Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Ile Thr Tyr Pro Tyr
                85                  90                  95

Thr Phe Gly Gly Gly Thr Lys Leu Glu Ile Lys
            100                 105

<210> SEQ ID NO 13
<211> LENGTH: 116
<212> TYPE: PRT
<213> ORGANISM: Mus musculus

<400> SEQUENCE: 13

Glu Ile Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Ser Asp Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Tyr Gly Ala Thr Ser Tyr Asn Gln Arg Phe
50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Gly Asp Ser Leu Phe Ala Tyr Trp Gly Gln Gly Thr Leu Val
            100                 105                 110

Thr Val Ser Ala
        115

<210> SEQ ID NO 14
<211> LENGTH: 107
<212> TYPE: PRT
<213> ORGANISM: Mus musculus

<400> SEQUENCE: 14

Asp Ile Val Met Thr Gln Ser Gln Glu Phe Met Ser Thr Ser Leu Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Leu
        35                  40                  45

Tyr Ser Ala Ser Ser Arg Tyr Ser Gly Val Pro Asp Arg Phe Thr Gly
50                  55                  60
```

Ser Gly Ser Gly Thr Asp Phe Thr Leu Thr Ile Asn Asn Met Gln Ser
 65                  70                  75                  80

Glu Asp Leu Ala Glu Tyr Phe Cys Gln Gln Tyr Ile Thr Tyr Pro Tyr
                 85                  90                  95

Thr Phe Gly Gly Gly Thr Lys Leu Glu Ile Lys
            100                 105

<210> SEQ ID NO 15
<211> LENGTH: 122
<212> TYPE: PRT
<213> ORGANISM: Mus musculus

<400> SEQUENCE: 15

Gln Val Gln Leu Gln Gln Pro Gly Ala Glu Leu Val Lys Pro Gly Ser
1               5                   10                  15

Pro Val Lys Leu Ser Cys Lys Ala Ser Tyr Phe Thr Phe Thr Ser Tyr
                20                  25                  30

Trp Met His Trp Val Arg Gln Arg Pro Gly Gln Gly Leu Glu Trp Ile
            35                  40                  45

Gly Glu Ile Asn Pro Ser Asn Gly His Thr Asn Tyr Asn Glu Lys Phe
    50                  55                  60

Glu Ser Lys Ala Thr Leu Thr Val Asp Arg Ser Ser Ser Thr Ala Tyr
65                  70                  75                  80

Met Gln Leu Ser Ser Leu Thr Ser Glu Asp Ser Ala Val Phe Tyr Cys
                85                  90                  95

Ala Asn Gly Val Glu Ser Tyr Asp Phe Asp Asp Ala Leu Asp Tyr Trp
            100                 105                 110

Gly Gln Gly Thr Ser Val Thr Val Ser Ser
        115                 120

<210> SEQ ID NO 16
<211> LENGTH: 107
<212> TYPE: PRT
<213> ORGANISM: Mus musculus

<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
                20                  25                  30

Leu Asn Trp Tyr Gln Gln Lys Pro Asp Gly Thr Ile Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Leu Pro Phe
                85                  90                  95

Thr Phe Gly Gly Gly Thr Lys Leu Glu Ile Lys
            100                 105

<210> SEQ ID NO 17
<211> LENGTH: 122
<212> TYPE: PRT
<213> ORGANISM: Mus musculus

<400> SEQUENCE: 17

Gln Val Gln Leu Gln Gln Pro Gly Ala Glu Leu Val Lys Pro Gly Ala

```
   1               5                  10                  15
Ser Val Lys Leu Ser Cys Lys Ala Ser Val Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly His Thr Asn Tyr Asn Glu Lys Phe
            50                  55                  60

Lys Thr Lys Ala Lys Leu Thr Val Asp Lys Ser Ser Ser Thr Ala Tyr
65                      70                  75                  80

Met Gln Leu Ser Ser Leu Thr Ser Glu Asp Ser Ala Val Tyr Phe Cys
                    85                  90                  95

Ala Asn Gly Val Glu Thr Tyr Asp Phe Asp Asp Ala Met Asp Tyr Trp
                100                 105                 110

Gly Gln Gly Thr Ser Val Thr Val Ser Ser
            115                 120

<210> SEQ ID NO 18
<211> LENGTH: 107
<212> TYPE: PRT
<213> ORGANISM: Mus musculus

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
            35                  40                  45

Tyr Phe Thr Ser Arg Leu His Ser Gly Val Pro Ser Arg Phe Ser Gly
            50                  55                  60

Ser Gly Ser Gly Thr Asp Tyr Ser Leu Thr Ile Ser Asn Leu Glu Gln
65                      70                  75                  80

Glu Asp Ile Ala Thr Tyr Phe Cys Gln Gln Gly Asp Thr Phe Pro Phe
                    85                  90                  95

Thr Phe Gly Gly Gly Thr Lys Leu Glu Ile Lys
                100                 105

<210> SEQ ID NO 19
<211> LENGTH: 120
<212> TYPE: PRT
<213> ORGANISM: Mus musculus

<400> SEQUENCE: 19

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Glu Met Asn Trp Val Lys Glu Ala Pro Gly Lys Gly Leu Lys Trp Met
            35                  40                  45

Gly Trp Ile Asn Thr Tyr Thr Gly Glu Ser Thr Tyr Ala Asp Asp Phe
            50                  55                  60

Lys Gly Arg Phe Ala Phe Ser Leu Glu Thr Ser Ala Ser Thr Val Tyr
65                      70                  75                  80

Leu Gln Ile Asn Asn Leu Lys Asp Glu Asp Val Ala Thr Tyr Phe Cys
                    85                  90                  95

Val Arg Asp Asp Tyr Gly Arg Ser Tyr Gly Phe Ala Tyr Trp Gly Gln
```

```
                100                 105                 110
Gly Thr Leu Val Thr Val Ser Ala
        115                 120

<210> SEQ ID NO 20
<211> LENGTH: 112
<212> TYPE: PRT
<213> ORGANISM: Mus musculus

<400> SEQUENCE: 20

Asn Ile Val Leu Thr Gln Ser Pro Ala Ser Leu Thr Val Ser Leu Gly
1               5                   10                  15

Gln Arg Ala Asn Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Thr Asp Asp Ala Ala Thr Tyr Tyr Cys His Gln Asn Asn
                85                  90                  95

Glu Asp Pro Pro Trp Thr Phe Gly Gly Gly Thr Lys Leu Glu Ile Lys
            100                 105                 110

<210> SEQ ID NO 21
<211> LENGTH: 114
<212> TYPE: PRT
<213> ORGANISM: Mus musculus

<400> SEQUENCE: 21

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Ile Thr Glu Thr Gly Glu Pro Thr Tyr Ala Asp Asp Phe
    50                  55                  60

Arg Gly Arg Phe Ala Phe Ser Leu Glu Thr Ser Ala Asn Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Phe Asp Gly Tyr Trp Gly Gln Gly Thr Thr Leu Thr Val
            100                 105                 110

Ser Ser

<210> SEQ ID NO 22
<211> LENGTH: 107
<212> TYPE: PRT
<213> ORGANISM: Mus musculus

<400> SEQUENCE: 22

Asp Ile Leu Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30
```

Leu Ala Trp Tyr Gln Gln Lys Arg Gly Lys Ser Pro Gln Phe Leu Val
            35                  40                  45

Tyr Asn Ala Lys Thr Leu Thr Glu Gly Val Pro Ser Arg Phe Arg Gly
 50                  55                  60

Ser Gly Ser Gly Thr Gln Phe Ser Leu Lys Ile Asn Ser Leu Gln Pro
 65                  70                  75                  80

Glu Asp Phe Gly Thr Tyr Tyr Cys Gln His His Tyr Gly Phe Pro Trp
                 85                  90                  95

Thr Phe Gly Gly Gly Thr Lys Leu Glu Ile Lys
            100                 105

<210> SEQ ID NO 23
<211> LENGTH: 118
<212> TYPE: PRT
<213> ORGANISM: Mus musculus

<400> SEQUENCE: 23

Asp Val Gln Leu Val Glu Ser Gly Gly Leu Val Gln Pro Gly Gly
 1               5                  10                  15

Ser Arg Lys Leu Ser Cys Ala Ala Ser Gly Phe Thr Phe Ser Thr Phe
                20                  25                  30

Gly Met His Trp Val Arg Gln Ala Pro Glu Lys Gly Leu Glu Trp Val
            35                  40                  45

Ala Tyr Ile Ser Ser Gly Ser Asn Ala Ile Tyr Ala Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Ser Pro Gly Tyr Gly Ala Trp Phe Ala Tyr Trp Gly Gln Gly Thr
            100                 105                 110

Leu Val Thr Val Ser Ala
        115

<210> SEQ ID NO 24
<211> LENGTH: 108
<212> TYPE: PRT
<213> ORGANISM: Mus musculus

<400> SEQUENCE: 24

Glu Asn Val Leu Thr Gln Ser Pro Ala Ile Met Ser Ala Ser Pro Gly
 1               5                  10                  15

Glu Lys Val Thr Met Thr Cys Arg Ala Ser Ser Ser Val Ser Ser Ala
                20                  25                  30

Tyr Leu His Trp Tyr Gln Gln Lys Ser Gly Ala Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Ala Tyr Pro
                 85                  90                  95

Tyr Thr Phe Gly Gly Gly Thr Lys Leu Glu Ile Lys
            100                 105

<210> SEQ ID NO 25
<211> LENGTH: 121

```
<212> TYPE: PRT
<213> ORGANISM: Mus musculus

<400> SEQUENCE: 25

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ser Met His Trp Val Lys Gln Ser His Ala Lys Ser Leu Glu Trp Ile
        35                  40                  45

Gly Val Ile Ser Thr Tyr Asn Gly Asn Thr Asn Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Arg Gly Tyr Tyr Gly Ser Ser Ser Trp Phe Gly Tyr Trp Gly
            100                 105                 110

Gln Gly Thr Leu Val Thr Val Ser Ala
        115                 120

<210> SEQ ID NO 26
<211> LENGTH: 107
<212> TYPE: PRT
<213> ORGANISM: Mus musculus

<400> SEQUENCE: 26

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asp
            20                  25                  30

Val Ala Trp Tyr Gln Gln Lys Pro Gly Gln Ser Pro Glu Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Ala Asp Phe Thr Leu Thr Ile Ser Asn Val Gln Ser
65                  70                  75                  80

Glu Asp Leu Ala Glu Tyr Phe Cys Gln Gln Tyr Asn Ser Phe Pro Tyr
                85                  90                  95

Thr Phe Gly Gly Gly Thr Lys Leu Glu Ile Lys
            100                 105

<210> SEQ ID NO 27
<211> LENGTH: 6
<212> TYPE: PRT
<213> ORGANISM: Mus musculus

<400> SEQUENCE: 27

Gly Gly Phe Ala Trp Asn
1               5

<210> SEQ ID NO 28
<211> LENGTH: 8
<212> TYPE: PRT
<213> ORGANISM: Mus musculus

<400> SEQUENCE: 28

Gly Tyr Ser Ile Thr Gly Gly Phe
1               5
```

```
<210> SEQ ID NO 29
<211> LENGTH: 9
<212> TYPE: PRT
<213> ORGANISM: Mus musculus

<400> SEQUENCE: 29

Gly Tyr Ser Ile Thr Gly Gly Phe Ala
1               5

<210> SEQ ID NO 30
<211> LENGTH: 16
<212> TYPE: PRT
<213> ORGANISM: Mus musculus

<400> SEQUENCE: 30

Tyr Ile Gly Tyr Gly Gly Ser Thr Ser Tyr Asn Pro Ser Leu Asn Ser
1               5                   10                  15

<210> SEQ ID NO 31
<211> LENGTH: 7
<212> TYPE: PRT
<213> ORGANISM: Mus musculus

<400> SEQUENCE: 31

Ile Gly Tyr Gly Gly Ser Thr
1               5

<210> SEQ ID NO 32
<211> LENGTH: 7
<212> TYPE: PRT
<213> ORGANISM: Mus musculus

<400> SEQUENCE: 32

Gly Asp Tyr Leu Phe Ala Tyr
1               5

<210> SEQ ID NO 33
<211> LENGTH: 5
<212> TYPE: PRT
<213> ORGANISM: Mus musculus

<400> SEQUENCE: 33

Asp Tyr Leu Phe Ala
1               5

<210> SEQ ID NO 34
<211> LENGTH: 9
<212> TYPE: PRT
<213> ORGANISM: Mus musculus

<400> SEQUENCE: 34

Ala Arg Gly Asp Tyr Leu Phe Ala Tyr
1               5

<210> SEQ ID NO 35
<211> LENGTH: 11
<212> TYPE: PRT
<213> ORGANISM: Mus musculus

<400> SEQUENCE: 35

Lys Ala Ser Gln Asp Val Asn Thr Ala Val Ala
1               5                   10
```

```
<210> SEQ ID NO 36
<211> LENGTH: 7
<212> TYPE: PRT
<213> ORGANISM: Mus musculus

<400> SEQUENCE: 36

Ser Gln Asp Val Asn Thr Ala
1               5

<210> SEQ ID NO 37
<211> LENGTH: 6
<212> TYPE: PRT
<213> ORGANISM: Mus musculus

<400> SEQUENCE: 37

Gln Asp Val Asn Thr Ala
1               5

<210> SEQ ID NO 38
<211> LENGTH: 7
<212> TYPE: PRT
<213> ORGANISM: Mus musculus

<400> SEQUENCE: 38

Ser Ala Ser Tyr Arg Tyr Thr
1               5

<210> SEQ ID NO 39
<211> LENGTH: 9
<212> TYPE: PRT
<213> ORGANISM: Mus musculus

<400> SEQUENCE: 39

Gln Gln His Tyr Ser Thr Pro Arg Thr
1               5

<210> SEQ ID NO 40
<211> LENGTH: 6
<212> TYPE: PRT
<213> ORGANISM: Mus musculus

<400> SEQUENCE: 40

His Tyr Ser Thr Pro Arg
1               5

<210> SEQ ID NO 41
<211> LENGTH: 11
<212> TYPE: PRT
<213> ORGANISM: Mus musculus

<400> SEQUENCE: 41

Arg Ala Ser Gly Asn Ile His Asn Tyr Leu Ala
1               5                   10

<210> SEQ ID NO 42
<211> LENGTH: 7
<212> TYPE: PRT
<213> ORGANISM: Mus musculus

<400> SEQUENCE: 42

Ser Gly Asn Ile His Asn Tyr
1               5

<210> SEQ ID NO 43
<211> LENGTH: 6
```

```
<212> TYPE: PRT
<213> ORGANISM: Mus musculus

<400> SEQUENCE: 43

Gly Asn Ile His Asn Tyr
1               5

<210> SEQ ID NO 44
<211> LENGTH: 7
<212> TYPE: PRT
<213> ORGANISM: Mus musculus

<400> SEQUENCE: 44

Asn Ala Lys Thr Leu Ala Asp
1               5

<210> SEQ ID NO 45
<211> LENGTH: 9
<212> TYPE: PRT
<213> ORGANISM: Mus musculus

<400> SEQUENCE: 45

Gln His Phe Trp Ser Thr Pro Arg Thr
1               5

<210> SEQ ID NO 46
<211> LENGTH: 6
<212> TYPE: PRT
<213> ORGANISM: Mus musculus

<400> SEQUENCE: 46

Phe Trp Ser Thr Pro Arg
1               5

<210> SEQ ID NO 47
<211> LENGTH: 5
<212> TYPE: PRT
<213> ORGANISM: Mus musculus

<400> SEQUENCE: 47

Ser Tyr Asp Met Ser
1               5

<210> SEQ ID NO 48
<211> LENGTH: 7
<212> TYPE: PRT
<213> ORGANISM: Mus musculus

<400> SEQUENCE: 48

Gly Phe Ala Phe Ser Ser Tyr
1               5

<210> SEQ ID NO 49
<211> LENGTH: 8
<212> TYPE: PRT
<213> ORGANISM: Mus musculus

<400> SEQUENCE: 49

Gly Phe Ala Phe Ser Ser Tyr Asp
1               5

<210> SEQ ID NO 50
<211> LENGTH: 17
<212> TYPE: PRT
<213> ORGANISM: Mus musculus
```

<400> SEQUENCE: 50

His Ile Gly Ser Gly Gly Gly Asn Ile Tyr Tyr Pro Asp Thr Val Lys
1               5                   10                  15

Gly

<210> SEQ ID NO 51
<211> LENGTH: 8
<212> TYPE: PRT
<213> ORGANISM: Mus musculus

<400> SEQUENCE: 51

Ile Gly Ser Gly Gly Gly Asn Ile
1               5

<210> SEQ ID NO 52
<211> LENGTH: 12
<212> TYPE: PRT
<213> ORGANISM: Mus musculus

<400> SEQUENCE: 52

Leu Ile Phe Thr Thr Gly Phe Tyr Gly Met Asp Tyr
1               5                   10

<210> SEQ ID NO 53
<211> LENGTH: 10
<212> TYPE: PRT
<213> ORGANISM: Mus musculus

<400> SEQUENCE: 53

Ile Phe Thr Thr Gly Phe Tyr Gly Met Asp
1               5                   10

<210> SEQ ID NO 54
<211> LENGTH: 14
<212> TYPE: PRT
<213> ORGANISM: Mus musculus

<400> SEQUENCE: 54

Ala Arg Leu Ile Phe Thr Thr Gly Phe Tyr Gly Met Asp Tyr
1               5                   10

<210> SEQ ID NO 55
<211> LENGTH: 11
<212> TYPE: PRT
<213> ORGANISM: Mus musculus

<400> SEQUENCE: 55

Arg Ala Ser Gln Asp Ile Ser Ser Tyr Leu Asn
1               5                   10

<210> SEQ ID NO 56
<211> LENGTH: 7
<212> TYPE: PRT
<213> ORGANISM: Mus musculus

<400> SEQUENCE: 56

Ser Gln Asp Ile Ser Ser Tyr
1               5

<210> SEQ ID NO 57
<211> LENGTH: 6
<212> TYPE: PRT
<213> ORGANISM: Mus musculus

<400> SEQUENCE: 57

Gln Asp Ile Ser Ser Tyr
1               5

<210> SEQ ID NO 58
<211> LENGTH: 7
<212> TYPE: PRT
<213> ORGANISM: Mus musculus

<400> SEQUENCE: 58

Tyr Thr Ser Arg Leu His Ser
1               5

<210> SEQ ID NO 59
<211> LENGTH: 9
<212> TYPE: PRT
<213> ORGANISM: Mus musculus

<400> SEQUENCE: 59

Gln Gln Gly Asn Ala Leu Pro Trp Thr
1               5

<210> SEQ ID NO 60
<211> LENGTH: 6
<212> TYPE: PRT
<213> ORGANISM: Mus musculus

<400> SEQUENCE: 60

Gly Asn Ala Leu Pro Trp
1               5

<210> SEQ ID NO 61
<211> LENGTH: 5
<212> TYPE: PRT
<213> ORGANISM: Mus musculus

<400> SEQUENCE: 61

Asp Tyr Asn Met Asn
1               5

<210> SEQ ID NO 62
<211> LENGTH: 7
<212> TYPE: PRT
<213> ORGANISM: Mus musculus

<400> SEQUENCE: 62

Gly Tyr Ser Phe Ser Asp Tyr
1               5

<210> SEQ ID NO 63
<211> LENGTH: 8
<212> TYPE: PRT
<213> ORGANISM: Mus musculus

<400> SEQUENCE: 63

Gly Tyr Ser Phe Ser Asp Tyr Asn
1               5

<210> SEQ ID NO 64
<211> LENGTH: 17
<212> TYPE: PRT
<213> ORGANISM: Mus musculus

<400> SEQUENCE: 64

Asn Ile Asp Pro Tyr Tyr Gly Ala Thr Ser Tyr Asn Gln Arg Phe Lys
1               5                   10                  15
Gly

<210> SEQ ID NO 65
<211> LENGTH: 8
<212> TYPE: PRT
<213> ORGANISM: Mus musculus

<400> SEQUENCE: 65

Ile Asp Pro Tyr Tyr Gly Ala Thr
1               5

<210> SEQ ID NO 66
<211> LENGTH: 7
<212> TYPE: PRT
<213> ORGANISM: Mus musculus

<400> SEQUENCE: 66

Gly Asp Ser Leu Phe Ala Tyr
1               5

<210> SEQ ID NO 67
<211> LENGTH: 5
<212> TYPE: PRT
<213> ORGANISM: Mus musculus

<400> SEQUENCE: 67

Asp Ser Leu Phe Ala
1               5

<210> SEQ ID NO 68
<211> LENGTH: 9
<212> TYPE: PRT
<213> ORGANISM: Mus musculus

<400> SEQUENCE: 68

Ala Arg Gly Asp Ser Leu Phe Ala Tyr
1               5

<210> SEQ ID NO 69
<211> LENGTH: 11
<212> TYPE: PRT
<213> ORGANISM: Mus musculus

<400> SEQUENCE: 69

Lys Ala Ser Gln Asn Val Gly Thr Asn Val Ala
1               5                   10

<210> SEQ ID NO 70
<211> LENGTH: 7
<212> TYPE: PRT
<213> ORGANISM: Mus musculus

<400> SEQUENCE: 70

Ser Gln Asn Val Gly Thr Asn
1               5

<210> SEQ ID NO 71
<211> LENGTH: 6
<212> TYPE: PRT
<213> ORGANISM: Mus musculus

<400> SEQUENCE: 71

```
Gln Asn Val Gly Thr Asn
1               5

<210> SEQ ID NO 72
<211> LENGTH: 7
<212> TYPE: PRT
<213> ORGANISM: Mus musculus

<400> SEQUENCE: 72

Ser Ala Ser Ser Arg Tyr Ser
1               5

<210> SEQ ID NO 73
<211> LENGTH: 9
<212> TYPE: PRT
<213> ORGANISM: Mus musculus

<400> SEQUENCE: 73

Gln Gln Tyr Ile Thr Tyr Pro Tyr Thr
1               5

<210> SEQ ID NO 74
<211> LENGTH: 6
<212> TYPE: PRT
<213> ORGANISM: Mus musculus

<400> SEQUENCE: 74

Tyr Ile Thr Tyr Pro Tyr
1               5

<210> SEQ ID NO 75
<211> LENGTH: 5
<212> TYPE: PRT
<213> ORGANISM: Mus musculus

<400> SEQUENCE: 75

Ser Tyr Trp Met His
1               5

<210> SEQ ID NO 76
<211> LENGTH: 7
<212> TYPE: PRT
<213> ORGANISM: Mus musculus

<400> SEQUENCE: 76

Tyr Phe Thr Phe Thr Ser Tyr
1               5

<210> SEQ ID NO 77
<211> LENGTH: 8
<212> TYPE: PRT
<213> ORGANISM: Mus musculus

<400> SEQUENCE: 77

Tyr Phe Thr Phe Thr Ser Tyr Trp
1               5

<210> SEQ ID NO 78
<211> LENGTH: 17
<212> TYPE: PRT
<213> ORGANISM: Mus musculus

<400> SEQUENCE: 78

Glu Ile Asn Pro Ser Asn Gly His Thr Asn Tyr Asn Glu Lys Phe Glu
```

1               5                   10                  15

Ser

<210> SEQ ID NO 79
<211> LENGTH: 8
<212> TYPE: PRT
<213> ORGANISM: Mus musculus

<400> SEQUENCE: 79

Ile Asn Pro Ser Asn Gly His Thr
1               5

<210> SEQ ID NO 80
<211> LENGTH: 13
<212> TYPE: PRT
<213> ORGANISM: Mus musculus

<400> SEQUENCE: 80

Gly Val Glu Ser Tyr Asp Phe Asp Asp Ala Leu Asp Tyr
1               5                   10

<210> SEQ ID NO 81
<211> LENGTH: 11
<212> TYPE: PRT
<213> ORGANISM: Mus musculus

<400> SEQUENCE: 81

Val Glu Ser Tyr Asp Phe Asp Asp Ala Leu Asp
1               5                   10

<210> SEQ ID NO 82
<211> LENGTH: 15
<212> TYPE: PRT
<213> ORGANISM: Mus musculus

<400> SEQUENCE: 82

Ala Asn Gly Val Glu Ser Tyr Asp Phe Asp Asp Ala Leu Asp Tyr
1               5                   10                  15

<210> SEQ ID NO 83
<211> LENGTH: 11
<212> TYPE: PRT
<213> ORGANISM: Mus musculus

<400> SEQUENCE: 83

Arg Ala Ser Gln Asp Ile Asn Asn Tyr Leu Asn
1               5                   10

<210> SEQ ID NO 84
<211> LENGTH: 7
<212> TYPE: PRT
<213> ORGANISM: Mus musculus

<400> SEQUENCE: 84

Ser Gln Asp Ile Asn Asn Tyr
1               5

<210> SEQ ID NO 85
<211> LENGTH: 6
<212> TYPE: PRT
<213> ORGANISM: Mus musculus

<400> SEQUENCE: 85

Gln Asp Ile Asn Asn Tyr

```
<210> SEQ ID NO 86
<211> LENGTH: 9
<212> TYPE: PRT
<213> ORGANISM: Mus musculus

<400> SEQUENCE: 86

Gln Gln Gly Asn Thr Leu Pro Phe Thr
1               5

<210> SEQ ID NO 87
<211> LENGTH: 6
<212> TYPE: PRT
<213> ORGANISM: Mus musculus

<400> SEQUENCE: 87

Gly Asn Thr Leu Pro Phe
1               5

<210> SEQ ID NO 88
<211> LENGTH: 7
<212> TYPE: PRT
<213> ORGANISM: Mus musculus

<400> SEQUENCE: 88

Val Tyr Thr Phe Thr Ser Tyr
1               5

<210> SEQ ID NO 89
<211> LENGTH: 8
<212> TYPE: PRT
<213> ORGANISM: Mus musculus

<400> SEQUENCE: 89

Val Tyr Thr Phe Thr Ser Tyr Trp
1               5

<210> SEQ ID NO 90
<211> LENGTH: 17
<212> TYPE: PRT
<213> ORGANISM: Mus musculus

<400> SEQUENCE: 90

Glu Ile Asn Pro Ser Asn Gly His Thr Asn Tyr Asn Glu Lys Phe Lys
1               5                   10                  15

Thr

<210> SEQ ID NO 91
<211> LENGTH: 8
<212> TYPE: PRT
<213> ORGANISM: Mus musculus

<400> SEQUENCE: 91

Ile Asn Pro Ser Asn Gly His Thr
1               5

<210> SEQ ID NO 92
<211> LENGTH: 13
<212> TYPE: PRT
<213> ORGANISM: Mus musculus

<400> SEQUENCE: 92

Gly Val Glu Thr Tyr Asp Phe Asp Asp Ala Met Asp Tyr
```

```
<210> SEQ ID NO 93
<211> LENGTH: 11
<212> TYPE: PRT
<213> ORGANISM: Mus musculus

<400> SEQUENCE: 93

Val Glu Thr Tyr Asp Phe Asp Asp Ala Met Asp
1               5                   10

<210> SEQ ID NO 94
<211> LENGTH: 15
<212> TYPE: PRT
<213> ORGANISM: Mus musculus

<400> SEQUENCE: 94

Ala Asn Gly Val Glu Thr Tyr Asp Phe Asp Asp Ala Met Asp Tyr
1               5                   10                  15

<210> SEQ ID NO 95
<211> LENGTH: 7
<212> TYPE: PRT
<213> ORGANISM: Mus musculus

<400> SEQUENCE: 95

Phe Thr Ser Arg Leu His Ser
1               5

<210> SEQ ID NO 96
<211> LENGTH: 9
<212> TYPE: PRT
<213> ORGANISM: Mus musculus

<400> SEQUENCE: 96

Gln Gln Gly Asp Thr Phe Pro Phe Thr
1               5

<210> SEQ ID NO 97
<211> LENGTH: 6
<212> TYPE: PRT
<213> ORGANISM: Mus musculus

<400> SEQUENCE: 97

Gly Asp Thr Phe Pro Phe
1               5

<210> SEQ ID NO 98
<211> LENGTH: 5
<212> TYPE: PRT
<213> ORGANISM: Mus musculus

<400> SEQUENCE: 98

Asn Tyr Glu Met Asn
1               5

<210> SEQ ID NO 99
<211> LENGTH: 7
<212> TYPE: PRT
<213> ORGANISM: Mus musculus

<400> SEQUENCE: 99

Gly Tyr Thr Phe Thr Asn Tyr
1               5
```

<210> SEQ ID NO 100
<211> LENGTH: 8
<212> TYPE: PRT
<213> ORGANISM: Mus musculus

<400> SEQUENCE: 100

Gly Tyr Thr Phe Thr Asn Tyr Glu
1               5

<210> SEQ ID NO 101
<211> LENGTH: 16
<212> TYPE: PRT
<213> ORGANISM: Mus musculus

<400> SEQUENCE: 101

Trp Ile Asn Thr Tyr Thr Gly Glu Ser Thr Tyr Ala Asp Asp Phe Lys
1               5                   10                  15

<210> SEQ ID NO 102
<211> LENGTH: 8
<212> TYPE: PRT
<213> ORGANISM: Mus musculus

<400> SEQUENCE: 102

Ile Asn Thr Tyr Thr Gly Glu Ser
1               5

<210> SEQ ID NO 103
<211> LENGTH: 11
<212> TYPE: PRT
<213> ORGANISM: Mus musculus

<400> SEQUENCE: 103

Asp Asp Tyr Gly Arg Ser Tyr Gly Phe Ala Tyr
1               5                   10

<210> SEQ ID NO 104
<211> LENGTH: 9
<212> TYPE: PRT
<213> ORGANISM: Mus musculus

<400> SEQUENCE: 104

Asp Tyr Gly Arg Ser Tyr Gly Phe Ala
1               5

<210> SEQ ID NO 105
<211> LENGTH: 13
<212> TYPE: PRT
<213> ORGANISM: Mus musculus

<400> SEQUENCE: 105

Val Arg Asp Asp Tyr Gly Arg Ser Tyr Gly Phe Ala Tyr
1               5                   10

<210> SEQ ID NO 106
<211> LENGTH: 15
<212> TYPE: PRT
<213> ORGANISM: Mus musculus

<400> SEQUENCE: 106

Arg Ala Ser Glu Ser Val Asp Ser Tyr Gly Asn Ser Phe Met His
1               5                   10                  15

<210> SEQ ID NO 107

```
<211> LENGTH: 11
<212> TYPE: PRT
<213> ORGANISM: Mus musculus

<400> SEQUENCE: 107

Ser Glu Ser Val Asp Ser Tyr Gly Asn Ser Phe
1               5                   10

<210> SEQ ID NO 108
<211> LENGTH: 10
<212> TYPE: PRT
<213> ORGANISM: Mus musculus

<400> SEQUENCE: 108

Glu Ser Val Asp Ser Tyr Gly Asn Ser Phe
1               5                   10

<210> SEQ ID NO 109
<211> LENGTH: 7
<212> TYPE: PRT
<213> ORGANISM: Mus musculus

<400> SEQUENCE: 109

Leu Ala Ser Lys Leu Glu Ser
1               5

<210> SEQ ID NO 110
<211> LENGTH: 10
<212> TYPE: PRT
<213> ORGANISM: Mus musculus

<400> SEQUENCE: 110

His Gln Asn Asn Glu Asp Pro Pro Trp Thr
1               5                   10

<210> SEQ ID NO 111
<211> LENGTH: 7
<212> TYPE: PRT
<213> ORGANISM: Mus musculus

<400> SEQUENCE: 111

Asn Asn Glu Asp Pro Pro Trp
1               5

<210> SEQ ID NO 112
<211> LENGTH: 5
<212> TYPE: PRT
<213> ORGANISM: Mus musculus

<400> SEQUENCE: 112

Asp Tyr Ser Met His
1               5

<210> SEQ ID NO 113
<211> LENGTH: 7
<212> TYPE: PRT
<213> ORGANISM: Mus musculus

<400> SEQUENCE: 113

Gly Tyr Thr Phe Thr Asp Tyr
1               5

<210> SEQ ID NO 114
<211> LENGTH: 8
<212> TYPE: PRT
```

<213> ORGANISM: Mus musculus

<400> SEQUENCE: 114

Gly Tyr Thr Phe Thr Asp Tyr Ser
1               5

<210> SEQ ID NO 115
<211> LENGTH: 17
<212> TYPE: PRT
<213> ORGANISM: Mus musculus

<400> SEQUENCE: 115

Trp Ile Ile Thr Glu Thr Gly Glu Pro Thr Tyr Ala Asp Asp Phe Arg
1               5                   10                  15
Gly

<210> SEQ ID NO 116
<211> LENGTH: 8
<212> TYPE: PRT
<213> ORGANISM: Mus musculus

<400> SEQUENCE: 116

Ile Ile Thr Glu Thr Gly Glu Pro
1               5

<210> SEQ ID NO 117
<211> LENGTH: 5
<212> TYPE: PRT
<213> ORGANISM: Mus musculus

<400> SEQUENCE: 117

Asp Phe Asp Gly Tyr
1               5

<210> SEQ ID NO 118
<211> LENGTH: 7
<212> TYPE: PRT
<213> ORGANISM: Mus musculus

<400> SEQUENCE: 118

Ala Arg Asp Phe Asp Gly Tyr
1               5

<210> SEQ ID NO 119
<211> LENGTH: 11
<212> TYPE: PRT
<213> ORGANISM: Mus musculus

<400> SEQUENCE: 119

Arg Ala Ser Glu Asn Ile Tyr Ser Tyr Leu Ala
1               5                   10

<210> SEQ ID NO 120
<211> LENGTH: 7
<212> TYPE: PRT
<213> ORGANISM: Mus musculus

<400> SEQUENCE: 120

Ser Glu Asn Ile Tyr Ser Tyr
1               5

<210> SEQ ID NO 121
<211> LENGTH: 6
<212> TYPE: PRT

<213> ORGANISM: Mus musculus

<400> SEQUENCE: 121

Glu Asn Ile Tyr Ser Tyr
1               5

<210> SEQ ID NO 122
<211> LENGTH: 7
<212> TYPE: PRT
<213> ORGANISM: Mus musculus

<400> SEQUENCE: 122

Asn Ala Lys Thr Leu Thr Glu
1               5

<210> SEQ ID NO 123
<211> LENGTH: 9
<212> TYPE: PRT
<213> ORGANISM: Mus musculus

<400> SEQUENCE: 123

Gln His His Tyr Gly Phe Pro Trp Thr
1               5

<210> SEQ ID NO 124
<211> LENGTH: 6
<212> TYPE: PRT
<213> ORGANISM: Mus musculus

<400> SEQUENCE: 124

His Tyr Gly Phe Pro Trp
1               5

<210> SEQ ID NO 125
<211> LENGTH: 5
<212> TYPE: PRT
<213> ORGANISM: Mus musculus

<400> SEQUENCE: 125

Thr Phe Gly Met His
1               5

<210> SEQ ID NO 126
<211> LENGTH: 7
<212> TYPE: PRT
<213> ORGANISM: Mus musculus

<400> SEQUENCE: 126

Gly Phe Thr Phe Ser Thr Phe
1               5

<210> SEQ ID NO 127
<211> LENGTH: 8
<212> TYPE: PRT
<213> ORGANISM: Mus musculus

<400> SEQUENCE: 127

Gly Phe Thr Phe Ser Thr Phe Gly
1               5

<210> SEQ ID NO 128
<211> LENGTH: 17
<212> TYPE: PRT
<213> ORGANISM: Mus musculus

```
<400> SEQUENCE: 128

Tyr Ile Ser Ser Gly Ser Asn Ala Ile Tyr Tyr Ala Asp Thr Val Lys
1               5                   10                  15

Gly

<210> SEQ ID NO 129
<211> LENGTH: 8
<212> TYPE: PRT
<213> ORGANISM: Mus musculus

<400> SEQUENCE: 129

Ile Ser Ser Gly Ser Asn Ala Ile
1               5

<210> SEQ ID NO 130
<211> LENGTH: 9
<212> TYPE: PRT
<213> ORGANISM: Mus musculus

<400> SEQUENCE: 130

Pro Gly Tyr Gly Ala Trp Phe Ala Tyr
1               5

<210> SEQ ID NO 131
<211> LENGTH: 7
<212> TYPE: PRT
<213> ORGANISM: Mus musculus

<400> SEQUENCE: 131

Gly Tyr Gly Ala Trp Phe Ala
1               5

<210> SEQ ID NO 132
<211> LENGTH: 11
<212> TYPE: PRT
<213> ORGANISM: Mus musculus

<400> SEQUENCE: 132

Ala Ser Pro Gly Tyr Gly Ala Trp Phe Ala Tyr
1               5                   10

<210> SEQ ID NO 133
<211> LENGTH: 12
<212> TYPE: PRT
<213> ORGANISM: Mus musculus

<400> SEQUENCE: 133

Arg Ala Ser Ser Ser Val Ser Ser Ala Tyr Leu His
1               5                   10

<210> SEQ ID NO 134
<211> LENGTH: 8
<212> TYPE: PRT
<213> ORGANISM: Mus musculus

<400> SEQUENCE: 134

Ser Ser Ser Val Ser Ser Ala Tyr
1               5

<210> SEQ ID NO 135
<211> LENGTH: 7
<212> TYPE: PRT
<213> ORGANISM: Mus musculus
```

```
<400> SEQUENCE: 135

Ser Ser Val Ser Ser Ala Tyr
1               5

<210> SEQ ID NO 136
<211> LENGTH: 7
<212> TYPE: PRT
<213> ORGANISM: Mus musculus

<400> SEQUENCE: 136

Ser Thr Ser Asn Leu Ala Ser
1               5

<210> SEQ ID NO 137
<211> LENGTH: 9
<212> TYPE: PRT
<213> ORGANISM: Mus musculus

<400> SEQUENCE: 137

Gln Gln Tyr Ser Ala Tyr Pro Tyr Thr
1               5

<210> SEQ ID NO 138
<211> LENGTH: 6
<212> TYPE: PRT
<213> ORGANISM: Mus musculus

<400> SEQUENCE: 138

Tyr Ser Ala Tyr Pro Tyr
1               5

<210> SEQ ID NO 139
<211> LENGTH: 17
<212> TYPE: PRT
<213> ORGANISM: Mus musculus

<400> SEQUENCE: 139

Val Ile Ser Thr Tyr Asn Gly Asn Thr Asn Tyr Asn Gln Lys Phe Lys
1               5                   10                  15

Gly

<210> SEQ ID NO 140
<211> LENGTH: 8
<212> TYPE: PRT
<213> ORGANISM: Mus musculus

<400> SEQUENCE: 140

Ile Ser Thr Tyr Asn Gly Asn Thr
1               5

<210> SEQ ID NO 141
<211> LENGTH: 12
<212> TYPE: PRT
<213> ORGANISM: Mus musculus

<400> SEQUENCE: 141

Arg Gly Tyr Tyr Gly Ser Ser Ser Trp Phe Gly Tyr
1               5                   10

<210> SEQ ID NO 142
<211> LENGTH: 10
<212> TYPE: PRT
<213> ORGANISM: Mus musculus
```

```
<400> SEQUENCE: 142

Gly Tyr Tyr Gly Ser Ser Ser Trp Phe Gly
1               5                   10

<210> SEQ ID NO 143
<211> LENGTH: 14
<212> TYPE: PRT
<213> ORGANISM: Mus musculus

<400> SEQUENCE: 143

Ala Arg Arg Gly Tyr Tyr Gly Ser Ser Ser Trp Phe Gly Tyr
1               5                   10

<210> SEQ ID NO 144
<211> LENGTH: 11
<212> TYPE: PRT
<213> ORGANISM: Mus musculus

<400> SEQUENCE: 144

Lys Ala Ser Gln Asn Val Gly Thr Asp Val Ala
1               5                   10

<210> SEQ ID NO 145
<211> LENGTH: 7
<212> TYPE: PRT
<213> ORGANISM: Mus musculus

<400> SEQUENCE: 145

Ser Gln Asn Val Gly Thr Asp
1               5

<210> SEQ ID NO 146
<211> LENGTH: 6
<212> TYPE: PRT
<213> ORGANISM: Mus musculus

<400> SEQUENCE: 146

Gln Asn Val Gly Thr Asp
1               5

<210> SEQ ID NO 147
<211> LENGTH: 7
<212> TYPE: PRT
<213> ORGANISM: Mus musculus

<400> SEQUENCE: 147

Ser Ala Ser Tyr Arg Tyr Ser
1               5

<210> SEQ ID NO 148
<211> LENGTH: 9
<212> TYPE: PRT
<213> ORGANISM: Mus musculus

<400> SEQUENCE: 148

Gln Gln Tyr Asn Ser Phe Pro Tyr Thr
1               5

<210> SEQ ID NO 149
<211> LENGTH: 6
<212> TYPE: PRT
<213> ORGANISM: Mus musculus

<400> SEQUENCE: 149
```

Tyr Asn Ser Phe Pro Tyr
1               5

<210> SEQ ID NO 150
<211> LENGTH: 449
<212> TYPE: PRT
<213> ORGANISM: homo sapiens

<400> SEQUENCE: 150

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220

Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
                245                 250                 255

Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Glu Phe Thr Cys Arg Ala
    290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Gly Ala Gly Ala Thr Ala Leu Val Phe Leu Ser Phe Cys
            340                 345                 350

Val Ile Phe Ile Val Val Arg Ser Cys Arg Lys Lys Ser Ala Arg Pro
        355                 360                 365

```
Ala Ala Asp Val Gly Asp Ile Gly Met Lys Asp Ala Asn Thr Ile Arg
        370                 375                 380

Gly Ser Ala Ser Gln Gly Asn Leu Thr Glu Ser Trp Ala Asp Asp Asn
385                 390                 395                 400

Pro Arg His His Gly Leu Ala Ala His Ser Ser Gly Glu Glu Arg Glu
                405                 410                 415

Ile Gln Tyr Ala Pro Leu Ser Phe His Lys Gly Glu Pro Gln Asp Leu
            420                 425                 430

Ser Gly Gln Glu Ala Thr Asn Asn Glu Tyr Ser Glu Ile Lys Ile Pro
        435                 440                 445

Lys
```

<210> SEQ ID NO 151
<211> LENGTH: 446
<212> TYPE: PRT
<213> ORGANISM: homo sapiens

<400> SEQUENCE: 151

```
Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
                20                  25                  30

Trp Ile Tyr Pro Gly Pro Val Val His Gly Tyr Trp Phe Arg Glu Gly
            35                  40                  45

Ala Asn Thr Asp Gln Asp Ala Pro Val Ala Thr Asn Asn Pro Ala Arg
        50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
        210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285
```

```
Glu Leu Pro Trp Val His Leu Arg Asp Ala Glu Phe Thr Cys Arg
    290                 295                 300

Ala Gln Asn Pro Leu Gly Ser Gln Val Tyr Leu Asn Val Ser Leu
305                 310                 315                 320

Gln Ser Lys Ala Thr Ser Gly Val Thr Gln Gly Val Val Gly Ala
                325                 330                 335

Gly Ala Thr Ala Leu Val Phe Leu Ser Phe Cys Val Ile Phe Val Val
                340                 345                 350

Val Arg Ser Cys Arg Lys Lys Ser Ala Arg Pro Ala Ala Gly Val Gly
                355                 360                 365

Asp Thr Gly Ile Glu Asp Ala Asn Ala Val Arg Gly Ser Ala Ser Gln
    370                 375                 380

Gly Pro Leu Thr Glu Pro Trp Ala Glu Asp Ser Pro Pro Asp Gln Pro
385                 390                 395                 400

Pro Pro Ala Ser Ala Arg Ser Ser Val Gly Glu Gly Glu Leu Gln Tyr
                405                 410                 415

Ala Ser Leu Ser Phe Gln Met Val Lys Pro Trp Asp Ser Arg Gly Gln
                420                 425                 430

Glu Ala Thr Asp Thr Glu Tyr Ser Glu Ile Lys Ile His Arg
    435                 440                 445

<210> SEQ ID NO 152
<211> LENGTH: 347
<212> TYPE: PRT
<213> ORGANISM: homo sapiens

<400> SEQUENCE: 152

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
                20                  25                  30

Tyr Asp Lys Asn Ser Pro Val His Gly Tyr Trp Phe Arg Glu Gly Ala
            35                  40                  45

Ile Ile Ser Gly Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
```

```
                 210                 215                 220
Ile Phe Pro Gly Asp Gly Ser Gly Lys Gln Glu Thr Arg Ala Gly Val
225                 230                 235                 240

Val His Gly Ala Ile Gly Gly Ala Gly Val Thr Ala Leu Leu Ala Leu
                245                 250                 255

Cys Leu Cys Leu Ile Phe Phe Ile Val Lys Thr His Arg Arg Lys Ala
            260                 265                 270

Ala Arg Thr Ala Val Gly Arg Asn Asp Thr His Pro Thr Thr Gly Ser
        275                 280                 285

Ala Ser Pro Lys His Gln Lys Lys Ser Lys Leu His Gly Pro Thr Glu
    290                 295                 300

Thr Ser Ser Cys Ser Gly Ala Ala Pro Thr Val Glu Met Asp Glu Glu
305                 310                 315                 320

Leu His Tyr Ala Ser Leu Asn Phe His Gly Met Asn Pro Ser Lys Asp
                325                 330                 335

Thr Ser Thr Glu Tyr Ser Glu Val Arg Thr Gln
                340                 345

<210> SEQ ID NO 153
<211> LENGTH: 535
<212> TYPE: PRT
<213> ORGANISM: homo sapiens

<400> SEQUENCE: 153

Glu Lys Pro Val Tyr Glu Leu Gln Val Gln Lys Ser Val Thr Val Gln
1               5                   10                  15

Glu Gly Leu Cys Val Leu Val Pro Cys Ser Phe Ser Tyr Pro Trp Arg
            20                  25                  30

Ser Trp Tyr Ser Ser Pro Pro Leu Tyr Val Tyr Trp Phe Arg Asp Gly
        35                  40                  45

Glu Ile Pro Tyr Tyr Ala Glu Val Val Ala Thr Asn Asn Pro Asp Arg
    50                  55                  60

Arg Val Lys Pro Glu Thr Gln Gly Arg Phe Arg Leu Leu Gly Asp Val
65                  70                  75                  80

Gln Lys Lys Asn Cys Ser Leu Ser Ile Gly Asp Ala Arg Met Glu Asp
                85                  90                  95

Thr Gly Ser Tyr Phe Phe Arg Val Glu Arg Gly Arg Asp Val Lys Tyr
            100                 105                 110

Ser Tyr Gln Gln Asn Lys Leu Asn Leu Glu Val Thr Ala Leu Ile Glu
        115                 120                 125

Lys Pro Asp Ile His Phe Leu Glu Pro Leu Glu Ser Gly Arg Pro Thr
    130                 135                 140

Arg Leu Ser Cys Ser Leu Pro Gly Ser Cys Glu Ala Gly Pro Pro Leu
145                 150                 155                 160

Thr Phe Ser Trp Thr Gly Asn Ala Leu Ser Pro Leu Asp Pro Glu Thr
                165                 170                 175

Thr Arg Ser Ser Glu Leu Thr Leu Thr Pro Arg Pro Glu Asp His Gly
            180                 185                 190

Thr Asn Leu Thr Cys Gln Met Lys Arg Gln Gly Ala Gln Val Thr Thr
        195                 200                 205

Glu Arg Thr Val Gln Leu Asn Val Ser Tyr Ala Pro Gln Thr Ile Thr
    210                 215                 220

Ile Phe Arg Asn Gly Ile Ala Leu Glu Ile Leu Gln Asn Thr Ser Tyr
225                 230                 235                 240
```

```
Leu Pro Val Leu Glu Gly Gln Ala Leu Arg Leu Cys Asp Ala Pro
            245                 250                 255

Ser Asn Pro Pro Ala His Leu Ser Trp Phe Gln Gly Ser Pro Ala Leu
        260                 265                 270

Asn Ala Thr Pro Ile Ser Asn Thr Gly Ile Leu Glu Leu Arg Arg Val
            275                 280                 285

Arg Ser Ala Glu Glu Gly Gly Phe Thr Cys Arg Ala Gln His Pro Leu
        290                 295                 300

Gly Phe Leu Gln Ile Phe Leu Asn Leu Ser Val Tyr Ser Leu Pro Gln
305                 310                 315                 320

Leu Leu Gly Pro Ser Cys Ser Trp Glu Ala Glu Gly Leu His Cys Arg
            325                 330                 335

Cys Ser Phe Arg Ala Arg Pro Ala Pro Ser Leu Cys Trp Arg Leu Glu
        340                 345                 350

Glu Lys Pro Leu Glu Gly Asn Ser Ser Gln Gly Ser Phe Lys Val Asn
        355                 360                 365

Ser Ser Ser Ala Gly Pro Trp Ala Asn Ser Ser Leu Ile Leu His Gly
    370                 375                 380

Gly Leu Ser Ser Asp Leu Lys Val Ser Cys Lys Ala Trp Asn Ile Tyr
385                 390                 395                 400

Gly Ser Gln Ser Gly Ser Val Leu Leu Leu Gln Gly Arg Ser Asn Leu
        405                 410                 415

Gly Thr Gly Val Val Pro Ala Ala Leu Gly Gly Ala Gly Val Met Ala
            420                 425                 430

Leu Leu Cys Ile Cys Leu Cys Leu Ile Phe Phe Leu Ile Val Lys Ala
            435                 440                 445

Arg Arg Lys Gln Ala Ala Gly Arg Pro Glu Lys Met Asp Asp Glu Asp
    450                 455                 460

Pro Ile Met Gly Thr Ile Thr Ser Gly Ser Arg Lys Lys Pro Trp Pro
465                 470                 475                 480

Asp Ser Pro Gly Asp Gln Ala Ser Pro Pro Gly Asp Ala Pro Pro Leu
            485                 490                 495

Glu Glu Gln Lys Glu Leu His Tyr Ala Ser Leu Ser Phe Ser Glu Met
        500                 505                 510

Lys Ser Arg Glu Pro Lys Asp Gln Glu Ala Pro Ser Thr Thr Glu Tyr
        515                 520                 525

Ser Glu Ile Lys Thr Ser Lys
    530                 535

<210> SEQ ID NO 154
<211> LENGTH: 411
<212> TYPE: PRT
<213> ORGANISM: homo sapiens

<400> SEQUENCE: 154

Gln Glu Arg Arg Phe Gln Leu Glu Gly Pro Glu Ser Leu Thr Val Gln
1               5                   10                  15

Glu Gly Leu Cys Val Leu Val Pro Cys Arg Leu Pro Thr Thr Leu Pro
            20                  25                  30

Ala Ser Tyr Tyr Gly Tyr Gly Tyr Trp Phe Leu Glu Gly Ala Asp Val
        35                  40                  45

Pro Val Ala Thr Asn Asp Pro Asp Glu Glu Val Gln Glu Glu Thr Arg
    50                  55                  60

Gly Arg Phe His Leu Leu Trp Asp Pro Arg Arg Lys Asn Cys Ser Leu
65                  70                  75                  80
```

Ser Ile Arg Asp Ala Arg Arg Asp Asn Ala Ala Tyr Phe Phe Arg
            85                  90                  95

Leu Lys Ser Lys Trp Met Lys Tyr Gly Tyr Thr Ser Ser Lys Leu Ser
        100                 105                 110

Val Arg Val Met Ala Leu Thr His Arg Pro Asn Ile Ser Ile Pro Gly
        115                 120                 125

Thr Leu Glu Ser Gly His Pro Ser Asn Leu Thr Cys Ser Val Pro Trp
    130                 135                 140

Val Cys Glu Gln Gly Thr Pro Pro Ile Phe Ser Trp Met Ser Ala Ala
145                 150                 155                 160

Pro Thr Ser Leu Gly Pro Arg Thr Thr Gln Ser Ser Val Leu Thr Ile
                165                 170                 175

Thr Pro Arg Pro Gln Asp His Ser Thr Asn Leu Thr Cys Gln Val Thr
            180                 185                 190

Phe Pro Gly Ala Gly Val Thr Met Glu Arg Thr Ile Gln Leu Asn Val
        195                 200                 205

Ser Ser Phe Lys Ile Leu Gln Asn Thr Ser Ser Leu Pro Val Leu Glu
    210                 215                 220

Gly Gln Ala Leu Arg Leu Leu Cys Asp Ala Asp Gly Asn Pro Pro Ala
225                 230                 235                 240

His Leu Ser Trp Phe Gln Gly Phe Pro Ala Leu Asn Ala Thr Pro Ile
                245                 250                 255

Ser Asn Thr Gly Val Leu Glu Leu Pro Gln Val Gly Ser Ala Glu Glu
            260                 265                 270

Gly Asp Phe Thr Cys Arg Ala Gln His Pro Leu Gly Ser Leu Gln Ile
        275                 280                 285

Ser Leu Ser Leu Phe Val His Trp Lys Pro Glu Gly Arg Ala Gly Gly
    290                 295                 300

Val Leu Gly Ala Val Trp Gly Ala Ser Ile Thr Thr Leu Val Phe Leu
305                 310                 315                 320

Cys Val Cys Phe Ile Phe Arg Val Lys Thr Arg Arg Lys Lys Ala Ala
                325                 330                 335

Gln Pro Val Gln Asn Thr Asp Asp Val Asn Pro Val Met Val Ser Gly
            340                 345                 350

Ser Arg Gly His Gln His Gln Phe Gln Thr Gly Ile Val Ser Asp His
        355                 360                 365

Pro Ala Glu Ala Gly Pro Ile Ser Glu Asp Glu Gln Glu Leu His Tyr
    370                 375                 380

Ala Val Leu His Phe His Lys Val Gln Pro Gln Glu Pro Lys Val Thr
385                 390                 395                 400

Asp Thr Glu Tyr Ser Glu Ile Lys Ile His Lys
                405                 410

<210> SEQ ID NO 155
<211> LENGTH: 483
<212> TYPE: PRT
<213> ORGANISM: homo sapiens

<400> SEQUENCE: 155

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly

```
            35                  40                  45
Tyr Trp Phe Arg Ala Gly Asp Arg Pro Tyr Gln Asp Ala Pro Val Ala
 50                  55                  60

Thr Asn Asn Pro Asp Arg Glu Val Gln Ala Glu Thr Gln Gly Arg Phe
 65                  70                  75                  80

Gln Leu Leu Gly Asp Ile Trp Ser Asn Asp Cys Ser Leu Ser Ile Arg
                 85                  90                  95

Asp Ala Arg Lys Arg Asp Lys Gly Ser Tyr Phe Phe Arg Leu Glu Arg
                100                 105                 110

Gly Ser Met Lys Trp Ser Tyr Lys Ser Gln Leu Asn Tyr Lys Thr Lys
                115                 120                 125

Gln Leu Ser Val Phe Val Thr Ala Leu Thr His Arg Pro Asp Ile Leu
                130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
                180                 185                 190

Leu Thr Leu Thr Pro Lys Pro Gln Asp His Gly Thr Ser Leu Thr Cys
                195                 200                 205

Gln Val Thr Leu Pro Gly Thr Gly Val Thr Thr Thr Ser Thr Val Arg
                210                 215                 220

Leu Asp Val Ser Tyr Pro Pro Trp Asn Leu Thr Met Thr Val Phe Gln
225                 230                 235                 240

Gly Asp Ala Thr Ala Ser Thr Ala Leu Gly Asn Gly Ser Ser Leu Ser
                245                 250                 255

Val Leu Glu Gly Gln Ser Leu Arg Leu Val Cys Ala Val Asn Ser Asn
                260                 265                 270

Pro Pro Ala Arg Leu Ser Trp Thr Arg Gly Ser Leu Thr Leu Cys Pro
                275                 280                 285

Ser Arg Ser Ser Asn Pro Gly Leu Leu Glu Leu Pro Arg Val His Val
                290                 295                 300

Arg Asp Glu Gly Glu Phe Thr Cys Arg Ala Gln Asn Ala Gln Gly Ser
305                 310                 315                 320

Gln His Ile Ser Leu Ser Leu Ser Leu Gln Asn Glu Gly Thr Gly Thr
                325                 330                 335

Ser Arg Pro Val Ser Gln Val Thr Leu Ala Ala Val Gly Gly Ala Gly
                340                 345                 350

Ala Thr Ala Leu Ala Phe Leu Ser Phe Cys Ile Ile Phe Ile Ile Val
                355                 360                 365

Arg Ser Cys Arg Lys Lys Ser Ala Arg Pro Ala Ala Gly Val Gly Asp
                370                 375                 380

Thr Gly Met Glu Asp Ala Lys Ala Ile Arg Gly Ser Ala Ser Gln Gly
385                 390                 395                 400

Pro Leu Thr Glu Ser Trp Lys Asp Gly Asn Pro Leu Lys Lys Pro Pro
                405                 410                 415

Pro Ala Val Ala Pro Ser Ser Gly Glu Glu Gly Glu Leu His Tyr Ala
                420                 425                 430

Thr Leu Ser Phe His Lys Val Lys Pro Gln Asp Pro Gln Gly Gln Glu
                435                 440                 445

Ala Thr Asp Ser Glu Tyr Ser Glu Ile Lys Ile His Lys Arg Glu Thr
450                 455                 460
```

```
Ala Glu Thr Gln Ala Cys Leu Arg Asn His Asn Pro Ser Ser Lys Glu
465                 470                 475                 480

Val Arg Gly

<210> SEQ ID NO 156
<211> LENGTH: 681
<212> TYPE: PRT
<213> ORGANISM: homo sapiens

<400> SEQUENCE: 156

Met Asp Gly Arg Phe Trp Ile Arg Val Gln Glu Ser Val Met Val Pro
1               5                   10                  15

Glu Gly Leu Cys Ile Ser Val Pro Cys Ser Phe Ser Tyr Pro Arg Gln
            20                  25                  30

Asp Trp Thr Gly Ser Thr Pro Ala Tyr Gly Tyr Trp Phe Lys Ala Val
        35                  40                  45

Thr Glu Thr Thr Lys Gly Ala Pro Val Ala Thr Asn His Gln Ser Arg
50                  55                  60

Glu Val Glu Met Ser Thr Arg Gly Arg Phe Gln Leu Thr Gly Asp Pro
65                  70                  75                  80

Ala Lys Gly Asn Cys Ser Leu Val Ile Arg Asp Ala Gln Met Gln Asp
                85                  90                  95

Glu Ser Gln Tyr Phe Phe Arg Val Glu Arg Gly Ser Tyr Val Arg Tyr
            100                 105                 110

Asn Phe Met Asn Asp Gly Phe Phe Leu Lys Val Thr Ala Leu Thr Gln
        115                 120                 125

Lys Pro Asp Val Tyr Ile Pro Glu Thr Leu Glu Pro Gly Gln Pro Val
130                 135                 140

Thr Val Ile Cys Val Phe Asn Trp Ala Phe Glu Glu Cys Pro Pro Pro
145                 150                 155                 160

Ser Phe Ser Trp Thr Gly Ala Ala Leu Ser Ser Gln Gly Thr Lys Pro
                165                 170                 175

Thr Thr Ser His Phe Ser Val Leu Ser Phe Thr Pro Arg Pro Gln Asp
            180                 185                 190

His Asn Thr Asp Leu Thr Cys His Val Asp Phe Ser Arg Lys Gly Val
        195                 200                 205

Ser Val Gln Arg Thr Val Arg Leu Arg Val Ala Tyr Ala Pro Arg Asp
210                 215                 220

Leu Val Ile Ser Ile Ser Arg Asp Asn Thr Pro Ala Leu Glu Pro Gln
225                 230                 235                 240

Pro Gln Gly Asn Val Pro Tyr Leu Glu Ala Gln Lys Gly Gln Phe Leu
                245                 250                 255

Arg Leu Leu Cys Ala Ala Asp Ser Gln Pro Pro Ala Thr Leu Ser Trp
            260                 265                 270

Val Leu Gln Asn Arg Val Leu Ser Ser Ser His Pro Trp Gly Pro Arg
        275                 280                 285

Pro Leu Gly Leu Glu Leu Pro Gly Val Lys Ala Gly Asp Ser Gly Arg
290                 295                 300

Tyr Thr Cys Arg Ala Glu Asn Arg Leu Gly Ser Gln Gln Arg Ala Leu
305                 310                 315                 320

Asp Leu Ser Val Gln Tyr Pro Pro Glu Asn Leu Arg Val Met Val Ser
                325                 330                 335

Gln Ala Asn Arg Thr Val Leu Glu Asn Leu Gly Asn Gly Thr Ser Leu
            340                 345                 350
```

```
Pro Val Leu Glu Gly Gln Ser Leu Cys Leu Val Cys Val Thr His Ser
        355                 360                 365

Ser Pro Pro Ala Arg Leu Ser Trp Thr Gln Arg Gly Gln Val Leu Ser
    370                 375                 380

Pro Ser Gln Pro Ser Asp Pro Gly Val Leu Glu Leu Pro Arg Val Gln
385                 390                 395                 400

Val Glu His Glu Gly Glu Phe Thr Cys His Ala Arg His Pro Leu Gly
                405                 410                 415

Ser Gln His Val Ser Leu Ser Leu Ser Val His Tyr Ser Pro Lys Leu
            420                 425                 430

Leu Gly Pro Ser Cys Ser Trp Glu Ala Glu Gly Leu His Cys Ser Cys
        435                 440                 445

Ser Ser Gln Ala Ser Pro Ala Pro Ser Leu Arg Trp Trp Leu Gly Glu
    450                 455                 460

Glu Leu Leu Glu Gly Asn Ser Ser Gln Asp Ser Phe Glu Val Thr Pro
465                 470                 475                 480

Ser Ser Ala Gly Pro Trp Ala Asn Ser Ser Leu Ser Leu His Gly Gly
                485                 490                 495

Leu Ser Ser Gly Leu Arg Leu Arg Cys Glu Ala Trp Asn Val His Gly
            500                 505                 510

Ala Gln Ser Gly Ser Ile Leu Gln Leu Pro Asp Lys Lys Gly Leu Ile
        515                 520                 525

Ser Thr Ala Phe Ser Asn Gly Ala Phe Leu Gly Ile Gly Ile Thr Ala
    530                 535                 540

Leu Leu Phe Leu Cys Leu Ala Leu Ile Ile Met Lys Ile Leu Pro Lys
545                 550                 555                 560

Arg Arg Thr Gln Thr Glu Thr Pro Arg Pro Arg Phe Ser Arg His Ser
                565                 570                 575

Thr Ile Leu Asp Tyr Ile Asn Val Val Pro Thr Ala Gly Pro Leu Ala
            580                 585                 590

Gln Lys Arg Asn Gln Lys Ala Thr Pro Asn Ser Pro Arg Thr Pro Leu
        595                 600                 605

Pro Pro Gly Ala Pro Ser Pro Glu Ser Lys Lys Asn Gln Lys Lys Gln
    610                 615                 620

Tyr Gln Leu Pro Ser Phe Pro Glu Pro Lys Ser Ser Thr Gln Ala Pro
625                 630                 635                 640

Glu Ser Gln Glu Ser Gln Glu Glu Leu His Tyr Ala Thr Leu Asn Phe
                645                 650                 655

Pro Gly Val Arg Pro Arg Pro Glu Ala Arg Met Pro Lys Gly Thr Gln
            660                 665                 670

Ala Asp Tyr Ala Glu Val Lys Phe Gln
        675                 680

<210> SEQ ID NO 157
<211> LENGTH: 670
<212> TYPE: PRT
<213> ORGANISM: homo sapiens

<400> SEQUENCE: 157

Asn Lys Asp Pro Ser Tyr Ser Leu Gln Val Gln Arg Gln Val Pro Val
1               5                   10                  15

Pro Glu Gly Leu Cys Val Ile Val Ser Cys Asn Leu Ser Tyr Pro Arg
                20                  25                  30

Asp Gly Trp Asp Glu Ser Thr Ala Ala Tyr Gly Tyr Trp Phe Lys Gly
```

```
            35                  40                  45
Arg Thr Ser Pro Lys Thr Gly Ala Pro Val Ala Thr Asn Asn Gln Ser
 50                  55                  60
Arg Glu Val Glu Met Ser Thr Arg Asp Arg Phe Gln Leu Thr Gly Asp
 65                  70                  75                  80
Pro Gly Lys Gly Ser Cys Ser Leu Val Ile Arg Asp Ala Gln Arg Glu
                 85                  90                  95
Asp Glu Ala Trp Tyr Phe Phe Arg Val Glu Arg Gly Ser Arg Val Arg
                100                 105                 110
His Ser Phe Leu Ser Asn Ala Phe Phe Leu Lys Val Thr Ala Leu Thr
            115                 120                 125
Lys Lys Pro Asp Val Tyr Ile Pro Glu Thr Leu Glu Pro Gly Gln Pro
130                 135                 140
Val Thr Val Ile Cys Val Phe Asn Trp Ala Phe Lys Lys Cys Pro Ala
145                 150                 155                 160
Pro Ser Phe Ser Trp Thr Gly Ala Ala Leu Ser Pro Arg Arg Thr Arg
                165                 170                 175
Pro Ser Thr Ser His Phe Ser Val Leu Ser Phe Thr Pro Ser Pro Gln
            180                 185                 190
Asp His Asp Thr Asp Leu Thr Cys His Val Asp Phe Ser Arg Lys Gly
            195                 200                 205
Val Ser Ala Gln Arg Thr Val Arg Leu Arg Val Ala Tyr Ala Pro Lys
210                 215                 220
Asp Leu Ile Ile Ser Ile Ser His Asp Asn Thr Ser Ala Leu Glu Leu
225                 230                 235                 240
Gln Gly Asn Val Ile Tyr Leu Glu Val Gln Lys Gly Gln Phe Leu Arg
                245                 250                 255
Leu Leu Cys Ala Ala Asp Ser Gln Pro Pro Ala Thr Leu Ser Trp Val
                260                 265                 270
Leu Gln Asp Arg Val Leu Ser Ser Ser His Pro Trp Gly Pro Arg Thr
            275                 280                 285
Leu Gly Leu Glu Leu Arg Gly Val Arg Ala Gly Asp Ser Gly Arg Tyr
            290                 295                 300
Thr Cys Arg Ala Glu Asn Arg Leu Gly Ser Gln Gln Gln Ala Leu Asp
305                 310                 315                 320
Leu Ser Val Gln Tyr Pro Pro Glu Asn Leu Arg Val Met Val Ser Gln
                325                 330                 335
Ala Asn Arg Thr Val Leu Glu Asn Leu Gly Asn Gly Thr Ser Leu Pro
                340                 345                 350
Val Leu Glu Gly Gln Ser Leu Arg Leu Val Cys Val Thr His Ser Ser
            355                 360                 365
Pro Pro Ala Arg Leu Ser Trp Thr Arg Trp Gly Gln Thr Val Gly Pro
            370                 375                 380
Ser Gln Pro Ser Asp Pro Gly Val Leu Glu Leu Pro Ile Gln Met
385                 390                 395                 400
Glu His Glu Gly Glu Phe Thr Cys His Ala Gln His Pro Leu Gly Ser
                405                 410                 415
Gln His Val Ser Leu Ser Leu Ser Val His Tyr Pro Pro Gln Leu Leu
            420                 425                 430
Gly Pro Ser Cys Ser Trp Glu Ala Glu Gly Leu His Cys Ser Cys Ser
            435                 440                 445
Ser Gln Ala Ser Pro Ala Pro Ser Leu Arg Trp Trp Leu Gly Glu Glu
450                 455                 460
```

Leu Leu Glu Gly Asn Ser Ser Gln Gly Ser Phe Glu Val Thr Pro Ser
465                 470                 475                 480

Ser Ala Gly Pro Trp Ala Asn Ser Ser Leu Ser Leu His Gly Gly Leu
                485                 490                 495

Ser Ser Gly Leu Arg Leu Arg Cys Lys Ala Trp Asn Val His Gly Ala
            500                 505                 510

Gln Ser Gly Ser Val Phe Gln Leu Leu Pro Gly Lys Leu Glu His Gly
        515                 520                 525

Gly Gly Leu Gly Leu Gly Ala Ala Leu Gly Ala Gly Val Ala Ala Leu
    530                 535                 540

Leu Ala Phe Cys Ser Cys Leu Val Val Phe Arg Val Lys Ile Cys Arg
545                 550                 555                 560

Lys Glu Ala Arg Lys Arg Ala Ala Ala Glu Gln Asp Val Pro Ser Thr
                565                 570                 575

Leu Gly Pro Ile Ser Gln Gly His Gln His Glu Cys Ser Ala Gly Ser
            580                 585                 590

Ser Gln Asp His Pro Pro Gly Ala Ala Thr Tyr Thr Pro Gly Lys
        595                 600                 605

Gly Glu Glu Gln Glu Leu His Tyr Ala Ser Leu Ser Phe Gln Gly Leu
    610                 615                 620

Arg Leu Trp Glu Pro Ala Asp Gln Glu Ala Pro Ser Thr Thr Glu Tyr
625                 630                 635                 640

Ser Glu Ile Lys Ile His Thr Gly Gln Pro Leu Arg Gly Pro Gly Phe
                645                 650                 655

Gly Leu Gln Leu Glu Arg Glu Met Ser Gly Met Val Pro Lys
            660                 665                 670

<210> SEQ ID NO 158
<211> LENGTH: 577
<212> TYPE: PRT
<213> ORGANISM: homo sapiens

<400> SEQUENCE: 158

Lys Glu Gln Lys Asp Tyr Leu Leu Thr Met Gln Lys Ser Val Thr Val
1               5                   10                  15

Gln Glu Gly Leu Cys Val Ser Val Leu Cys Ser Phe Ser Tyr Pro Gln
                20                  25                  30

Asn Gly Trp Thr Ala Ser Asp Pro Val His Gly Tyr Trp Phe Arg Ala
            35                  40                  45

Gly Asp His Val Ser Arg Asn Ile Pro Val Ala Thr Asn Asn Pro Ala
50                  55                  60

Arg Ala Val Gln Glu Glu Thr Arg Asp Arg Phe His Leu Leu Gly Asp
65                  70                  75                  80

Pro Gln Asn Lys Asp Cys Thr Leu Ser Ile Arg Asp Thr Arg Glu Ser
                85                  90                  95

Asp Ala Gly Thr Tyr Val Phe Cys Val Glu Arg Gly Asn Met Lys Trp
            100                 105                 110

Asn Tyr Lys Tyr Asp Gln Leu Ser Val Asn Val Thr Ala Ser Gln Asp
        115                 120                 125

Leu Leu Ser Arg Tyr Arg Leu Glu Val Pro Glu Ser Val Thr Val Gln
    130                 135                 140

Glu Gly Leu Cys Val Ser Val Pro Cys Ser Val Leu Tyr Pro His Tyr
145                 150                 155                 160

Asn Trp Thr Ala Ser Ser Pro Val Tyr Gly Ser Trp Phe Lys Glu Gly

```
            165                 170                 175
Ala Asp Ile Pro Trp Asp Ile Pro Val Ala Thr Asn Thr Pro Ser Gly
            180                 185                 190

Lys Val Gln Glu Asp Thr His Gly Arg Phe Leu Leu Leu Gly Asp Pro
            195                 200                 205

Gln Thr Asn Asn Cys Ser Leu Ser Ile Arg Asp Ala Arg Lys Gly Asp
            210                 215                 220

Ser Gly Lys Tyr Tyr Phe Gln Val Glu Arg Gly Ser Arg Lys Trp Asn
225                 230                 235                 240

Tyr Ile Tyr Asp Lys Leu Ser Val His Val Thr Ala Leu Thr His Met
                245                 250                 255

Pro Thr Phe Ser Ile Pro Gly Thr Leu Glu Ser Gly His Pro Arg Asn
            260                 265                 270

Leu Thr Cys Ser Val Pro Trp Ala Cys Glu Gln Gly Thr Pro Pro Thr
            275                 280                 285

Ile Thr Trp Met Gly Ala Ser Val Ser Ser Leu Asp Pro Thr Ile Thr
            290                 295                 300

Arg Ser Ser Met Leu Ser Leu Ile Pro Gln Pro Gln Asp His Gly Thr
305                 310                 315                 320

Ser Leu Thr Cys Gln Val Thr Leu Pro Gly Ala Gly Val Thr Met Thr
                325                 330                 335

Arg Ala Val Arg Leu Asn Ile Ser Tyr Pro Pro Gln Asn Leu Thr Met
            340                 345                 350

Thr Val Phe Gln Gly Asp Gly Thr Ala Ser Thr Thr Leu Arg Asn Gly
            355                 360                 365

Ser Ala Leu Ser Val Leu Glu Gly Gln Ser Leu His Leu Val Cys Ala
370                 375                 380

Val Asp Ser Asn Pro Pro Ala Arg Leu Ser Trp Thr Trp Gly Ser Leu
385                 390                 395                 400

Thr Leu Ser Pro Ser Gln Ser Ser Asn Leu Gly Val Leu Glu Leu Pro
            405                 410                 415

Arg Val His Val Lys Asp Glu Gly Glu Phe Thr Cys Arg Ala Gln Asn
            420                 425                 430

Pro Leu Gly Ser Gln His Ile Ser Leu Ser Leu Ser Leu Gln Asn Glu
            435                 440                 445

Tyr Thr Gly Lys Met Arg Pro Ile Ser Gly Val Thr Leu Gly Ala Phe
            450                 455                 460

Gly Gly Ala Gly Ala Thr Ala Leu Val Phe Leu Tyr Phe Cys Ile Ile
465                 470                 475                 480

Phe Val Val Val Arg Ser Cys Arg Lys Lys Ser Ala Arg Pro Ala Val
                485                 490                 495

Gly Val Gly Asp Thr Gly Met Glu Asp Ala Asn Ala Val Arg Gly Ser
            500                 505                 510

Ala Ser Gln Gly Pro Leu Ile Glu Ser Pro Ala Asp Asp Ser Pro Pro
            515                 520                 525

His His Ala Pro Pro Ala Leu Ala Thr Pro Ser Pro Glu Glu Gly Glu
            530                 535                 540

Ile Gln Tyr Ala Ser Leu Ser Phe His Lys Ala Arg Pro Gln Tyr Pro
545                 550                 555                 560

Gln Glu Gln Glu Ala Ile Gly Tyr Glu Tyr Ser Glu Ile Asn Ile Pro
                565                 570                 575

Lys
```

<210> SEQ ID NO 159
<211> LENGTH: 353
<212> TYPE: PRT
<213> ORGANISM: Macaca fascicularis

<400> SEQUENCE: 159

```
Gln Arg Asn Asn Gln Lys Asn Tyr Pro Leu Thr Met Gln Glu Ser Val
  1               5                  10                  15

Thr Val Gln Gln Gly Leu Cys Val His Val Leu Cys Ser Phe Ser Tyr
             20                  25                  30

Pro Trp Tyr Gly Trp Ile Ser Ser Asp Pro Val His Gly Tyr Trp Phe
         35                  40                  45

Arg Ala Gly Ala His Thr Asp Arg Asp Ala Pro Val Ala Thr Asn Asn
 50                  55                  60

Pro Ala Arg Ala Val Arg Glu Asp Thr Arg Asp Arg Phe His Leu Leu
 65                  70                  75                  80

Gly Asp Pro Gln Thr Lys Asn Cys Thr Leu Ser Ile Arg Asp Ala Arg
                 85                  90                  95

Ser Ser Asp Ala Gly Thr Tyr Phe Phe Arg Val Glu Thr Gly Lys Thr
            100                 105                 110

Lys Trp Asn Tyr Lys Tyr Ala Pro Leu Ser Val His Val Thr Ala Leu
        115                 120                 125

Thr His Arg Pro Asn Ile Leu Ile Pro Gly Thr Leu Glu Ser Gly Cys
130                 135                 140

Pro Arg Asn Leu Thr Cys Ser Val Pro Trp Ala Cys Glu Gln Gly Thr
145                 150                 155                 160

Ala Pro Met Ile Ser Trp Met Gly Thr Ser Val Ser Pro Leu Asp Pro
                165                 170                 175

Ser Thr Thr Arg Ser Ser Val Leu Thr Leu Ile Pro Gln Pro Gln Asp
            180                 185                 190

His Gly Thr Ser Leu Thr Cys Gln Val Thr Phe Pro Gly Ala Ser Val
        195                 200                 205

Thr Thr Asn Lys Thr Ile His Leu Asn Val Ser Tyr Pro Pro Gln Asn
210                 215                 220

Leu Thr Met Thr Val Phe Gln Gly Asn Asp Thr Val Ser Ile Val Leu
225                 230                 235                 240

Gly Asn Gly Ser Ser Val Ser Val Pro Glu Gly Pro Ser Leu Arg Leu
                245                 250                 255

Val Cys Ala Val Asp Ser Asn Pro Pro Ala Arg Leu Ser Leu Ser Trp
            260                 265                 270

Gly Gly Leu Thr Leu Cys Pro Ser Gln Pro Ser Asn Pro Gly Val Leu
        275                 280                 285

Glu Leu Pro Arg Val His Leu Arg Asp Glu Glu Glu Phe Thr Cys Arg
290                 295                 300

Ala Gln Asn Leu Leu Gly Ser Gln Gln Val Ser Leu Asn Val Ser Leu
305                 310                 315                 320

Gln Ser Lys Ala Thr Ser Gly Leu Thr Gln Gly Ala Val Gly Ala Gly
                325                 330                 335

Ala Thr Ala Leu Val Phe Leu Ser Phe Cys Val Ile Phe Val Val Val
            340                 345                 350

Pro
```

<210> SEQ ID NO 160
<211> LENGTH: 446

```
<212> TYPE: PRT
<213> ORGANISM: homo sapiens

<400> SEQUENCE: 160

Gln Thr Ser Lys Leu Leu Thr Met Gln Ser Val Thr Val Gln Glu
1               5                   10                  15

Gly Leu Cys Val His Val Pro Cys Ser Phe Ser Tyr Pro Ser His Gly
                20                  25                  30

Trp Ile Tyr Pro Gly Pro Val Val His Gly Tyr Trp Phe Arg Glu Gly
            35                  40                  45

Ala Asn Thr Asp Gln Asp Ala Pro Val Ala Thr Asn Asn Pro Ala Arg
        50                  55                  60

Ala Val Trp Glu Glu Thr Arg Asp Arg Phe His Leu Leu Gly Asp Pro
65                  70                  75                  80

His Thr Glu Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
            100                 105                 110

Tyr Lys His His Arg Leu Ser Val Asn Val Thr Ala Leu Thr His Arg
        115                 120                 125

Pro Asn Ile Leu Ile Pro Gly Thr Leu Glu Ser Gly Cys Pro Gln Asn
130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
            165                 170                 175

Arg Ser Ser Val Leu Thr Leu Ile Pro Gln Pro Gln Asp His Gly Thr
        180                 185                 190

Ser Leu Thr Cys Gln Val Thr Phe Pro Gly Ala Ser Val Thr Thr Asn
    195                 200                 205

Lys Thr Val His Leu Asn Val Ser Tyr Pro Pro Gln Asn Leu Thr Met
210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
            245                 250                 255

Val Asp Ala Val Asp Ser Asn Pro Pro Ala Arg Leu Ser Leu Ser Trp
        260                 265                 270

Arg Gly Leu Thr Leu Cys Pro Ser Gln Pro Ser Asn Pro Gly Val Leu
    275                 280                 285

Glu Leu Pro Trp Val His Leu Arg Asp Glu Ala Glu Phe Thr Cys Arg
290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly Val Val Gly Gly Ala
            325                 330                 335

Gly Ala Thr Ala Leu Val Phe Leu Ser Phe Cys Val Ile Phe Val Val
        340                 345                 350

Val Arg Ser Cys Arg Lys Lys Ser Ala Arg Pro Ala Ala Gly Val Gly
    355                 360                 365

Asp Thr Gly Ile Glu Asp Ala Asn Ala Val Arg Gly Ser Ala Ser Gln
370                 375                 380

Gly Pro Leu Thr Glu Pro Trp Ala Glu Asp Ser Pro Pro Asp Gln Pro
385                 390                 395                 400
```

```
Pro Pro Ala Ser Ala Arg Ser Ser Val Gly Glu Gly Glu Leu Gln Tyr
            405                 410                 415

Ala Ser Leu Ser Phe Gln Met Val Lys Pro Trp Asp Ser Arg Gly Gln
            420                 425                 430

Glu Ala Thr Asp Thr Glu Tyr Ser Glu Ile Lys Ile His Arg
            435                 440                 445

<210> SEQ ID NO 161
<211> LENGTH: 280
<212> TYPE: PRT
<213> ORGANISM: homo sapiens

<400> SEQUENCE: 161

Met Glu Trp Ser Trp Val Phe Leu Phe Phe Leu Ser Val Thr Thr Gly
1               5                   10                  15

Val His Ser Gly Lys Pro Ile Pro Asn Pro Leu Leu Gly Leu Asp Ser
                20                  25                  30

Thr Gln Thr Ser Lys Leu Leu Thr Met Gln Ser Ser Val Thr Val Gln
            35                  40                  45

Glu Gly Leu Cys Val His Val Pro Cys Ser Phe Ser Tyr Pro Ser His
50                  55                  60

Gly Trp Ile Tyr Pro Gly Pro Val Val His Gly Tyr Trp Phe Arg Glu
65                  70                  75                  80

Gly Ala Asn Thr Asp Gln Asp Ala Pro Val Ala Thr Asn Asn Pro Ala
                85                  90                  95

Arg Ala Val Trp Glu Glu Thr Arg Asp Arg Phe His Leu Leu Gly Asp
            100                 105                 110

Pro His Thr Lys Asn Cys Thr Leu Ser Ile Arg Asp Ala Arg Arg Ser
            115                 120                 125

Asp Ala Gly Arg Tyr Phe Phe Arg Met Glu Lys Gly Ser Ile Lys Trp
        130                 135                 140

Asn Tyr Lys His His Arg Leu Ser Val Asn Val Thr Ala Ala Thr Ser
145                 150                 155                 160

Gly Val Thr Gln Gly Val Val Gly Gly Ala Gly Ala Thr Ala Leu Val
                165                 170                 175

Phe Leu Ser Phe Cys Val Ile Phe Val Val Val Arg Ser Cys Arg Lys
            180                 185                 190

Lys Ser Ala Arg Pro Ala Ala Gly Val Gly Asp Thr Gly Ile Glu Asp
        195                 200                 205

Ala Asn Ala Val Arg Gly Ser Ala Ser Gln Gly Pro Leu Thr Glu Pro
    210                 215                 220

Trp Ala Glu Asp Ser Pro Pro Asp Gln Pro Pro Pro Ala Ser Ala Arg
225                 230                 235                 240

Ser Ser Val Gly Glu Gly Glu Leu Gln Tyr Ala Ser Leu Ser Phe Gln
                245                 250                 255

Met Val Lys Pro Trp Asp Ser Arg Gly Gln Glu Ala Thr Asp Thr Glu
            260                 265                 270

Tyr Ser Glu Ile Lys Ile His Arg
        275                 280

<210> SEQ ID NO 162
<211> LENGTH: 265
<212> TYPE: PRT
<213> ORGANISM: homo sapiens

<400> SEQUENCE: 162
```

```
Met Glu Trp Ser Trp Val Phe Leu Phe Phe Leu Ser Val Thr Thr Gly
1               5                   10                  15

Val His Ser Gly Lys Pro Ile Pro Asn Pro Leu Leu Gly Leu Asp Ser
                20                  25                  30

Thr Leu Thr His Arg Pro Asn Ile Leu Ile Pro Gly Thr Leu Glu Ser
            35                  40                  45

Gly Cys Pro Gln Asn Leu Thr Cys Ser Val Pro Trp Ala Cys Glu Gln
50                  55                  60

Gly Thr Pro Pro Met Ile Ser Trp Ile Gly Thr Ser Val Ser Pro Leu
65                  70                  75                  80

Asp Pro Ser Thr Thr Arg Ser Ser Val Leu Thr Leu Ile Pro Gln Pro
                85                  90                  95

Gln Asp His Gly Thr Ser Leu Thr Cys Gln Val Thr Phe Pro Gly Ala
            100                 105                 110

Ser Val Thr Thr Asn Lys Thr Val His Leu Asn Val Ser Tyr Pro Pro
            115                 120                 125

Gln Asn Leu Thr Met Thr Val Phe Gln Gly Asp Gly Thr Val Ala Thr
        130                 135                 140

Ser Gly Val Thr Gln Gly Val Val Gly Gly Ala Gly Ala Thr Ala Leu
145                 150                 155                 160

Val Phe Leu Ser Phe Cys Val Ile Phe Val Val Val Arg Ser Cys Arg
                165                 170                 175

Lys Lys Ser Ala Arg Pro Ala Ala Gly Val Gly Asp Thr Gly Ile Glu
                180                 185                 190

Asp Ala Asn Ala Val Arg Gly Ser Ala Ser Gln Gly Pro Leu Thr Glu
            195                 200                 205

Pro Trp Ala Glu Asp Ser Pro Pro Asp Gln Pro Pro Pro Ala Ser Ala
210                 215                 220

Arg Ser Ser Val Gly Glu Gly Glu Leu Gln Tyr Ala Ser Leu Ser Phe
225                 230                 235                 240

Gln Met Val Lys Pro Trp Asp Ser Arg Gly Gln Glu Ala Thr Asp Thr
                245                 250                 255

Glu Tyr Ser Glu Ile Lys Ile His Arg
            260                 265

<210> SEQ ID NO 163
<211> LENGTH: 246
<212> TYPE: PRT
<213> ORGANISM: homo sapiens

<400> SEQUENCE: 163

Met Glu Trp Ser Trp Val Phe Leu Phe Phe Leu Ser Val Thr Thr Gly
1               5                   10                  15

Val His Ser Gly Lys Pro Ile Pro Asn Pro Leu Leu Gly Leu Asp Ser
                20                  25                  30

Thr Ser Thr Val Leu Gly Asn Gly Ser Ser Leu Ser Leu Pro Glu Gly
            35                  40                  45

Gln Ser Leu Arg Leu Val Cys Ala Val Asp Ala Val Asp Ser Asn Pro
50                  55                  60

Pro Ala Arg Leu Ser Leu Ser Trp Arg Gly Leu Thr Leu Cys Pro Ser
65                  70                  75                  80

Gln Pro Ser Asn Pro Gly Val Leu Glu Leu Pro Trp Val His Leu Arg
                85                  90                  95

Asp Ala Ala Glu Phe Thr Cys Arg Ala Gln Asn Pro Leu Gly Ser Gln
```

```
                    100                 105                 110
Gln Val Tyr Leu Asn Val Ser Leu Gln Ser Lys Ala Thr Ser Gly Val
                115                 120                 125

Thr Gln Gly Val Val Gly Ala Gly Ala Thr Ala Leu Val Phe Leu
            130                 135                 140

Ser Phe Cys Val Ile Phe Val Val Arg Ser Cys Arg Lys Lys Ser
145                 150                 155                 160

Ala Arg Pro Ala Ala Gly Val Gly Asp Thr Gly Ile Glu Asp Ala Asn
                165                 170                 175

Ala Val Arg Gly Ser Ala Ser Gln Gly Pro Leu Thr Glu Pro Trp Ala
            180                 185                 190

Glu Asp Ser Pro Pro Asp Gln Pro Pro Ala Ser Ala Arg Ser Ser
                195                 200                 205

Val Gly Glu Gly Glu Leu Gln Tyr Ala Ser Leu Ser Phe Gln Met Val
                210                 215                 220

Lys Pro Trp Asp Ser Arg Gly Gln Glu Ala Thr Asp Thr Glu Tyr Ser
225                 230                 235                 240

Glu Ile Lys Ile His Arg
                245

<210> SEQ ID NO 164
<211> LENGTH: 575
<212> TYPE: PRT
<213> ORGANISM: homo sapiens

<400> SEQUENCE: 164

Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
                20                  25                  30

Pro Val Asp Ser Gln Thr Asp Ser Asp Pro Val His Gly Tyr Trp Phe
            35                  40                  45

Arg Ala Gly Asn Asp Ile Ser Trp Lys Ala Pro Val Ala Thr Asn Asn
        50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
                100                 105                 110

Lys Trp Asn Tyr Lys Tyr Asp Gln Leu Ser Val Asn Val Thr Ala Leu
            115                 120                 125

Thr His Arg Pro Asn Ile Leu Ile Pro Gly Thr Leu Glu Ser Gly Cys
        130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220
```

```
Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
            245                 250                 255

Val Cys Ala Val Asp Ser Asn Pro Pro Ala Arg Leu Ser Trp Thr Trp
        260                 265                 270

Arg Ser Leu Thr Leu Tyr Pro Ser Gln Pro Ser Asn Pro Leu Val Leu
    275                 280                 285

Glu Leu Gln Val His Leu Gly Asp Glu Gly Glu Phe Thr Cys Arg Ala
290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Gly Gly Ser Ser Pro Lys Ser Cys Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
    370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
        435                 440                 445

Cys Lys Val Ser Asn Lys Ala Leu Pro Ala Pro Ile Glu Lys Thr Ile
    450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510

Gly Gln Pro Glu Asn Asn Tyr Lys Thr Thr Pro Pro Val Leu Asp Ser
        515                 520                 525

Asp Gly Ser Phe Phe Leu Tyr Ser Lys Leu Thr Val Asp Lys Ser Arg
    530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 165
<211> LENGTH: 567
<212> TYPE: PRT
<213> ORGANISM: homo sapiens

<400> SEQUENCE: 165

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
            20                  25                  30
```

```
Trp Ile Tyr Pro Gly Pro Val His Gly Tyr Trp Phe Arg Glu Gly
        35                  40                  45

Ala Asn Thr Asp Gln Asp Ala Pro Val Ala Thr Asn Asn Pro Ala Arg
50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
                100                 105                 110

Tyr Lys His His Arg Leu Ser Val Asn Val Thr Ala Leu Thr His Arg
            115                 120                 125

Pro Asn Ile Leu Ile Pro Gly Thr Leu Glu Ser Gly Cys Pro Gln Asn
        130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175

Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
        195                 200                 205

Lys Thr Val His Leu Asn Val Ser Tyr Pro Pro Gln Asn Leu Thr Met
210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
                245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
        275                 280                 285

Glu Leu Pro Trp Val His Leu Arg Asp Ala Ala Glu Phe Thr Cys Arg
290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly Gly Gly Ser Ser
                325                 330                 335

Pro Lys Ser Cys Asp Lys Thr His Thr Cys Pro Pro Cys Pro Ala Pro
            340                 345                 350

Glu Leu Leu Gly Gly Pro Ser Val Phe Leu Phe Pro Pro Lys Pro Lys
        355                 360                 365

Asp Thr Leu Met Ile Ser Arg Thr Pro Glu Val Thr Cys Val Val Val
        370                 375                 380

Asp Val Ser His Glu Asp Pro Glu Val Lys Phe Asn Trp Tyr Val Asp
385                 390                 395                 400

Gly Val Glu Val His Asn Ala Lys Thr Lys Pro Arg Glu Glu Gln Tyr
                405                 410                 415

Asn Ser Thr Tyr Arg Val Val Ser Val Leu Thr Val Leu His Gln Asp
            420                 425                 430

Trp Leu Asn Gly Lys Glu Tyr Lys Cys Lys Val Ser Asn Lys Ala Leu
        435                 440                 445
```

```
Pro Ala Pro Ile Glu Lys Thr Ile Ser Lys Ala Lys Gly Gln Pro Arg
    450                 455                 460
Glu Pro Gln Val Tyr Thr Leu Pro Pro Ser Arg Glu Glu Met Thr Lys
465                 470                 475                 480
Asn Gln Val Ser Leu Thr Cys Leu Val Lys Gly Phe Tyr Pro Ser Asp
                485                 490                 495
Ile Ala Val Glu Trp Glu Ser Asn Gly Gln Pro Glu Asn Asn Tyr Lys
            500                 505                 510
Thr Thr Pro Pro Val Leu Asp Ser Asp Gly Ser Phe Phe Leu Tyr Ser
        515                 520                 525
Lys Leu Thr Val Asp Lys Ser Arg Trp Gln Gln Gly Asn Val Phe Ser
530                 535                 540
Cys Ser Val Met His Glu Ala Leu His Asn His Tyr Thr Gln Lys Ser
545                 550                 555                 560
Leu Ser Leu Ser Pro Gly Lys
                565

<210> SEQ ID NO 166
<211> LENGTH: 330
<212> TYPE: PRT
<213> ORGANISM: homo sapiens

<400> SEQUENCE: 166

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Ala Glu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Ser Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
```

-continued

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 167
<211> LENGTH: 330
<212> TYPE: PRT
<213> ORGANISM: homo sapiens

<400> SEQUENCE: 167

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

```
                    290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 168
<211> LENGTH: 330
<212> TYPE: PRT
<213> ORGANISM: homo sapiens

<400> SEQUENCE: 168

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 169
<211> LENGTH: 330
<212> TYPE: PRT
<213> ORGANISM: homo sapiens

<400> SEQUENCE: 169

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 170
<211> LENGTH: 233
<212> TYPE: PRT
<213> ORGANISM: homo sapiens

<400> SEQUENCE: 170

```
Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
210                 215                 220

Ile Ile Tyr His Cys Lys His Lys Leu
225                 230

<210> SEQ ID NO 171
<211> LENGTH: 452
<212> TYPE: PRT
<213> ORGANISM: Artificial
<220> FEATURE:
<223> OTHER INFORMATION: Chimeric

<400> SEQUENCE: 171

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125
```

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys
    450

<210> SEQ ID NO 172
<211> LENGTH: 452
<212> TYPE: PRT
<213> ORGANISM: Artificial
<220> FEATURE:
<223> OTHER INFORMATION: Chimeric

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Trp Met Asn Trp Val Arg Gln Ala Pro Gly Gln Gly Leu Glu Trp Met
         35                   40                  45
Gly Arg Ile Asp Pro Tyr Asp Ser Glu Thr His Tyr Ala Gln Lys Leu
 50                   55                  60
Gln Gly Arg Val Thr Met Thr Thr Asp Thr Ser Thr Ser Thr Ala Tyr
 65              70                  75                      80
Met Glu Leu Arg Ser Leu Arg Ser Asp Asp Thr Ala Val Tyr Tyr Cys
                 85                  90                  95
Ala Arg Gly Gly Tyr Asp Phe Asp Val Gly Thr Leu Tyr Trp Phe Phe
            100                 105                110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
            210                 215                 220
Ser Lys Tyr Gly Pro Pro Cys Pro Pro Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly Lys
```

<210> SEQ ID NO 173
<211> LENGTH: 452
<212> TYPE: PRT
<213> ORGANISM: Artificial
<220> FEATURE:
<223> OTHER INFORMATION: Chimeric

<400> SEQUENCE: 173

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Met Asn Trp Val Arg Gln Met Pro Gly Lys Gly Leu Glu Trp Met
        35                  40                  45

Gly Arg Ile Asp Pro Tyr Asp Ser Glu Thr His Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val

```
                355                 360                 365
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
        450

<210> SEQ ID NO 174
<211> LENGTH: 452
<212> TYPE: PRT
<213> ORGANISM: Artificial
<220> FEATURE:
<223> OTHER INFORMATION: Chimeric

<400> SEQUENCE: 174

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Asn Trp Val Gln Gln Ala Pro Gly Lys Gly Leu Glu Trp Met
        35                  40                  45

Gly Arg Ile Asp Pro Tyr Asp Ser Glu Thr His Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
```

```
                260                 265                 270
Gln Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly Lys
    450

<210> SEQ ID NO 175
<211> LENGTH: 452
<212> TYPE: PRT
<213> ORGANISM: Artificial
<220> FEATURE:
<223> OTHER INFORMATION: Chimeric

<400> SEQUENCE: 175

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Trp Met Asn Trp Val Arg Gln Ala Pro Gly Gln Gly Leu Glu Trp Met
        35                  40                  45
Gly Arg Ile Asp Pro Tyr Asp Ser Glu Thr His Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Gly Tyr Asp Phe Asp Val Gly Thr Leu Tyr Trp Phe Phe
            100                 105                 110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
```

```
                165                 170                 175
Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 176
<211> LENGTH: 214
<212> TYPE: PRT
<213> ORGANISM: Artificial
<220> FEATURE:
<223> OTHER INFORMATION: Chimeric

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
```

```
                 65                  70                  75                  80
Glu Asp Phe Ala Thr Tyr Tyr Cys Gln His His Tyr Gly Thr Pro Arg
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 177
<211> LENGTH: 124
<212> TYPE: PRT
<213> ORGANISM: Artificial
<220> FEATURE:
<223> OTHER INFORMATION: Chimeric

<400> SEQUENCE: 177

Glu Val Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Thr Ser Tyr
                 20                  25                  30

Trp Met Asn Trp Val Arg Gln Met Pro Gly Lys Gly Leu Glu Trp Met
             35                  40                  45

Gly Arg Ile Asp Pro Tyr Asp Ser Glu Thr His Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Asp Phe Asp Val Gly Thr Leu Tyr Trp Phe Phe
             100                 105                 110

Asp Val Trp Gly Gln Gly Thr Thr Val Thr Val Ser
         115                 120

<210> SEQ ID NO 178
<211> LENGTH: 124
<212> TYPE: PRT
<213> ORGANISM: Artificial
<220> FEATURE:
<223> OTHER INFORMATION: Chimeric

<400> SEQUENCE: 178

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                 20                  25                  30
```

Trp Met Asn Trp Val Arg Gln Ala Pro Gly Gln Gly Leu Glu Trp Met
         35                  40                  45

Gly Arg Ile Asp Pro Tyr Asp Ser Glu Thr His Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Thr Ala Val Tyr Tyr Cys
                 85                  90                  95

Ala Arg Gly Gly Tyr Asp Phe Asp Val Gly Thr Leu Tyr Trp Phe Phe
             100                 105                 110

Asp Val Trp Gly Gln Gly Thr Thr Val Thr Val Ser
         115                 120

<210> SEQ ID NO 179
<211> LENGTH: 124
<212> TYPE: PRT
<213> ORGANISM: Artificial
<220> FEATURE:
<223> OTHER INFORMATION: Chimeric

<400> SEQUENCE: 179

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Thr Ser Tyr
             20                  25                  30

Trp Met Asn Trp Val Arg Gln Met Pro Gly Lys Gly Leu Glu Trp Met
         35                  40                  45

Gly Arg Ile Asp Pro Tyr Asp Ser Glu Thr His Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Gly Tyr Asp Phe Asp Val Gly Thr Leu Tyr Trp Phe Phe
             100                 105                 110

Asp Val Trp Gly Gln Gly Thr Thr Val Thr Val Ser
         115                 120

<210> SEQ ID NO 180
<211> LENGTH: 124
<212> TYPE: PRT
<213> ORGANISM: Artificial
<220> FEATURE:
<223> OTHER INFORMATION: Chimeric

<400> SEQUENCE: 180

Glu Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Ser Tyr
             20                  25                  30

Trp Met Asn Trp Val Gln Gln Ala Pro Gly Lys Gly Leu Glu Trp Met
         35                  40                  45

Gly Arg Ile Asp Pro Tyr Asp Ser Glu Thr His Tyr Ala Glu Lys Phe
 50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120

<210> SEQ ID NO 181
<211> LENGTH: 124
<212> TYPE: PRT
<213> ORGANISM: Artificial
<220> FEATURE:
<223> OTHER INFORMATION: Chimeric

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Asn Trp Val Arg Gln Ala Pro Gly Gln Gly Leu Glu Trp Met
        35                  40                  45

Gly Arg Ile Asp Pro Tyr Asp Ser Glu Thr His Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Phe Asp Val Gly Thr Leu Tyr Trp Phe Phe
            100                 105                 110

Asp Val Trp Gly Gln Gly Thr Thr Val Thr Val Ser
            115                 120

<210> SEQ ID NO 182
<211> LENGTH: 107
<212> TYPE: PRT
<213> ORGANISM: Artificial
<220> FEATURE:
<223> OTHER INFORMATION: Chimeric

<400> SEQUENCE: 182

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Arg
                85                  90                  95

Thr Phe Gly Gly Gly Thr Lys Val Glu Ile Lys
            100                 105

<210> SEQ ID NO 183
<211> LENGTH: 119
<212> TYPE: PRT
<213> ORGANISM: Artificial
<220> FEATURE:
<223> OTHER INFORMATION: Chimeric

```
<400> SEQUENCE: 183

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

Ala Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Thr Leu Tyr
65                  70                  75                  80

Leu Glu Ile Ser Ser Leu Arg Ser Glu Asp Thr Ala Met Tyr Tyr Cys
                85                  90                  95

Thr Arg His Gly Asp Tyr Pro Arg Phe Phe Asp Val Trp Gly Ala Gly
            100                 105                 110

Thr Thr Val Thr Val Ser Ser
            115

<210> SEQ ID NO 184
<211> LENGTH: 106
<212> TYPE: PRT
<213> ORGANISM: Artificial
<220> FEATURE:
<223> OTHER INFORMATION: Chimeric

<400> SEQUENCE: 184

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Ile
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Tyr Thr
                85                  90                  95

Phe Gly Gly Gly Thr Lys Leu Glu Ile Lys
            100                 105
```

COMBINATION THERAPY USING ANTIBODY TO HUMAN SIGLEC-9 AND ANTIBODY TO HUMAN NKG2A FOR TREATING CANCER

CROSS-REFERENCE TO RELATED APPLICATIONS

This application is the U.S. national stage application of International Patent Application No. PCT/EP2018/068532, filed Jul. 9, 2018, which claims the benefit of U.S. Provisional Application No. 62/530,454 filed Jul. 10, 2017, the disclosures of which are incorporated herein by reference in their entirety; including any drawings and sequence listing.

REFERENCE TO THE SEQUENCE LISTING

The present application is being filed along with a Sequence Listing in electronic format. The Sequence Listing is provided as a file entitled "Sig793 PCT_ST25 txt", created Jul. 3, 2018, which is 156 KB in size. The information in the electronic format of the Sequence Listing is incorporated herein by reference in its entirety.

FIELD OF THE INVENTION

This invention relates to agents that bind human Siglec proteins having inhibitory activity in NK and/or other immune cells, and that neutralize the inhibitory activity of such Siglec. Such agents can be used for the treatment of cancers.

BACKGROUND OF THE INVENTION

NK cells are mononuclear cell that develop in the bone marrow from lymphoid progenitors, and morphological features and biological properties typically include the expression of the cluster determinants (CDs) CD16, CD56, and/or CD57; the absence of the alpha/beta or gamma/delta TCR complex on the cell surface; the ability to bind to and kill target cells that fail to express "self" major histocompatibility complex (MHC)/human leukocyte antigen (HLA) proteins; and the ability to kill tumor cells or other diseased cells that express ligands for activating NK receptors. NK cells are characterized by their ability to bind and kill several types of tumor cell lines without the need for prior immunization or activation. NK cells can also release soluble proteins and cytokines that exert a regulatory effect on the immune system; and can undergo multiple rounds of cell division and produce daughter cells with similar biologic properties as the parent cell. Normal, healthy cells are protected from lysis by NK cells.

Based on their biological properties, various therapeutic and vaccine strategies have been proposed in the art that rely on a modulation of NK cells. However, NK cell activity is regulated by a complex mechanism that involves both stimulating and inhibitory signals. Briefly, the lytic activity of NK cells is regulated by various cell surface receptors that transduce either positive or negative intracellular signals upon interaction with ligands on the target cell. The balance between positive and negative signals transmitted via these receptors determines whether or not a target cell is lysed (killed) by a NK cell. NK cell stimulatory signals can be mediated by Natural Cytotoxicity Receptors (NCR) such as NKp30, NKp44, and NKp46; as well as NKG2C receptors, NKG2D receptors, certain activating Killer Ig-like Receptors (KIRs), and other activating NK receptors (Lanier, Annual Review of Immunology 2005; 23:225-74). NK cell inhibitory signals can be mediated by receptors like CD94/NKG2-A, as well as certain inhibitory KIRs, which recognize major histocompatibility complex (MHC) class I-molecules (Wagtmann et al. (1995) Immunity 5:439-449). These inhibitory receptors bind to polymorphic determinants of MHC class I molecules (including HLA class I) present on other cells and inhibit NK cell-mediated lysis.

The lytic activity of NK cells can also be regulated by siglec polypeptides. Siglecs (sialic-acid-binding immunoglobulin-like lectins) are a subset of I-type lectins that bind to sialoglycans and are predominantly expressed on cells of the hematopoietic system in a manner dependent on cell type and differentiation. Whereas sialic acid is ubiquitously expressed, typically at the terminal position of glycoproteins and lipids, only very specific, distinct sialoglycan structures are recognized by individual Siglec receptors, depending on identity and linkage to subterminal carbohydrate moieties. Siglecs have only low general affinity to the common mammalian sialoside structures containing the N-acetylneuraminic acid (Neu5Ac) $\alpha$2-6 and $\alpha$2-3 linkages.

Siglecs are generally divided into two groups, a first subset made up of Siglec-1, -2, -4 and -15, and the CD33-related group of Siglecs which includes Siglec-3, -5, -6, -7, -8, -9, -10, -11, -12, -14 and -16. The CD33-related Siglecs are characterized, inter alia, by low evolutionary conservation and rapidly evolving sequence by multiple mechanisms.

Siglec-7 (CD328), a type 1 trans-membrane protein first cloned and characterized in 1999 by the Moretta group in Genoa, Italy, and belonging to the human CD33-related Siglec receptors, is characterized by a sialic acid binding N-terminal V-set Ig domain, two C2-set Ig domains and an intracytoplasmic region containing one immune-receptor tyrosine based inhibitory motif (ITIM) and one ITIM-like motif. Siglec-7 is constitutively expressed on NK cells, dendritic cells, monocytes and neutrophils. The extracellular domain of this receptor preferentially binds a (2,8)-linked disialic acids and branched $\alpha$ 2,6-sialyl residues, such as those displayed by ganglioside GD3.

Siglec-9 (CD329) was characterized in 2000 by the Varki group (see, e.g., Angata et al. J Biol Chem 2000; 275:22127-22135) and is expressed on monocytes, neutrophils, dendritic cells, CD34+ cells and NK cells. Siglec-9 (as well as Siglec-8) have been found to have differential specificity for sialoside ligands that contain both sialic acid and sulfate, with the position of the sulfate being an important determinant of specificity. Siglec-9 has been found to bind MUC16 that is overexpressed on cancer cells. Like Siglec-7, Siglec 9 also contains a sialic acid binding N-terminal V-set Ig domain, two C2-set Ig domains and an intracytoplasmic region containing one immune-receptor tyrosine based inhibitory motif (ITIM) and one ITIM-like motif. N-terminal V-set Ig domain of human Siglec-9 shares an overall amino acid sequence identity of about 77% with N-terminal V-set Ig domain of human Siglec-7, and these two siglecs display different sialic acids binding specificities.

Binding assays have reported that, similar to Siglec-7, Siglec-9 recognized sialic acid in either the $\alpha$2,3- or $\alpha$2,6-glycosidic linkage to galactose. Using a Siglec-9 specific mAb, Zhang et al. ((2000) J. Biol. Chem. Vol. 275, No. 29: 22121-22126) reported that Siglec-9 was found to be expressed at high or intermediate levels by monocytes, neutrophils, and a minor population of CD16+, CD56– cells. However, weaker expression was observed on ~50% of B cells and NK cells and minor subsets of CD8+ T cells and CD4+ T cells. The authors concluded that despite their high degree of sequence similarity, Siglec-7 and Siglec-9 have distinct expression profiles.

Despite the interesting expression profile of Siglec-9 on NK and other immune cells, and the potential therapeutic interest in neutralizing Siglec-9, to date no candidate therapeutic agents that specifically neutralize Siglec-9 have been advanced or proposed for therapeutic use. Engagement of Siglec-9 on cells of the myelomonocytic lineage by tumor-associated sialic acid ligands has been reported to inhibit immunosurveillance and tumor cell killing by NK cells as well as by neutrophils, specialized granulocytes that recognize and directly kill microorganisms (Laubli et al. (2014) Proc. Nat. Acad. Sci. USA 111(39): 14211-14216). Carlin et al. ((2009) Blood 113: 3333-3336) reported that mimicry of host sialylated glycans allows a bacterial pathogen to engage neutrophil Siglec-9 and dampen the innate immune response. Carlin et al. described anti-Siglec-9 antibody 191240 (R&D Systems, Inc.) as binding to the sialic acid binding site on Siglec-9 and inhibiting the interaction with sialic acid. Carlin et al. further reported that unlike a non-blocking antibody (clone E10-286, BD Biosciences inc.), clone 191240 enhanced the activation of neutrophils towards bacterial cells. Similarly, Laubli et al. (2014), supra, reported that the anti-Siglec-9 antibody clone 191240 was able to enhance killing of tumor cells by neutrophils, compared to clone E10-286 that did not enhance killing of tumor cells by neutrophils.

Anti-Siglec-7 antibodies have been described in European Patent 1238282B1 (Moretta et al) and Vitale et al. ((1999) Proc. Nat. Acad. Sci. 96(26):15091-96), referring to the murine anti-siglec-7 antibody QA79, as well as in Falco et al. (1999) J. Exp. Med. 190:793-801 report an anti-Siglec-7 antibody Z176.

Hudak et al. (2014) Nat. Chem. Biol. 10:69-77 reported that blocking anti-Siglec-7 antibodies inhibited the Siglec-7 mediated protection of tumor target cells from lysis by NK cells. However, when turning to Siglec-9, anti-Siglec-9 antibodies (clone 191240 was used) were not able to inhibit the Siglec-9 mediated protection of tumor target cells from lysis by NK cells purified from human donors (see, Hudak et al (2014)), despite the ability to enhance killing of tumor cells by neutrophils (see, Laubli et al. (2014)). The bivalent binding antibody clone E10-286, reported in Laubli et al. (2014) as non-blocking and not enhancing killing of tumor cells by neutrophils, also failed to inhibit the Siglec-9 mediated protection of tumor target cells from lysis by primary NK cells (Jandus et al. (2014) J. Clin. Invest. 124(4): 1810-18020).

Despite the interest in Siglec-7 and -9, no therapeutic agents targeting these receptors have been developed. There is therefore a need for agents that target these receptors for use in treating diseases such as cancer.

SUMMARY OF THE INVENTION

In one aspect, the invention arises from the discovery of high affinity binder antibodies that act as potent neutralizers of human Siglecs, notably on NK cells which express lower levels of cell surface Siglec compared to neutrophils and/or other cells, and that act as inhibitory cell surface receptors in effector lymphocytes (Siglec-7, Siglec-9).

In another aspect, the invention arises from the discovery that antibodies that bind and neutralize the inhibitory activity of human Siglec-9 (and that optionally further bind and neutralize the inhibitory activity of human Siglec-7) exhibit a highly increased ability to cause immune-mediated (e.g. NK cell mediated) elimination of target cells (e.g. tumor cells, infected cells) when used in combination with an agent that neutralizes the activity of the human NKG2A polypeptide. In particular, the inventors have observed that Siglec polypeptides are inhibiting the cytotoxic activity of NKG2A-expressing NK cells towards HLA-E expressing tumor cells when the inhibitory activity of NKG2A is neutralized.

In one embodiment, the disclosure provides agents that inhibit the activity of a Siglec-9 polypeptide (e.g., a Siglec-9 expressed at the surface of a cell), including agents (e.g. antibody agents) that are competitive and non-competitive inhibitors of Siglec-9. The respective agents have particularly high potency in neutralization of the inhibitory activity of a Siglec, with or without substantially blocking the interaction between the Siglec and a sialic acid ligand thereof. In one embodiment, provided is a method of treating an individual having a cancer or an infectious disease, the method comprising administering to the individual an agent that inhibits Siglec-9 and/or Siglec-7 in combination with an agent that neutralizes the inhibitory activity of human NKG2A polypeptide. In one embodiment, provided is an agent that inhibits Siglec-9 and/or Siglec-7, for use in treating or preventing a cancer or an infectious disease, optionally, wherein the cancer or infectious disease is characterized by cells (e.g. tumor cell, infected cells) expressing HLA-E, optionally wherein the agent that inhibits of Siglec-9 and/or Siglec-7 is administered in combination with an agent that neutralizes the inhibitory activity of a human NKG2A polypeptide. In one embodiment, the agent that inhibits of Siglec-9 and/or Siglec-7 is an antibody agent that neutralizes the inhibitory activity of a Siglec-9 polypeptide (and optionally further a Siglec-7 polypeptide). In one embodiment, provided is use of an agent (e.g. an antibody agent) that neutralizes the inhibitory activity of a Siglec-9 polypeptide (and optionally further a Siglec-7 polypeptide) in combination with an agent (e.g. an antibody agent) that neutralizes the inhibitory activity of a human NKG2A polypeptide, optionally for the treatment of cancer or an infectious disease. In one embodiment, provided is an agent that inhibits Siglec-9 and/or Siglec-7, for use in potentiating the therapeutic activity of an agent (e.g., an antibody) that neutralizes the inhibitory activity of human NKG2A polypeptide. In one embodiment, provided is an agent (e.g., an antibody) that neutralizes the inhibitory activity of human NKG2A polypeptide, for use in treating or preventing a cancer or an infectious disease, optionally, wherein the cancer or infectious disease is characterized by cells (e.g. tumor cell, infected cells) expressing a sialic acid ligand of a Siglec-9 and/or Siglec-7 (e.g., a sialic acid comprising a Neu5Acα2-3Galb1-4GlcNAcb structure), optionally wherein the agent that neutralizes the inhibitory activity of a human NKG2A polypeptide is administered in combination with an inhibitor of Siglec-9 and/or Siglec-7. In one embodiment, provided is an agent (e.g., an antibody) that neutralizes the inhibitory activity of human NKG2A polypeptide, for use in potentiating the therapeutic activity of an inhibitor of Siglec-9 and/or Siglec-7. In one embodiment, the agent that neutralizes the inhibitory activity of human NKG2A polypeptide is an antibody that binds a NKG2A polypeptide and neutralizes the inhibitory activity of human NKG2A polypeptide. In one embodiment, the agent that neutralizes the inhibitory activity of human NKG2A polypeptide is an antibody that binds HLA-E and inhibits the interaction between NKG2A and HLA-E, thereby neutralizing the inhibitory activity of human NKG2A polypeptide.

In one embodiment, the disclosure provides a method of treating an individual having a cancer or an infectious disease, the method comprising administering to the individual an agent that neutralizes the inhibitory activity of a Siglec-9 polypeptide (and optionally further a Siglec-7 polypeptide) in combination with an agent that neutralizes the inhibitory activity of a human NKG2A polypeptide. In one embodiment, the agent that neutralizes the inhibitory activity of a Siglec-9 polypeptide is an antibody having the characteristics as further described herein. In one embodiment, provided is a method for treating or preventing a cancer in an individual, the method comprising administering to an individual: (a) a therapeutically active amount of an agent that inhibits a human NKG2A polypeptide, and (b) a therapeutically active amount of an agent that inhibits a human Siglec-9 and/or Siglec-7 polypeptide. In one embodiment, the cancer is a solid tumor. In one embodiment, the cancer is a hematological tumor. In one embodiment, the cancer comprises malignant cells that express HLA-E at their surface. In one embodiment, the agent that inhibits a human NKG2A polypeptide is an antibody that neutralizes the inhibitory activity of NKG2A. In one embodiment, the agent that inhibits a human Siglec-9 polypeptide is an anti-Siglec-9 antibody that neutralizes the inhibitory activity of Siglec-9. The individual can be specified to be a human.

In one embodiment, provided is method of activating or potentiating the activity of a tumor-infiltrating lymphocyte cell (e.g. an NK cell) in an individual, the method comprising administering to an individual: (a) a therapeutically active amount of an agent that inhibits a human NKG2A polypeptide, and (b) a therapeutically active amount of an agent that inhibits a human Siglec-9 polypeptide. In one embodiment, provided is method of activating or potentiating the activity of a tumor-infiltrating NK cell in an individual, the method comprising administering to an individual: (a) a therapeutically active amount of an agent that inhibits a human NKG2A polypeptide, and (b) a therapeutically active amount of an agent that inhibits a human Siglec-9 polypeptide. In one embodiment, provided is method of increasing the ability of NK cells (e.g. NKG2A-expressing NK cells) to cause the death of the HLA-E-expressing cell (e.g. a cancer cell; an infected cell) in an individual, the method comprising administering to an individual: (a) a therapeutically active amount of an agent that inhibits a human NKG2A polypeptide, and (b) a therapeutically active amount of an agent that inhibits a human Siglec-9 polypeptide.

In one aspect provided is a composition comprising an agent (e.g. an antibody) that inhibits a human NKG2A polypeptide and an agent (e.g. an antibody) that inhibits a human Siglec-9 polypeptide.

In one aspect, the compositions and method herein are for use in the treatment or prevention of a cancer, optionally a solid tumor, optionally a haematological malignancy, optionally an HLA-E positive tumor, e.g., characterized by tumor cells bearing HLA-E at their surface. In one embodiment the cancer is an advanced and/or refractory solid tumor. In one non-limiting embodiment, the cancer is selected from the group consisting of head and neck squamous cell carcinoma (HNSCC), non-small cell lung cancer (NSCLC), kidney cancer, pancreatic or esophagus adenocarcinoma, breast cancer, renal cell carcinoma (RCC), melanoma, colorectal cancer, and ovarian cancer.

In one embodiment, the anti-Siglec-9 antibody is administered in an amount that results in the neutralization of the inhibitory activity of human Siglec-9 in a human individual (in vivo), e.g., an amount that results in the neutralization of the inhibitory activity of human Siglec-9 on NK cells in a human individual, optionally for at least one week, two weeks, three weeks or one month following administration the anti-Siglec-9 antibody. In one embodiment, the anti-NKG2A antibody is administered in an amount that results in the neutralization of the inhibitory activity of human CD94/NKG2A in a human individual (in vivo), e.g., an amount that results in the neutralization of the inhibitory activity of human CD94/NKG2A on NK cells in a human individual, optionally for at least one week, two weeks, three weeks or one month following administration of the anti-NKG2A antibody.

In one embodiment, the Siglec inhibitor (the agent that inhibits a Siglec-9 polypeptide) is a protein comprising an immunoglobulin antigen binding domain that specifically binds to a human Siglec-9 protein, e.g. an antibody or antibody fragment, or a protein comprising such. In one embodiment, the Siglec inhibitor specifically binds to human Siglec-9 protein without binding to human Siglec-7 and/or other human Siglecs of Table 1 (exemplified by mAbsA, -B, -C, -D, -E and -F). In one embodiment, the Siglec inhibitor specifically binds to human Siglec-9 protein and to human Siglec-7 protein, optionally further without binding to other human Siglecs of Table 1 (exemplified by mAbs4, -5, -6). In one embodiment, the Siglec inhibitor is an antibody or antibody fragment that specifically binds to human Siglec-9 protein, to human Siglec-7 protein and to human Siglec-12 protein, optionally further without binding to other human Siglecs of Table 1 (exemplified by mAbs1, -2 and -3). In one embodiment, the Siglec inhibitor is an antibody or antibody fragment that is capable of bivalent binding to a human Siglec-9 protein (the inhibitor comprises two antigen binding domains that each are capable of binding to a human Siglec-9 protein).

In one embodiment, an antibody that binds to human Siglec-9 protein is an isolated antibody or antibody fragment that specifically binds to a human Siglec-9 polypeptide and neutralizes the inhibitory activity of the Siglec-9 polypeptide, optionally wherein the antibody or antibody fragment does not substantially block the interaction between the Siglec-9 polypeptide and a sialic acid ligand thereof (exemplified by mAbs 1, 2 and 3, see Example 10), optionally wherein the antibody or antibody fragment blocks the interaction between the Siglec-9 polypeptide and a sialic acid ligand thereof (exemplified by mAbs A, B and C, see Example 10). Optionally, the Siglec-9 polypeptide is expressed at the surface of a cell, e.g., an effector lymphocyte, an NK cell, e.g., a primary NK cell, a $CD56^{dim}$ NK cell from a human individual. Optionally, the Siglec-9 polypeptide is expressed at the surface of a monocyte-derived dendritic cell. In one embodiment, the antibody further binds to a human Siglec-7 polypeptide and neutralizes the inhibitory activity of the Siglec-7 polypeptide, optionally further wherein the antibody does not substantially block the interaction between the Siglec-7 polypeptide and a sialic acid ligand thereof. Optionally, the Siglec-7 polypeptide is expressed at the surface of a cell, e.g., a monocyte-derived dendritic cell. In another embodiment, the antibody does not bind to a human Siglec-7 polypeptide.

In one aspect, the antibody that specifically bind human Siglec-9 enhances the activity (e.g. cytotoxicity) of NK cells (e.g. primary NK cells) towards a sialic-acid ligand-bearing target cell. Unlike some antibodies that can enhance cytotoxicity only in neutrophils, Siglec transfectants and/or other cells that express or are made to express high levels of Siglec-9 at their cell surface, the antibodies described herein are functional even in cells that express low levels of Siglec-9 such as NK cells in a human (e.g. $CD56^{dim}$ NK cells). The ability to enhance the cytotoxicity of such Siglec-9 low-expressing NK cells has the advantage of being able to additionally mobilize this population of cells against disease target cells, e.g. tumor cells and/or bacterial cells.

In one embodiment, an antibody that binds to human Siglec-9 protein is an antibody or antibody fragment (or a protein that comprises such a fragment) that specifically binds human Siglec-9 and that enhances and/or restores the cytotoxicity of NK cells (primary NK cells) in a standard 4-hour in vitro cytotoxicity assay in which NK cells that express Siglec-9 are incubated with target cells that express a sialic acid ligand of Siglec-9. In one embodiment the target cells are labeled with $^{51}$Cr prior to addition of NK cells, and then the killing (cytotoxicity) is estimated as proportional to the release of $^{51}$Cr from the cells to the medium. Optionally, an assay can be carried out according to the methods in the Examples herein, see, e.g. Example 8. In one embodiment, the antibody or antibody fragment is capable of restoring cytotoxicity of NK cells that express Siglec-9 to at least the level observed with NK cells that do not express Siglec-9 (e.g. as determined according to the methods of the Examples herein).

In one embodiment, an antibody that binds to human Siglec-9 enhances and/or restores the cytotoxicity of NK cells (primary NK cells; NKG2A-expressing cells) in the presence of an antibody that binds and neutralizes the inhibitory activity of NKG2A in a cytotoxicity assay (e.g. a CD137 expression assay) in which NK cells that express Siglec-9 are incubated with target cells that express a sialic acid ligand of Siglec-9.

In any aspect herein, NK cells (e.g. primary NK cells) can be specified as being fresh NK cells purified from donors, optionally incubated overnight at 37° C. before use. In any aspect herein, NK cells or primary NK cells can be specified as being Siglec-9 expressing, e.g., for use in assays the cells can be gated on Siglec-9 by flow cytometry. See, e.g. NK cells as described Example 8, herein. In any aspect herein, NK cells or primary NK cells can be specified as being NKG2A expressing, e.g., for use in assays the cells can be gated on NKG2A by flow cytometry.

In another embodiment, an antibody that binds to human Siglec-9 protein is an antibody or antibody fragment (or a protein that comprises such a fragment) that specifically binds human Siglec-9 and that neutralizes the inhibitory activity of the Siglec-9 polypeptide in a monocyte-derived dendritic cell (moDC). In one embodiment, the moDC bear sialic acid ligands of Siglec-9 at their surface. In one embodiment, the moDC bear at their surface Siglec-9 polypeptides that are engaged in cis-interactions with sialic acids. In one embodiment, the antibody increases activation or signaling in a moDC. In one embodiment, the antibody neutralizes the inhibitory activity of the Siglec-9 polypeptide in a moDC bearing sialic acid ligands of Siglec-9, wherein the moDC is a cell in which treatment of the moDC with neuramidase to remove sialic acid ligands results in a lower $EC_{50}$ for antibody binding to the moDC.

Optionally, anti-Siglec-9 antibodies can bind both Siglec-7 and Siglec-9 polypeptides with comparable affinity. Such antibodies have advantageous pharmacological characteristics. As shown herein, NK cells can express both the inhibitory Siglec-7 and the inhibitory Siglec-9 protein, yet Siglec-7 and Siglec-9 can also have different expression profiles across different cell populations. Furthermore, it has been shown that tumor cells can express the natural ligands (glycans) for Siglec-7 and for Siglec-9. Consequently, a therapeutic agent that inhibits of one Siglec but not the other may not be maximally efficient in neutralizing Siglec-mediated restriction of the activity of NK and/or other immune cell populations (e.g. myeloid-derived dendritic cells). Inhibition of both Siglec 7 and 9 can therefore be advantageous. However, Siglec-9 shares an overall amino acid sequence identity of only about 77% with N-terminal V-set Ig domain of human Siglec-7. Moreover, these two siglecs display different sialic acids binding specificities. In one embodiment, an antibody or antibody fragment (or a protein that comprises such a fragment) that binds human Siglec-7 (in addition to Siglec-9) neutralizes the inhibitory activity of the Siglec-7 polypeptide in a neutrophil; in one embodiment the antibody or antibody fragment enhances and/or restores the cytotoxicity of neutrophils towards target cells that express a sialic acid ligand of Siglec-7. In one embodiment, an antibody or antibody fragment (or a protein that comprises such a fragment) that binds human Siglec-7 (in addition to Siglec-9) neutralizes the inhibitory activity of the Siglec-7 polypeptide in a monocyte-derived dendritic cell (moDC). In one embodiment, the moDC bear sialic acid ligands of Siglec-7 at their surface. In one embodiment, the moDC bear at their surface Siglec-7 polypeptides that are engaged in cis-interactions with sialic acids. In one embodiment, the antibody increases activation or signaling in a moDC. In one embodiment, the antibody neutralizes the inhibitory activity of the Siglec-7 polypeptide in a moDC bearing sialic acid ligands of Siglec-7, wherein the moDC is a cell in which treatment of the moDC with neuramidase to remove sialic acid ligands results in a lower $EC_{50}$ for antibody binding to the moDC.

In one aspect, an antibody that neutralizes the inhibitory activity of Siglec-7 and Siglec-9 is capable of specifically binding to the inhibitory human Siglec-7 polypeptide and the human Siglec-9 polypeptide with comparable affinity. The antibodies that bind Siglec-7 and Siglec-9 with comparable affinity can, for example, in certain embodiments, have increased ability to block the interactions between each of the Siglecs and a sialic acid ligand(s) thereof (exemplified by mAbs4, 5 and 6, see Example 6). The antibodies that bind Siglec-9 can in other embodiments be characterized as neutralizing the inhibitory activity of Siglec-9, without substantially blocking the interactions between Siglec-9 and a sialic acid ligand(s) thereof, particularly a sialic acid comprising a Neu5Aca2-3Galb1-4GlcNAcb structure (exemplified by mAbs1, 2 and 3, see Example 9).

As shown herein, human Siglec-9 binds to both Sia1 (Neu5Aca2-3Galb1-4GlcNAcb) and Sia2 (6'-Sialyllactose), while Siglec-7 bind only to Sia2. In one aspect antibodies are capable of blocking the interaction of such Siglec polypeptide(s) a sialic acid ligand of both Siglec-9 and Siglec-7, e.g., a Sia2 sialic acid. In one embodiment, the sialic acid is a sialylated trisaccharide. In one embodiment, the sialic acid comprises a 6'-Sialyllactose structure.

In another aspect, an antibody binds a human Siglec-9 polypeptide and neutralizes the inhibitory activity thereof, wherein the antibody is capable of blocking the interaction of both Sia1 (Neu5Aca2-3Galb1-4GlcNAcb) and Sia2 (6'-Sialyllactose) with a Siglec-9 polypeptide (exemplified by mAbs1, 2 and 3, see Example 9).

In one embodiment, an antibody that is capable of binding Siglec-7 and Siglec-9 has an $EC_{50}$ for binding to human Siglec-7 polypeptide that differs by less than 1-log from its $EC_{50}$ for binding to human Siglec-9 polypeptide, as determined by flow cytometry for binding to cells expressing at their surface Siglec-7 or Siglec-9 (e.g., CHO cells transfected with one of the respective Siglec but that do not express the other Siglec). In one embodiment, the antibody has an $EC_{50}$ for binding to human Siglec-7 polypeptide and a human Siglec-9 polypeptide that differs by no more than 0.5 log, 0.3 log, 0.2 log or 0.1 log, as determined by flow cytometry for binding to cells expressing at their surface Siglec-7 or Siglec-9. The cells expressing at their surface Siglec-7 or Siglec-9 can be characterized as expressing the respective siglec at comparable levels of expression.

In one embodiment, the antibodies further bind to non-human primate Siglec with a comparable affinity as for human Siglec-9. In one embodiment, the antibody has an $EC_{50}$ for binding to human Siglec-9 polypeptide and a non-human primate Siglec that differs by no more than 1-log, 0.5 log, 0.3 log, 0.2 log or 0.1 log, as determined by flow cytometry for binding to cells expressing at their surface the respective siglec polypeptide (e.g., CHO cells transfected with the respective Siglec).

In one embodiment, an antibody that neutralizes the activity of human Siglec-9 has an $EC_{50}$ for binding to a human Siglec-9 polypeptide and a non-human primate Siglec that differs by no more than 1-log, 0.5 log, 0.3 log, 0.2 log or 0.1 log, as determined by flow cytometry for binding to cells expressing at their surface the Siglec-9 (e.g., CHO cells transfected with the Siglec).

In one embodiment, the antibody has a KD for binding affinity, as determined by, e.g., surface plasmon resonance (SPR) screening (such as by analysis with a BIAcore™ SPR analytical device), that differs by no more than 10-fold, 5-fold, 3-fold or 2-fold for binding to a human Siglec-7 polypeptide and to a human Siglec-9 polypeptide (and optionally further a non-human primate Siglec).

In one embodiment, an antibody has a KD of about $1\times10^{-8}$ M to about $1\times10^{-10}$ M, or about $1\times10^{-9}$ M to about $1\times10^{-11}$ M, for binding to a human a human Siglec-9 polypeptide (and optionally further a human Siglec-7 polypeptide and/or non-human primate Siglec). In one embodiment, an anti-Siglec-9 antibody has a KD of about $1\times10^{-8}$ M to about $1\times10^{-10}$ M, or about $1\times10^{-9}$ M to about $1\times10^{-11}$ M, for binding (e.g., monovalent affinity) to a human a human Siglec-9 polypeptide, wherein the antibody does not have substantial binding to a human Siglec-7 polypeptide.

In one embodiment, the antibodies furthermore do not substantially bind any of human Siglecs-3, -5, -6, -8, -10, -11 and -12. In one embodiment, the antibodies furthermore do not substantially bind any of Siglecs-14 and -16. In one embodiment, the antibodies furthermore do not substantially bind human Siglec-6. In one embodiment, the antibodies furthermore do not substantially bind human Siglec-12.

In any of the embodiments herein, the anti-Siglec antibodies can be characterized by binding to polypeptides expressed on the surface of a cell (e.g., an NK cell, a cell made to express Siglec-7 and/or Siglec-9, e.g., a recombinant CHO host cell made to express Siglec-7 and/or Siglec-9 at its surface, as shown in the Examples), and optionally further wherein the antibody binds with high affinity as determined by flow cytometry. For example, an antibody can be characterized by an $EC_{50}$, as determined by flow cytometry, of no more than 5 μg/ml, optionally no more than 1 μg/ml, no more than 0.5 μg/ml, no more than 0.2 μg/ml or no more than 0.1 μg/ml, for binding to primary NK cells (e.g., NK cells purified from a biological sample from a human individual or donor), optionally $CD56^{dim}$ NK cells. EC50 can be determined, for example, according to the methods of Example 9, e.g., 4 or more healthy human donors tested, stainings acquired on a BD FACS Canto II and analyzed using the FlowJo software, and $EC_{50}$ calculated using a 4-parameter logistic fit.

In another aspect, an antibody or antibody fragment (e.g. an antigen binding domain or a protein comprising such) that specifically binds to a human Siglec-7 and/or -9 polypeptide is capable of a neutralizing the inhibitory activity of such Siglec(s) in immune cells and capable of blocking the interaction of such Siglec polypeptide(s) with a sialic acid ligand thereof. In one embodiment, the sialic acid is a sialylated trisaccharide. In one embodiment, the sialic acid comprises a Neu5Aca2-3Galb1-4GlcNAcb structure. In one embodiment, the sialic acid comprises a 6'-Sialyllactose structure. In one embodiment, the antibody or antibody fragment specifically binds to a human Siglec-7 and/or -9 polypeptide and is capable of a neutralizing the inhibitory activity of such Siglec(s) in human NK cells (e.g. human primary NK cells; $CD56^{dim}$ NK cells), in human monocytes, in human dendritic cells, in human macrophages (notably immunosuppressive or M2 macrophages), CD8 T cells, and/or in human neutrophils. In one embodiment, the antibody or antibody fragment specifically binds to a human Siglec-7 and/or -9 polypeptide and is capable of a neutralizing the inhibitory activity of such Siglec(s) in immunosuppressive macrophages (e.g. M2 macrophages) from a human donor, wherein the antibody or antibody fragment reduces the immunosuppressive activity or capacity of the macrophages.

As discussed, human Siglec-9 binds to both Sia1 (Neu5Aca2-3Galb1-4GlcNAcb) and Sia2 (6'-Sialyllactose), while Siglec-7 bind only to Sia2. In certain aspects antibodies are capable blocking the interaction of a Siglec-9 polypeptide(s) with a sialic acid that is a ligand of Siglec-9 but not Siglec-7, e.g., a Sia1 sialic acid. In one embodiment, the sialic acid is a sialylated trisaccharide. In one embodiment, the sialic acid comprises a Neu5Aca2-3Galb1-4GlcNAcb structure. In one embodiment the antibody does not substantially block the interaction of a Siglec-7 polypeptide(s) with a sialic acid that is a ligand of Siglec-7 but not Siglec-9, e.g., a 6'-Sialyllactose-containing sialic acid.

Fragments and derivatives of such antibodies arc can also be used in accordance with the methods herein. In one embodiment, the antibody comprises an antigen-binding domain (e.g., a single antigen binding domain, a domain made up of a heavy and a light chain variable domain, etc.) capable of binding to the human Siglec-7 polypeptide and/or human Siglec-9 polypeptide. In one embodiment, the antigen-binding domain binds human Siglec-9 polypeptide and not human Siglec-7 polypeptide (exemplified by mAbsA, -B, -C, -D, -E and -F). In one embodiment, the antigen-binding domain binds both human Siglec-9 polypeptide and human Siglec-7 polypeptide (exemplified by mAbs1, -2, -3, -4, -5 and -6). In one embodiment, provided is a protein (e.g. antibody, multimeric and/or multispecific protein) or nucleic acid encoding such antigen binding domain.

In one embodiment, the neutralizing anti-Siglec antibody relieves the inhibitory activity exerted by Siglec-7 and/or -9 in immune cells, enhancing the ability of lymphocytes to effectively recognize and/or eliminate cancer cells that express sialic acid ligands of Siglec-7 and/or sialic acid ligands of Siglec-9. The antibodies (or antibody fragments) reduce the ability of cancer cells to escape lysis due to expression of one or the other types of ligand, and they therefore enhance tumor surveillance by the immune system. In the NK compartment, Siglec-9 is expressed primarily on $CD56^{dim}$ NK cells, while siglec-7 is expressed on $CD56^{dim}$ and $CD56^{bright}$ NK cells. $CD56^{dim}$ NK cells ($CD56^{dim}CD16^{+}KIR^{+}$) represent about 90% of peripheral blood and spleen NK cells, express perforin and granzymes, and are the major cytotoxic subset, whereas $CD56^{bright}$ NK cells (CD56$^{bright}$CD16$^{dim/-}$KIR$^-$) constitute the majority of NK cells in lymph nodes and tonsils and, upon activation, primarily respond with cytokine production. In one embodiment, provided is an antibody or antibody fragment that specifically binds human Siglec-9 and relieves the inhibitory activity exerted by Siglec-9 in human NK cells (e.g. human primary NK cells; CD56$^{dim}$ NK cells), enhancing the ability of the NK cells to effectively recognize and/or eliminate cancer cells that express sialic acid ligands of Siglec-9. In one embodiment, provided is an antibody or antibody fragment that specifically binds human Siglec-7 and Siglec-9 and relieves the inhibitory activity exerted by Siglec-7 and Siglec-9 in human NK cells (e.g. human primary NK cells; CD56$^{dim}$ NK cells), enhancing the ability of the NK cells to effectively recognize and/or eliminate cancer cells that express sialic acid ligands of Siglec-7 and Siglec-9.

In any embodiment, an anti-Siglec antibody can bind both Siglec-7 and Siglec-9 and can neutralize both Siglec-7 and Siglec-9-mediated inhibition of lymphocyte (e.g., NK cell, CD8+ T cell) cytotoxicity. In one aspect, the antibody increases lymphocyte activation in the presence of a target cell (e.g., a cell that expresses a ligand of Siglec-7 and/or a ligand of Siglec-9, a tumor cell). In one embodiment, the antibody increases cytotoxicity of NK cells, as assessed in a standard in vitro cytotoxicity assay in which NK cells that express Siglec-9 are purified from human donors and incubated with target cells that express a sialic acid ligand of Siglec-9. In one embodiment, increased activation or neutralization of inhibition of cytotoxicity is assessed by increase in a marker of cytotoxicity/cytotoxic potential, e.g., CD107 and/or CD137 expression (mobilization). In one embodiment, increased activation or neutralization of inhibition of cytotoxicity is assessed by increase in $^{51}$Cr release in a $^{51}$Cr release assay. The Siglec-7 may comprise an amino acid sequence of SEQ ID NO: 1. The Siglec-9 may comprise an amino acid sequence of SEQ ID NO: 2. In another embodiment, the Siglec-9 comprises an amino acid sequence of SEQ ID NO: 160.

In any embodiment, an antibody is capable of binding to both a Siglec-9 polypeptide comprising the amino acid sequence of SEQ ID NO: 2 (bearing a lysine at position 100, representative of about 49% of the population) and to a Siglec-9 polypeptide comprising the amino acid sequence of SEQ ID NO: 160 (bearing a glutamic acid at position corresponding to residue 100 of SEQ ID NO: 2), representative of about 36% of the population). In any embodiment an antibody or antibody fragment of the disclosure can be specified as being capable of neutralizing the inhibitory activity of Siglec-9 in individuals who express (or whose cells express) a Siglec-9 polypeptide comprising the amino acid sequence of SEQ ID NO: 2, as well as in individuals who express (or whose cells express) a Siglec-9 polypeptide comprising the amino acid sequence of SEQ ID NO: 160.

In any embodiment, an anti-Siglec-9 antibody can be capable of neutralizing the inhibitory activity of both a Siglec-9 polypeptide comprising the amino acid sequence of SEQ ID NO: 2 and a Siglec-9 polypeptide comprising the amino acid sequence of SEQ ID NO: 160. In one embodiment, an antibody or antibody fragment (or a protein that comprises such fragment) binds a human Siglec-9 polypeptide and is capable of neutralizing the inhibitory activity of Siglec-9 polypeptide in NK cells that express a Siglec-9 polypeptide comprising the amino acid sequence of SEQ ID NO: 2, and in NK cells that express a Siglec-9 polypeptide comprising the amino acid sequence of SEQ ID NO: 160. In one embodiment, the antibody increases cytotoxicity of NK cells, as assessed in a standard in vitro cytotoxicity assay in which NK cells that express the particular Siglec-9 are purified from human donors and incubated with target cells that express a sialic acid ligand of the Siglec-9.

In one aspect, the anti-Siglec antibody is a tetrameric (e.g., full length, F(ab)'2 fragment) antibody or antibody fragment that is capabling of binding in bivalent fashion to an epitope present on the extracellular domain of a Siglec. The antibody or antibody fragment that binds a Siglec in bivalent fashion can comprise two antigen binding domains that each are capable of binding a Siglec-9 polypeptide, or that each are capable of binding to an epitope present on both Siglec-7 and -9 polypeptides. In another aspect of any of the embodiments herein, the antibody binds to a Siglec in monovalent manner and lacks agonist activity at each Siglec, e.g., Siglec-7 and/or Siglec-9. In one embodiment, the antibody that binds a Siglec in monovalent manner is a Fab fragment. In any of the embodiments herein, the antibody that binds to a Siglec in monovalent or bivalent manner is free of agonist activity at the Siglec9. For therapeutic use, an antibody is preferably a non-depleting antibody. Optionally the antibody comprises an Fc domain capable of being bound by the human neonatal Fc receptor (FcRn) but which substantially lacks binding, via its Fc domain, to a human FcγR (e.g., CD16' optionally one or more of, or each of, human CD16A, CD16B, CD32A, CD32B and/or CD64 polypeptides). Optionally the antibody comprises an Fc domain of human IgG1, IgG2, IgG3 of IgG4 isotype comprising an amino acid modification (e.g. one or more substitutions) that decrease the binding affinity of the antibody for one or more of, or each of, human CD16A, CD16B, CD32A, CD32B and/or CD64 polypeptides.

In one embodiment, the antibody comprises one or more (e.g., two) antigen binding domain that binds to Siglec-9, optionally further to Siglec-7. In one specific embodiment, the antibody is a tetrameric, optionally full-length, antibody that comprises two identical antigen binding domains (optionally, two heavy and light chain variable region pairs), and that binds and neutralizes the inhibitory activity of Siglec-9, optionally further Siglec-7, comprises an Fc domain capable of being bound by the human neonatal Fc receptor (FcRn) and that substantially lacks binding to a human FOR (e.g., CD16; optionally one or more of, or each of, human CD16A, CD16B, CD32A, CD32B and/or CD64 polypeptides).

In any of the embodiments herein, upon binding to a Siglec on a human lymphocyte, the monoclonal antibody has the ability to enhance or reconstitute lysis of a target human cell bearing a sialic acid ligand of the Siglec on the target cell surface, and/or has the ability to increase lymphocyte activation (e.g., as determined by an increase in CD107 and/or CD137 expression on a lymphocyte), when said target cell comes into contact with said lymphocyte, e.g., an effector lymphocyte, an NK or a CD8+ T cell from a human individual, e.g. a CD56$^{dim}$ NK cell. In one embodiment, provided is an antibody that neutralizes a first Siglec expressed by a first subset of lymphocytes (e.g. Siglec-9 expressed on CD56$^{dim}$ NK cells), and that neutralizes a second Siglec expressed by a second subset of lymphocytes (Siglec-7 expressed on CD56$^{bright}$ NK cells). The first and second subset of human lymphocytes (e.g., NK cells, CD8+ T cells, monocytes, dendritic cells, macrophages, immunosuppressive or M2 macrophages) can for example be characterized by different cell surface markers or different functional properties, or the ability to lyse or recognize (e.g., be activated by) different target cells. In one embodiment, the antibody reduces (blocks) binding of a Siglec to a sialoside ligand thereof (e.g., a ligand present on tumor cells).

In any of the embodiments herein, the sialoside or sialic acid ligand of a Siglec is a natural ligand, e.g., a sialic acid ligand (a ligand comprising a sialic acid) is known to bind to the Siglec polypeptide to which the antibody binds. Sialic acids, a family of nine-carbon acidic monosaccharides, are typically found to be terminating branches of N-glycans, 0-glycans, and glycolipids. Siglecs are believed to recognize many aspects of the sialic acid molecule, like the acid sialic linkage from the 2-position, the arrangements of sialic acids and their way of presentation. In any of the embodiments herein, the ligand of a Siglec comprises mainly a 5-N-acetylneuraminic acid (Neu5Ac) derivative, and can comprises other sialic acid derivatives, like 5-N-glycolylneuraminic acid (Neu5Gc) derivatives. In one embodiment, the ligand of Siglec-9 and/or Siglec-7 is a sialic acid present on a glycoprotein (e.g., a mucin) or a glycolipid. In one embodiment, the ligand of Siglec-7 comprises a α2,8-linked disialic acid presented on b-series gangliosides, e.g., GD2, GD3 and GT1b. In one embodiment, the ligand of Siglec-7 comprises an internally branched alpha2,6-linked disialic gangliosides, e.g., DSGb5. In one embodiment, the ligand of Siglec-9 is a ligand present on, or comprises, a mucin, e.g., MUC1. In one embodiment, the ligand of Siglec-9 is a sialoglycan ligand that contains both sialic acid and sulfate.

In one aspect, an antibody binds to a common determinant present on an extracellular domain of as first and a second human CD33-related Siglec. In one aspect of any embodiment herein, an antibody binds to a determinant present on Siglec-9 but not on Siglec-7. In one aspect of any embodiment herein, an antibody binds to a common determinant present on Siglec-7 and on Siglec-9. Optionally, the determinant bound by an antibody is not present on one or more other Siglecs, e.g., one or more of (or all of) Siglecs-3, -5, -6, -8, -10, -11 and -12.

In any of the embodiments herein, the antibody binds to an extracellular domain of the Siglec. In certain of the embodiments herein, particularly where the antibody blocks the interaction between a Siglec and a sialic acid ligand thereof, the antibody may bind at least partially within or near the sialic acid binding domain of the Siglec. In other embodiments herein, particularly where the antibody does not block the interaction between a Siglec and a sialic acid ligand thereof, the antibody may bind outside the sialic acid binding domain of the Siglec.

In any of the embodiments herein, upon binding to a Siglec on a human lymphocyte (e.g., a primary NK cell), the monoclonal antibody has the ability to reconstitute lysis of a target human cell bearing a sialic acid ligand of the Siglec on the target cell surface, when said target cell comes into contact with said lymphocyte.

In any of the embodiments herein, the anti-Siglec antibody has a KD (e.g. for monovalent binding, as determined according to the methods disclosed in the Examples here) of less than $10^{-8}$ M, preferably less than $10^{-9}$ M for binding to a Siglec polypeptide (e.g., human Siglec-7 and/or human Siglec-9). Insofar as the Siglec-7 and -9 binding sites are believed to be generally masked at the cellular surface due to cis interactions with abundantly expressed low affinity sialic acids, trans interactions can occur with antibodies expressing higher affinity than the ligands that compete with cis. In one embodiment, the neutralizing anti-Siglec antibody is capable of displacing the binding of a sialoside ligand to a Siglec (e.g., Siglec-7 and/or Siglec-9).

The anti-Siglec antibody may be a human or humanized antibody or antibody fragment, or a derivative thereof, which has any of the foregoing properties, alone or in any suitable combination.

The anti-Siglec antibody may compete for binding to an epitope on Siglec-9 bound by mAb-A, -B, -C, -D, -E and/or -F, (e.g., that competes for binding to an epitope on a Siglec-9 polypeptide with an antibody having the heavy and light chain CDRs or variable regions of any of mAb-A, -B, -C, -D, -E and/or -F).

The anti-Siglec antibody may compete for binding to an epitope on Siglec-7 and/or Siglec-9 bound by mAbs-1, -2, -3, -4, -5 and/or -6, (e.g., that competes for binding to an epitope on a Siglec-7 and/or Siglec-9 polypeptide with an antibody having the heavy and light chain CDRs or variable regions of any of mAbs-1, -2, -3, -4, -5 or -6).

In one aspect, the anti-Siglec antibodies have reduced binding to a Siglec-7 polypeptide having a mutation at residue N82, P83, A84, R85, A86 and/or V87 (e.g. the mutations as set forth in Table 3). In one aspect, the anti-Siglec-7 antibodies have reduced binding to a Siglec-7 polypeptide having a mutation at residue N81, D100, H102 and/or T103 (e.g. the mutations as set forth in Table 3). In one aspect, the anti-Siglec-7 antibodies have reduced binding to a Siglec-7 polypeptide having a mutation at residue W88, E89, E90, R92 (e.g. the mutations as set forth in Table 3). Residue positions for mutations are with reference to the Siglec-7 polypeptide of SEQ ID NO: 1. Optionally, the antibody does not lose binding for one or more other mutant Siglec-7 polypeptides of Table 3, e.g., one or more (or all of) mutants M6, M8, M15 or M16.

In one aspect, the anti-Siglec antibodies have reduced binding to a Siglec-9 polypeptide having a mutation at residue N78, P79, A80, R81, A82 and/or V83 (e.g. the mutations as set forth in Table 3). In one aspect, the anti-Siglec-9 antibodies have reduced binding to a Siglec-9 polypeptide having a mutation at residue N77, D96, H98 and/or T99 (e.g. the mutations as set forth in Table 3). In one aspect, the anti-Siglec-9 antibodies have reduced binding to a Siglec-9 polypeptide having a mutation at residue W84, E85, E86 and/or R88 (e.g. the mutations as set forth in Table 3). Residue positions for mutations are with reference to the Siglec-9 polypeptide of SEQ ID NO: 2. Optionally, the antibody does not lose binding for one or more other mutant Siglec-9 polypeptides of Table 3, e.g., one or more (or all of) mutants M6, M8, M15 or M16.

In one aspect, the anti-Siglec antibodies have reduced binding to a Siglec-9 polypeptide having a mutation at residue S47, H48, G49, W50, I51, Y52, P53 and/or G54 (e.g. the mutations as set forth in Table 3). Residue positions for mutations are with reference to the Siglec-9 polypeptide of SEQ ID NO: 2. Optionally, the antibody does not lose binding for one or more other mutant Siglec-9 polypeptides of Table 3, e.g., mutants 9, 10 and/or 11, or one or more (or all of) mutants M7 or M8.

In one aspect, the anti-Siglec antibodies have reduced binding to a Siglec-9 polypeptide having a mutation at residue P55, H58, E122, G124, S125 and/or K127 (e.g. the mutations as set forth in Table 3). Residue positions for mutations are with reference to the Siglec-9 polypeptide of SEQ ID NO: 2. Optionally, the antibody does not lose binding for one or more other mutant Siglec-9 polypeptides of Table 3, e.g., mutants 9, 10 and/or 11.

In one aspect, the anti-Siglec antibodies have reduced binding to a Siglec-9 polypeptide having a mutation at residue K131 and/or H132 (e.g. the mutations as set forth in Table 3). Residue positions for mutations are with reference to the Siglec-9 polypeptide of SEQ ID NO: 2. Optionally, the antibody does not lose binding for one or more other mutant Siglec-9 polypeptides of Table 3, e.g., mutants 9, 10 and/or 11, or one or more (or all of) mutants M8 or M15.

In one aspect, the anti-Siglec antibodies have reduced binding to a Siglec-9 polypeptide having a mutation at residue R63, A66, N67, T68, D69, Q70 and/or D71 (e.g. the mutations as set forth in Table 3). Residue positions for mutations are with reference to the Siglec-9 polypeptide of SEQ ID NO: 2. Optionally, the antibody does not lose binding for one or more other mutant Siglec-9 polypeptides of Table 3, e.g., mutants 9, 10 and/or 11, or one or more (or all of) mutants M6, M15 or M16.

The anti-Siglec antibody may comprise the heavy and light chain CDR1, 2 and 3 of, or that binds the same epitope and/or competes for binding to a Siglec-7 and/or Siglec-9 polypeptide with, an antibody selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

(g) a monoclonal antibody comprising (i) a heavy chain comprising CDR 1, 2 and 3 of the heavy chain variable region of SEQ ID NO: 15 and (ii) a light chain comprising CDR 1, 2 and 3 of the light chain variable region of SEQ ID NO: 16;

(h) a monoclonal antibody comprising (i) a heavy chain comprising CDR 1, 2 and 3 of the heavy chain variable region of SEQ ID NO: 17 and (ii) a light chain comprising CDR 1, 2 and 3 of the light chain variable region of SEQ ID NO: 18;

(i) a monoclonal antibody comprising (i) a heavy chain comprising CDR 1, 2 and 3 of the heavy chain variable region of SEQ ID NO: 19 and (ii) a light chain comprising CDR 1, 2 and 3 of the light chain variable region of SEQ ID NO: 20;

(j) a monoclonal antibody comprising (i) a heavy chain comprising CDR 1, 2 and 3 of the heavy chain variable region of SEQ ID NO: 21 and (ii) a light chain comprising CDR 1, 2 and 3 of the light chain variable region of SEQ ID NO: 22;

(k) a monoclonal antibody comprising (i) a heavy chain comprising CDR 1, 2 and 3 of the heavy chain variable region of SEQ ID NO: 23 and (ii) a light chain comprising CDR 1, 2 and 3 of the light chain variable region of SEQ ID NO: 24; and (l) a monoclonal antibody comprising (i) a heavy chain comprising CDR 1, 2 and 3 of the heavy chain variable region of SEQ ID NO: 25 and (ii) a light chain comprising CDR 1, 2 and 3 of the light chain variable region of SEQ ID NO: 26.

The anti-Siglec antibody may have a heavy chain having one, two or three CDRs of the heavy chain of an antibody selected from the group consisting of antibody mAb-A, -B, -C, -D, -E and -F; and a light chain having one, two or three CDRs of the light chain of the respective antibody selected from the group consisting of antibody mAb-A, -B, -C, -D, -E and -F.

The anti-Siglec antibody may comprise: a heavy chain CDR1 comprising the amino acid sequence SYWMH (SEQ ID NO: 75); a heavy chain CDR2 comprising the amino acid sequence EINPSNGHTNYNEKFES (SEQ ID NO: 78); a heavy chain CDR3 comprising the amino acid sequence GVESYDFDDALDY (SEQ ID NO: 80); a light chain CDR1 comprising the amino acid sequence RASQDINNYLN (SEQ ID NO: 83); a light chain CDR2 comprising the amino acid sequence YTSRLHS (SEQ ID NO: 57); a light chain CDR3 comprising the amino acid sequence QQGNTLPFT (SEQ ID NO: 86); and human heavy and light chain framework sequences.

The anti-Siglec antibody may comprise: a heavy chain CDR1 comprising the amino acid sequence SYWMH (SEQ ID NO: 75); a heavy chain CDR2 comprising the amino acid sequence EINPSNGHTNYNEKFKT (SEQ ID NO: 90); a heavy chain CDR3 comprising the amino acid sequence GVETYDFDDAMDY (SEQ ID NO: 92); a light chain CDR1 comprising the amino acid sequence RASQDINNYLN (SEQ ID NO: 83); a light chain CDR2 comprising the amino acid sequence FTSRLHS (SEQ ID NO: 95); a light chain CDR3 comprising the amino acid sequence QQGDTFPFT (SEQ ID NO: 96); and human heavy and light chain framework sequences.

The anti-Siglec antibody may comprise: a heavy chain CDR1 comprising the amino acid sequence NYEMN (SEQ ID NO: 98); a heavy chain CDR2 comprising the amino acid sequence WINTYTGESTYADDFK (SEQ ID NO: 101); a heavy chain CDR3 comprising the amino acid sequence DDYGRSYGFAY (SEQ ID NO: 103); a light chain CDR1 comprising the amino acid sequence RASESVDSYGNSFMH (SEQ ID NO: 106); a light chain CDR2 comprising the amino acid sequence LASKLES (SEQ ID NO: 109); a light chain CDR3 comprising the amino acid sequence HQNNEDPPWT (SEQ ID NO: 110); and human heavy and light chain framework sequences.

The anti-Siglec antibody may comprise: a heavy chain CDR1 comprising the amino acid sequence DYSMH (SEQ ID NO: 112); a heavy chain CDR2 comprising the amino acid sequence WIITETGEPTYADDFRG (SEQ ID NO: 115); a heavy chain CDR3 comprising the amino acid sequence DFDGY (SEQ ID NO: 117); a light chain CDR1 comprising the amino acid sequence RASENIYSYLA (SEQ ID NO: 119); a light chain CDR2 comprising the amino acid sequence NAKTLTE (SEQ ID NO: 122); a light chain CDR3 comprising the amino acid sequence QHHYGFPWT (SEQ ID NO: 123); and human heavy and light chain framework sequences.

The anti-Siglec antibody may comprise: a heavy chain CDR1 comprising the amino acid sequence TFGMH (SEQ ID NO: 125); a heavy chain CDR2 comprising the amino acid sequence YISSGSNAIYYADTVKG (SEQ ID NO:

128); a heavy chain CDR3 comprising the amino acid sequence PGYGAWFAY (SEQ ID NO: 130); a light chain CDR1 comprising the amino acid sequence RASSSVSAYLH (SEQ ID NO: 133); a light chain CDR2 comprising the amino acid sequence STSNLAS (SEQ ID NO: 136; a light chain CDR3 comprising the amino acid sequence QQYSAYPYT (SEQ ID NO: 137); and human heavy and light chain framework sequences.

The anti-Siglec antibody may comprise: a heavy chain CDR1 comprising the amino acid sequence DYSMH (SEQ ID NO: 112); a heavy chain CDR2 comprising the amino acid sequence VISTYNGNTNYNQKFKG (SEQ ID NO: 139); a heavy chain CDR3 comprising the amino acid sequence RGYYGSSSWFGY (SEQ ID NO: 141); a light chain CDR1 comprising the amino acid sequence KASQNVGTDVA (SEQ ID NO: 144); a light chain CDR2 comprising the amino acid sequence SASYRYS (SEQ ID NO: 147; a light chain CDR3 comprising the amino acid sequence QQYNSFPYT (SEQ ID NO: 148 and human heavy and light chain framework sequences.

The anti-Siglec antibody may have a heavy and/or light chain having one, two or three CDRs of the respective heavy and/or light chain of an antibody selected from the group consisting of antibody mAbs-1, -2, -3, -4, -5 and -6.

In one aspect of any of the embodiments, binding to a Siglec can be specified as being cellular Siglec, where the Siglec is expressed at the surface of a cell, for example a native or modified cellular Siglec, a Siglec expressed by a recombinant host cell, a Siglec expressed by an NK cell, a CD8 T cell, etc.

The compound that inhibits a NKG2A polypeptide (anti-NKG2A agent) can be characterized as a compound that increases the ability of an NKG2A-expressing NK cell and/or T cell to cause the death of the HLA-E-expressing cell (e.g. a HLA-E expressing tumor cell). Optionally, the compound that inhibits a NKG2A polypeptide is a polypeptide, optionally an antibody (e.g. monoclonal antibody), that binds a NKG2A polypeptide.

In one embodiment, the anti-NKG2A agent reduces the inhibitory activity of NKG2A by blocking binding of its ligand, HLA-E, i.e., the anti-NKG2A agent interferes with the binding of NKG2A by HLA-E. The antibody having the heavy chain of any of SEQ ID NOS: 171-175 and the light chain of SEQ ID NO: 176 is an example of such an antibody. In one embodiment, the anti-NKG2A agent reduces the inhibitory activity of NKG2A without blocking binding of its ligand, HLA-E, i.e., the anti-NKG2A agent is a non-competitive antagonist and does not interfere with the binding of NKG2A by HLA-E. The antibody having the heavy and light chain variable regions of SEQ ID NOS: 177 and 178 respectively is an example of such an antibody.

In one embodiment, the anti-NKG2A agent binds with a significantly higher affinity to NKG2A than to one or more activating NKG2 receptors. For example, in one embodiment, the agent is antibody which binds with a significantly higher affinity to NKG2A than to NKG2C. In an additional or alternative embodiment, the agent is antibody which binds with a significantly higher affinity to NKG2A than to NKG2E. In an additional or alternative embodiment, the agent is antibody which binds with a significantly higher affinity to NKG2A than to NKG2H.

In one embodiment, the anti-NKG2A agent competes with the antibody having the heavy chain variable region comprising an amino acid sequence of any of SEQ ID NOS: 171-175 and the light chain variable region comprising an amino acid sequence of SEQ ID NO: 176, or the antibody having the heavy and light chain variable regions of SEQ ID NOS: 177 and 178 respectively, in binding to CD94/NKG2A. The agent can be, e.g., a human or humanized anti-NKG2A antibody, for example monalizumab (IPH2201, Innate Pharma).

In one embodiment, the anti-NKG2A antibody is a humanized antibody having the heavy chain CDRs of any of the heavy chains of any of SEQ ID NOS: 171-175 and the light chain CDRs of the light chain of SEQ ID NO: 176 respectively. In one embodiment, the anti-NKG2A antibody is a humanized antibody having the heavy chain variable region of any of the heavy chains of any of SEQ ID NOS: 171-175 and the light chain variable region of the light chain of SEQ ID NO: 176 respectively.

In one aspect of any of the embodiments of the invention, provided is a protein (e.g. an antibody or antibody fragment according to any of the embodiments herein) that binds a Siglec-9 polypeptide and that further binds a human NKG2A polypeptide and neutralizes the inhibitory activity of the NKG2A polypeptide. Examples of such proteins include, e.g., a multispecific (e.g. bispecific, tri-specific) antibodies.

The disclosure also relates to nucleic acid encoding the human or humanized antibody or antibody fragment having any of the foregoing properties, a vector comprising such a nucleic acid, a cell comprising such a vector, and methods of producing antibodies according to the disclosure. Also provided are compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The invention further relates various new and useful methods making and using such antibodies, nucleic acids, vectors, cells, organisms, and/or compositions, such as in the modulation of Siglec-mediated biological activities, for example in the treatment of diseases related thereto, notably cancers and infectious disease.

These aspects are more fully described in, and additional aspects, features, and advantages will be apparent from, the description of the invention provided herein.

BRIEF DESCRIPTION OF THE DRAWINGS

FIG. 9 shows that mAbs 1, 2, 4, 5 and 6 blocked Siglec-7 interaction with Sia2, but mAb3 did not. FIG. 10 shows that all mAbs block the Siglec-9 interaction with Sia2, while mAb1, mAb2 and mAb3 showed low ability to inhibit the Siglec-9 interaction with Sia1, and thus did not substantially block the Sia1 interaction.

FIG. 11 shows the structure of the Siglec-9 N-terminal V-set Ig-like domain, with the residues substituted in Siglec-9 mutant M9, M10 and M11 shown in dark shading. FIG. 12 shows the structure of the Siglec-9 N-terminal V-set Ig-like domain, with the residues substituted in Siglec-9 mutant M6 and M7 shown in dark shading. FIG. 13 shows the structure of the Siglec-9 N-terminal V-set Ig-like domain, with the residues substituted in Siglec-9 mutant M16 shown in dark shading. FIG. 14 shows the structure of the Siglec-9 N-terminal V-set Ig-like domain, with the residues substituted in Siglec-9 mutant M8 shown in dark shading. In each of FIGS. 11-14, the sialic acid ligand binding site is shown in light shading.

DETAILED DESCRIPTION

Definitions

Figure 1:
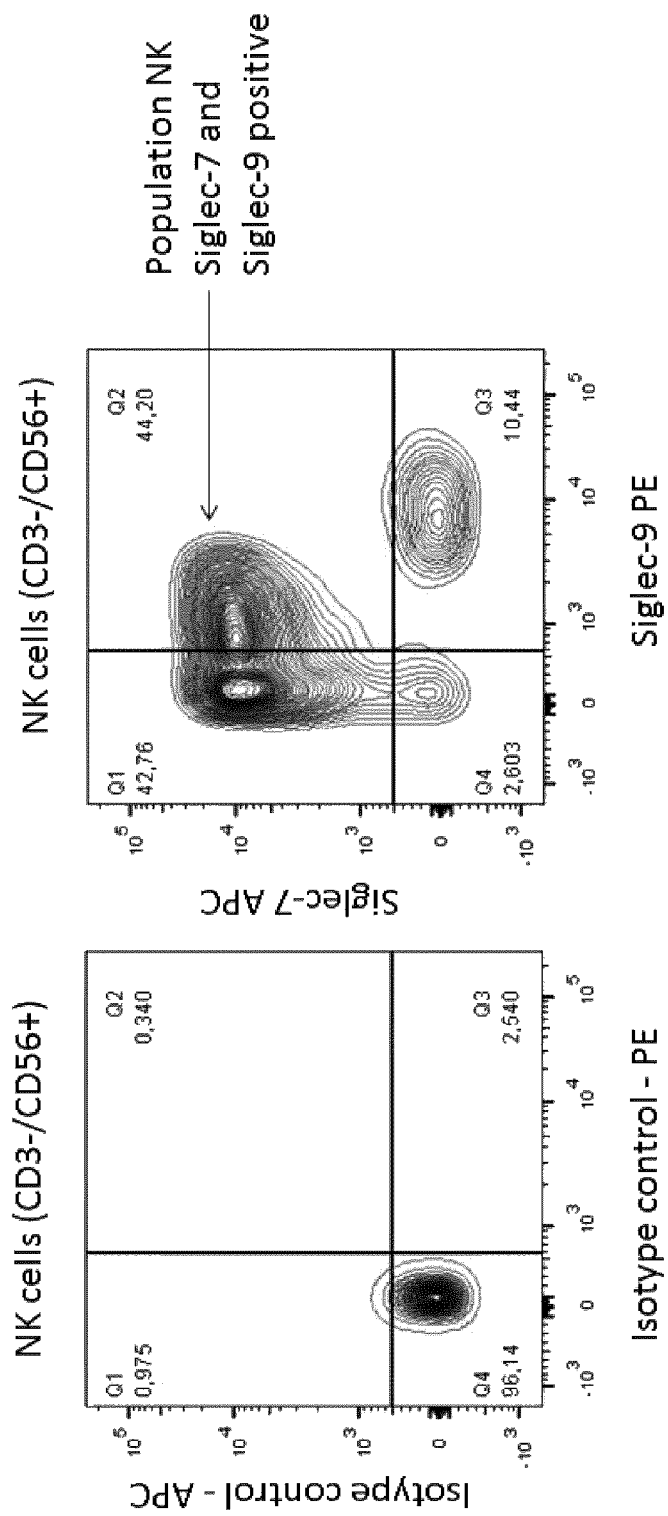
FIG. 1 shows binding of anti-Siglec antibodies to NK cells. Siglec MFI:Mean of fluorescence intensity. A significant fraction (about 44%) of NK cells expressed both Siglec-7 and Siglec-9, suggesting that a large proportion of NK cells can be inhibited by each of (or both of) these receptors, as a function of the glycan ligands present, for example on tumor cells.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

Human Siglec-7 (shown in Genbank accession number NP_055200.1, the entire disclosure of which is incorporated herein by reference) is a member of the CD33-related Siglec family (Angata and Varki, Glycobiology 10 (4), 431-438 (2000)). Human Siglec-7 comprises 467 amino acids, having the following amino acid sequence:

```
                                            (SEQ ID NO: 1)
mllllllpll wgrervegqk snrkdysltm qssvtvqegm cvhvrcsfsy pvdsqtdsdp vhgywfragn diswkapvat nnpawavqee trdrfhllgd pqtknctlsi rdarmsdagr yffrmekgni kwnykydqls vnvtalthrp nilipgtles gcfqnltcsv pwaceqgtpp miswmgtsvs plhpsttrss vltlipqpqh hgtsltcqvt lpgagvttnr tiqlnvsypp qnltvtvfqg egtastalgn ssslsvlegq slrlvcavds npparlswtw rsltlypsqp snplvlelqv hlgdegeftc raqnslgsqh vslnlslqqe ytgkmrpvsg vllgavggag atalvflsfc vifivvrscr kksarpaadv gdigmkdant irgsasqgnl teswaddnpr hhglaahssg eereiqyapl sfhkgepqdl sgqeatnney seikipk.
```

Human Siglec-9 (shows in Genbank accession number NP055256.1 the entire disclosure of which is incorporated herein by reference) is a member of the CD33-related Siglec family (Angata and Varki, J. Biol. Chem. 275 (29), 22127-22135 (2000)). Human Siglec-9 comprises 463 amino acids, having the following amino acid sequence:

```
                                            (SEQ ID NO: 2)
MLLLLLPLLW GRERAEGQTS KLLTMQSSVT VQEGLCVHVP

CSFSYPSHGW IYPGPWHGY WFREGANTDQ DAPVATNNPA

RAVWEETRDR FHLLGDPHTK NCTLSIRDAR RSDAGRYFFR

MEKGSIKWNY KHHRLSVNVT ALTHRPNILI PGTLESGCPQ

NLTCSVPWAC EQGTPPMISW IGTSVSPLDP STTRSSVLTL

IPQPQDHGTS LTCQVTFPGA SVTTNKTVHL NVSYPPQNLT
```

```
MTVFQGDGTV STVLGNGSSL SLPEGQSLRL VCAVDAVDSN

PPARLSLSWR GLTLCPSQPS NPGVLELPWV HLRDAAEFTC

RAQNPLGSQQ VYLNVSLQSK ATSGVTQGVV GGAGATALVF

LSFCVIFVVV RSCRKKSARP AAGVGDTGIE DANAVRGSAS

QGPLTEPWAE DSPPDQPPPA SARSSVGEGE LQYASLSFQM

VKPWDSRGQE ATDTEYSEIK IHR.
```

In the context of the present disclosure, "neutralize Siglec-mediated inhibition of NK cell cytotoxicity", "neutralize Siglec-mediated inhibition of T cell cytotoxicity" or "neutralize the inhibitory activity of a Siglec", refers to a process in which a Siglec (e.g., Siglec-7, Siglec-9) is inhibited in its capacity to negatively affect intracellular processes leading to lymphocyte responses such as cytokine release and cytotoxic responses. This can be measured for example in a standard NK- or T-cell based cytotoxicity assay, in which the capacity of a therapeutic compound to stimulate killing of sialic-acid ligand positive cells by Siglec positive lymphocytes is measured. In one embodiment, an antibody preparation causes at least a 10% augmentation in the cytotoxicity of a Siglec-restricted lymphocyte, optionally at least a 40% or 50% augmentation in lymphocyte cytotoxicity, or optionally at least a 70% augmentation in NK cytotoxicity, and referring to the cytotoxicity assays described. In one embodiment, an antibody preparation causes at least a 10% augmentation in cytokine release by a Siglec-restricted lymphocyte, optionally at least a 40% or 50% augmentation in cytokine release, or optionally at least a 70% augmentation in cytokine release, and referring to the cytotoxicity assays described. In one embodiment, an antibody preparation causes at least a 10% augmentation in cell surface expression of a marker of cytotoxicity (e.g., CD107 and/or CD137) by a Siglec-restricted lymphocyte, optionally at least a 40% or 50% augmentation, or optionally at least a 70% augmentation in cell surface expression of a marker of cytotoxicity (e.g., CD107 and/or CD137).

The ability of an anti-Siglec antibody to "block" the binding of a Siglec molecule to a sialic acid ligand means that the antibody, in an assay using soluble or cell-surface associated Siglec and sialic acid molecules, can detectably reduce the binding of a Siglec molecule to a sialic acid molecule in a dose-dependent fashion, where the Siglec molecule detectably binds to the sialic acid molecule in the absence of the antibody.

NKG2A (OMIM 161555, the entire disclosure of which is herein incorporated by reference) is a member of the NKG2 group of transcripts (Houchins, et al. (1991) J. Exp. Med. 173:1017-1020). NKG2A is encoded by 7 exons spanning 25 kb, showing some differential splicing. Together with CD94, NKG2A forms the heterodimeric inhibitory receptor CD94/NKG2A, found on the surface of subsets of NK cells, α/β T cells, γ/δ T cells, and NKT cells. Similar to inhibitory KIR receptors, it possesses an ITIM in its cytoplasmic domain. As used herein, "NKG2A" refers to any variant, derivative, or isoform of the NKG2A gene or encoded protein. Human NKG2A comprises 233 amino acids in 3 domains, with a cytoplasmic domain comprising residues 1-70, a transmembrane region comprising residues 71-93, and an extracellular region comprising residues 94-233, of the following sequence:

```
(SEQ ID NO: 170)
MDNQGVIYSDLNLPPNPKRQQRKPKGNKSSILATEQEITYAEL

NLQKASQDFQGNDKTYHCKDLPSAPEKLIVGILGIICLILMAS

VVTIVVIPSTLIQRHNNSSLNTRTQKARHCGHCPEEWITYSNS

CYYIGKERRTWEESLLACTSKNSSLLSIDNEEEMKFLSIISPS

SWIGVFRNSSHHPWVTMNGLAFKHEIKDSDNAELNCAVLQVNR

LKSAQCGSSIIYHCKHKL.
```

NKG2C (OMIM 602891, the entire disclosure of which is herein incorporated by reference) and NKG2E (OMIM 602892, the entire disclosure of which is herein incorporated by reference) are two other members of the NKG2 group of transcripts (Gilenke, et al. (1998) Immunogenetics 48:163-173). The CD94/NKG2C and CD94/NKG2E receptors are activating receptors found on the surface of subsets of lymphocytes such as NK cells and T-cells.

HLA-E (OMIM 143010, the entire disclosure of which is herein incorporated by reference) is a nonclassical MHC molecule that is expressed on the cell surface and regulated by the binding of peptides, e.g., such as fragments derived from the signal sequence of other MHC class I molecules. Soluble versions of HLA-E have also been identified. In addition to its T-cell receptor binding properties, HLA-E binds subsets of natural killer (NK) cells, natural killer T-cells (NKT) and T cells (α/β and γ/δ), by binding specifically to CD94/NKG2A, CD94/NKG2B, and CD94/NKG2C (see, e.g., Braud et al. (1998) Nature 391:795-799, the entire disclosure of which is herein incorporated by reference). Surface expression of HLA-E protects target cells from lysis by CD94/NKG2A+ NK, T, or NKT cell clones. As used herein, "HLA-E" refers to any variant, derivative, or isoform of the HLA-E gene or encoded protein.

In the context of the present disclosure, "NKG2A" or "CD94/NKG2A positive lymphocyte" refers to cells of the lymphoid lineage (e.g. NK-, NKT- and T-cells) expressing CD94/NKG2A on the cell-surface, which can be detected by e.g. flow-cytometry using antibodies that specifically recognize a combined epitope on CD94 and NKG2A or and epitope on NKG2A alone. "NKG2A positive lymphocyte" also includes immortal cell lines of lymphoid origin (e.g. NKL, NK-92).

In the context of the present disclosure, "reduces the inhibitory activity of NKG2A", "neutralizes NKG2A" or "neutralizes the inhibitory activity of NKG2A" refers to a process in which CD94/NKG2A is inhibited in its capacity to negatively affect intracellular processes leading to lymphocyte responses such as cytokine release and cytotoxic responses. This can be measured for example in a NK- or T-cell based cytotoxicity assay, in which the capacity of a therapeutic compound to stimulate killing of HLA-E positive cells by CD94/NKG2A positive lymphocytes is measured. In one embodiment, an antibody preparation causes at least a 10% augmentation in the cytotoxicity of a CD94/NKG2A-restricted lymphocyte, optionally at least a 40% or 50% augmentation in lymphocyte cytotoxicity, optionally at least a 70% augmentation in NK cytotoxicity", and referring to the cytotoxicity assays described. If an anti-NKG2A antibody reduces or blocks CD94/NKG2A interactions with HLA-E, it may increase the cytotoxicity of CD94/NKG2A-restricted lymphocytes. This can be evaluated, for example, in a standard 4-hour in vitro cytotoxicity assay using, e.g., NK cells that express CD94/NKG2A, and target cells that express HLA-E. Such NK cells do not efficiently kill targets that express HLA-E because CD94/NKG2A recognizes HLA-E, leading to initiation and propagation of inhibitory signaling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). Chromium release and/or other parameters to assess the ability of the antibody to stimulate lymphocytes to kill target cells such as P815, K562 cells, or appropriate tumor cells are also disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference. The target cells are labeled with $^{51}$Cr prior to addition of NK cells, and then the killing is estimated as proportional to the release of $^{51}$Cr from the cells to the medium, as a result of killing. The addition of an antibody that prevents CD94/NKG2A from binding to HLA-E results in prevention of the initiation and propagation of inhibitory signaling via CD94/NKG2A. Therefore, addition of such agents results in increases in lymphocyte-mediated killing of the target cells. This step thereby identifies agents that prevent CD94/NKG2A-induced negative signaling by, e.g., blocking ligand binding. In a particular $^{51}$Cr-release cytotoxicity assay, CD94/NKG2A-expressing NK effector-cells can kill HLA-E-negative LCL 721.221 target cells, but less well HLA-E-expressing LCL 721.221-Cw3 control cells. In contrast, YTS effector-cells that lack CD94/NKG2A kill both cell-lines efficiently. Thus, NK effector cells kill less efficiently HLA-E$^+$ LCL 721.221-Cw3 cells due to HLA-E-induced inhibitory signaling via CD94/NKG2A. When NK cells are pre-incubated with blocking anti-CD94/NKG2A antibodies according to the present invention in such a $^{51}$Cr-release cytotoxicity assay, HLA-E-expressing LCL 721.221-Cw3 cells are more efficiently killed, in an antibody-concentration-dependent fashion. The inhibitory activity (i.e. cytotoxicity enhancing potential) of an anti-NKG2A antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference. Activation of NK cell cytotoxicity can be assessed for example by measuring an increase in cytokine production (e.g. IFN-γ production) or cytotoxicity markers (e.g. CD107 or CD137 mobilization). In an exemplary protocol, IFN-y production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-y or PE-IgG1 (Pharmingen). GM-CSF and IFN-y production from polyclonal activated NK cells are measured in supernatants using ELISA (GM-CSF: DuoSet Elisa, R&D Systems, Minneapolis, Minn., IFN-y: OptEIA set, Pharmingen).

Whenever within this whole specification "treatment of cancer" or the like is mentioned with reference to anti-Siglec binding agent (e.g., antibody), there is meant: (a) method of treatment of cancer, said method comprising the step of administering (for at least one treatment) an anti-Siglec binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-Siglec binding agent for the treatment of cancer, or an anti-Siglec binding agent, for use in said treatment (especially in a human); (c) the use of an anti-Siglec binding agent for the manufacture of a pharmaceutical preparation for the treatment of cancer, a method of using an anti-Siglec binding agent for the manufacture of a pharmaceutical preparation for the treatment of cancer, comprising admixing an anti-Siglec binding agent with a pharmaceutically acceptable carrier, or a pharmaceutical preparation comprising an effective dose of an anti-Siglec binding agent that is appropriate for the treatment of cancer; or (d) any combination of a), b), and c), in accordance with the subject matter allowable for patenting in a country where this application is filed.

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The terms "antibody" or "immunoglobulin," as used interchangeably herein, include whole antibodies and any antigen binding fragment or single chains thereof. A typical antibody comprises at least two heavy (H) chains and two light (L) chains interconnected by disulfide bonds. Each heavy chain is comprised of a heavy chain variable region ($V_H$) and a heavy chain constant region. The heavy chain constant region is comprised of three domains, CH1, CH2, and CH3. Each light chain is comprised of a light chain variable region ($V_L$) and a light chain constant region. The light chain constant region is comprised of one domain, CL. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. Several of these are further divided into subclasses or isotypes, such as IgG1, IgG2, IgG3, IgG4, and the like. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

A "cross-reactive" anti-Siglec antibody is an antibody that binds more than one Siglec molecule with specificity and/or affinity. For example, a monoclonal antibody can be cross-reactive with Siglec-7 and Siglec-9.

The term "specifically binds to" means that an antibody can bind preferably in a competitive binding assay to the binding partner, e.g., Siglec-7, Siglec-9, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody, it means that the antibody competes with the monoclonal antibody in a binding assay using either recombinant Siglec molecules or surface expressed Siglec molecules. For example, if a test antibody reduces the binding of a reference antibody to a Siglec polypeptide or Siglec-expressing cell in a binding assay, the antibody is said to "compete" respectively with the reference antibody.

The term "affinity", as used herein, means the strength of the binding of an antibody to an epitope. The affinity of an antibody is given by the dissociation constant Kd, defined as [Ab]×[Ag]/[Ab−Ag], where [Ab−Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "deplete" or "depleting", with respect to Siglec-expressing cells (e.g., Siglec-7 or Siglec-9 expressing lymphocytes) means a process, method, or compound that results in killing, elimination, lysis or induction of such killing, elimination or lysis, so as to negatively affect the number of such Siglec-expressing cells present in a sample or in a subject. "Non-depleting", with reference to a process, method, or compound means that the process, method, or compound is not depleting.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g., the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "hypervariable region" when used herein refers to the amino acid residues of an antibody that are responsible for antigen binding. The hypervariable region generally comprises amino acid residues from a "complementarity-determining region" or "CDR" (e.g., residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g., residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Therapeutic Agents

Agents that Inhibit Siglec

The anti-Siglec agents useful for the treatment of disease (e.g. cancer, infectious disease) bind an extra-cellular portion of the human Siglec-9 protein (and optionally further binding the human Siglec-7 protein, with or without further Siglec-12 binding) and reduces the inhibitory activity of the human Siglec expressed on the surface of a Siglec positive immune cell. In one embodiment the agent inhibits the ability of a sialic acid molecule to cause inhibitory signaling by a Siglec in a neutrophil, a dendritic cell, a macrophage, an M2 macrophage, an NK cell and/or a CD8+ T cell.

In one embodiment, the anti-Siglec agent described herein can be used to increase the cytotoxicity of NK cells and/or neutrophils in a human or from a human donor toward a target cell (e.g. a cancer cell) that bears ligands of the Siglec. NK cells and neutrophils are specialized granulocytes that recognize and directly kill microorganisms and cancer cells. Sialic acid expressing at the surface of tumor cells is shown to reduce the cytotoxicity of NK cells towards tumor cells. The antibodies can be used to enhance NK cell cytotoxicity, for example to restore the level of cytotoxicity to substantially that observed in an NK cell or neutrophil that does not express at its surface the particular Siglec.

Sialic acids are also highly expressed on dendritic cells and have been described to modulate several DC functions, including responsiveness to TLR stimulation. The blockade of sialic acid synthesis lowers the activation threshold of moDCs for TLR stimulation and Siglec-E deletion enhanced dendritic cell responses to several microbial TLR ligands. Siglec-9 being the closest human orthologous member of Siglec-E in mice, the blocking anti-Siglec-9 antibodies may enhance dendritic cell activation and modulate DC-T interactions. The modification of antigens with sialic acids regulates the generation of antigen-specific regulatory T (Treg) cells and prevents formation of effector CD4+ and CD8+ T cells via dendritic cells. The phagocytic capacity of dendritic cells can also be improved by a 2,6-sialic acid deficiency.

Siglec-7 and -9 are both expressed on type M1 and M2 macrophages, and the knockdown of Siglec-9 has been described to modulate various surface expression markers (e.g. CCR7 and CD200R) suggesting a modulation of macrophage functions by Siglec-9. Indeed, various Siglec-9 mutants (mutation in ITIM domain) were transfected in macrophage cell line and demonstrated that Siglec-9 enhances the production of the anti-inflammatory cytokine IL-10. Binding of Siglec-9 with a soluble ligand can also induce macrophages to display a tumor-associated macrophage-like phenotype, with increased expression of the checkpoint ligand PD-L1.

In one embodiment the agent competes with a sialic acid molecule in binding to a Siglec, i.e., the agent blocks the interaction between Siglec and a sialic acid ligand thereof.

In one aspect of the invention, the agent is an antibody selected from a full-length antibody, an antibody fragment, and a synthetic or semi-synthetic antibody-derived molecule.

In one aspect of the invention, the agent is an antibody selected from a fully human antibody, a humanized antibody, and a chimeric antibody.

In one aspect of the invention, the agent is a fragment of an antibody selected from IgA, an IgD, an IgG, an IgE and an IgM antibody.

In one aspect of the invention, the agent is a fragment of an antibody comprising a constant domain selected from IgG1, IgG2, IgG3 and IgG4.

In one aspect of the invention, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment.

In one aspect of the invention, the agent is a synthetic or semisynthetic antibody-derived molecule selected from a scFV, a dsFV, a minibody, a diabody, a triabody, a kappa body, an IgNAR; and a multispecific antibody.

In one aspect, the antibody or antigen binding domain binds to Siglec-7 and/or -9 with a binding affinity (e.g., KD) at least 100-fold lower than to a further human Siglec, e.g., Siglecs-3, -5, -6, -8, -10, -11 and/or -12. In one aspect, the antibody or antigen binding domain binds to Siglec-9 but not to Siglec-7; in one embodiment, the antibody binds a human Siglec-9 polypeptide with a binding affinity (e.g., KD) at least 100-fold lower than to human Siglec-7 polypeptide. In another aspect, the antibody binds both a human Siglec-9 polypeptide and to human Siglec-7 polypeptide with a binding affinity (e.g., KD) that does not differ by more than 1-log from one another, and wherein the binding affinities for said Siglec-7 and Siglec-9 are at least 100-fold lower than to a further human Siglec, e.g., Siglecs-3, -5, -6, -8, -10, -11 and/or -12. Affinity can be determined for example by Surface Plasmon Resonance, for binding to recombinant Siglec polypeptides.

In one aspect, the antibody is in purified or at least partially purified form. In one aspect of the invention, the antibody is in essentially isolated form.

The antibodies may be produced by a variety of techniques known in the art. Typically, they are produced by immunization of a non-human animal, preferably a mouse, with an immunogen comprising a Siglec polypeptide, preferably a human Siglec polypeptide. The Siglec polypeptide may comprise the full length sequence of a human Siglec-9 and/or Siglec-7 polypeptide, or a fragment or derivative thereof, typically an immunogenic fragment, i.e., a portion of the polypeptide comprising an epitope exposed on the surface of cells expressing a Siglec polypeptide. Such fragments typically contain at least about 7 consecutive amino acids of the mature polypeptide sequence, even more preferably at least about 10 consecutive amino acids thereof. Fragments typically are essentially derived from the extracellular domain of the receptor. In one embodiment, the immunogen comprises a wild-type human Siglec polypeptide in a lipid membrane, typically at the surface of a cell. In a specific embodiment, the immunogen comprises intact cells, particularly intact human cells, optionally treated or lysed. In another embodiment, the polypeptide is a recombinant Siglec polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to Siglec polypeptide gene products. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to Siglec polypeptides, e.g., Siglec-expressing cells.

Hybridomas that are confirmed to produce a monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

Antibodies can be titrated on Siglecs for the concentration required to achieve maximal binding to a Siglec polypeptide. "EC50" with respect to binding to a Siglec polypeptide (or cell expressing such), refers to the efficient concentration of anti-Siglec antibody which produces 50% of its maximum response or effect with respect to binding to a Siglec polypeptide (or cell expressing such).

Once antibodies are identified that are capable of binding Siglec and/or having other desired properties, they will also typically be assessed, using standard methods including those described herein, for their ability to bind to other polypeptides, including other Siglec polypeptides and/or unrelated polypeptides. Ideally, the antibodies only bind with substantial affinity to Siglec, e.g., human Siglec-7 and/or human Siglec-9, and do not bind at a significant level to unrelated polypeptides, notably polypeptides other than CD33-related Siglecs, or Siglecs other than the desired Siglecs (e.g., Siglec-7 and/or Siglec-9). However, it will be appreciated that, as long as the affinity for Siglec is substantially greater (e.g., 5×, 10×, 50×, 100×, 500×, 1000×, 10,000×, or more) than it is for other Siglecs and/or other, unrelated polypeptides), then the antibodies are suitable for use in the present methods.

The anti-Siglec antibodies can be prepared as non-depleting antibodies such that they have reduced, or substantially lack specific binding to human Fcγ receptors. Such antibodies may comprise constant regions of various heavy chains that are known not to bind, or to have low binding affinity for, Fcγ receptors. One such example is a human IgG4 constant region. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any antibody isotype can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The DNA encoding an antibody that binds an epitope present on Siglec polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding a monoclonal antibodies can be readily isolated and sequenced using conventional procedures (e. g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

A "common determinant" designates a determinant or epitope that is shared by several gene products of the human inhibitory Siglec receptors, notably of the CD33-related Siglecs. An antibody can bind a common determinant shared by at least Siglec-7 and Siglec-9. In one embodiment, the common determinant may optionally be absent on one or more, or all of, the CD33-related Siglecs, particularly Siglecs-3, -5, -6, -8, -10, -11 and -12. In one embodiment the common determinant is absent on Siglecs-3, -5, -6, -8, -10, -11 and -12.

The identification of one or more antibodies that bind(s) to siglec polypeptides (e.g., Siglec-7 and/or Siglec-9, particularly substantially or essentially the same epitope as monoclonal antibody mAbsA, -B, -C, -D, -E or -F (Siglec-9 specific) or mAbs1, -2, -3, -4, -5 or -6 (Siglec-7/9 specific), can be readily determined using any one of a variety of immunological screening assays in which antibody competition can be assessed. Many such assays are routinely practiced and are well known in the art (see, e. g., U.S. Pat. No. 5,660,827, which is incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (mAbA, -B, -C, -D, -E or -F or mAb1, -2, -3, -4, -5 or -6, for example) and test antibodies are admixed (or pre-adsorbed) and applied to a sample containing Siglec polypeptides. Protocols based upon western blotting and the use of BIACORE analysis are suitable for use in such competition studies.

In certain embodiments, one pre-mixes the control antibodies (mAbA, -B, -C, -D, -E or -F or mAb1, -2, -3, -4, -5 or -6, for example) with varying amounts of the test antibodies (e.g., about 1:10 or about 1:100) for a period of time prior to applying to the Siglec antigen sample. In other embodiments, the control and varying amounts of test antibodies can simply be admixed during exposure to the Siglec antigen sample. As long as one can distinguish bound from free antibodies (e. g., by using separation or washing techniques to eliminate unbound antibodies) and mAbA, -B, -C, -D, -E, -F, -1, -2, -3, -4, -5 or -6 from the test antibodies (e. g., by using species-specific or isotype-specific secondary antibodies or by specifically labeling mAbA, -B, -C, -D, -E, -F, -1, -2, -3, -4, -5 or -6 with a detectable label) one can determine if the test antibodies reduce the binding of mAbA, -B, -C, -D, -E, -F, -1, -2, -3, -4, -5 or -6 to the antigens, indicating that the test antibody competes for binding and/or recognizes a common binding site on a Siglec as mAb1, mAbA, -B, -C, -D, -E, -F, -1, -2, -3, -4, -5 or -6. The binding of the (labeled) control antibodies in the absence of a completely irrelevant antibody can serve as the control high value. The control low value can be obtained by incubating the labeled (mAbA, -B, -C, -D, -E, -F, -1, -2, -3, -4, -5 or -6) antibodies with unlabelled antibodies of exactly the same type (mAbA, -B, -C, -D, -E, -F, -1, -2, -3, -4, -5 or -6), where competition would occur and reduce binding of the labeled antibodies. In a test assay, a significant reduction in labeled antibody reactivity in the presence of a test antibody is indicative of a test antibody that recognizes substantially the same region on a Siglec, and that that "cross-reacts" or competes with the labeled (mAbA, -B, -C, -D, -E, -F, -1, -2, -3, -4, -5 or -6) antibody. Any test antibody that reduces the binding of mAbA, -B, -C, -D, -E, -F, -1, -2, -3, -4, -5 or -6 to Siglec antigens by at least about 50%, such as at least about 60%, or more preferably at least about 80% or 90% (e. g., about 65-100%), at any ratio of mAbA, -B, -C, -D, -E, -F, -1, -2, -3, -4, -5 or -6:test antibody between about 1:10 and about 1:100 is considered to be an antibody competes with the respective mAbA, -B, -C, -D, -E, -F, -1, -2, -3, -4, -5 or -6. Preferably, such test antibody will reduce the binding of the respective mAbA, -B, -C, -D, -E, -F, -1, -2, -3, -4, -5 or -6 to the Siglec antigen by at least about 90% (e.g., about 95%).

Competition can also be assessed by, for example, a flow cytometry test. In such a test, cells bearing one or more given Siglec polypeptide(s) can be incubated first with mAbA, -B, -C, -D, -E, -F, -1, -2, -3, -4, -5 or -6, for example, and then with the test antibody labeled with a fluorochrome or biotin. The antibody is said to compete with mAbA, -B, -C, -D, -E, -F, -1, -2, -3, -4, -5 or -6 if the binding obtained upon preincubation with a saturating amount of mAbA, -B, -C, -D, -E, -F, -1, -2, -3, -4, -5 or -6 is about 80%, preferably about 50%, about 40% or less (e.g., about 30%, 20% or 10%) of the binding (as measured by mean of fluorescence) obtained by the antibody without preincubation with the respective mAbA, —B, —C, -D, -E, -F, -1, -2, -3, -4, -5 or -6. Alternatively, an antibody is said to compete with a mAbA, -B, -C, -D, -E, -F, -1, -2, -3, -4, -5 or -6 if the binding obtained with a respective labeled mAbA, -B, -C, -D, -E, -F, -1, -2, -3, -4, -5 or -6 antibody (by a fluorochrome or biotin) on cells preincubated with a saturating amount of test antibody is about 80%, preferably about 50%, about 40%, or less (e. g., about 30%, 20% or 10%) of the binding obtained without preincubation with the test antibody.

A simple competition assay in which a test antibody is pre-adsorbed and applied at saturating concentration to a surface onto which a Siglec antigen is immobilized may also be employed. The surface in the simple competition assay is preferably a BIACORE chip (or other media suitable for surface plasmon resonance analysis). The control antibody (e.g., mAbA, -B, -C, -D, -E, -F, -1, -2, -3, -4, -5 or -6) is then brought into contact with the surface at a Siglec-saturating concentration and the Siglec and surface binding of the control antibody is measured. This binding of the control antibody is compared with the binding of the control antibody to the Siglec-containing surface in the absence of test antibody. In a test assay, a significant reduction in binding of the Siglec-containing surface by the control antibody in the presence of a test antibody is indicative that the test antibody competes for binding and thus may recognize the same region on a Siglec as the control antibody such that the test antibody "cross-reacts" with the control antibody. Any test antibody that reduces the binding of control (such as mAbA, -B, -C, -D, -E, -F, -1, -2, -3, -4, -5 or -6) antibody to a Siglec antigen by at least about 30% or more, preferably about 40%, can be considered to be an antibody that competes for binding to a Siglec as a control (e.g., a respective mAbA, -B, -C, -D, -E, -F, -1, -2, -3, -4, -5 or -6). Preferably, such a test antibody will reduce the binding of the control antibody (e.g., mAbA, -B, -C, -D, -E, -F, -1, -2, -3, -4, -5 or -6) to the Siglec antigen by at least about 50% (e. g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the Siglec antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/ characterization methods, an epitope region for an anti-Siglec antibody may be determined by epitope "foot-printing" using chemical modification of the exposed amines/carboxyls in the Siglec protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e. g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e. g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g., by using trypsin in a ratio of about 1:50 to Siglec or o/n digestion at and pH 7-8, followed by mass spectrometry (MS) analysis for peptide identification. The peptides protected from trypsin cleavage by the anti-Siglec binder can subsequently be identified by comparison of samples subjected to trypsin digestion and samples incubated with antibody and then subjected to digestion by e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the Siglec polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fagerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody of the invention can be identified in one or more of the exemplary competition assays described herein.

Cross-blocking assays can also be used to evaluate whether a test antibody affects the binding of the natural or non-natural sialic acid ligand for human Siglec (e.g., Siglec-7 and/or Siglec-9). For example, to determine whether a humanized anti-Siglec antibody preparation reduces or blocks Siglec-7 interactions with sialic acid, the following test can be performed: A dose-range of anti-human Siglec-9 Fab is co-incubated 30 minutes at room temperature with the human Siglec-Fc (e.g., Siglec-7 Fc and/or Siglec-9 Fc) at a fixed dose, then added on sialic acid ligand expressing cell lines for 1 h. After washing cells two times in staining buffer, a PE-coupled goat anti-mouse IgG Fc fragment secondary antibodies diluted in staining buffer is added to the cells and plates are incubated for 30 additional minutes at 4° C. Cells are washed two times and analyzed on an Accury C6 flow cytometer equipped with an HTFC plate reader. In the absence of test antibodies, the Siglec-Fc binds to the cells. In the presence of an antibody preparation pre-incubated with Siglec-Fc (e.g., Siglec-7 Fc and/or Siglec-9 Fc) that blocks Siglec-binding to sialic acid, there is a reduced binding of Siglec-Fc to the cells. However, it will be appreciated that reconstitution of NK cell lytic activity toward sialic acid ligand-expressing target cells can be assessed directly without the need to assess blockade of the Siglec-sialic acid ligand interaction.

Optionally, antibodies can be specified to be antibodies other than any one or more of antibodies E10-286 (BD Biosciences Corp.), clone 191240, QA79 disclosed in European Patent 1238282B1 (Moretta et al., Universita degli Studi di Genova), or Z176 referenced in Falco et al. (1999) J. Exp. Med. 190:793-801, or derivatives of the foregoing, e.g., that comprise the antigen binding region or heavy and/or light chain CDRs, in whole or in part. Optionally, antibodies of the disclosure can be specified to be antibodies other than any one or more of antibodies 3A11, 1H9 and 2B4 disclosed in PCT application No. PCT/EP2015/070550 filed 9 Sep. 2015 (Innate Pharma). In other embodiments, the above-mentioned antibodies may, depending on the nature of the antibody, be modified so as to have the characteristics of the antibodies of the present disclosure.

Provided herein are antibodies that bind the extracellular domain, e.g., the N-terminal V-set domain or the Ig-like C2-type domain 1 or 2 of human Siglec-9, for example antibodies that bind the epitopes shown in the Examples herein.

In one aspect, the antibodies bind substantially the same epitope as antibody mAb1, -2, -3, -4, -5, -6, -A, -B, -C, -D, -E or -F. In one embodiment, the antibodies bind to an epitope of Siglec-9 and/or Siglec-7 that at least partially overlaps with, or includes at least one residue in, the epitope bound by antibody mAb1, -2, -3, -4, -5, -6, -A, -B, -C, -D, -E or -F. The residues bound by the antibody can be specified as being present on the surface of the of the Siglec-9 and/or Siglec-7 polypeptide, e.g. in a Siglec-9 or Siglec-7 polypeptide expressed on the surface of a cell. The amino acid residues on Siglec-9 and/or Siglec-7 bound by the antibody can for example be selected from the group consisting of the residues listed in Table 3.

Binding of anti-Siglec antibody to cells transfected with Siglec-9 mutants can be measured and compared to the ability of anti-Siglec antibody to bind wild-type Siglec-9 polypeptide (e.g., SEQ ID NO: 2). For antibodies that additionally bind Siglec-7, binding of anti-Siglec antibody can additionally or alternatively be conducted using cells transfected with Siglec-7 mutants (e.g. of Table 3) and compared to the ability of anti-Siglec antibody to bind wild-type Siglec-7 polypeptide (e.g., SEQ ID NO: 1). A reduction in binding between an anti-Siglec antibody and a mutant Siglec-9 and/or Siglec-7 polypeptide (e.g., a mutant Siglec-9 or Siglec-7 of Table 3) means that there is a reduction in binding affinity (e.g., as measured by known methods such FACS testing of cells expressing a particular mutant, or by Biacore™ (SPR) testing of binding to mutant polypeptides) and/or a reduction in the total binding capacity of the anti-Siglec antibody (e.g., as evidenced by a decrease in Bmax in a plot of anti-Siglec antibody concentration versus polypeptide concentration). A significant reduction in binding indicates that the mutated residue is directly involved in binding to the anti-Siglec antibody or is in close proximity to the binding protein when the anti-Siglec antibody is bound to Siglec-9.

In some embodiments, a significant reduction in binding means that the binding affinity and/or capacity between an anti-Siglec antibody and a mutant Siglec-9 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type Siglec-9 polypeptide. In certain embodiments, binding is reduced below detectable limits. In some embodiments, a significant reduction in binding is evidenced when binding of an anti-Siglec antibody to a mutant Siglec-9 polypeptide is less than 50% (e.g., less than 45%, 40%, 35%, 30%, 25%, 20%, 15% or 10%) of the binding observed between the anti-Siglec antibody and a wild-type Siglec-9 polypeptide.

In some embodiments, anti-Siglec antibodies are provided that exhibit significantly lower binding for a mutant Siglec-9 and/or Siglec-7 polypeptide in which a residue in a segment comprising an amino acid residue bound by antibody mAb1, -2, -3, -A, -B, -C, -D, -E or -F is substituted with a different amino acid. In one embodiment, the mutant is a mutant selected from mutants M6, M8, M9, M10, M11, M15 and M16 of Table 3, compared to binding to a wild-type Siglec polypeptide (e.g. the Siglec-9 polypeptide of SEQ ID NO: 2). In one embodiment, the mutant is a mutant selected from mutants M6, M8, M9, M10, M11, M15 and M16 of Table 3, compared to binding to a wild-type Siglec-7 polypeptide (e.g. the polypeptide of SEQ ID NO: 1).

In one aspect, the anti-Siglec antibodies bind an epitope on human Siglec-9 comprising one, two, three, four, five or six of the residues selected from the group consisting of N78, P79, A80, R81, A82 and/or V83 (with reference to SEQ ID NO: 2).

In one aspect, the anti-Siglec antibodies bind an epitope on human Siglec-9 comprising one, two, three or four of the residues selected from the group consisting of N77, D96, H98 and/or T99 (with reference to SEQ ID NO: 2).

In one aspect, the anti-Siglec antibodies bind an epitope on human Siglec-9 comprising one, two, three or four of the residues selected from the group consisting of W84, E85, E86 and/or R88 (with reference to SEQ ID NO: 2).

In one aspect, the anti-Siglec antibodies bind an epitope on human Siglec-9 comprising one, two, three, four, five, six, seven or eight of the residues selected from the group consisting of S47, H48, G49, W50, I51, Y52, P53 and/or G54 (with reference to SEQ ID NO: 2).

In one aspect, the anti-Siglec antibodies bind an epitope on human Siglec-9 comprising one or both of the residues K131 and/or H132 (with reference to SEQ ID NO: 2).

In one aspect, the anti-Siglec antibodies bind an epitope on human Siglec-9 comprising one, two, three, four, five, six or seven of the residues selected from the group consisting of R63, A66, N67, T68, D69, Q70 and/or D71 (with reference to SEQ ID NO: 2).

In one aspect, the anti-Siglec antibodies bind an epitope on human Siglec-9 comprising one, two, three, four, five or six of the residues selected from the group consisting of P55, H58, E122, G124, S125 and/or K127 (with reference to SEQ ID NO: 2).

In one aspect, the anti-Siglec antibodies bind an epitope on human Siglec-7 comprising one, two, three, four, five or six of the residues selected from the group consisting of N82, P83, A84, R85, A86 and/or V87 (with reference to SEQ ID NO: 1).

In one aspect, the anti-Siglec antibodies bind an epitope on human Siglec-7 comprising one, two, three or four of the residues selected from the group consisting of N81, D100, H102 and/or T103 (with reference to SEQ ID NO: 1).

In one aspect, the anti-Siglec antibodies bind an epitope on human Siglec-7 comprising one, two, three or four of the residues selected from the group consisting of W88, E89, E90, R92 (with reference to SEQ ID NO: 1).

Once an antigen-binding compound having the desired binding for Siglecs is obtained it may be assessed for its ability to inhibit Siglec (e.g., Siglec-7 and/or Siglec-9). For example, if an anti-Siglec antibody reduces or blocks Siglec activation induced by a sialic acid ligand (e.g., as present on a cell), it can increase the cytotoxicity of Siglec-restricted lymphocytes. This can be evaluated by a typical cytotoxicity assay, examples of which are described below.

The ability of an antibody to reduce Siglec-mediated signaling can be tested in a standard 4-hour in vitro cytotoxicity assay using, e.g., NK cells that express Siglec-7 or Siglec-9, and target cells that express a sialic acid ligand of the respective Siglec. Such NK cells do not efficiently kill targets that express the sialic acid ligand because Siglec-7 or -9 recognizes the sialic acid ligand, leading to initiation and propagation of inhibitory signaling that prevents lymphocyte-mediated cytolysis. Such an assay can be carried out according to the methods in the Examples herein, see, e.g. Example 8, using primary NK cells, as fresh NK cells purified from donors, incubated overnight at 37° C. before use. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). The target cells are labeled with $^{51}$Cr prior to addition of NK cells, and then the killing is estimated as proportional to the release of $^{51}$Cr from the cells to the medium, as a result of killing. The addition of an antibody that prevents Siglec-7 and/or -9 from binding to the sialic acid ligand results in prevention of the initiation and propagation of inhibitory signaling via the Siglec. Therefore, addition of such agents results in increases in lymphocyte-mediated killing of the target cells. This step thereby identifies agents that prevent Siglec-7 or -9-induced negative signaling by, e.g., blocking ligand binding. In a particular $^{51}$Cr-release cytotoxicity assay, Siglec-7 or -9− expressing NK effector-cells can kill sialic acid ligand-negative target cells (e.g., cells treated with sialidase), but less well sialic acid ligand-expressing control cells. Thus, NK effector cells kill less efficiently sialic acid ligand positive cells due to sialic acid-induced inhibitory signaling via the particular Siglec. When NK cells are pre-incubated with blocking anti-Siglec antibodies in such a $^{51}$Cr-release cytotoxicity assay, sialic acid ligand-expressing cells are more efficiently killed, in an antibody-concentration-dependent fashion. The assay can be carried out separately for each Siglec, e.g., Siglec-7 and Siglec-9.

The inhibitory activity (i.e., cytotoxicity enhancing potential) of an antibody can also be assessed in any of a number of other ways, e.g., by its effect on intracellular free calcium as described, e.g., in Sivori et al., J. Exp. Med. 1997; 186:1129-1136, the disclosure of which is herein incorporated by reference, or by the effect on markers of NK cell cytotoxicity activation, such as degranulation marker CD107 or CD137 expression. NK, T, or NKT cell activity can also be assessed using any cell based cytotoxicity assays, e.g., measuring any other parameter to assess the ability of the antibody to stimulate NK cells to kill target cells such as P815, K562 cells, or appropriate tumor cells as disclosed in Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference.

In one embodiment, an antibody preparation causes at least a 10% augmentation in the cytotoxicity of a Siglec-restricted lymphocyte, preferably at least a 40% or 50% augmentation in NK cytotoxicity, or more preferably at least a 70% augmentation in NK cytotoxicity.

The activity of a cytotoxic lymphocyte can also be addressed using a cytokine-release assay, wherein NK cells are incubated with the antibody to stimulate the cytokine production of the NK cells (for example IFN-y and TNF-α production). In an exemplary protocol, IFN-y production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-y or PE-IgG1 (Pharmingen). GM-CSF and IFN-y production from polyclonal activated NK cells are measured in supernatants using ELISA (GM-CSF: DuoSet Elisa, R&D Systems, Minneapolis, Minn., IFN-y: OptEIA set, Pharmingen).

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g., bispecific) antibodies formed from antibody fragments. Included, inter alia, are a nanobody, domain antibody, single domain antibody or a "dAb".

In certain embodiments, the DNA of a hybridoma producing an antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Optionally an antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for Siglec receptors and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

In one embodiment, the anti-Siglec antibodies can be prepared such that they do not have substantial specific binding to human Fcγ receptors, e.g., any one or more of CD16A, CD16B, CD32A, CD32B and/or CD64). Such antibodies may comprise constant regions of various heavy chains that are known to lack or have low binding to Fcγ receptors. Alternatively, antibody fragments that do not comprise (or comprise portions of) constant regions, such as F(ab')2 fragments, can be used to avoid Fc receptor binding. Fc receptor binding can be assessed according to methods known in the art, including for example testing binding of an antibody to Fc receptor protein in a BIACORE assay. Also, generally any antibody IgG isotype can be used in which the Fc portion is modified (e.g., by introducing 1, 2, 3, 4, 5 or more amino acid substitutions) to minimize or eliminate binding to Fc receptors (see, e.g., WO 03/101485, the disclosure of which is herein incorporated by reference). Assays such as cell based assays, to assess Fc receptor binding are well known in the art, and are described in, e.g., WO 03/101485.

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297A mutation, the LALA mutations, (Strohl, W., 2009, Curr. Opin. Biotechnol. vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g. N297A, N297S mutation), which results in aglycosylated/non-glycosylated antibodies. Other silent mutations include: substitutions at residues L234 and G237 (L234A/G237A); substitutions at residues S228, L235 and R409 (S228P/L235E/R409K,T,M,L); substitutions at residues H268, V309, A330 and A331 (H268Q/V309L/A330S/A331S); substitutions at residues C220, C226, C229 and P238 (C220S/C226S/C229S/P238S); substitutions at residues C226, C229, E233, L234 and L235 (C226S/C229S/E233P/L234V/L235A; substitutions at residues K322, L235 and L235 (K322A/L234A/L235A); substitutions at residues L234, L235 and P331 (L234F/L235E/P331S); substitutions at residues 234, 235 and 297; substitutions at residues E318, K320 and K322 (L235E/E318A/K320A/K322A); substitutions at residues (V234A, G237A, P238S); substitutions at residues 243 and 264; substitutions at residues 297 and 299; substitutions such that residues 233, 234, 235, 237, and 238 defined by the EU numbering system, comprise a sequence selected from PAAAP, PAAAS and SAAAS (see WO2011/066501).

In one embodiment, the antibody can comprise one or more specific mutations in the Fc region that result in improved stability of an antibody of the disclosure, e.g. comprising multiple aromatic amino acid residues and/or having high hydrophobicity. For example, such an antibody can comprise an Fc domain of human IgG1 origin, comprises a mutation at Kabat residue(s) 234, 235, 237, 330 and/or 331. One example of such an Fc domain comprises substitutions at Kabat residues L234, L235 and P331 (e.g., L234A/L235E/P331S or (L234F/L235E/P331S). Another example of such an Fc domain comprises substitutions at Kabat residues L234, L235, G237 and P331 (e.g., L234A/L235E/G237A/P331S). Another example of such an Fc domain comprises substitutions at Kabat residues L234, L235, G237, A330 and P331 (e.g., L234A/L235E/G237A/A330S/P331S). In one embodiment, the antibody comprises an Fc domain, optionally of human IgG1 isotype, comprising: a L234$X_1$ substitution, a L235$X_2$ substitution, and a P331X₃ substitution, wherein X₁ is any amino acid residue other than leucine, X₂ is any amino acid residue other than leucine, and X₃ is any amino acid residue other than proline; optionally wherein X₁ is an alanine or phenylalanine or a conservative substitution thereof; optionally wherein X₂ is glutamic acid or a conservative substitution thereof; optionally wherein X₃ is a serine or a conservative substitution thereof. In another embodiment, the antibody comprises an Fc domain, optionally of human IgG1 isotype, comprising: a L234X₁ substitution, a L235X₂ substitution, a G237X₄ substitution and a P331X₄ substitution, wherein X₁ is any amino acid residue other than leucine, X₂ is any amino acid residue other than leucine, X₃ is any amino acid residue other than glycine, and X₄ is any amino acid residue other than proline; optionally wherein X₁ is an alanine or phenylalanine or a conservative substitution thereof; optionally wherein X₂ is glutamic acid or a conservative substitution thereof; optionally, X₃ is alanine or a conservative substitution thereof; optionally X₄ is a serine or a conservative substitution thereof. In another embodiment, the antibody comprises an Fc domain, optionally of human IgG1 isotype, comprising: a L234X₁ substitution, a L235X₂ substitution, a G237X₄ substitution, G330X₄ substitution, and a P331X₅ substitution, wherein X₁ is any amino acid residue other than leucine, X₂ is any amino acid residue other than leucine, X₃ is any amino acid residue other than glycine, X₄ is any amino acid residue other than alanine, and X₅ is any amino acid residue other than proline; optionally wherein X₁ is an alanine or phenylalanine or a conservative substitution thereof; optionally wherein X₂ is glutamic acid or a conservative substitution thereof; optionally, X₃ is alanine or a conservative substitution thereof; optionally, X₄ is serine or a conservative substitution thereof; optionally X₅ is a serine or a conservative substitution thereof. In the shorthand notation used here, the format is: Wild type residue: Position in polypeptide: Mutant residue, wherein residue positions are indicated according to EU numbering according to Kabat.

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

```
                                        (SEQ ID NO: 166)
A S T K G P S V F P L A P S S K

S T S G G T A A L G C L V K D Y

F P E P V T V S W N S G A L T S

G V H T F P A V L Q S S G L Y S

L S S V V T V P S S S L G T Q T

Y I C N V N H K P S N T K V D K

R V E P K S C D K T H T C P P C

P A P E A E G G P S V F L F P P

K P K D T L M I S R T P E V T C

V V V D V S H E D P E V K F N W

Y V D G V E V H N A K T K P R E

E Q Y N S T Y R V V S V L T V L

H Q D W L N G K E Y K C K V S N
```

```
K A L P A S I E K T I S K A K G

Q P R E P Q V Y T L P P S R E E

M T K N Q V S L T C L V K G F Y

P S D I A V E W E S N G Q P E N

N Y K T T P P V L D S D G S F F

L Y S K L T V D K S R W Q Q G N

V F S C S V M H E A L H N H Y T

Q K S L S L S P G K.
```

In one embodiment, an antibody comprises a heavy chain constant region comprising the amino acid sequence below, or an amino acid sequence at least 90%, 95% or 99% identical thereto but retaining the amino acid residues at Kabat positions 234, 235 and 331 (underlined):

```
                                        (SEQ ID NO: 167)
A S T K G P S V F P L A P S S

K S T S G G T A A L G C L V K

D Y F P E P V T V S W N S G A

L T S G V H T F P A V L Q S S

G L Y S L S S V V T V P S S S

L G T Q T Y I C N V N H K P S

N T K V D K R V E P K S C D K

T H T C P P C P A P E F E G G

P S V F L F P P K P K D T L M

I S R T P E V T C V V V D V S

H E D P E V K F N W Y V D G V

E V H N A K T K P R E E Q Y N

S T Y R V V S V L T V L H Q D

W L N G K E Y K C K V S N K A

L P A S I E K T I S K A K G Q

P R E P Q V Y T L P P S R E E

M T K N Q V S L T C L V K G F

Y P S D I A V E W E S N G Q P

E N N Y K T T P P V L D S D G

S F F L Y S K L T V D K S R W

Q Q G N V F S C S V M H E A L

H N H Y T Q K S L S L S P G K .
```

In one embodiment, an antibody comprises a heavy chain constant region comprising the amino acid sequence below, or an amino acid sequence at least 90%, 95% or 99% identical thereto but retaining the amino acid residues at Kabat positions 234, 235, 237, 330 and 331 (underlined):

(SEQ ID NO: 168)
A S T K G P S V F P L A P S S

K S T S G G T A A L G C L V K

D Y F P E P V T V S W N S G A

L T S G V H T F P A V L Q S S

G L Y S L S S V V T V P S S S

L G T Q T Y I C N V N H K P S

N T K V D K R V E P K S C D K

T H T C P P C P A P E A E G A

P S V F L F P P K P K D T L M

I S R T P E V T C V V V D V S

H E D P E V K F N W Y V D G V

E V H N A K T K P R E E Q Y N

S T Y R V V S V L T V L H Q D

W L N G K E Y K C K V S N K A

L P S S I E K T I S K A K G Q

P R E P Q V Y T L P P S R E E

M T K N Q V S L T C L V K G F

Y P S D I A V E W E S N G Q P

E N NY K T T P P V L D S D G

S F F L Y S K L T V D K S R W

Q Q G N V F S C S V M H E A L

H N H Y T Q K S L S L S P G K.

In one embodiment, an antibody comprises a heavy chain constant region comprising the amino acid sequence below, or a sequence at least 90%, 95% or 99% identical thereto but retaining the amino acid residues at Kabat positions 234, 235, 237 and 331 (underlined):

(SEQ ID NO: 169)
A S T K G P S V F P L A P S S

K S T S G G T A A L G C L V K

D Y F P E P V T V S W N S G A

L T S G V H T F P A V L Q S S

G L Y S L S S V V T V P S S S

L G T Q T Y I C N V N H K P S

N T K V D K R V E P K S C D K

T H T C P P C P A P E A E G A

P S V F L F P P K P K D T L M

I S R T P E V T C V V V D V S

H E D P E V K F N W Y V D G V

E V H N A K T K P R E E Q Y N

S T Y R V V S V L T V L H Q D

W L N G K E Y K C K V S N K A

L P S I E K T I S K A K G Q

P R E P Q V Y T L P P S R E E

M T K N Q V S L T C L V K G F

Y P S D I A V E W E S N G Q P

E N N Y K T T P P V L D S D G

S F F L Y S K L T V D K S R W

Q Q G N V F S C S V M H E A L

H N H Y T Q K S L S L S P G K.

Fc silent antibodies result in no or low ADCC activity, meaning that an Fc silent antibody exhibits an ADCC activity that is below 50% specific cell lysis. Preferably an antibody substantially lacks ADCC activity, e.g., the Fc silent antibody exhibits an ADCC activity (specific cell lysis) that is below 5% or below 1%. Fc silent antibodies can also result in lack of FcγR-mediated cross-linking of Siglec-9 and/or Siglec-7 at the surface of a cell (e.g. an NK cell, a T cell, a monocyte, a dendritic cell, a macrophage).

In one embodiment, the antibody has a substitution in a heavy chain constant region at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330, 331 and 409 (numbering of residues in the heavy chain constant region is according to EU numbering according to Kabat). In one embodiment, the antibody comprises a substitution at residues 234, 235 and 322. In one embodiment, the antibody has a substitution at residues 234, 235 and 331. In one embodiment, the antibody has a substitution at residues 234, 235, 237 and 331. In one embodiment, the antibody has a substitution at residues 234, 235, 237, 330 and 331. In one embodiment, the Fc domain is of human IgG1 subtype. Amino acid residues are indicated according to EU numbering according to Kabat.

Antibody CDR Sequences

The amino acid sequence of the heavy and light chain variable regions of antibodies mAb1, -2, -3, -4, -5, -6, -A, -B, -C, -D, -E and -F are shown in Table B. In a specific embodiment, provided is an antibody that binds essentially the same epitope or determinant as monoclonal antibodies mAb1, -2, -3, -4, -5, -6, -A, -B, -C, -D, -E or -F; optionally the antibody comprises the hypervariable region of antibody mAb1, -2, -3, -4, -5, -6, -A, -B, -C, -D, -E or -F. In any of the embodiments herein, antibody mAb1, -2, -3, -4, -5, -6, -A, -B, -C, -D, -E or -F can be characterized by the amino acid sequences and/or nucleic acid sequences encoding it. In one embodiment, the monoclonal antibody comprises the VH and/or VL, or the Fab or F(ab')$_2$ portion of mAb1, -2, -3, -4, -5, -6, -A, -B, -C, -D, -E or -F. Also provided is a monoclonal antibody that comprises the heavy chain variable region of mAb1. According to one embodiment, the monoclonal antibody comprises the three CDRs of the heavy chain variable region of mAb1, -2, -3, -4, -5, -6, -A, -B, -C, -D, -E or -F. Also provided is a monoclonal antibody that further comprises the variable light chain variable region of the respective mAb1, -2, -3, -4, -5, -6, -A, -B, -C, -D, -E or -F, or one, two or three of the CDRs of the light chain variable region of the respective mAb1, -2, -3, -4, -5, -6, -A, —B, —C, -D, -E or -F. Optionally any one or more of said light or heavy chain CDRs may contain one, two, three, four or five or more amino acid modifications (e.g., substitutions, insertions or deletions). Optionally, provided is an antibody where any of the light and/or heavy chain variable regions comprising part or all of an antigen binding region of antibody mAb1 are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

An exemplary antibody comprises: a HCDR1 region of mAb1 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR2 region of mAb1 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a HCDR3 region of mAb1 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR1 region of mAb1 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR2 region of mAb1 comprising an amino acid sequence as set forth in Table A-1, or a sequence of at least 4, 5, 6, 7, 8, 9 or 10 contiguous amino acids thereof, optionally wherein one or more of these amino acids may be substituted by a different amino acid; a LCDR3 region of mAb1 comprising an amino acid sequence as set forth in Table A-1, or a sequence of at least 4, 5, 6, 7, 8, 9 or 10 contiguous amino acids thereof, optionally wherein one or more of these amino acids may be deleted or substituted by a different amino acid.

TABLE A-1

| mAb | CDR definition | HCDR1 SEQ ID | Sequence | HCDR2 SEQ ID | Sequence | HCDR3 SEQ ID | Sequence |
|---|---|---|---|---|---|---|---|
| mAb1 | Kabat | 27 | GGFAWN | 30 | YIGYGGSTSYNPSLNS | 32 | GDYLFAY |
| | Chotia | 28 | GYSITGGF | | YGG | 33 | DYLFA |
| | IMGT | 29 | GYSITGGFA | 31 | IGYGGST | 34 | ARGDYLFAY |

| mAb | CDR definition | LCDR1 SEQ | Sequence | LCDR2 SEQ ID | Sequence | LCDR3 SEQ ID | Sequence |
|---|---|---|---|---|---|---|---|
| mAb1 | Kabat | 35 | KASQDVNTAVA | 38 | SASYRYT | 39 | QQHYSTPRT |
| | Chotia | 36 | SQDVNTA | | SAS | 40 | HYSTPR |
| | IMGT | 37 | QDVNTA | | SAS | 39 | QQHYSTPRT |

Another exemplary antibody comprises: a HCDR1 region of mAb3 comprising an amino acid sequence as set forth in Table A-3, or a sequence of at least 4, 5, 6, 7, 8, 9 or 10 contiguous amino acids thereof, optionally wherein one or more of these amino acids may be substituted by a different amino acid; a HCDR2 region of mAb3 comprising an amino acid sequence as set forth in Table A-3, or a sequence of at least 4, 5, 6, 7, 8, 9 or 10 contiguous amino acids thereof, optionally wherein one or more of these amino acids may be substituted by a different amino acid; a HCDR3 region of mAb3 comprising an amino acid sequence as set forth in Table A-3, or a sequence of at least 4, 5, 6, 7, 8, 9 or 10 contiguous amino acids thereof, optionally wherein one or more of these amino acids may be substituted by a different amino acid; a LCDR1 region of mAb3 comprising an amino acid sequence as set forth in Table A-3, or a sequence of at least 4, 5, 6, 7, 8, 9 or 10 contiguous amino acids thereof, optionally wherein one or more of these amino acids may be substituted by a different amino acid; a LCDR2 region of mAb3 comprising an amino acid sequence as set forth in Table A-3, or a sequence of at least 4, 5, 6, 7, 8, 9 or 10 contiguous amino acids thereof, optionally wherein one or more of these amino acids may be substituted by a different amino acid; a LCDR3 region of mAb3 comprising an amino acid sequence as set forth in Table A-3, or a sequence of at least 4, 5, 6, 7, 8, 9 or 10 contiguous amino acids thereof, optionally wherein one or more of these amino acids may be deleted or substituted by a different amino acid.

TABLE A-3

| mAb | CDR definition | HCDR1 SEQ ID | Sequence | HCDR2 SEQ ID | Sequence | HCDR3 SEQ ID | Sequence |
|---|---|---|---|---|---|---|---|
| mAb3 | Kabat | 27 | GGFAWN | 30 | YIGYGGSTSYNPSLNS | 32 | GDYLFAY |
| | Chotia | 28 | GYSITGGF | | YGG | 33 | DYLFA |
| | IMGT | 29 | GYSITGGFA | 31 | IGYGGST | 34 | ARGDYLFAY |

| mAb | CDR definition | LCDR1 SEQ | Sequence | LCDR2 SEQ ID | Sequence | LCDR3 SEQ ID | Sequence |
|---|---|---|---|---|---|---|---|
| mAb3 | Kabat | 41 | RASGNIHNYLA | 38 | NAKTLAD | 45 | QHFWSTPRT |
| | Chotia | 42 | SGNIHNY | | NAK | 46 | FWSTPR |
| | IMGT | 43 | GNIHNY | | NAK | 45 | QHFWSTPRT |

Another exemplary antibody comprises: a HCDR1 region of mAb4 comprising an amino acid sequence as set forth in Table A-4, or a sequence of at least 4, 5, 6, 7, 8, 9 or 10 contiguous amino acids thereof, optionally wherein one or more of these amino acids may be substituted by a different amino acid; a HCDR2 region of mAb4 comprising an amino acid sequence as set forth in Table A-4, or a sequence of at least 4, 5, 6, 7, 8, 9 or 10 contiguous amino acids thereof, optionally wherein one or more of these amino acids may be substituted by a different amino acid; a HCDR3 region of mAb4 comprising an amino acid sequence as set forth in Table A-4, or a sequence of at least 4, 5, 6, 7, 8, 9 or 10 contiguous amino acids thereof, optionally wherein one or more of these amino acids may be substituted by a different amino acid; a LCDR1 region of mAb4 comprising an amino acid sequence as set forth in Table A-4, or a sequence of at least 4, 5, 6, 7, 8, 9 or 10 contiguous amino acids thereof, optionally wherein one or more of these amino acids may be substituted by a different amino acid; a LCDR2 region of mAb4 comprising an amino acid sequence as set forth in Table A-4, or a sequence of at least 4, 5, 6, 7, 8, 9 or 10 contiguous amino acids thereof, optionally wherein one or more of these amino acids may be substituted by a different amino acid; a LCDR3 region of mAb4 comprising an amino acid sequence as set forth in Table A-4, or a sequence of at least 4, 5, 6, 7, 8, 9 or 10 contiguous amino acids thereof, optionally wherein one or more of these amino acids may be deleted or substituted by a different amino acid.

TABLE A-4

| mAb | CDR definition | HCDR1 SEQ ID | Sequence | HCDR2 SEQ ID | Sequence | HCDR3 SEQ ID | Sequence |
|---|---|---|---|---|---|---|---|
| mAb4 | Kabat | 47 | SYDMS | 50 | HIGSGGGNIYYPDTVKG | 52 | LIFTTGFYGMDY |
| | Chotia | 48 | GFAFSSY | | SGGG | 53 | IFTTGFYGMD |
| | IMGT | 49 | GFAFSSYD | 51 | IGSGGGNI | 54 | ARLIFTTGFYGMDY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAb4 | Kabat | 55 | RASQDISSYLN | 58 | YTSRLHS | 59 | QQGNALPWT |
| | Chotia | 56 | SQDISSY | | YTS | 60 | GNALPW |
| | IMGT | 57 | QDISSY | | YTS | 59 | QQGNALPWT |

Another exemplary antibody comprises: a HCDR1 region of mAb5 comprising an amino acid sequence as set forth in Table A-5, or a sequence of at least 4, 5, 6, 7, 8, 9 or 10 contiguous amino acids thereof, optionally wherein one or more of these amino acids may be substituted by a different amino acid; a HCDR2 region of mAb5 comprising an amino acid sequence as set forth in Table A-5, or a sequence of at least 4, 5, 6, 7, 8, 9 or 10 contiguous amino acids thereof, optionally wherein one or more of these amino acids may be substituted by a different amino acid; a HCDR3 region of mAb5 comprising an amino acid sequence as set forth in Table A-5, or a sequence of at least 4, 5, 6, 7, 8, 9 or 10 contiguous amino acids thereof, optionally wherein one or more of these amino acids may be substituted by a different amino acid; a LCDR1 region of mAb5 comprising an amino acid sequence as set forth in Table A-5, or a sequence of at least 4, 5, 6, 7, 8, 9 or 10 contiguous amino acids thereof, optionally wherein one or more of these amino acids may be substituted by a different amino acid; a LCDR2 region of mAb5 comprising an amino acid sequence as set forth in Table A-5, or a sequence of at least 4, 5, 6, 7, 8, 9 or 10 contiguous amino acids thereof, optionally wherein one or more of these amino acids may be substituted by a different amino acid; a LCDR3 region of mAb5 comprising an amino acid sequence as set forth in Table A-5, or a sequence of at least 4, 5, 6, 7, 8, 9 or 10 contiguous amino acids thereof, optionally wherein one or more of these amino acids may be deleted or substituted by a different amino acid.

TABLE A-5

| mAb | CDR definition | HCDR1 SEQ ID | Sequence | HCDR2 SEQ ID | Sequence | HCDR3 SEQ ID | Sequence |
|---|---|---|---|---|---|---|---|
| mAb5 | Kabat | 61 | DYNMN | 64 | NIDPYYGATSYNQRFKG | 66 | GDSLFAY |
|  | Chotia | 62 | GYSFSDY |  | PYYG | 67 | DSLFA |
|  | IMGT | 63 | GYSFSDYN | 65 | IDPYYGAT | 68 | ARGDSLFAY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAb5 | Kabat | 69 | KASQNVGTNVA | 72 | SASSRYS | 73 | QQYITYPYT |
|  | Chotia | 70 | SQNVGTN |  | SAS | 74 | YITYPY |
|  | IMGT | 71 | QNVGTN |  | SAS | 73 | QQYITYPYT |

Another exemplary antibody comprises: a HCDR1 region of mAbA comprising an amino acid sequence as set forth in Table A-7, or a sequence of at least 4, 5, 6, 7, 8, 9 or 10 contiguous amino acids thereof, optionally wherein one or more of these amino acids may be substituted by a different amino acid; a HCDR2 region of mAbA comprising an amino acid sequence as set forth in Table A-7 or a sequence of at least 4, 5, 6, 7, 8, 9 or 10 contiguous amino acids thereof, optionally wherein one or more of these amino acids may be substituted by a different amino acid; a HCDR3 region of mAbA comprising an amino acid sequence as set forth in Table A-7, or a sequence of at least 4, 5, 6, 7, 8, 9 or 10 contiguous amino acids thereof, optionally wherein one or more of these amino acids may be substituted by a different amino acid; a LCDR1 region of mAbA comprising an amino acid sequence as set forth in Table A-7, or a sequence of at least 4, 5, 6, 7, 8, 9 or 10 contiguous amino acids thereof, optionally wherein one or more of these amino acids may be substituted by a different amino acid; a LCDR2 region of mAbA comprising an amino acid sequence as set forth in Table A-7, or a sequence of at least 4, 5, 6, 7, 8, 9 or 10 contiguous amino acids thereof, optionally wherein one or more of these amino acids may be substituted by a different amino acid; a LCDR3 region of mAbA comprising an amino acid sequence as set forth in Table A-7, or a sequence of at least 4, 5, 6, 7, 8, 9 or 10 contiguous amino acids thereof, optionally wherein one or more of these amino acids may be deleted or substituted by a different amino acid.

TABLE A-7

| mAb | CDR definition | HCDR1 SEQ ID | Sequence | HCDR2 SEQ ID | Sequence | HCDR3 SEQ ID | Sequence |
|---|---|---|---|---|---|---|---|
| mAbA | Kabat | 75 | SYWMH | 78 | EINPSNGHTNYNEKFES | 80 | GVESYDFDDALDY |
|  | Chotia | 76 | YFTFTSY |  | PSNG | 81 | VESYDFDDALD |
|  | IMGT | 77 | YFTFTSYW | 79 | INPSNGHT | 82 | ANGVESYDFDDALDY |

TABLE A-7-continued

| mAb | CDR definition | LCDR1 SEQ ID | Sequence | LCDR2 SEQ ID | Sequence | LCDR3 SEQ ID | Sequence |
|---|---|---|---|---|---|---|---|
| mAbA | Kabat | 83 | RASQDINNYLN | 58 | YTSRLHS | 86 | QQGNTLPFT |
| | Chotia | 84 | SQDINNY | | YTS | 87 | GNTLPF |
| | IMGT | 85 | QDINNY | | YTS | 86 | QQGNTLPFT |

Another exemplary antibody comprises: a HCDR1 region of mAbB comprising an amino acid sequence as set forth in Table A-8, or a sequence of at least 4, 5, 6, 7, 8, 9 or 10 contiguous amino acids thereof, optionally wherein one or more of these amino acids may be substituted by a different amino acid; a HCDR2 region of mAbB comprising an amino acid sequence as set forth in Table A-8 or a sequence of at least 4, 5, 6, 7, 8, 9 or 10 contiguous amino acids thereof, optionally wherein one or more of these amino acids may be substituted by a different amino acid; a HCDR3 region of mAbB comprising an amino acid sequence as set forth in Table A-8, or a sequence of at least 4, 5, 6, 7, 8, 9 or 10 contiguous amino acids thereof, optionally wherein one or more of these amino acids may be substituted by a different amino acid; a LCDR1 region of mAbB comprising an amino acid sequence as set forth in Table A-8, or a sequence of at least 4, 5, 6, 7, 8, 9 or 10 contiguous amino acids thereof, optionally wherein one or more of these amino acids may be substituted by a different amino acid; a LCDR2 region of mAbB comprising an amino acid sequence as set forth in Table A-8, or a sequence of at least 4, 5, 6, 7, 8, 9 or 10 contiguous amino acids thereof, optionally wherein one or more of these amino acids may be substituted by a different amino acid; a LCDR3 region of mAbB comprising an amino acid sequence as set forth in Table A-8, or a sequence of at least 4, 5, 6, 7, 8, 9 or 10 contiguous amino acids thereof, optionally wherein one or more of these amino acids may be deleted or substituted by a different amino acid.

Another exemplary antibody comprises: a HCDR1 region of mAbC comprising an amino acid sequence as set forth in Table A-9, or a sequence of at least 4, 5, 6, 7, 8, 9 or 10 contiguous amino acids thereof, optionally wherein one or more of these amino acids may be substituted by a different amino acid; a HCDR2 region of mAbC comprising an amino acid sequence as set forth in Table A-9 or a sequence of at least 4, 5, 6, 7, 8, 9 or 10 contiguous amino acids thereof, optionally wherein one or more of these amino acids may be substituted by a different amino acid; a HCDR3 region of mAbC comprising an amino acid sequence as set forth in Table A-9, or a sequence of at least 4, 5, 6, 7, 8, 9 or 10 contiguous amino acids thereof, optionally wherein one or more of these amino acids may be substituted by a different amino acid; a LCDR1 region of mAbC comprising an amino acid sequence as set forth in Table A-9, or a sequence of at least 4, 5, 6, 7, 8, 9 or 10 contiguous amino acids thereof, optionally wherein one or more of these amino acids may be substituted by a different amino acid; a LCDR2 region of mAbC comprising an amino acid sequence as set forth in Table A-9, or a sequence of at least 4, 5, 6, 7, 8, 9 or 10 contiguous amino acids thereof, optionally wherein one or more of these amino acids may be substituted by a different amino acid; a LCDR3 region of mAbC comprising an amino acid sequence as set forth in Table A-9, or a sequence of at least 4, 5, 6, 7, 8, 9 or 10 contiguous amino acids thereof, optionally wherein one or more of these amino acids may be deleted or substituted by a different amino acid.

TABLE A-8

| mAb | CDR definition | HCDR1 SEQ ID | Sequence | HCDR2 SEQ ID | Sequence | HCDR3 SEQ ID | Sequence |
|---|---|---|---|---|---|---|---|
| mAbB | Kabat | 75 | SYWMH | 90 | EINPSNGHTNYNEKFKT | 92 | GVETYDFDDAMDY |
| | Chotia | 88 | VYTFTSY | | PSNG | 93 | VETYDFDDAMD |
| | IMGT | 89 | VYTFTSYW | 91 | INPSNGHT | 94 | ANGVETYDFDDAMDY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAbB | Kabat | 83 | RASQDINNYLN | 95 | FTSRLHS | 96 | QQGDTFPFT |
| | Chotia | 84 | SQDINNY | | YTS | 97 | GDTFPF |
| | IMGT | 85 | QDINNY | | FTS | 96 | QQGDTFPFT |

TABLE A-9

| mAb | CDR definition | HCDR1 SEQ ID | Sequence | HCDR2 SEQ ID | Sequence | HCDR3 SEQ ID | Sequence |
|---|---|---|---|---|---|---|---|
| mAbC | Kabat | 98 | NYEMN | 101 | WINTYTGESTYADDFK | 103 | DDYGRSYGFAY |
|  | Chotia | 99 | GYTFTNY |  | TYTG | 104 | DYGRSYGFA |
|  | IMGT | 100 | GYTFTNYE | 102 | INTYTGES | 105 | VRDDYGRSYGFAY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAbC | Kabat | 106 | RASESVDSYGNSFMH | 109 | LASKLES | 110 | HQNNEDPPWT |
|  | Chotia | 107 | SESVDSYGNSF |  | LAS | 111 | NNEDPPW |
|  | IMGT | 108 | ESVDSYGNSF |  | LAS | 110 | HQNNEDPPWT |

Another exemplary antibody comprises: a HCDR1 region of mAbD comprising an amino acid sequence as set forth in Table A-10, or a sequence of at least 4, 5, 6, 7, 8, 9 or 10 contiguous amino acids thereof, optionally wherein one or more of these amino acids may be substituted by a different amino acid; a HCDR2 region of mAbD comprising an amino acid sequence as set forth in Table A-10 or a sequence of at least 4, 5, 6, 7, 8, 9 or 10 contiguous amino acids thereof, optionally wherein one or more of these amino acids may be substituted by a different amino acid; a HCDR3 region of mAbD comprising an amino acid sequence as set forth in Table A-10, or a sequence of at least 4, 5, 6, 7, 8, 9 or 10 contiguous amino acids thereof, optionally wherein one or more of these amino acids may be substituted by a different amino acid; a LCDR3 region of mAbD comprising an amino acid sequence as set forth in Table A-10, or a sequence of at least 4, 5, 6, 7, 8, 9 or 10 contiguous amino acids thereof, optionally wherein one or more of these amino acids may be deleted or substituted by a different amino acid.

TABLE A-10

| mAb | CDR definition | HCDR1 SEQ ID | Sequence | HCDR2 SEQ ID | Sequence | HCDR3 SEQ ID | Sequence |
|---|---|---|---|---|---|---|---|
| mAbD | Kabat | 112 | DYSMH | 115 | WIITETGEPTYADDFRG | 117 | DFDGY |
|  | Chotia | 113 | GYTFTDY |  | TETG |  | FDG |
|  | IMGT | 114 | GYTFTDYS | 116 | HTETGEP | 118 | ARDFDGY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAbD | Kabat | 119 | RASENIYSYLA | 122 | NAKTLTE | 123 | QHHYGFPWT |
|  | Chotia | 120 | SENIYSY |  | NAK | 124 | HYGFPW |
|  | IMGT | 121 | ENIYSY |  | NAK | 123 | QHHYGFPWT | forth in Table A-10, or a sequence of at least 4, 5, 6, 7, 8, 9 or 10 contiguous amino acids thereof, optionally wherein one or more of these amino acids may be substituted by a different amino acid; a LCDR1 region of mAbD comprising an amino acid sequence as set forth in Table A-10, or a sequence of at least 4, 5, 6, 7, 8, 9 or 10 contiguous amino acids thereof, optionally wherein one or more of these amino acids may be substituted by a different amino acid; a LCDR2 region of mAbD comprising an amino acid sequence as set Another exemplary antibody comprises: a HCDR1 region of mAbE comprising an amino acid sequence as set forth in Table A-11, or a sequence of at least 4, 5, 6, 7, 8, 9 or 10 contiguous amino acids thereof, optionally wherein one or more of these amino acids may be substituted by a different amino acid; a HCDR2 region of mAbE comprising an amino acid sequence as set forth in Table A-11 or a sequence of at least 4, 5, 6, 7, 8, 9 or 10 contiguous amino acids thereof, optionally wherein one or more of these amino acids may be substituted by a different amino acid; a HCDR3 region of mAbE comprising an amino acid sequence as set forth in Table A-11, or a sequence of at least 4, 5, 6, 7, 8, 9 or 10 contiguous amino acids thereof, optionally wherein one or more of these amino acids may be substituted by a different amino acid; a LCDR1 region of mAbE comprising an amino acid sequence as set forth in Table A-11, or a sequence of at least 4, 5, 6, 7, 8, 9 or 10 contiguous amino acids thereof, optionally wherein one or more of these amino acids may be substituted by a different amino acid; a LCDR2 region of mAbE comprising an amino acid sequence as set forth in Table A-11, or a sequence of at least 4, 5, 6, 7, 8, 9 or 10 contiguous amino acids thereof, optionally wherein one or more of these amino acids may be substituted by a different amino acid; a LCDR3 region of mAbE comprising an amino acid sequence as set forth in Table A-11, or a sequence of at least 4, 5, 6, 7, 8, 9 or 10 contiguous amino acids thereof, optionally wherein one or more of these amino acids may be deleted or substituted by a different amino acid.

amino acid; a HCDR2 region of mAbF comprising an amino acid sequence as set forth in Table A-12 or a sequence of at least 4, 5, 6, 7, 8, 9 or 10 contiguous amino acids thereof, optionally wherein one or more of these amino acids may be substituted by a different amino acid; a HCDR3 region of mAbF comprising an amino acid sequence as set forth in Table A-12, or a sequence of at least 4, 5, 6, 7, 8, 9 or 10 contiguous amino acids thereof, optionally wherein one or more of these amino acids may be substituted by a different amino acid; a LCDR1 region of mAbF comprising an amino acid sequence as set forth in Table A-12, or a sequence of at least 4, 5, 6, 7, 8, 9 or 10 contiguous amino acids thereof, optionally wherein one or more of these amino acids may be substituted by a different amino acid; a LCDR2 region of mAbF comprising an amino acid sequence as set forth in Table A-12, or a sequence of at least 4, 5, 6, 7, 8, 9 or 10 contiguous amino acids thereof, optionally wherein one or more of these amino acids may be substituted by a different

TABLE A-11

| mAb | CDR definition | HCDR1 SEQ ID | Sequence | HCDR2 SEQ ID | Sequence | HCDR3 SEQ ID | Sequence |
|---|---|---|---|---|---|---|---|
| mAbE | Kabat | 125 | TFGMH | 128 | YISSGSNAIYYADTVKG | 130 | PGYGAWFAY |
| | Chotia | 126 | GFTFSTF | | SGSN | 131 | GYGAWFA |
| | IMGT | 127 | GFTFSTFG | 129 | ISSGSNAI | 132 | ASPGYGAWFAY |

| mAb | CDR definition | LCDR1 SEQ ID | Sequence | LCDR2 SEQ ID | Sequence | LCDR3 SEQ ID | Sequence |
|---|---|---|---|---|---|---|---|
| mAbE | Kabat | 133 | RASSSVSSAYLH | 136 | STSNLAS | 137 | QQYSAYPYT |
| | Chotia | 134 | SSSVSSAY | | STS | 138 | YSAYPY |
| | IMGT | 135 | SSVSSAY | | STS | 137 | QQYSAYPYT |

Another exemplary antibody comprises: a HCDR1 region of mAbF comprising an amino acid sequence as set forth in Table A-12, or a sequence of at least 4, 5, 6, 7, 8, 9 or 10 contiguous amino acids thereof, optionally wherein one or more of these amino acids may be substituted by a different amino acid; a LCDR3 region of mAbF comprising an amino acid sequence as set forth in Table A-12, or a sequence of at least 4, 5, 6, 7, 8, 9 or 10 contiguous amino acids thereof, optionally wherein one or more of these amino acids may be deleted or substituted by a different amino acid.

TABLE A-12

| mAb | CDR definition | HCDR1 SEQ ID | Sequence | HCDR2 SEQ ID | Sequence | HCDR3 SEQ ID | Sequence |
|---|---|---|---|---|---|---|---|
| mAbF | Kabat | 112 | DYSMH | 139 | VISTYNGNTNYNQKFKG | 141 | RGYYGSSSWFGY |
| | Chotia | 113 | GYTFTDY | | TYNG | 142 | GYYGSSSWFG |
| | IMGT | 114 | GYTFTDYS | 140 | ISTYNGNT | 143 | ARRGYYGSSSWFGY |

TABLE A-12-continued

| mAb | CDR definition | LCDR1 SEQ ID | Sequence | LCDR2 SEQ ID | Sequence | LCDR3 SEQ ID | Sequence |
|---|---|---|---|---|---|---|---|
| mAbF | Kabat | 144 | KASQNVGTDVA | 147 | SASYRYS | 148 | QQYNSFPYT |
|  | Chotia | 145 | SQNVGTD |  | SAS | 149 | YNSFPY |
|  | IMGT | 146 | QNVGTD |  | SAS | 148 | QQYNSFPYT |

In any of the embodiments herein, any of the HCDR1, 2, 3 and LCDR1, 2, 3 sequences can optionally be specified as all (or each, independently) being those of the Kabat numbering system (as indicated in Table A-1 to A-12 for each CDR), those of the Chotia numbering system as indicated in Table A-1 to A-12 for each CDR), those of the IMGT numbering system as indicated in Table A-1 to A-12 for each CDR), or any other suitable numbering system.

In another aspect, any of the CDRs 1, 2 and 3 of the heavy and light chains of mAbA, mAbB, mAbC, mAbD, mAbE, mAbF, mAb1, mAb2, mAb3, mAb4, mAb5 or mAb6 may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In any of the antibodies, e.g., mAbA, mAbB, mAbC, mAbD, mAbE, mAbF, mAb1, mAb2, mAb3, mAb4, mAb5 or mAb6, the specified variable region and CDR sequences may comprise sequence modifications, e.g., a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the properties set forth herein) using the assays described herein.

The sequences of the CDRs, according to IMGT, Kabat and Chothia definitions systems, are summarized in Tables A-1 to A-12. The sequences of the variable regions of the antibodies according to the invention are listed in Table B below. In any embodiment herein, a VL or VH sequence can be specified or numbered so as to further comprise or lack a signal peptide or any part thereof.

In one embodiment, the antibodies are antibody fragments that retain their binding and/or functional properties.

TABLE B

|  | SEQ ID NO: | Amino Acid Sequence |
|---|---|---|
| mAb1 VH | 3 | DVQLQESGPGLVKPSQSLSLTCTVTGYSITGGFAWNWIRQFPGNTLEWMGYIGYGGSTSYNPSLNSRISITRDTSKNHFFLQFNSVTTDDSATYYCARGDYLFAYWGQGTLVTVSA |
| mAb1 VL | 4 | DIVMTQSHKFMSTSVGDRVSITCKASQDVNTAVAWYQQKPGQSPKLLIYSASYRYTGVPDRFTGSGSGTDFTFTISSVQAEDLAVYYCQQHYSTPRTFGGGTKLEIK |
| mAb2 VH | 5 | EVQLQESGPGLVKPSQSLSLTCTVTGYSITGGFAWNWIRQFPGNTLEWMGYIGYGGSTSYNPSLNSRISITRDTSKNHFFLQFNSVTTEDSATYYCARGDYLFAYWGQGTLVTVSA |
| mAb2 VL | 6 | DIVMTQSHKFMSTSVGDRVSITCKASQDVNTAVAWYQQKPGQSPKLLIYSASYRYTGVPDRFTGSGSGTDFTFTISSVQAEDLAVYYCQQHYSTPRTFGGGTKLEIK |
| mAb3 VH | 7 | EVQLLETGPGLVKPSQSLSLTCTVTGYSITGGFAWNWIRQFPGNTLEWMGYIGYGGSTSYNPSLNSRISITRDTSKNHFFLQFNSVTTEDSATYYCARGDYLFAYWGQGTLVTVSA |
| mAb3 VL | 8 | DILMTQSPASLSASVGETVSITCRASGNIHNYLAWYLQRQGKSPQLLVYNAKTLADGVPSRFSGTGSGTQFSLKINSLQPEDFGSYYCQHFWSTPRTFGGGTKLEIK |
| mAb4 VH | 9 | DVQLVESGGDLVKPGGSLKLSCAASGFAFSSYDMSWVRQSPEKRLEWIAHIGSGGGNIYYPDTVKGRFTISRDNAKNTLYLQMRSLKSEDTAMYYCARLIFTTGFYGMDYWGQGTSVTVSS |
| mAb4 VL | 10 | DIQMTQTTSSLSASLGDRVTISCRASQDISSYLNWYQQKPDGTIKLLIYYTSRLHSGVPSRFSGSGSGTDYSLTISNLDQDDIATYFCQQGNALPWTFGGGTKLEIK |

TABLE B-continued

| | SEQ ID NO: | Amino Acid Sequence |
|---|---|---|
| mAb5 VH | 11 | EIQLQQSGPELEKPGASVKISCKASGYSFSDYNMNWVKQSNGKSLEWIGNIDPYYGATSYNQRFKGKATLTVDKSSSTAYMQLKSLTSEDSAVYYCARGDSLFAYWGHGTLVTVSA |
| mAb5 VL | 12 | DIVMTQSQEFMSTSLGDRVSVTCKASQNVGTNVAWYQQKPGQSPKALLYSASSRYSGVPDRFTGSGSGTDFTLTISNVQSEDLAEYFCQQYITYPYTFGGGTKLEIK |
| mAb6 VH | 13 | EIQLQQSGPELEKPGASVKISCKASGYSFSDYNMNWVKQSNGKSLEWIGNIDPYYGATSYNQRFKGKATLTVDKSSSTAYMQLKSLTSEDSAVYYCARGDSLFAYWGQGTLVTVSA |
| mAb6 VL | 14 | DIVMTQSQEFMSTSLGDRVSVTCKASQNVGTNVAWYQQKPGQSPKALLYSASSRYSGVPDRFTGSGSGTDFTLTINNMQSEDLAEYFCQQYITYPYTFGGGTKLEIK |
| mAbA VH | 15 | QVQLQQPGAELVKPGSPVKLSCKASYFTFTSYWMHWVRQRPGQGLEWIGEINPSNGHTNYNEKFESKATLTVDRSSSTAYMQLSSLTSEDSAVFYCANGVESYDFDDALDYWGQGTSVTVSS |
| mAbA VL | 16 | DIQMTQTTSSLSASLGDRVTISCRASQDINNYLNWYQQKPDGTIKLLIYYTSRLHSGVPSRFSGSGSGTDYSLTINNLEQEDIATYFCQQGNTLPFTFGGGTKLEIK |
| mAbB VH | 17 | QVQLQQPGAELVKPGASVKLSCKASVYTFTSYWMHWVRQRPGQGLEWIGEINPSNGHTNYNEKFKTKAKLTVDKSSSTAYMQLSSLTSEDSAVYFCANGVETYDFDDAMDYWGQGTSVTVSS |
| mAbB VL | 18 | DIQMTQTTSSLSASLGDRVTISCRASQDINNYLNWYQQKPDGTVKLLIYFTSRLHSGVPSRFSGSGSGTDYSLTISNLEQEDIATYFCQQGDTFPFTFGGGTKLEIK |
| mAbC VH | 19 | QIQLVQSGPELKKPGETVKISCKASGYTFTNYEMNWVKEAPGKGLKWMGWINTYTGESTYADDFKGRFAFSLETSASTVYLQINNLKDEDVATYFCVRDDYGRSYGFAYWGQGTLVTVSA |
| mAbC VL | 20 | NIVLTQSPASLTVSLGQRANISCRASESVDSYGNSFMHWYQQKPGQPPKLLIYLASKLESGVPARFSGSGSRTDFTLTIDPVETDDAATYYCHQNNEDPPWTFGGGTKLEIK |
| mAbD VH | 21 | QIQLVQSGPELKKPGETVKISCKASGYTFTDYSMHWVKQAPGKGLKWMGWIITETGEPTYADDFRGRFAFSLETSANTAYLQINNLKNEDTATYFCARDFDGYWGQGTTLTVSS |
| mAbD VL | 22 | DILMTQSPASLSASVGETVTITCRASENIYSYLAWYQQKRGKSPQFLVYNAKTLTEGVPSRFRGSGSGTQFSLKINSLQPEDFGTYYCQHHYGFPWTFGGGTKLEIK |
| mAbE VH | 23 | DVQLVESGGGLVQPGGSRKLSCAASGFTFSTFGMHWVRQAPEKGLEWVAYISSGSNAIYYADTVKGRFTISRDNPKNTLFLQMTSLRSEDTAMYYCASPGYGAWFAYWGQGTLVTVSA |
| mAbE VL | 24 | ENVLTQSPAIMSASPGEKVTMTCRASSSVSSAYLHWYQQKSGASPKLWIYSTSNLASGVPARFSGSGSGTSYSLTISSVEAEDAATYYCQQYSAYPYTFGGGTKLEIK |
| mAbF VH | 25 | QVQLQQSGPEVVRPGVSVKISCKGSGYTFTDYSMHWVKQSHAKSLEWIGVISTYNGNTNYNQKFKGKATMTVDKSSSTAYMELARLTSEDSAIYYCARRGYYGSSSWFGYWGQGTLVTVSA |
| mAbF VL | 26 | DIVMTQSQKFMSTSVGDRVSVTCKASQNVGTDVAWYQQKPGQSPEALIYSASYRYSGVPDRFTGSGSGADFTLTISNVQSEDLAEYFCQQYNSFPYTFGGGTKLEIK |

NKG2A Inhibition

Neutralization of the inhibitory activity of human NKG2A polypeptide can be achieved by inhibition the HLA-E-mediated activation of NKG2A in NK and/or T cells. Examples of agents that neutralizes the inhibitory activity of human NKG2A polypeptide includes antibodies that bind HLA-E and that inhibit the interaction between NKG2A and HLA-E. Alternatively, antibodies may bind an extra-cellular portion of human CD94/NKG2A receptor and reduce the inhibitory activity of human CD94/NKG2A receptor expressed on the surface of a CD94/NKG2A positive lymphocyte. In one embodiment the NKG2A-binding agent competes with HLA-E in binding to CD94/NKG2A, i.e. the agent blocks the interaction between CD94/NKG2A and its ligand HLA-E. In another embodiment the agent does not compete with HLA-E in binding to CD94/NKG2A; i.e. the agent is capable of binding CD94/NKG2A simultaneously with HLA-E. Such an antibody may bind a combined epitope on CD94 and NKG2A or and epitope on NKG2A alone.

In one aspect the anti-NKG2A agent is an antibody selected from a fully human antibody, a humanized antibody, and a chimeric antibody. In one aspect, the agent comprises a constant domain derived from a human IgG1, IgG2, IgG3 or IgG4 antibody. In one aspect, the agent is a fragment of an antibody selected from IgA, an IgD, an IgG, an IgE and an IgM antibody. In one aspect, the agent is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment. In one aspect, the agent is a synthetic or semisynthetic antibody-derived molecule selected from a scFV, a dsFV, a minibody, a diabody, a triabody, a kappa body, an IgNAR; and a multispecific antibody.

Optionally, the anti-NKG2A antibodies do not demonstrate substantial specific binding to human Fcγ receptors, e.g. CD16. Such antibodies may comprise constant regions of various heavy chains that are known to have no or low binding to human Fc receptors. One such example is a human IgG4 constant region. In one embodiment, the IgG4 antibody comprises a modification to prevent the formation of half antibodies (fab arm exchange) in vivo, e.g., the antibody comprises an IgG4 heavy chain comprising a serine to proline mutation in residue 241, corresponding to position 228 according to the EU-index (Kabat et al., "Sequences of proteins of immunological interest", 5th ed., NIH, Bethesda, M L, 1991). Such modified IgG4 antibodies will remain intact in vivo and maintain a bivalent (high affinity) binding to NKG2A, as opposed to native IgG4 that will undergo fab arm exchange in vivo such that they bind to NKG2A in monovalent manner which can alter binding affinity. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any human antibody type (e.g. IgG1, IgG2, IgG3 or IgG4) can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The present invention thus concerns antibodies or other agents binding to NKG2A. In one aspect, the antibody binds to NKG2A with a KD at least 100-fold lower than to human NKG2C and/or NKG2E.

In one aspect of the invention, the agent reduces CD94/NKG2A-mediated inhibition of a CD94/NKG2A-expressing lymphocyte by interfering with CD94/NKG2A signalling by, e.g., interfering with the binding of HLA-E by NKG2A, preventing or inducing conformational changes in the CD94/NKG2A receptor, and/or affecting dimerization and/or clustering of the CD94/NKG2A receptor.

In one aspect, the agent binds to an extracellular portion of NKG2A with a KD at least 100 fold lower than to NKG2C. In a further preferred aspect, the agent binds to an extracellular portion of NKG2A with a KD at least 150, 200, 300, 400, or 10,000 fold lower than to NKG2C. In another aspect of the invention, the agent binds to an extracellular portion of NKG2A with a KD at least 100 fold lower than to NKG2C, NKG2E and/or NKG2H molecules. In a further preferred aspect, the agent binds to an extracellular portion of NKG2A with a KD at least 150, 200, 300, 400, or 10,000 fold lower than to NKG2C, NKG2C and/or NKG2H molecules. This can be measured, for instance, in BiaCore experiments, in which the capacity of agents to bind the extracellular portion of immobilized CD94/NKG2A (e.g. purified from CD94/NKG2 expressing cells, or produced in a bio-system) is measured and compared to the binding of agents to similarly produced CD94/NKG2C and/or other CD94/NKG2 variants in the same assay. Alternatively, the binding of agents to cells that either naturally express, or over-express (e.g. after transient or stable transfection), CD94/NKG2A can be measured and compared to binding of cells expressing CD94/NKG2C and/or other CD94/NKG2 variants. Anti-NKG2A antibodies may optionally bind NKG2B, which is an NKG2A splice variant forming an inhibitory receptor together with CD94. In one embodiment, affinity can be measured using the methods disclosed in U.S. Pat. No. 8,206,709, for example by assessing binding to covalently immobilized NKG2A-CD94-Fc fusion protein by Biacore as shown in Example 8 of U.S. Pat. No. 8,206,709, the disclosure of which is incorporate herein by reference.

The anti-NKG2A antibody can be a humanized antibody, for example comprising a VH human acceptor framework from a human acceptor sequence selected from, e.g., VH1_18, VH5_a, VH5_51, VH1_f, and VH1_46, and a JH6 J-segment, or other human germline VH framework sequences known in the art. The VL region human acceptor sequence may be, e.g., VKI_O2/JK4.

In one embodiment, the antibody is a humanized antibody based on antibody Z270. Different humanized Z270 VH chains are shown in SEQ ID NOS: 171-175 (variable region domain residues underlined). HumZ270VH6 (SEQ ID NO: 171) is based on VH5_51; HumZ270VH1 (SEQ ID NO: 172) is based on VH1_18; humZ270VH5 (SEQ ID NO: 173) is based on VH5_a; humZ270VH7 (SEQ ID NO: 174) is based on VH1_f; and humZ270VH8 (SEQ ID NO: 175) is based on VH1_46; all with a JH6 J-segment. Each of these antibodies retains high affinity binding to NKG2A, with low likelihood of a host immune response against the antibody as the 6 C-terminal amino acid residues of the Kabat CDR-H2 of each of the humanized constructs are identical to the human acceptor framework. Using the alignment program VectorNTI, the following sequence identities between humZ270VH1 and humZ270VH5, -6, -7, and -8 were obtained: 78.2% (VH1 vs. VH5), 79.0% (VH1 vs. VH6), 88.7% (VH1 vs. VH7), and 96.0% (VH1 vs. VH8).

In one aspect, the agent comprises (i) a heavy chain variable region of any of SEQ ID NOS: 177-181, or an amino acid sequence at least 50%, 60%, 70%, 80%, 90%, 95%, 98% or 99% identical thereto, and (ii) a light chain variable region of SEQ ID NO: 182, or an amino acid sequence at least 50%, 60%, 70%, 80%, 90%, 95%, 98% or 99% identical thereto. In one aspect, the agent comprises (i) a heavy chain comprising the amino acid sequence of any of SEQ ID NOS: 171-175, or an amino acid sequence at least 50%, 60%, 70%, 80%, 90%, 95%, 98% or 99% identical thereto, and (ii) a light chain comprising the amino acid sequence of SEQ ID NO: 176, or an amino acid sequence at least 50%, 60%, 70%, 80%, 90%, 95%, 98% or 99% identical thereto. The antibody having the heavy chain of any of SEQ ID NOS: 171-175 and a light chain of SEQ ID NO: 176 neutralizes the inhibitory activity of NKG2A, but does not substantially bind the activating receptors NKG2C, NKGE or NKG2H. This antibody furthermore competes with HLA-E for binding to NKG2A on the surface of a cell. In one aspect, the agent comprises HCDR1, HCDR2 and/or HCDR3 sequences derived from the heavy chain having the amino acid sequence of any of SEQ ID NO: 171-175. In one aspect of the invention, the agent comprises LCDR1, LCDR2 and/or LCDR3 sequences derived from the light chain having the amino acid sequence of SEQ ID NO: 176.

```
Heavy Chains
VH6:
                                      (SEQ ID NO: 171)
EVQLVQSGAEVKKPGESLKISCKGSGYSFTSYWMNWVRQMPGKGLEWMG

RIDPYDSETHYSPSFQGQVTISADKSISTAYLQWSSLKASDTAMYYCAR

GGYDFDVGTLYWFFDVWGQGTTVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHY

TQKSLSLSLGK
```

-continued

VH1:
(SEQ ID NO: 172)
QVQLVQSGAEVKKPGASVKVSCKASGYTFTSYWMNWVRQAPGQGLEWMG

RIDPYDSETHYAQKLQGRVTMTTDTSTSTAYMELRSLRSDDTAVYYCAR

GGYDFDVGTLYWFFDVWGQGTTVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSV

FLFPPKPKD TLMISRTPEVTCVVVDVSQEDPEVQFNWYVDGVEVHNAK

TKPREEQFNSTYRVVSVLTVLHQDWLNGKEYKCKVSNKGLPSSIEKTIS

KAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNH

YTQKSLSLSLGK

VH5:
(SEQ ID NO: 173)
EVQLVQSGAEVKKPGESLRISCKGSGYSFTSYWMNWVRQMPGKGLEWMG

RIDPYDSETHYSPSFQGHVTISADKSISTAYLQWSSLKASDTAMYYCAR

GGYDFDVGTLYWFFDVWGQGTTVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHY

TQKSLSLSLGK

VH7:
(SEQ ID NO: 174)
EVQLVQSGAEVKKPGATVKISCKVSGYTFTSYWMNWVQQAPGKGLEWMG

RIDPYDSETHYAEKFQGRVTITADTSTDTAYMELSSLRSEDTAVYYCAT

GGYDFDVGTLYWFFDVWGQGTTVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHY

TQKSLSLSLGK

VH8:
(SEQ ID NO: 175)
QVQLVQSGAEVKKPGASVKVSCKASGYTFTSYWMNWVRQAPGQGLEWMG

RIDPYDSETHYAQKFQGRVTMTRDTSTSTVYMELSSLRSEDTAVYYCAR

GGYDFDVGTLYWFFDVWGQGTTVTVSSASTKGPSVFPLAPCSRSTSEST

AALGCLVKDYFPEPVTVSWNSGALTSGVHTFPAVLQSSGLYSLSSVVTV

PSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISK

AKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHY

TQKSLSLSLGK

Light chain
(SEQ ID NO: 176)
DIQMTQSPSSLSASVGDRVTITCRASENIYSYLAWYQQKPGKAPKLLIY

NAKTLAEGVPSRFSGSGSGTDFTLTISSLQPEDFATYYCQHHYGTPRTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain variable regions
VH6:
(SEQ ID NO: 177)
EVQLVQSGAEVKKPGESLKISCKGSGYSFTSYWMNWVRQMPGKGLEWMG

RIDPYDSETHYSPSFQGQVTISADKSISTAYLQWSSLKASDTAMYYCAR

GGYDFDVGTLYWFFDVWGQGTTVTVS

VH1:
(SEQ ID NO: 178)
QVQLVQSGAEVKKPGASVKVSCKASGYTFTSYWMNWVRQAPGQGLEWMG

RIDPYDSETHYAQKLQGRVTMTTDTSTSTAYMELRSLRSDDTAVYYCAR

GGYDFDVGTLYWFFDVWGQGTTVTVS

VH5:
(SEQ ID NO: 179)
EVQLVQSGAEVKKPGESLRISCKGSGYSFTSYWMNWVRQMPGKGLEWMG

RIDPYDSETHYSPSFQGHVTISADKSISTAYLQWSSLKASDTAMYYCAR

GGYDFDVGTLYWFFDVWGQGTTVTVS

VH7:
(SEQ ID NO: 180)
EVQLVQSGAEVKKPGATVKISCKVSGYTFTSYWMNWVQQAPGKGLEWMG

RIDPYDSETHYAEKFQGRVTITADTSTDTAYMELSSLRSEDTAVYYCAT

GGYDFDVGTLYWFFDVWGQGTTVTVS

VH8:
(SEQ ID NO: 181)
QVQLVQSGAEVKKPGASVKVSCKASGYTFTSYWMNWVRQAPGQGLEWMG

RIDPYDSETHYAQKFQGRVTMTRDTSTSTVYMELSSLRSEDTAVYYCAR

GGYDFDVGTLYWFFDVWGQGTTVTVS

Light chain variable region
(SEQ ID NO: 182)
DIQMTQSPSSLSASVGDRVTITCRASENIYSYLAWYQQKPGKAPKLLIY

NAKTLAEGVPSRFSGSGSGTDFTLTISSLQPEDFATYYCQHHYGTPRTF

GGGTKVEIK

In one aspect, the anti-NKG2A antibody is an antibody comprising a CDR-H1 corresponding to residues 31-35 of SEQ ID NOS: 171-175, a CDR-H2 corresponding to residues 50-60 (optionally 50-66 when including amino acids of human origin) of SEQ ID NOS: 171-175, and a CDR-H3 corresponding to residues 99-114 (95-102 according to Kabat) of SEQ ID NOS: 171-175. In one embodiment, the CDR-H2 corresponding to residues 50-66 of SEQ ID NOS: 171-175. Optionally, a CDR may comprise one, two, three, four, or more amino acid substitutions.

In one aspect, the anti-NKG2A antibody is an antibody comprising a CDR-L1 corresponding to residues 24-34 of SEQ ID NO: 176, a CDR-L2 corresponding to residues 50-56 of SEQ ID NO: 176, and an CDR-L3 corresponding to residues 89-97 of SEQ ID NO: 176. Optionally, a CDR may comprise one, two, three, four, or more amino acid substitutions.

In one aspect, the anti-NKG2A antibody is an antibody comprising a CDR-H1 corresponding to residues 31-35 of SEQ ID NOS: 171-175, a CDR-H2 corresponding to residues 50-60 (optionally 50-66) of SEQ ID NOS: 171-175, and a CDR-H3 corresponding to residues 99-114 (95-102 according to Kabat) of SEQ ID NOS: 171-175, a CDR-L1 corresponding to residues 24-34 of SEQ ID NO: 176, a CDR-L2 corresponding to residues 50-56 of SEQ ID NO: 176, and an CDR-L3 corresponding to residues 89-97 of SEQ ID NO: 176.

In one aspect, the agent comprises HCDR1, HCDR2 and/or HCDR3 sequences derived from the VH having the amino acid sequence of SEQ ID NO: 183. In one aspect of the invention, the agent comprises LCDR1, LCDR2 and/or LCDR3 sequences derived from the VL having the amino acid sequence of SEQ ID NO: 184. In one aspect, the agent comprises HCDR1, HCDR2 and/or HCDR3 sequences derived from the VH having the amino acid sequence of SEQ ID NO: 183, and LCDR1, LCDR2 and/or LCDR3 sequences derived from the VL having the amino acid sequence of SEQ ID NO: 184. The antibody having the heavy chain of SEQ ID NO: 183 and a light chain of SEQ ID NO: 184 neutralizes the inhibitory activity of NKG2A, and also binds the activating receptors NKG2C, NKG2E or NKG2H. The antibody does not compete with HLA-E for binding to NKG2A on the surface of a cell (i.e. it is a non-competitive antagonist of NKG2A).

```
                                            (SEQ ID NO: 183)
EVQLVESGGGLVKPGGSLKLSCAASGFTFSSYAMSWVRQSPEKRLEWVA

EISSGGSYTYYPDTVTGRFTISRDNAKNTLYLEISSLRSEDTAMYYCTR

HGDYPRFFDVWGAGTTVTVSS.

(SEQ ID NO: 184)
QIVLTQSPALMSASPGEKVTMTCSASSSVSYIYWYQQKPRSSPKPWIYL

TSNLASGVPARFSGSGSGTSYSLTISSMEAEDAATYYCQQWSGNPYTFG

GGTKLEIK.
```

In one aspect, the agent comprises amino acid residues 31-35, 50-60, 62, 64, 66, and 99-108 of the variable-heavy ($V_H$) domain (SEQ ID NO: 183) and amino acid residues 24-33, 49-55, and 88-96 of the variable-light ($V_L$) domain (SEQ ID NO: 184), optionally with one, two, three, four, or more amino acid substitutions.

In one aspect, the agent is a fully human antibody which has been raised against the CD94/NKG2A epitope to which any of the aforementioned antibodies bind.

In one aspect, the agent is the anti-NKG2A antibody having the heavy chain variable region of SEQ ID NO: 178 and the light chain variable region of SEQ ID NO: 182, or an antibody having the heavy chain of SEQ ID NO: 172 and the light chain of SEQ ID NO: 176. For example, the agent may be monalizumab (Innate Pharma SA, Medimmune and AstraZeneca).

It will be appreciated that, while the aforementioned antibodies can be used, other antibodies can recognize and be raised against any part of the NKG2A polypeptide so long as the antibody causes the neutralization of the inhibitory activity of NKG2A. For example, any fragment of NKG2A, preferably but not exclusively human NKG2A, or any combination of NKG2A fragments, can be used as immunogens to raise antibodies, and the antibodies can recognize epitopes at any location within the NKG2A polypeptide, so long as they can do so on NKG2A expressing NK cells as described herein. Optionally, the epitope is the epitope specifically recognized by antibody having the heavy chain of any of SEQ ID NOS: 171-175 and the light chain of SEQ ID NO: 176.

In one aspect, the agent competes with humZ270 antibody disclosed in U.S. Pat. No. 8,206,709 (the disclosure of which is incorporated herein by reference) in binding to the extracellular portion of human CD94/NKG2A receptor. Competitive binding can be measured, for instance, in BiaCore experiments, in which the capacity of agents is measured, for binding the extracellular portion of immobilized CD94/NKG2A receptor (e.g. purified from CD94/NKG2 expressing cells, or produced in a bio-system) saturated with humZ270. Alternatively, the binding of agents to cells is measured that either naturally express, or over-express (e.g. after transient or stable transfection), CD94/NKG2A receptor, and which have been pre-incubated with saturating doses of Z270. In one embodiment, competitive binding can be measured using the methods disclosed in U.S. Pat. No. 8,206,709, for example by assessing binding to Ba/F3-CD94-NKG2A cells by flow cytometry as shown in Example 15 of U.S. Pat. No. 8,206,709, the disclosure of which is incorporate herein by reference.

Antibody Formulations

An antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g., freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof.

Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: *The Science and Practice of Pharmacy*, 19$^{th}$ edition, 1995.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions according to the invention may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies of this invention. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Also provided are kits which include a pharmaceutical composition containing an anti-NKG2A antibody, and an anti-Siglec-9 (optionally further anti-Siglec-7) antibody, and a pharmaceutically-acceptable carrier, in a therapeutically effective amount adapted for use in the preceding methods. The kits optionally also can include instructions, e.g., comprising administration schedules, to allow a practitioner (e.g., a physician, nurse, or patient) to administer the composition contained therein to administer the composition to a patient having cancer (e.g., a solid tumor). The kit also can include a syringe.

Optionally, the kits include multiple packages of the single-dose pharmaceutical compositions each containing an effective amount of the anti-NKG2A and/or anti-Siglec-9 antibody for a single administration in accordance with the methods provided above. Instruments or devices necessary for administering the pharmaceutical composition(s) also may be included in the kits. For instance, a kit may provide one or more pre-filled syringes containing an amount of the anti-NKG2A, anti-Siglec-9 antibody.

In one embodiment, the present invention provides a kit for treating a cancer in a human patient, the kit comprising:

(a) a dose of an anti-Siglec-9 antibody comprising the CDR1, CDR2 and CDR3 domains of a heavy chain of any of mAbA, mAbB, mAbC, mAbD, mAbE, mAbF, mAb1, mAb2, mAb3, mAb4, mAb5 or mAb6, and the CDR1, CDR2 and CDR3 domains of a light chain of the respective mAbA, mAbB, mAbC, mAbD, mAbE, mAbF, mAb1, mAb2, mAb3, mAb4, mAb5 or mAb6;

(b) a dose of an NKG2A antibody; and (c) optionally, instructions for using the anti-NKG2A antibody and anti-Siglec-9 antibody in any of the methods described herein.

In one embodiment, the present invention provides a kit for treating a cancer in a human patient, the kit comprising:

(a) a dose of an anti-NKG2A antibody comprising the CDR1, CDR2 and CDR3 domains of a heavy chain having the sequence set forth herein, and the CDR1, CDR2 and CDR3 domains of a light chain having the sequence set forth herein;

(b) a dose of an Siglec-9 antibody; and (c) optionally, instructions for using the anti-NKG2A antibody and anti-Siglec-9 antibody in any of the methods described herein.

Diagnosis and Treatment of Malignancies

Methods of treating an individual, notably a human patient, via the inhibition of Siglec-9 and NKG2A (e.g. using an anti-Siglec antibody and an anti-NKG2A antibody as described herein) are also provided for. In one embodiment, the invention provides for the use of an antibody or antibody fragment as described herein in the preparation of a pharmaceutical composition for administration to a human patient. Typically, the patient suffers from, or is at risk for, cancer or infections disease, e.g., a bacterial or a viral disease.

For example, in one aspect, the invention provides a method of potentiating the activity of Siglec-7 and/or -9-restricted immune cell in an individual (e.g. having a cancer or an infectious disease), in a patient in need thereof, comprising the step of administering to said individual (i) a neutralizing anti-Siglec-7 and/or -9 antibody and (ii) a NKG2A-neutralizing antibody. The antibody can be for example a human or humanized anti-Siglec-7 and/or -9 antibody, which antibody reduces or prevents sialic acid-mediated activation of the Siglec-7 and/or -9 receptors. In one embodiment, the method directed at increasing the activity of such lymphocytes in patients having a disease in which increased lymphocyte (e.g., NK and/or CD8+ T cell) activity is beneficial, which involves, affects or is caused by cells susceptible to lysis by NK or CD8+ T cells, or which is caused or characterized by insufficient NK or CD8+ T cell activity, such as a cancer or an infectious disease. For example, in one aspect, the invention provides a method of enhancing the activity (e.g. cellular activation, anti-tumor immunity or activity, cytokine production, proliferation) of Siglec-7 and/or -9-restricted immune cells, for example an NK cell (e.g. CD56$^{bright}$ cell), a T cell, a monocyte, a dendritic cell, a macrophage (e.g., an immunosuppressive or M2 macrophage), in a patient in need thereof, comprising the step of administering a neutralizing anti-Siglec-7 and/or -9 antibody of the disclosure to said patient.

In one embodiment, the antibodies of the disclosure are used in the treatment of a tumor characterized by expression of the ST3GAL6 and/or ST3GAL1 enzyme (or, e.g., a high level of ST3GAL6 and/or ST3GAL1 enzyme activity), optionally overexpression of the ST3GAL6 enzyme (compared to expression in, e.g., healthy tissue, in healthy individuals).

More specifically, the methods and compositions herein are utilized for the treatment of a variety of cancers and other proliferative diseases. Because these methods operate by enhancing an immune response via blockade of inhibitory receptors on lymphocytes, they are applicable to a very broad range of cancers. In one embodiment, a human patient treated with an anti-Siglec antibody of the disclosure has liver cancer, bone cancer, pancreatic cancer, skin cancer, cancer of the head or neck (e.g. Head and Neck Squamous Cell Carcinoma), breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present invention is also applicable to treatment of metastatic cancers. Patients can be tested or selected for one or more of the above described clinical attributes prior to, during or after treatment.

The anti-Siglec antibody based treatment can also be used to treat or prevent infectious diseases, including preferably any infections caused by infection by viruses, bacteria, protozoa, molds or fungi. Such viral infectious organisms include, but are not limited to, hepatitis type A, hepatitis type B, hepatitis type C, influenza, varicella, adenovirus, herpes simplex type I (HSV-1), herpes simplex type 2 (HSV-2), rinderpest, rhinovirus, echovirus, rotavirus, respiratory syncytial virus, papilloma virus, papilloma virus, cytomegalovirus, echinovirus, arbovirus, huntavirus, coxsackie virus, mumps virus, measles virus, rubella virus, polio virus and human immunodeficiency virus type I or type 2 (HIV-1, HIV-2). Bacteria constitute another preferred class of infectious organisms including but are not limited to the following: *Staphylococcus; Streptococcus*, including *S. pyogenes*; Enterococcl; *Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponerna; Camplyobacter, Pseudomonas* including *P. aeruginosa; Legionella; Neisseria* including *N. gonorrhoeae* and *N. meningitides; Flavobacterium* including *F. meningosepticum* and *F. odoraturn; Brucella; Bordetella* including *B. pertussis* and *B. bronchiseptica; Escherichia* including *E. coli, Klebsiella; Enterobacter, Serratia* including *S. marcescens* and *S. liquefaciens; Edwardsiella; Proteus* including *P. mirabilis* and *P. vulgaris; Streptobacillus*; Rickettsiaceae including *R. fickettsfi, Chlamydia* including *C. psittaci* and *C. trachomatis; Mycobacterium* including *M. tuberculosis, M. intracellulare, M. folluiturn, M. laprae, M. avium, M. bovis, M. africanum, M. kansasii, M. intracellulare*, and *M. lepraernurium*; and *Nocardia*. Protozoa may include but are not limited to, *leishmania*, kokzidioa, and *trypanosoma*. Parasites include but are not limited to, *chlamydia* and *rickettsia*.

The antibody compositions may be used to treat individuals regardless of the residue present at position 100 in Siglec-9 (reference to SEQ ID NO: 2) or position 104 in Siglec-7 (reference to SEQ ID NO: 1) in the alleles expressed by the individuals. Siglec-9 bearing a lysine at position 100 (e.g. SEQ ID NO: 2) is representative of about 49% of the population) while Siglec-9 bearing a glutamic acid at position 100 (e.g. SEQ ID NO: 160) is representative of about 36% of the population. In one embodiment, the antibody compositions are used to treat individuals having a lysine at position 100 in Siglec-9 (reference to SEQ ID NO: 2) and individuals having a glutamic acid at position 100 in Siglec-9. In one embodiment, the same administration regimen is used to treat individuals whose cells (e.g. NK cells, neutrophils, etc.) express a lysine at position 100 in Siglec-9 (reference to SEQ ID NO: 2) and individuals whose cells express a glutamic acid at position 100 in Siglec-9. In one embodiment, the administration regimen comprises the same mode of administration, the same dosage and the same frequency of administration irrespective of the particular allele of Siglec-7 and/or -9 expressed in an individual.

The antibody compositions may be used in combined treatments with one or more other further therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents.

In the treatment methods, the anti-Siglec-9 agent and the NKG2A-neutralizing agent can be administered separately, together or sequentially, or in a cocktail. In some embodiments, the antigen-binding compound is administered prior to the administration of the NKG2A-neutralizing agent. For example, the anti-Siglec-9 agent can be administered approximately 0 to 30 days prior to the administration of the NKG2A-neutralizing agent. In some embodiments, an anti-Siglec-9 agent is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the NKG2A-neutralizing agent. In some embodiments, an anti-Siglec-9 agent is administered concurrently with the administration of the therapeutic agents. In some embodiments, an anti- Siglec-9 agent is administered after the administration of the NKG2A-neutralizing agent. For example, an anti-Siglec-9 agent can be administered approximately 0 to 30 days after the administration of the NKG2A-neutralizing agent. In some embodiments, an anti-Siglec-9 agent is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the NKG2A-neutralizing agent.

In other aspects, methods are provided for identifying Siglec-7+ and/or Siglec-9+ NK cells and/or T cells, e.g., CD8 T cells, CD56$^{bright}$ NK cells, CD56$^{dim}$ NK cells, optionally in each case wherein the cells are NKG2A-expressing cells. Assessing the co-expression of Siglec-7 and/or Siglec-9 on NK cells and/or T cells can be used in diagnostic or prognostic methods. For example, a biological sample can be obtained from an individual (e.g., from a blood sample, from cancer or cancer-adjacent tissue obtained from a cancer patient) and analyzed for the presence of Siglec-7 and/or Siglec-9+ NK and/or T cells. The expression of Siglec-9 on such cells can, for example, be used to identify individuals having NK and/or T cells, for example tumor infiltrating NK and/or T cells, optionally NKG2A-expressing cells, which are inhibited by Siglec-9 polypeptides. The expression of both Siglec-7 and Siglec-9 on such cells can, for example, be used to identify individuals having NK and/or T cells, for example tumor infiltrating NK and/or T cells which are inhibited by both Siglec polypeptides and NKG2A polypeptides. The method can, for example, be useful as a prognostic for response to treatment with an agent that neutralizes Siglec-9 and an agent that neutralizes NKG2A. Expression of Siglec-9 (and optionally further NKG2A) on such cells can indicate an individual suitable for treatment with an antibody of the disclosure.

In certain aspects provided is a method of potentiating and/or modulating the activity of lymphocytes (e.g., NK cells, CD8+ T cells) activity in a subject in need thereof, for example a method of potentiating NK cell activity by modulating CD56$^{dim}$ NK cells (the major cytotoxic subset) and optionally further CD56$^{bright}$ NK cells (the majority of NK cells in lymph nodes and tonsils and, upon activation, primarily respond with cytokine production), which method comprises administering to the subject an effective amount of an anti-Siglec-9 agent and NKG2A-neutralizing agent as described herein. In one embodiment, the subject is a patient suffering from cancer. For example, the patient may be suffering from a hematopoietic cancer, e.g., acute myeloid leukaemia, chronic myeloid leukaemia, multiple myeloma, or non-Hodgkin's lymphoma. Alternatively, the patient may be suffering from a solid tumor, e.g., colorectal cancer, head and neck cancer, renal cancer, ovarian cancer, lung cancer, breast cancer or malignant melanoma. In another embodiment, the subject is a patient suffering from an infectious disease.

In certain optional aspects, an individual can be identified for treatment with a NKG2A-neutralizing agent and Siglec-9− (optionally further Siglec-7-) neutralizing agent by assessing, in a tumor sample from the individual, the presence (e.g. tumor tissue and/or tumor adjacent tissue) of HLA-E, optionally further assessing the presence of a ligand of Siglec-9 (and optionally further Siglec-7).

In certain optional aspects, an individual can be identified for treatment with a NKG2A-neutralizing agent and Siglec-9− (optionally further Siglec-7-) neutralizing agent by assessing in a tumor sample from the individual (e.g. tumor tissue and/or tumor adjacent tissue), the presence of Siglec-9 (e.g. on myeloid-derived dendritic cells and/or on neutrophils in the tumor environment). In certain optional aspects, an individual can be identified for treatment with a NKG2A-neutralizing agent and a Siglec-7- and Siglec-9− neutralizing agent by assessing in a tumor sample from the individual (e.g. tumor tissue and/or tumor adjacent tissue), the presence of Siglec-7 (e.g. on myeloid-derived dendritic cells and/or on neutrophils, e.g. in the tumor environment).

In certain optional aspects, an individual can be identified for treatment with a NKG2A-neutralizing agent and Siglec-9− (optionally further Siglec-7-) neutralizing agent by assessing in a tumor sample from the individual (e.g. tumor tissue and/or tumor adjacent tissue), the presence of HLA-E (e.g. on tumor cells) and optionally further Siglec-9 and/or Siglec-7 (e.g. on myeloid-derived dendritic cells and/or on neutrophils, e.g. in the tumor environment).

In one embodiment of any of the therapeutic uses or cancer treatment or prevention methods herein, the treatment or prevention of a cancer in an individual comprises:

a) determining the Siglec-7 and/or Siglec-9 polypeptide status of immune cells (e.g. myeloid-derived dendritic cells, neutrophils, NK cells, T cells) in tumor tissue or tumor adjacent tissue from the individual having a cancer, and b) upon a determination that Siglec-7 and/or Siglec-9 polypeptides are expressed by (e.g. on the surface of) cells in tumor tissue or tumor adjacent tissue from the individual, administering to the individual an agent that neutralizes the inhibitory activity of a human NKG2A polypeptide and an agent that inhibits a human Siglec-9 (and optionally further Siglec-7) polypeptide.

In one embodiment, a determination that a biological sample (e.g., a sample comprising tumor cells, tumor tissue and/or tumor adjacent tissue) prominently expresses HLA-E polypeptide (as assessed by assessing HLA-E nucleic acids or polypeptides) indicates that the individual has a cancer that can be treated with an agent that inhibits NKG2A in combination with an agent that inhibits a human Siglec-9 (and optionally further Siglec-7) polypeptide.

In one embodiment of any of the therapeutic uses or cancer treatment or prevention methods herein, the treatment or prevention of a cancer in an individual comprises:

a) determining the HLA-E polypeptide status of malignant cells within the individual having a cancer, and b) upon a determination that HLA-E polypeptides are expressed by (e.g. on the surface of) malignant cells (e.g. tumor cells), administering to the individual an agent that neutralizes the inhibitory activity of a human NKG2A polypeptide and an agent that inhibits a human Siglec-9 (and optionally further Siglec-7) polypeptide.

In one embodiment of any of the methods, determining the HLA-E polypeptide status or determining the level of expression in step (a) comprises determining the level of expression of a HLA-E nucleic acid or polypeptide of malignant cells in a biological sample and comparing the level to a reference level (e.g. a value, weak or strong cell surface staining, etc.). The reference level may, for example, correspond to a healthy individual, to an individual deriving no/low clinical benefit from treatment with a NKG2A-neutralizing antibody (optionally in combination with an agent that inhibits a human Siglec-9 polypeptide), or to an individual deriving substantial clinical benefit from treatment with a NKG2A-neutralizing antibody (optionally in combination with an agent that inhibits a human Siglec-9 polypeptide). A determination that a biological sample expresses HLA-E nucleic acid or polypeptide at a level that is increased (e.g. a high value, strong surface staining, a level that corresponds to that of an individual deriving substantial clinical benefit from treatment with a NKG2A-neutralizing antibody, a level that is higher than that corresponding to an individual deriving no/low clinical benefit from treatment with a NKG2A-neutralizing antibody, etc.) indicates that the individual has a cancer that can be treated with an anti-NKG2A antibody in combination with an agent that inhibits a human Siglec-9 polypeptide, e.g. according to the treatment methods described herein.

In one embodiment provided is a method for identifying an individual having a cancer for whom treatment with an anti-NKG2A agent is suitable, the method comprising:

a) determining the NKG2A and Siglec-9 polypeptide status of tumor infiltrating lymphocytes (e.g. NK cells) from the individual, and b) wherein a determination that NKG2A and Siglec-9 polypeptides are expressed on the surface of a significant proportion of tumor infiltrating lymphocytes (e.g. NK cells) from the individual, optionally TILs of a pre-defined subset (e.g. CD8 T cells, NK cells), indicates that treatment with an agent that neutralizes the inhibitory activity of a human NKG2A polypeptide and an agent that inhibits a human Siglec-9 polypeptide is suitable for the individual.

EXAMPLES

Example 1: A Human NK Cell Subset that Co-Expresses Both Siglec-7 and Siglec-9

Among the CD33-related Siglecs, Siglec-7 (CD328) and Siglec-9 (CD329) share the property of binding to sialic acids, including glycans overexpressed by cancer cells, and are thought to function as inhibitory receptors in the immune cells in which they are expressed. To investigate the expression of Siglecs on lymphocytes, distribution of Siglec-7 and Siglec-9 were studied on human NK cells.

Siglec-7 and Siglec-9 expression on NK cells was determined by flow cytometry on fresh NK cells purified from human donors. The NK population was determined as CD3-CD56+ cells (anti CD3 Pacific blue—BD Pharmingen #558124; anti CD56-PE-Vio770—Milteny #130 100 676). Anti-Siglec-7 antibody (clone 194211—IgG1 APC—R&D Systems #FAB11381A), anti-Siglec-9 antibody (clone 191240—IgG2A PE—R&D Systems #FAB1139P) and isotype controls IgG1 APC and IgG2A APC were used. NK cells were incubated 30 min with 50 ul of staining Ab mix, washed twice with staining buffer, and fluorescence was revealed with Canto II (HTS).

Results are shown in FIG. 1. A representative result is shown. MFI:Mean of fluorescence intensity. A significant fraction (about 44%) of NK cells expressed both Siglec-7 and Siglec-9, suggesting that a large proportion of NK cells can be inhibited by each of (or both of) these receptors, as a function of the glycan ligands present, for example on tumor cells.

Example 2: Generation of Anti-Siglec Antibodies

To obtain anti-human Siglec-7 and Siglec-9 antibodies, Balb/c mice were immunized with a human Siglec-7 Fc and human Siglec-9 Fc extracellular domain recombinant protein. Two different immunizations were done.

In a first immunization with Siglec-7 Fc and Siglec-9 Fc proteins, mice received 2 injections of an emulsion of 30 µg of each protein and Complete Freund Adjuvant, intraperitoneally. Then, mice received a boost with 7.5 µg of each protein, intravenously. Two different fusions (fusion 1 and 2) were done. Immune spleen cells were fused 3 days after the boost with X63.Ag8.653 immortalized B cells, and cultured in the presence of irradiated spleen cells. Hybridomas were plated in semi-solid methylcellulose-containing medium and growing clones were picked using a clonepix 2 apparatus (Molecular Devices).

A second immunization was carried out, again with Siglec-7 Fc and Siglec-9 Fc proteins. Mice received 3 injections of an emulsion of 30 µg of each protein and Complete Freund Adjuvant, intraperitoneally. Then, mice received a boost with 5 µg of each protein, intravenously. Three different fusions (fusion 3, 4 and 5) were done. Immune spleen cells were fused 3 days after the boost with X63.Ag8.653 immortalized B cells, and cultured in the presence of irradiated spleen cells. Hybridomas were plated in medium in P96. Siglec-7 Fc and Siglec-9 Fc proteins used in this immunization (and in the Examples hereafter) were produced in CHO cells. The Siglec-7 Fc protein had the following amino acid sequence:

(SEQ ID NO: 164)
QKSNRKDYSLTMQSSVTVQEGMCVHVRCSFSYPVDSQTDSDPVHGYWFR
AGNDISWKAPVATNNPAWAVQEETRDRFHLLGDPQTKNCTLSIRDARMS
DAGRYFFRMEKGNIKWNYKYDQLSVNVTALTHRPNILIPGTLESGCFQN
LTCSVPWACEQGTPPMISWMGTSVSPLHPSTTRSSVLTLIPQPQHHGTS
LTCQVTLPGAGVTTNRTIQLNVSYPPQNLTVTVFQGEGTASTALGNSSS
LSVLEGQSLRLVCAVDSNPPARLSWTWRSLTLYPSQPSNPLVLELQVHL
GDEGEFTCRAQNSLGSQHVSLNLSLQQEYTGKMRPVSGVLLGAVGGGGS
SPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLT
VDKSRWQQGNVFSCSVMHEALHNHYTQKSLSLSPGK.

The Siglec-9 Fc protein had the following amino acid sequence:

(SEQ ID NO: 165)
QTSKLLTMQSSVTVQEGLCVHVPCSFSYPSHGWIYPGPVVHGYWFREGA
NTDQDAPVATNNPARAVWEETRDRFHLLGDPHTKNCTLSIRDARRSDAG
RYFFRMEKGSIKWNYKHHRLSVNVTALTHRPNILIPGTLESGCPQNLTC
SVPWACEQGTPPMISWIGTSVSPLDPSTTRSSVLTLIPQPQDHGTSLTC
QVTFPGASVTTNKTVHLNVSYPPQNLTMTVFQGDGTVSTVLGNGSSLSL
PEGQSLRLVCAVDAVDSNPPARLSLSWRGLTLCPSQPSNPGVLELPWVH
LRDAAEFTCRAQNPLGSQQVYLNVSLQSKATSGVTQGGGGSSPKSCDKT
HTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVK
GFYPSDIAVEWESNGQPENNYKTTPPVLDSDGSFFLYSKLTVDKSRWQQ
GNVFSCSVMHEALHNHYTQKSLSLSPGK.

Primary screen: Supernatant (SN) of growing clones of both immunizations were tested in a primary screen by flow cytometry using parental and huSiglec-7, huSiglec-9 and cynoSiglec-expressing CHO cell lines. HuSiglec-7,—and cynoSiglec-expressing CHO were stained with 0.5 μM and 0.05 μM CFSE, respectively. For the flow cytometry screening, all cells were equally mixed and the presence of reacting antibodies in supernatants was revealed by Goat anti-mouse polyclonal antibody (pAb) labeled with alexa fluor 647.

Results: 20, 19 and more than 80 antibodies were selected in the respective fusions that bind to human Siglec-7 and/or Siglec-9 and/or Siglec-cyno in fusion 1, 2 and 3/4/5, respectively. Different cross reactive anti-Siglec-7, Siglec-9 and Siglec-Cyno antibodies and anti-Siglec-9 antibodies (that did not bind Siglec-7) from the 3 different fusions were cloned and produced as chimeric human IgG1 antibodies with a heavy chain N297Q (Kabat EU numbering) mutation which results in lack of N-linked glycosylation and diminished binding to Fcγ receptors.

Figure 2:
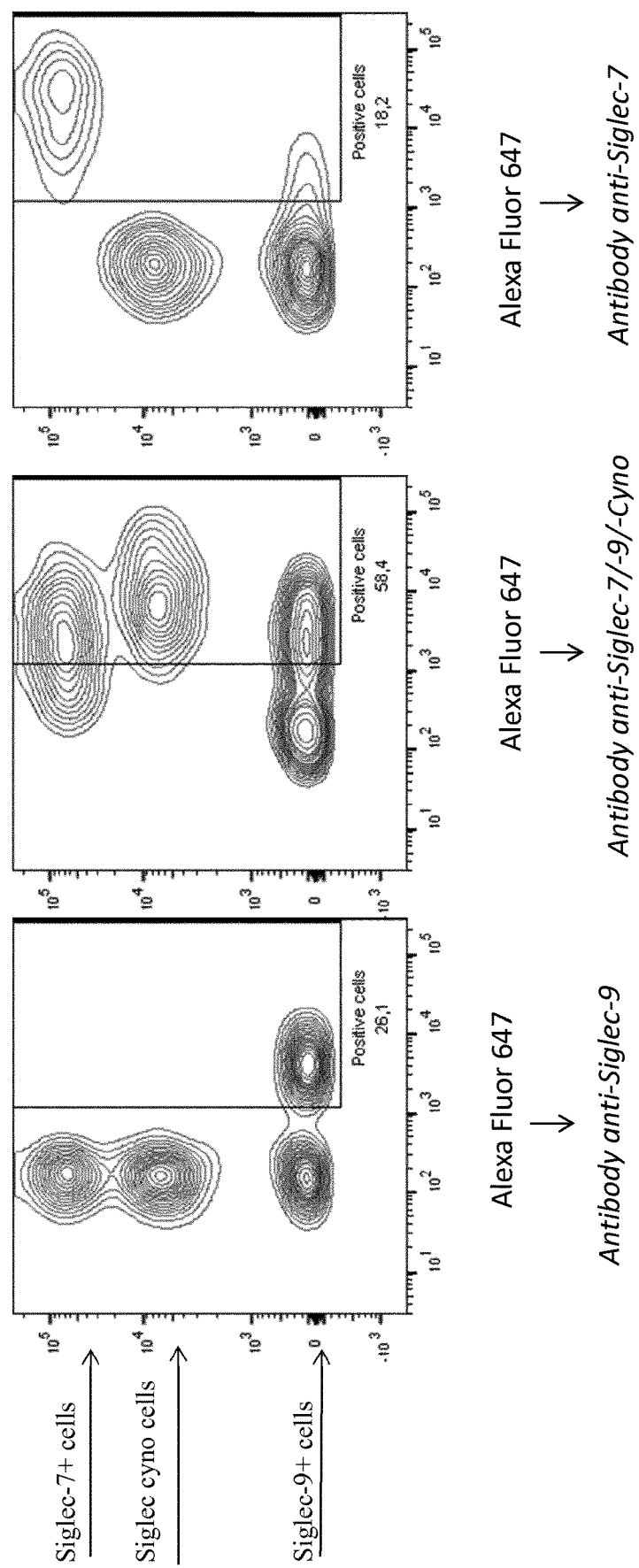
FIG. 2 shows representative results from flow cytometry for examples of antibodies that bind to Siglec-7 but not Siglec-9 or cynomolgus Siglec (right panel), that bind to each of Siglec-7, Siglec-9 and cynomolgus Siglec (middle panel), and that bind to Siglec-9 but not Siglec-7 or cynomolgus Siglec (left panel).

FIG. 2 shows representative results from flow cytometry for examples of antibodies that bind to Siglec-7 but not Siglec-9 or cynomolgus Siglec (right panel), that bind to each of Siglec-7, Siglec-9 and cynomolgus Siglec (middle panel), and that bind to Siglec-9 but not Siglec-7 or cynomolgus Siglec (left panel).

TABLE 1

Siglec sequences

| Name | NCBI Reference Sequence | Sequence (AA) |
|---|---|---|
| Human Siglec-7 | NM_014385.3; NP_055200.1 | QKSNRKDYSLTMQSSVTVQEGMCVHVRCSFSYPVDSQTDSDPVHGYWFRAGNDIS WKAPVATNNPAWAVQEETRDRFHLLGDPQTKNCTLSIRDARMSDAGRYFFRMEKG NIKWNYKYDQLSVNVTALTHRPNILIPGTLESGCFQNLTCSVPWACEQGTPPMIS WMGTSVSPLHPSTTRSSVLTLIPQPQHHGTSLTCQVTLPGAGVTTNRTIQLNVSY PPQNLTVTVFQGEGTASTALGNSSSLSVLEGQSLRLVCAVDSNPPARLSWTWRSL TLYPSQPSNPLVLELQVHLGDEGEFTCRAQNSLGSQHVSLNLSLQQEYTGKMRPV SGVLLGAVGGAGATALVFLSFCVIFIVVRSCRKKSARPAADVGDIGMKDANTIRG SASQGNLTESWADDNPRHHGLAAHSSGEEREIQYAPLSFHKGEPQDLSGQEATNN EYSEIKIPK (SEQ ID NO: 150) |
| Human Siglec-9 | NM_014441.2; NP_055256.1 | QTSKLLTMQSSVTVQEGLCVHVPCSFSYPSHGWIYPGPVVHGYWFREGANTDQDA PVATNNPARAVWEETRDRFHLLGDPHTKNCTLSIRDARRSDAGRYFFRMEKGSIK WNYKHHRLSVNVTALTHRPNILIPGTLESGCPQNLTCSVPWACEQGTPPMISWIG TSVSPLDPSTTRSSVLTLIPQPQDHGTSLTCQVTFPGASVTTNKTVHLNVSYPPQ NLTMTVFQGDGTVSTVLGNGSSLSLPEGQSLRLVCAVDAVSNPPARLSLSWRGL TLCPSQPSNPGVLELPWVHLRDAAEFTCRAQNPLGSQQVYLNVSLQSKATSGVTQ GVVGGAGATALVFLSFCVIFVVVRSCRKKSARPAAGVGDTGIEDANAVRGSASQG PLTEPWAEDSPPDQPPPASARSSVGEGELQYASLSFQMVKPWDSRGQEATDTEYS EIKIHR (SEQ ID NO: 151) |
| Human Siglec-3 | NM_001772.3; NP_001763.3 | DPNFWLQVQESVTVQEGLCVLVPCTFFHPIPYYDKNSPVHGYWFREGAIISGDSP VATNKLDQEVQEETQGRFRLLGDPSRNNCSLSIVDARRRDNGSYFFRMERGSTKY SYKSPQLSVHVTDLTHRPKILIPGTLEPGHSKNLTCSVSWACEQGTPPIFSWLSA APTSLGPRTTHSSVLIITPRPQDHGTNLTCQVKFAGAGVTTERTIQLNVTYVPQN PTTGIFPGDGSGKQETRAGVVHGAIGGAGVTALLALCLCLIFFIVKTHRRKAART AVGRNDTHPTTGSASPKHQKKSKLHGPTETSSCSGAAPTVEMDEELHYASLNFFI GMNPSKDTSTEYSEVRTQ (SEQ ID NO: 152) |
| Human Siglec-5 | NM_003830.3 | EKPVYELQVQKSVTVQEGLCVLVPCSFSYPWRSWYSSPPLYVYWFRDGEIPYYAE VVATNNPDRRVKPETQGRFRLLGDVQKKNCSLSIGDARMEDTGSYFFRVERGRDV KYSYQQNKLNLEVTALIEKPDIHFLEPLESGRPTRLSCSLPGSCEAGPPLTFSWT GNALSPLDPETTRSSELTLTPRPEDHGTNLTCQMKRQGAQVTTERTVQLNVSYAP QTITIFRNGIALEILQNTSYLPVLEGQALRLLCDAPSNPPAHLSWFQGSPALNAT PISNTGILELRRVRSAEEGGFTCRAQHPLGFLQIFLNLSVYSLPQLLGPSCSWEA EGLHCRCSFRARPAPSLCWRLEEKPLEGNSSQGSFKVNSSSAGPWANSSLILHGG LSSDLKVSCKAWNIYGSQSGSVLLLQGRSNLGTGVVPAALGGAGVMALLCICLCL IFFLIVKARRKQAAGRPEKMDDEDPIMGTITSGGSRKKPWPDSPGDQASPPGDAPP LEEQKELHYASLSFSEMKSREPKDQEAPSTTEYSEIKTSK (SEQ ID NO: 153) |
| Human Siglec-6 | NM_198845.4 | QERRFQLEGPESLTVQEGLCVLVPCRLPTTLPASYYGYGYWFLEGADVPVATNDP DEEVQEETRGRFHLLWDPRRKNCSLSIRDARRRDNAAYFFRLKSKWMKYGYTSSK LSVRVMALTHRPNISIPGTLESGHPSNLTCSVPWVCEQGTPPIFSWMSAAPTSLG PRTTQSSVLTITPRPQDHSTNLTCQVTFPGAGVTMERTIQLNVSSFKILQNTSSL PVLEGQALRLLCDADGNPPAHLSWFQGFPALNATPISNTGVLELPQVGSAEEGDF TCRAQHPLGSLQISLSLFVHWKPEGRAGGVLGAVWGASITTLVFLCVCFIFRVKT RRKKAAQPVQNTDDVNPVMVSGSRGHQHQFQTGIVSDHPAEAGPISEDEQELHYA VLHFHKVQPQEPKVTDTEYSEIKIHK (SEQ ID NO: 154) |
| Human Siglec-8 | NM_014442.2 | MEGDRQYGDGYLLQVQELVTVQEGLCVHVPCSFSYPQDGWTDSDPVHGYWFRAGD RPYQDAPVATNNPDREVQAETQGRFQLLGDIWSNDCSLSIRDARKRDKGSYFFRL ERGSMKWSYKSQLNYKTKQLSVFVTALTHRPDILILGTLESGHSRNLTCSVPWAC KQGTPPMISWIGASVSSPGPTTARSSVLTLTPKPQDHGTSLTCQVTLPGTGVTTT STVRLDVSYPPWNLTMTVFQGDATASTALGNGSSLSVLEGQSLRLVCAVNSNPPA RLSWTRGSLTLCPSRSSNPGLLELPRVHVRDEGEFTCRAQNAQGSQHISLSLSLQ NEGTGTSRPVSQVTLAAVGGAGATALAFLSFCIIFIIVRSCRKKSARPAAGVGDT GMEDAKAIRGSASQGPLTESWKDGNPLKKPPPAVAPSSGEEGELHYATLSFHKVK PQDPQGQEATDSEYSEIKIHKRETAETQACLRNHNPSSKEVRG (SEQ ID NO: 155) |

TABLE 1-continued

Siglec sequences

| Name | NCBI Reference Sequence | Sequence (AA) |
|---|---|---|
| Human Siglec-10 | NM_033130.4 | MDGRFWIRVQESVMVPEGLCISVPCSFSYPRQDWTGSTPAYGYWFKAVTETTKGA PVATNHQSREVEMSTRGRFQLTGDPAKGNCSLVIRDAQMQDESQYFFRVERGSYV RYNFMNDGFFLKVTALTQKPDVYIPETLEPGQPVTVICVFNWAFEECPPPSFSWT GAALSSQGTKPTTSHFSVLSFTPRPQDHNTDLTCHVDFSRKGVSVQRTVRLRVAY APRDLVISISRDNTPALEPQPQGNVPYLEAQKGQFLRLLCAADSQPPATLSWVLQ NRVLSSSHPWGPRPLGLELPGVKAGDSGRYTCRAENRLGSQQRALDLSVQYPPEN LRVMVSQANRTVLENLGNGTSLPVLEGQSLCLVCTHSSPPARLSWTQRGQVLSP SQPSDPGVLELPRVQVEHEGEFTCHARHPLGSQHVSLSLSVHYSPKLLGPSCSWE AEGLHCSCSSQASPAPSLRWWLGEELLEGNSSQDSFEVTPSSAGPWANSSLSLHG GLSSGLRLRCEAWNVHGAQSGSILQLPDKKGLISTAFSNGAFLGIGITALLFLCL ALIIMKILPKRRTQTETPRPRFSRHSTILDYINVVPTAGPLAQKRNQKATPNSPR TPLPPGAPSPESKKNQKKQYQLPSFPEPKSSTQAPESQESQEELHYATLNFPGVR PRPEARMPKGTQADYAEVKFQ (SEQ ID NO: 156) |
| Human Siglec-11 | NM_052884.2 | NKDPSYSLQVQRQVPVPEGLCVIVSCNLSYPRDGWDESTAAYGYWFKGRTSPKTG APVATNNQSREVEMSTRDRFQLTGDPGKGSCSLVIRDAQREDEAWYFFRVERGSR VRHSFLSNAFFLKVTALTKKPDVYIPETLEPGQPVTVICVFNWAFKKCPAPSFSW TGAALSPRRTRPSTSHFSVLSFTPSPQDHDTDLTCHVDFSRKGVSAQRTVRLRVA YAPKDLIISISHDNTSALELQGNVIYLEVQKGQFLRLLCAADSQPPATLSWVLQD RVLSSSHPWGPRTLGLELRGVRAGDSGRYTCRAENRLGSQQQALDLSVQYPPENL RVMVSQANRTVLENLGNGTSLPVLEGQSLRLVCTHSSPPARLSWTRWGQTVGPS QPSDPGVLELPPIQMEHEGEFTCHAQHPLGSQHVSLSLSVHYPPQLLGPSCSWEA EGLHCSCSSQASPAPSLRWWLGEELLEGNSSQGSFEVTPSSAGPWANSSLSLHGG LSSGLRLRCKAWNVHGAQSGSVFQLLPGKLEHGGGLGLGAALGAGVAALLAFCSC LVVFRVKICRKEARKRAAAEQDVPSTLGPISQGHQHECSAGSSQDHPPPGAATYT PGKGEEQELHYASLSFQGLRLWEPADQEAPSTTEYSEIKIHTGQPLRGPGFGLQL EREMSGMVPK (SEQ ID NO: 157) |
| Human Siglec-12 | NM_053003.3 | KEQKDYLLTMQKSVTVQEGLCVSVLCSFSYPQNGWTASDPVHGYWFFRAGDHVSRN IPVATNNPARAVQEETRDRFHLLGDPQNKDCTLSIRDTRESDAGTYVFCVERGNM KWNYKYDQLSVNVTASQDLLSRYRLEVPESVTVQEGLCVSVPCSVLYPHYNWTAS SPVYGSWFKEGADIPWDIPVATNTPSGKVQEDTHGRFLLLGDPQTNNCSLSIRDA RKGDSGKYYFQVERGSRKWNYIYDKLSVHVTALTHMPTFSIPGTLESGHPRNLTC SVPWACEQGTPPTITWMGASVSSLDPTITRSSMLSLIPQPQDHGTSLTCQVTLPG AGVTMTRAVRLNISYPPQNLTMTVFQGDGTASTTLRNGSALSVLEGQSLHLVCAV DSNPPARLSWTWGSLTLSPSQSSNLGVLELPRVHVKDEGEFTCRAQNPLGSQHIS LSLSLQNEYTGKMRPISGVTLGAFGGAGATALVFLYFCIIFVVVRSCRKKSARPA VGVGDTGMEDANAVRGSASQGPLIESPADDSPPHHAPPALATPSPEEGEIQYASL SFHKARPQYPQEQEAIGYEYSEINIPK (SEQ ID NO: 158) |
| Cynomolgus Siglec | XM_005590087.1 | QRNNQKNYPLTMQESVTVQQGLCVHVLCSFSYPWYGWISSDPVHGYWFRAGAHTD RDAPVATNNPARAVREDTRDRFHLLGDPQTKNCTLSIRDARSSDAGTYFFRVETG KTKWNYKYAPLSVHVTALTHRPNILIPGTLESGCPRNLTCSVPWACEQGTAPMIS WMGTSVSPLDPSTTRSSVLTLIPQPQDHGTSLTCQVTFPGASVTTNKTIHLNVSY PPQNLTMTVFQGNDTVSIVLGNGSSVSVPEGPSLRLVCAVDSNPPARLSLSWGGL TLCPSQSNPGVLELPRVHLRDEEEFTCRAQNLLGSQQVSLNVSLQSKATSGLTQ GAVGAGATALVFLSFCVIFVVVP (SEQ ID NO: 159) |
| Human Siglec-9 K100E/ A315E allele | | QTSKLLTMQSSVTVQEGLCVHVPCSFSYPSHGWIYPGPVVHGYWFREGANTDQDA PVATNNPARAVWEETRDRFHLLGDPHTENCTLSIRDARRSDAGRYFFRMEKGSIK WNYKHHRLSVNVTALTHRPNILIPGTLESGCPQNLTCSVPWACEQGTPPMISWIG TSVSPLDPSTTRSSVLTLIPQPQDHGTSLTCQVTFPGASVTTNKTVHLNVSYPPQ NLTMTVFQGDGTVSTVLGNGSSLSLPEGQSLRLVCAVDAVDSNPPARLSLSWRGL TLCPSQPSNPGVLELPWVHLRDEAEFTCRAQNPLGSQQVYLNVSLQSKATSGVTQ GVVGGAGATALVFLSFCVIFVVVRSCRKKSARPAAGVGDTGIEDANAVRGSASQG PLTEPWAEDSPPDQPPPASARSSVGEGELQYASLSFQMVKPWDSRGQEATDTEYS EIKIHR (SEQ ID NO: 160) |
| Human Siglec-9 N-terminal V-set Ig-like domain | | MEWSWVFLFFLSVTTGVHSGKPIPNPLLGLDSTQTSKLLTMQSSVTVQEGLCVHV PCSFSYPSHGWIYPGPVVHGYWFREGANTDQDAPVATNNPARAVWEETRDRFHLL GDPHTKNCTLSIRDARRSDAGRYFFRMEKGSIKWNYKHHRLSVNVTAATSGVTQG VVGGAGATALVFLSFCVIFVVVRSCRKKSARPAAGVGDTGIEDANAVRGSASQGP LTEPWAEDSPPDQPPPASARSSVGEGELQYASLSFQMVKPWDSRGQEATDTEYSE IKIHR (SEQ ID NO: 161) |
| Human Siglec-9 Ig-like C2-type domain 1 | | MEWSWVFLFFLSVTTGVHSGKPIPNPLLGLDSTLTHRPNILIPGTLESGCPQNLT CSVPWACEQGTPPMISWIGTSVSPLDPSTTRSSVLTLIPQPQDHGTSLTCQVTFP GASVTTNKTVHLNVSYPPQNLTMTVFQGDGTVATSGVTQGVVGGAGATALVFLSF CVIFVVVRSCRKKSARPAAGVGDTGIEDANAVRGSASQGPLTEPWAEDSPPDQPP PASARSSVGEGELQYASLSFQMVKPWDSRGQEATDTEYSEIKIHR (SEQ ID NO: 162) |

TABLE 1-continued

Siglec sequences

| Name | NCBI Reference Sequence | Sequence (AA) |
|---|---|---|
| Human Siglec-9 Ig-like C2-type domain 2 | | MEWSWVFLFFLSVTTGVHSGKPIPNPLLGLDSTSTVLGNGSSLSLPEGQSLRLVC AVDAVDSNPPARLSLSWRGLTLCPSQPSNPGVLELPWVHLRDAAEFTCRAQNPLG SQQVYLNVSLQSKATSGVTQGWGGAGATALVFLSFCVIFVVVRSCRKKSARPAAG VGDTGIEDANAVRGSASQGPLTEPWAEDSPPDQPPPASARSSVGEGELQYASLSF QMVKPWDSRGQEATDTEYSEIKIHR (SEQ ID NO: 163) |

Example 3: Binding to CD33-Related Siglecs

CD33-related Siglecs that share sequence similarity to Siglec-7 and -9 are generally divided into two groups, a first subset made up of Siglec-1, -2, -4 and -15, and the CD33-related group of Siglecs which includes Siglec-3, -5, -6, -7, -8, -9, -10, -11, -12, -14 and -16. Since other CD33-related Siglecs have different biological functions and/or are not thought to be involved in tumor surveillance, antibodies were further screened to assess whether it is possible to obtain cross-reactive Siglec-7/9 antibodies that do not bind to other CD33-related Siglecs.

Cells expressing Siglec-3, -5, -6, -8, -10, -11 and -12 were generated and a representative subset of the cross-reactive Siglec-7/9 antibodies were tested by flow cytometry for binding to the cells. Amino acid sequences and Genbank references for different Siglec used herein are shown below in Table 1, above.

Briefly, HuSiglec-expressing CHO cell lines (that expressed one of the Siglecs) were used. For the flow cytometry screening, antibodies were incubated 1 hour with each HuSiglec-expressing CHO cell lines (CHO HuSiglec-3 cell line, CHO HuSiglec-5 cell line, CHO HuSiglec-6 cell line, CHO HuSiglec-8 cell line, CHO HuSiglec-10 cell line, CHO HuSiglec-11 cell line, CHO HuSiglec-12 cell line), washed twice in staining buffer, revealed by Goat anti-mouse polyclonal antibody (pAb) labeled with PE, washed twice with staining buffer and stainings were acquired on a HTFC cytometer and analyzed using the FlowJo software.

Results showed that none of the anti-Siglec-9 antibodies mAbA, mAbB, mAbC, mAbD, mAbE and mAbF bound to any of the Siglecs-3, -5, -6, -7, -8, -10, -11 or -12.

Results showed that some cross-reactive Siglec-7/9 antibodies can be capable of also binding to Siglec-12 or Siglec-6 in addition to Siglec-7 and -9. mAb1, mAb2 and mAb3 bound to Siglec-12 in addition to Siglec-7 and -9, while mAb3, mAb4, mAb5 and mAb6 did not bind to Siglec-12. None of the exemplary antibodies mAb1, mAb2, mAb3, mAb4, mAb5 or mAb6 bound to any of the Siglecs-3, -5, -6, -8, -10, or -11.

Example 4: Titration of Antibodies for Binding to Siglecs

Binding of antibodies on human Siglec-7, human Siglec-9 and Cynomolgus Siglec-9 was tested by titration experiment by flow cytometry on CHO cells transfected with human Siglec-7 and human Siglec-9 and Cynomolgus Siglec-9. Cells were incubated 1 h in Staining Buffer (SB) with primary antibodies at 20 μg/ml and a series of dilution of 1:5. They were washed three times with SB, then incubated 30 min with a Goat F(ab')$^2$ Anti-human IgG (Fc) PE (Beckman Coulter #IM05510), and washed twice with SB. Fluorescence was revealed with HTFC Intellicyt cytometer.

Six antibodies shown below from the 5 fusions in the 2 immunizations were found to have comparable binding affinity for human Siglec-7 and human Siglec-9 as expressed by cells, and furthermore for cynomolgus Siglec. The $EC_{50}$ values (pg/ml) for binding for each antibody are shown below.

| | | mAb1 | mAb2 | mAb3 | mAb4 | mAb5 | mAb6 |
|---|---|---|---|---|---|---|---|
| $EC_{50}$ (μg/ml) | Siglec-7 | 0.21 | 0.17 | 0.22 | 0.17 | 0.22 | 0.33 |
| | Siglec-9 | 0.11 | 0.08 | 0.23 | 0.28 | 0.26 | 0.31 |
| | Siglec-Cyno | 0.67 | 0.53 | 0.85 | 0.17 | 0.14 | 0.17 |

Example 5: Siglec-9 Binding Affinity by Surface Plasmon Resonance (SPR)

Biacore™ T100 General Procedure and Reagents

SPR measurements were performed on a Biacore™ T200 apparatus (Biacore™ GE Healthcare) at 25° C. In all Biacore™ experiments HBS-EP+ (Biacore™ GE Healthcare) and NaOH 10 mM served as running buffer and regeneration buffer respectively. Sensorgrams were analyzed with Biacore™ T200 Evaluation software. Human siglec-9 and -7 multimeric proteins were cloned, produced and purified at Innate Pharma.

Immobilization of Protein-A

Proteins were immobilized covalently to carboxyl groups in the dextran layer on a Sensor Chip CM5. The chip surface was activated with EDC/NHS (N-ethyl-N'-(3-dimethylaminopropyl) carbodiamide hydrochloride and N-hydroxysuccinimide (Biacore™ GE Healthcare). Proteins were diluted to 10 μg/ml in coupling buffer (10 mM acetate, pH 4.2 & 5.0) and injected until the appropriate immobilization level was reached (i.e., 600 to 2000RU). Deactivation of the remaining activated groups was performed using 100 mM ethanolamine pH 8 (Biacore™, GE Healthcare).

Affinity Study

The affinity study was carried out according to a standard Kinetic protocol recommended by the manufacturer (Biacore™ GE Healthcare kinetic wizard). Serial dilutions of anti-Siglec-9 and -7/9 antibody Fab fragments ranging from 600 nM to 0.975 nM were sequentially injected over the immobilized Siglec-9 Fc and Siglec-7 Fc proteins and allowed to dissociate for 10 min before regeneration. The entire sensorgram sets were fitted using the 1:1 kinetic binding model. Monovalent affinities and kinetic association and dissociation rate constants are shown below in Table 2 below.

TABLE 2

| FAB | KD (nM) (1:1 Binding) | Koff $^{(10-3)}$ 1/S |
|---|---|---|
| Fab binding on Siglec-9 Fc protein | | |
| Fab.A (Fab of mAbA) | 0.04 | 0.025 |
| Fab.B (Fab of mAbB) | 0.37 | 0.31 |
| Fab.C (Fab of mAbC) | 0.55 | 0.43 |
| Fab.D (Fab of mAbD) | 4.12 | 0.11 |
| Fab.E (Fab of mAbE) | 1 | 1.9 |
| Fab.F (Fab of mAbF) | 1 | 0.46 |
| Fab1 (Fab of mAb1) | 0.4 | 0.16 |
| Fab2 (Fab of mAb2) | 0.8 | 0.17 |
| Fab binding on Siglec-7 Fc protein | | |
| Fab1 | 0.06 | 0.04 |
| Fab2 | 0.07 | 0.04 |

Example 6: Titration on Monocyte-Derived Dendritic Cells

Generation of Monocyte-Derived Dendritic Cells (moDCs):

Monocyte-derived dendritic cells were generated from peripheral blood mononuclear cells. PBMCs were isolated from buffy coats, obtained from healthy donors. Monocytes were purified using the kit Monocyte Isolation Kit II (Miltenyi Biotec) and were differentiated in moDC for a total of 6 days in RPMI medium (GIBCO) supplemented with 10% inactivated FBS (GIBCO), Glutamine (GIBCO), MEM NEAA (GIBCO), Sodium pyruvate (GIBCO), IL-4 (20 ng/ml)(Peprotech) and GM-CSF (400 ng/ml)(Miltenyi Biotec). Cells were cultured in a humidified CO2 incubator at 37° C. and the cytokines were renewed on day 4.

moDC were desialylated for 2 hours with 25 mU neuraminidase (Roche Diagnostics). Desialylation was controlled before and after neuraminidase treatment: moDCs cells were incubated 1 h in Staining Buffer (SB) with mouse Siglec-7 Fc (IPH) and mouse Siglec-9 Fc recombinant protein (IPH) at 10 ug/ml, washed twice with SB, incubated 30 min with a Goat F(ab')2 Anti-Mouse IgG (Fc) PE (Jackson ImmunoResearch), washed twice with SB, and fluorescence was revealed with Canto II (HTS).

Titrations

Binding on moDCs and neuraminidase treated moDCs was tested in a titration experiment by flow cytometry. Cells were incubated 1 h in Staining Buffer (SB) with primary antibodies at 10 µg/ml and a series of dilution of 1:10. They were washed two times with SB, then incubated 30 min with a Goat F(ab')$^2$ Anti-Human IgG (Fc) PE (Jackson ImmunoResearch), and washed twice with SB. Fluorescence was revealed with HTFC Intellicyt cytometer.

Results

Figure 3:
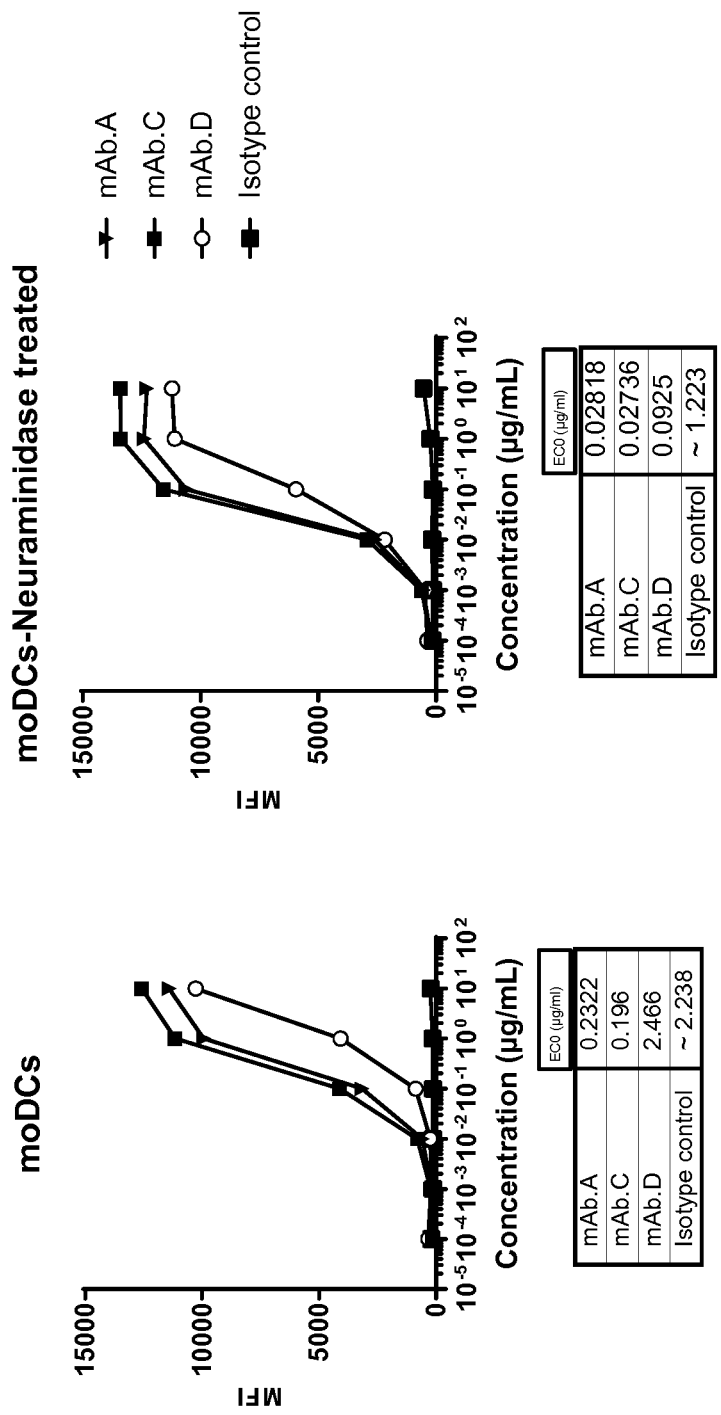
FIG. 3 shows titration by flow cytometry binding of antibodies mAbA, mAbC and mAbD to moDC (left hand panel) and neuramidase-treated moDC (right hand panel), accompanied by their respective $EC_{50}$ values. The $EC_{50}$ were highly enhanced (10 fold) after neuraminidase treatment, suggesting that Siglec-9 expressed on moDCs were engaged in cis interaction with their sialic acid ligands before neuraminidase treatment. However, the plateau phase level is not modified, suggesting than the antibodies can bind all Siglec-9 (bound and unbound) conformations on cell surface and inhibits cis-interactions and signalling in monoDCs, as well as in other cell types (e.g., monocytes and macrophages M1 and M2).

The $EC_{50}$ were highly enhanced (10 fold) after neuraminidase treatment, suggesting that Siglec-9 expressed on moDCs were engaged in cis interaction with their sialic acid ligands before neuraminidase treatment. However, the plateau phase level is not modified, suggesting than the high affinity antibodies can bind all Siglec-9 (bound and unbound) conformations on cell surface and inhibits cis-interactions and signalling in monoDCs, as well as in other cell types (e.g., NK cells, CD8 T cells, monocytes and macrophages M1 and M2). Results are shown in FIG. 3 for representative antibodies mAbA, mAbC and mAbD in moDC (left hand panel) and neuramidase-treated moDC (right hand panel), accompanied by their respective $EC_{50}$ values.

Example 7: Evaluation of Ability of Antibodies to Neutralize Siglec Activity in NK Cells Anti-Siglec-7/9 antibodies tested in the first and second immunizations were tested for blockade of Siglec activity in an NK cell activation assay using primary NK cells (fresh NK cells purified from human donors, incubated overnight at 37° C. before use). Increase of CD137 expression in 24 hours is correlated with the activation of several lymphocytes including NK cells (Kohrt et al. (2011) Blood 117(8): 2423-2432). The effect of anti-Siglec-7/9 antibody and desialylation of target cells on NK cells activation was determined by analysis of CD137 expression on NK cells by flow cytometry. Each of the anti-Siglec-7/9 mAbs mAb1, mAb2, mAb3, mAb4, mAb5 and mAb6 induced an increase of CD137 expression at 24 hours.

The effects of anti-Siglec-7/9 antibodies was then studied by cytotoxicity assays ($Cr^{51}$) with YTS Siglec-9* effector cell line (the human NK cell line YTS transfected with human Siglec-9) as effector and Ramos cell line as target. This test measures the cytotoxicity of YTS Siglec-9* cell line by directly quantifying the lysis of $^{51}Cr$-loaded target cells. Briefly, target cells are first labeled with radioactive $^{51}Cr$ isotope and then co-incubated for 4 h at 37° C. with effector cells. During this time, target cells that are sensitive to YTS cells are lysed releasing $^{51}Cr$ into the medium. The $^{51}Cr$ in the recovered supernatant is measured by liquid scintillation counting. The results obtained allow evaluating the percent lysis of target cells by NK cells. The assay was carried out in 96 U well plates in completed RPMI, 200 µL final/well, with an E:T ratio 5/1. Anti-Siglec-7/9 antibodies and isotype control were added at 10 µg/ml and a series of dilution of 1:10.

Figure 4A:
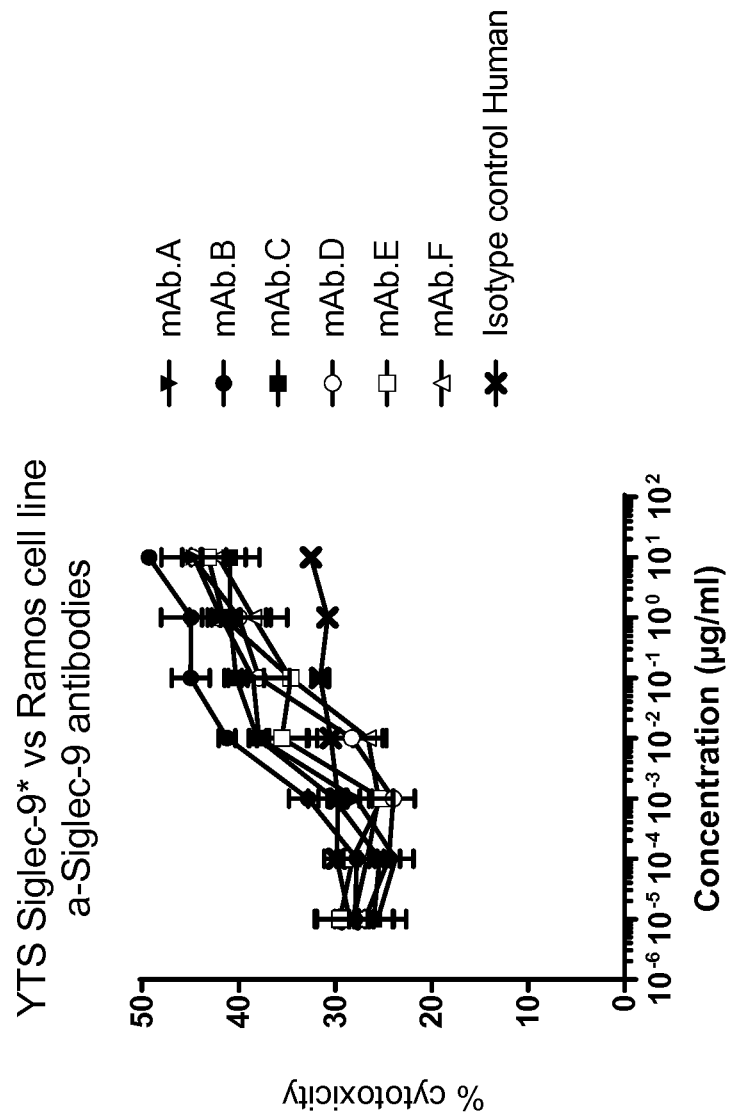
FIG. 4 shows dose dependent induction of an increase of YTS Siglec-9* cytotoxicity among Siglec-7 and -9 cross-reactive antibodies (FIG. 4B) and among the Siglec-9 mono-specific (non-Siglec-7 binding) antibodies (FIG. 4A).
Figure 4B:
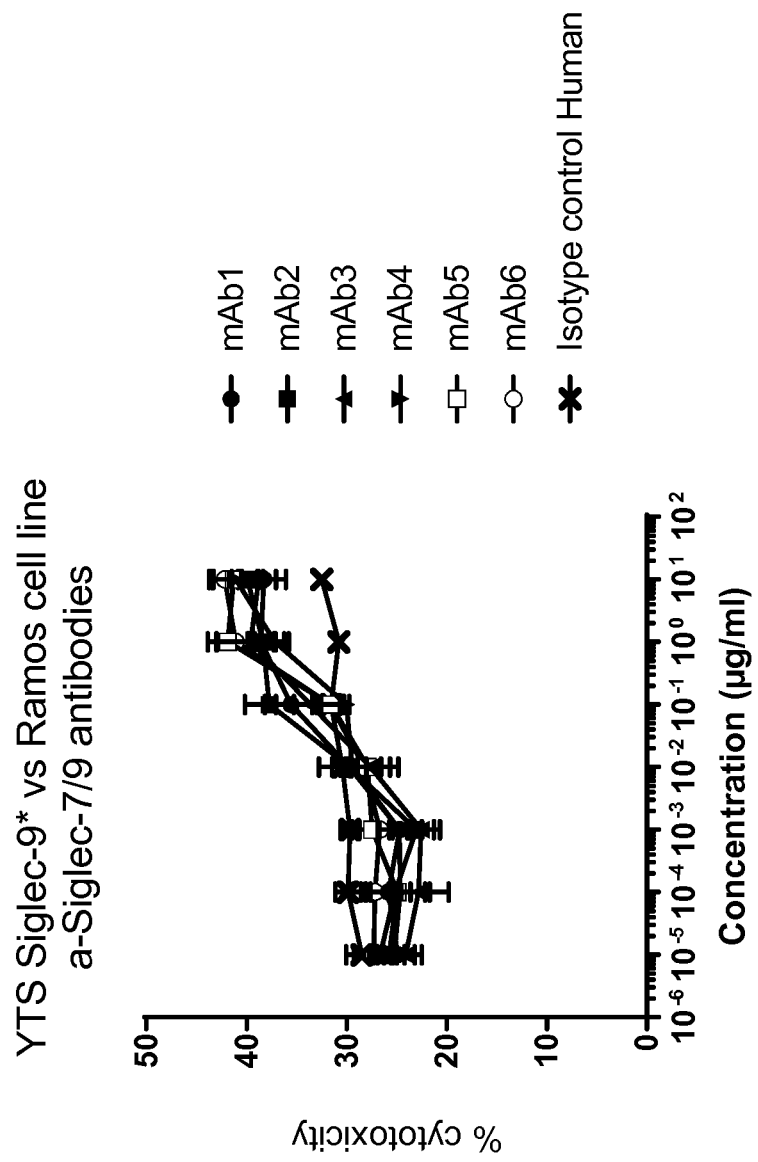

Each of the anti-Siglec-7/9 mAbs mAb1, mAb2, mAb3, mAb4, mAb5 and mAb6 induced an increase of YTS Siglec-9* cytotoxicity in a dose dependent manner. As a control, this effect was not observed on wild type YTS cell line (no Siglec-9 expression). Similarly, each of the anti-Siglec-9 mAbs mAbA, mAbB, mAbC, mAbD, mAbE and mAbF induce an increase of YTS Siglec-9* cytotoxicity in a dose dependent manner. FIG. 4 shows dose dependent induction of an increase of YTS Siglec-9* cytotoxicity among Siglec-7 and -9 cross-reactive antibodies (FIG. 4B) and among the Siglec-9 monospecific (non-Siglec-7 binding) antibodies (FIG. 4A).

Example 8: Detailed Study of Siglec-9 Neutralization in Primary Human NK Cells (Low Siglec-9 Expression)

We considered the possibility that the inability of prior antibodies to neutralize Siglec-9 in NK cells might be related to differences in Siglec-9 expression in primary NK cells compared for example to neutrophils and other cells that express much higher levels of Siglec-9 at their surface, and Siglec-7 expressed in differing NK cell subsets. In order to investigate whether antibodies could be obtained that neutralize Siglec-9 in NK cells, we studied and selected antibodies in primary NK cells from a number of human donors, gated on Siglec-9 by flow cytometry. The effect of anti-Siglec-9 antibodies was studied by cytotoxicity by assessing tumor cell lysis in a classical $^{51}$Cr release assay and by activation assays by assessing CD137 surface expression on NK cells. In each case, primary NK cells (as fresh NK cells purified from donors) were used as effector cells and HT29 colorectal cancer cell line were used as target.

Part 1: Cytotoxicity Assay: Purified NK Vs HT29 Tumor Cells in Two Human Donors

The cytotoxicity assay measured the cytotoxicity of NK cells by directly quantifying the lysis of $^{51}$Cr-loaded target cells. Briefly, target cells were first labeled with radioactive $^{51}$Cr isotope and then co-incubated for 4 h at 37° C. with effector cells. During this time, target cells that are sensitive to NK cells were lysed releasing $^{51}$Cr into the medium. The $^{51}$Cr in the recovered supernatant were measured by liquid scintillation counting. The results obtained allow the evaluation the percent lysis of target cells by NK cells. The assay was carried out in 96 U well plates in completed RPMI, 200 μL final/well, with an E:T ratio 8/1. Anti-Siglec-9 antibodies and isotype control were added at 10 μg/ml.

Figure 5:
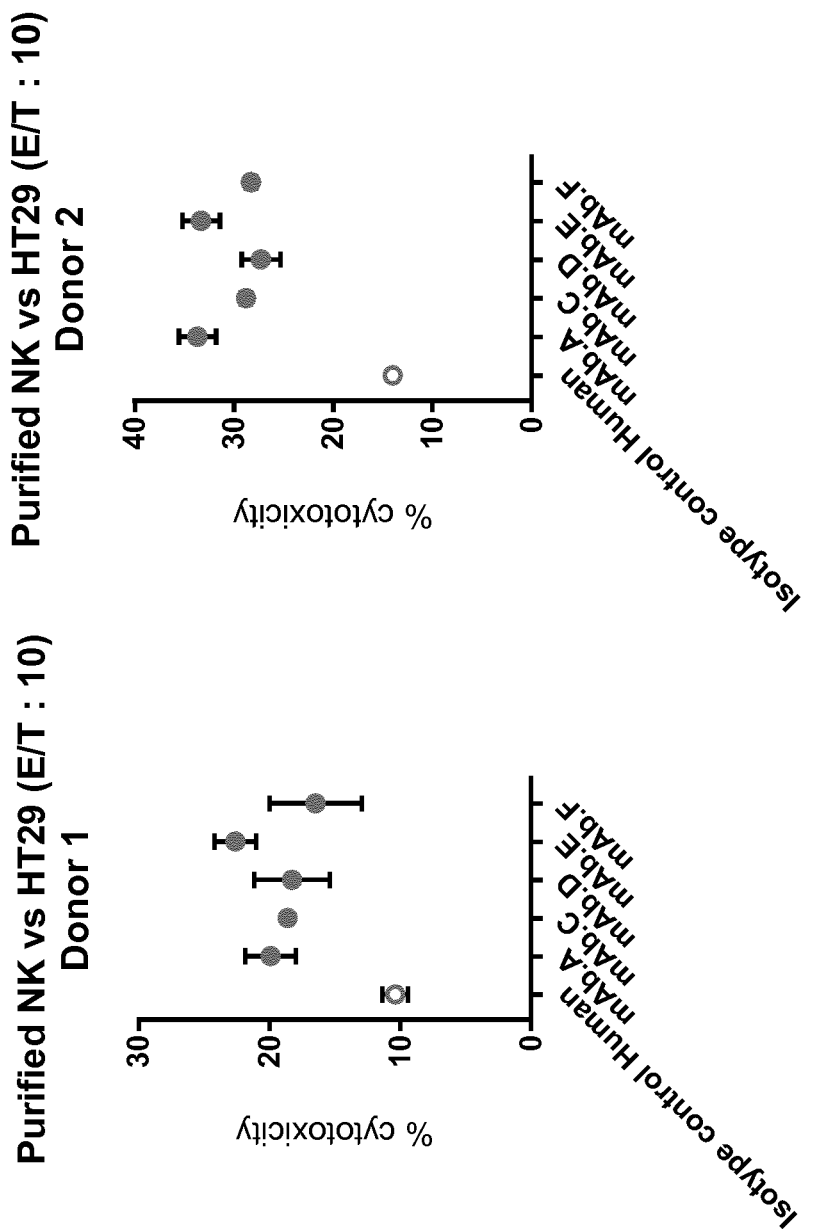
FIG. 5 shows the increase of primary NK cell cytotoxicity mediated by antibody mAbA, mAbC, mAbD, mAbE, and mAbF in two different human donors (donors D1 (left hand panel) and D2 (right hand panel)), in a classical $^{51}$Cr release assay, using primary NK cells (as fresh NK cells purified from donors) and HT29 colorectal cancer cells.

Each of the anti-Siglec9 antibodies mAbA, mAbB, mAbC, mAbD, mAbE, and mAbF and anti-Siglec7/9 antibodies mAb1, mAb2, mAb3, mAb4, mAb5 and mAb6 induced an increase of NK cells cytotoxicity. FIG. 5 is a representative figure showing the increase of primary NK cell cytotoxicity mediated by antibody mAbA, mAbC, mAbD, mAbE, and mAbF in two different human donors (donors D1 (left hand panel) and D2 (right hand panel)).

Part 2: Activation Assay (CD137): Purified NK Vs HT29, mAb Comparison in a Single Human Donor The effect of the anti-Siglec-7/9 and anti-Siglec-9 antibodies on NK cells activation was determined by analysis of CD137 expression on Siglec-9 positive NK cells by flow cytometry. Effector cells were primary NK cells (fresh NK cells purified from donors, incubation overnight at 37° C. before use) and target cells (HT29 cell line) were mixed at a ratio 1:1. The CD137 assay was carried out in 96 U well plates in completed RPMI, 200 μL final/well. Antibodies were pre-incubated 30 minutes at 37° C. with effector cells and then target cells were co-incubated overnight at 37° C. The following steps were: spin 3 min at 500 g; wash twice with Staining Buffer (SB); addition of 50 μL of staining Ab mix (anti CD3 Pacific blue—BD Pharmingen; anti-CD56-PE-Vio770 (Miltenyi); anti-CD137-APC (Miltenyi), anti Siglec-9 K8-PE (Biolegend); incubation 30 min at 4° C.; wash twice with SB; resuspended pellet with SB; and fluorescence revealed with Canto II (HTS).

Figure 6:
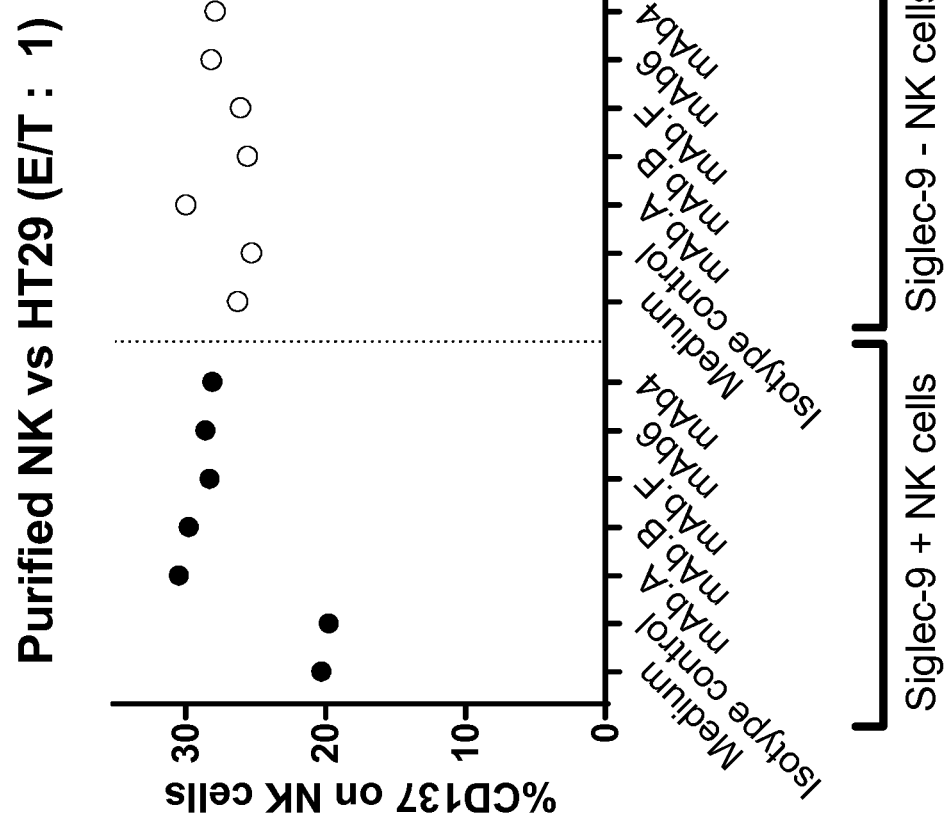
FIG. 6 shows increase of % of Siglec-9-positive NK cells expressing CD137 mediated by several anti-Siglec-9 and anti Siglec-7/9 antibodies mAbA, mAbB, mAbF, mAb6 and mAb4 in one human donor, in the presence of HT29 tumor cells. The anti-Siglec-9 antibodies fully restored cytotoxicity of Siglec-9-expressing primary human NK cells to the level observed in Siglec-9-negative primary human NK cells from the same donor.

Negative controls were NK cells vs HT29 alone and in presence of isotype control. FIG. 6 is a representative figure showing the increase of % of Siglec-9-positive NK cells expressing CD137 mediated by several anti-Siglec-9 and anti Siglec-7/9 antibodies mAbA, mAbB, mAbF, mAb6 and mAb4 in one human donor. As a control, % of Siglec-9-negative NK cells expressing CD137 were not affected by these antibodies. As can be seen in the figure, the anti-Siglec-9 antibodies fully restored cytotoxicity of Siglec-9-expressing primary human NK cells to the level observed in Siglec-9-negative primary human NK cells from the same donor.

Part 3: Activation Assay (CD137): Purified NK Vs HT29, mAbA and mAb1 in 6 Human Donors Experiments were reproduced with 6 donors by using one anti Siglec-9 (mAb.A) and one anti Siglec-7/9 (mAb1). In absence of antibodies (the "medium" setting), the % of NK expressing CD137 varied among donors between 6% and 27% (see (FIG. 7, left hand panel)). Data were normalized to be a relative change compared to the control medium value from each experiment: $((X-X_{medium}))/X_{medium}$ (%).

Figure 7:
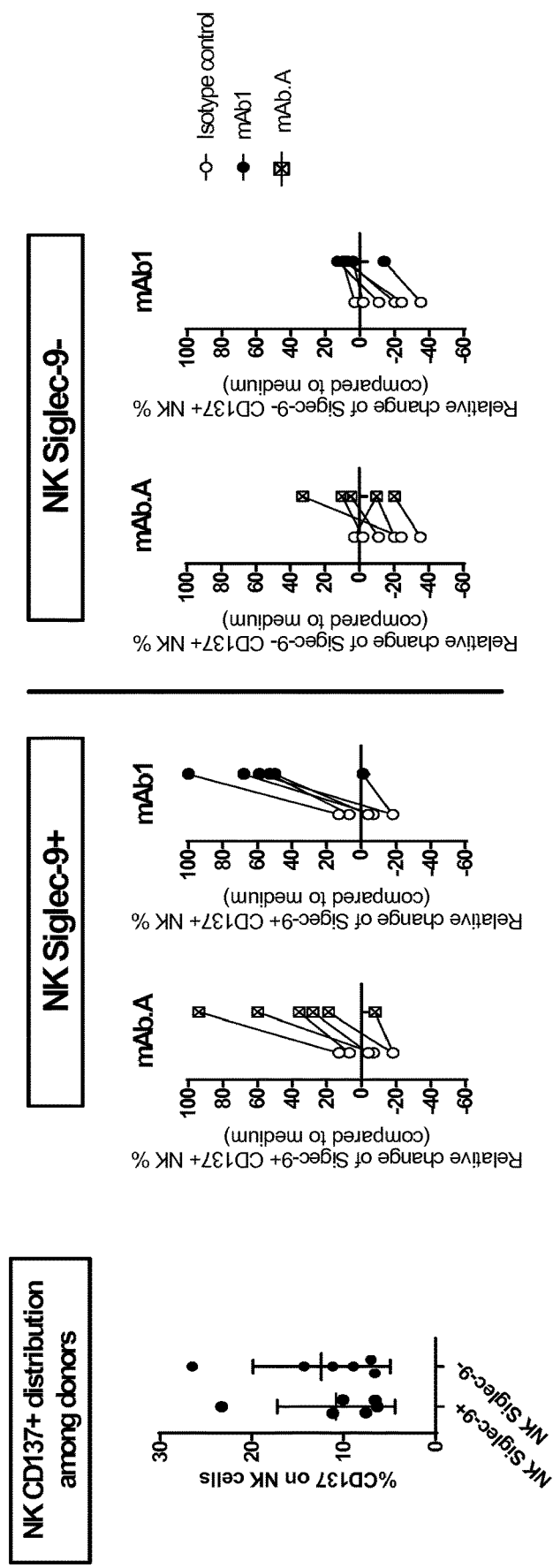
FIG. 7 shows that antibodies mAbA and mAb1 induce an increase of Siglec-9-positive CD137+ NK cells (%) (middle panel) but not Siglec-9-negative CD137+ NK cells (%) (right hand panel). The % of NK expressing CD137 in the absence of antibodies is shown in the left hand panel.

As shown in FIG. 7, mAbA and mAb1 induced an increase of Siglec-9+CD137+ NK % (FIG. 7, middle panel) and not Siglec-9-CD137+ NK % (FIG. 7, right hand panel).

Example 9: Titration on Primary NK Cells

Binding of antibodies on fresh purified human NK cells was tested by titration experiment by flow cytometry. Cells were incubated 1 h in Staining Buffer (SB) with primary antibodies at 10 μg/ml and a series of dilution of 1:10. They were washed three times with SB, then incubated 30 min with a Goat F(ab')$^2$ Anti-Human IgG (Fc) PE (Jackson ImmunoResearch). Stainings were acquired on a BD FACS Canto II and analyzed using the FlowJo software. EC$_{50}$ values are shown in the table below in μg/ml (calculated using a 4-parameter logistic fit).

|  | Mean EC50 (μg/ml) - 4 donors |
| --- | --- |
| mAb1 | 0.05 |
| mAb2 | 0.07 |
| mAb3 | 0.19 |
| mAb4 | 0.61 |
| mAb5 | 1.27 |
| mAb6 | 1.30 |
| mAbA | 0.08 |
| mAbB | 0.10 |
| mAbC | 0.09 |
| mAbE | 0.01 |
| mAbF | 0.30 |

Example 10: Blockade of Siglec Binding to Sialic Acid Ligands

Part A: Blockade of Siglec-9 Binding to Sialic Acid Expressing Tumor Cells by Flow Cytometry A dose-range of anti-human Siglec-9 Fab were co-incubated 30 minutes at room temperature with the human Siglec-9 Fc fusion recombinant protein at a fixed dose, then added on various sialic acid expressing cell lines K562 E6 (K562 cell line transfected with human HLA-E) and Ramos for 1 hour. After washing cells two times in staining buffer, a PE-coupled goat anti-mouse IgG Fc fragment secondary antibodies (Jackson ImmunoResearch) diluted in staining buffer were added to the cells and plates were incubated for 30 additional minutes at 4° C. Cells were washed two times and analyzed on an Accury C6 flow cytometer equipped with an HTFC plate reader. Mean of fluorescence vs. ratio of Fab and Siglec-9 Fc fusion recombinant protein was plotted on graphs.

Figure 8:
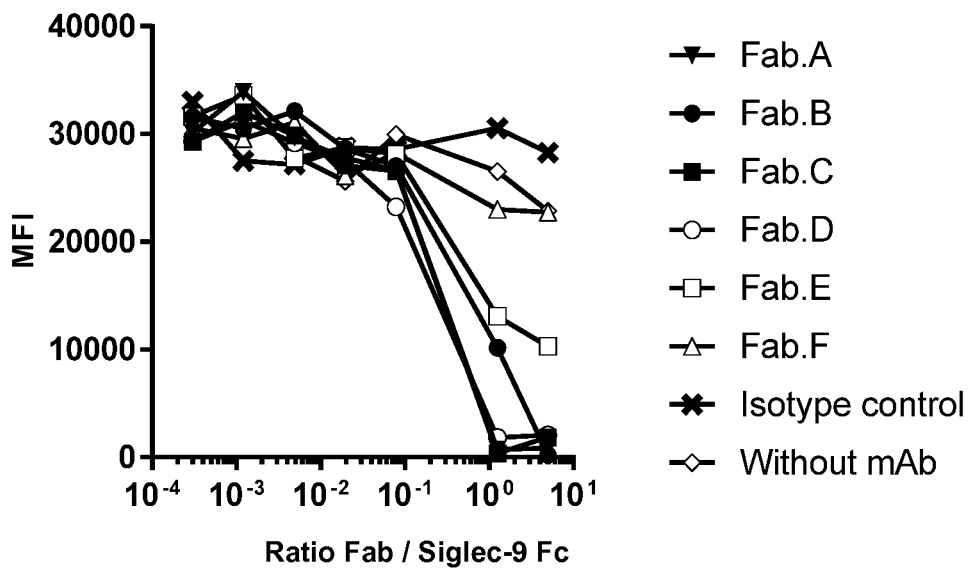
FIG. 8 shows binding of Siglec-9-Fc protein to Ramos cells in the presence of antibodies (top panel). The anti-Siglec/9 mAbs mAbA, mAbB, mAbC, and mAbD each inhibited binding of Siglec-9-Fc protein to the Ramos cells, while mAbE showed partial inhibition and mAbF did not inhibit binding. Binding of Siglec-9-Fc protein to K562 cells in the presence of antibodies is shown in the bottom panel. The anti-Siglec/9 mAbs mAbA, mAbB, mAbC and mAbD each inhibited binding of Siglec-9-Fc protein to the Ramos cells, while both mAbE and mAbF showed partial inhibition.
Figure 8:
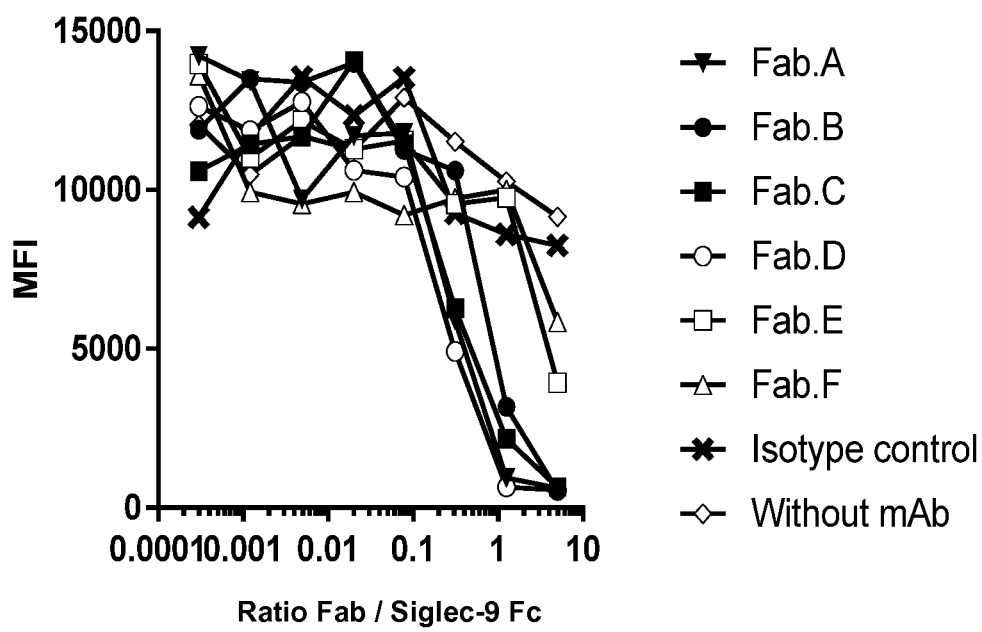

Results are shown in FIG. 8. On the top panel, shown is binding of Siglec-9-Fc protein to Ramos cells in the presence of antibodies. The anti-Siglec/9 mAbs mAbA, mAbB, mAbC, and mAbD each inhibited binding of Siglec-9-Fc protein to the Ramos cells, while mAbE showed a partial ability to inhibit binding of Siglec-9-Fc protein to the Ramos cells, and mAbF did not significantly inhibit binding of Siglec-9-Fc protein to the Ramos cells. In FIG. 8, bottom panel, shown is binding of Siglec-9-Fc protein to K562 cells in the presence of antibodies. The anti-Siglec/9 mAbs mAbA, mAbB, mAbC and mAbD each inhibited binding of Siglec-9-Fc protein to the Ramos cells, while both mAbE and mAbF showed a partial ability to inhibit binding of Siglec-9-Fc protein to the K562 cells, and only at significantly higher concentrations of antibody. In conclusion, the antibody mAbA, mAbB, mAbC, and mAbD block totally the binding of Siglec-9 to its sialic acid ligands on tumor cells while antibodies mAbE blockade depend on sialic acid expressing cell line and mAbF does not block the binding.

Part B: Blockade of Siglec-7 and -9 Binding to Sialylated Ligands by ELISA Assays Sialic acids are nine-carbon carboxylated monosaccharides on glycosylated proteins and lipids formed. Several enzymes including sialyltransferases (catalyzing their biosynthesis) and sialidases also termed as neuraminidases (catalyzing their cleavage), regulate their occurrence in the mammalian system. In cancer, altered sialic acid profile plays dominant role enhancing tumor growth, metastasis and evading immune surveillance, leading to cancer cell survival (Bork et al., J Pharm Sci. 2009 October; 98(10):3499-508). Increased sialylations together with altered enzyme profile regulating sialylation has been reported in several cancers. The ST3GAL6 enzyme is overexpressed in multiple myeloma cell lines and patients and is associated in vitro with expression of α-2,3-linked sialic acid on the surface of multiple myeloma cells. In vivo, ST3GAL6 knockdown is associated with reduced homing and engraftment of multiple myeloma cells to the bone marrow niche, along with decreased tumor burden and prolonged survival (Glavey et al., Blood. 2014 Sep. 11; 124(11):1765-76). High ST3GAL1 enzyme expression in glioma is associated with higher tumor grades of the mesenchymal molecular classification (Chong et al., Natl Cancer Inst. 2015 Nov. 7; 108(2). Aberrant promoter methylation play a role in modulation of several sialyl transferases expression in cancer (Vojta et al., Biochim Biophys Acta. 2016 Jan. 12). In bladder cancer, aberrant ST6GAL1 promoter methylation induces ST6Gal1 expression loss (Antony et al., BMC Cancer. 2014 Dec. 2; 14:901).

Siglec-7 and Siglec-9 bind to various sialic acid linkages. A sialoside library printed on chip identified sialoside ligands common to several Siglec and one selective Siglec-7 ligand (Rillahan et al., ACS Chem Biol. 2013 Jul. 19; 8(7):1417-22). In view of the possible differential recognition of sialosides by Siglec-7 and Siglec-9, targeting both Siglec-7 and -9 on immune cells could allow targeting of several cancer types given the various sialyl transferases and sialic acid.

Blocking of the interaction between Siglec-7 and -9 and sialylated ligands by anti Siglec-7/9 antibodies was tested on ELISA assays. Siglec proteins were Siglec-7 human Fc and Siglec-9 Human Fc recombinant proteins, and ligands were biotinylated polymers with sialylated trisaccharides (Neu5Aca2-3Galb1-4GlcNAcb-PAA-biotin Glycotech #01-077 referred to as "Sia1" and 6'-Sialyllactose-PAA-biotin Glycotech #01-039 (referred to as "Sia2"). Briefly, Protein A was coated on ELISA plates over night at 4° C. After 3 washes and saturation, Siglec-7 Fc and Siglec-9 Fc were added at 0.8 μg/well at RT for 1H30. After 3 washes, mAbs were added at 20 ug/ml and a series of dilution of 1:5. After 3 washes, biotinylated sialylated polymers were added for 3 hours at room temperature. After 3 washes, Streptavidin-Peroxidase (Beckman) was added at 1:1000. Finally, binding of sialylated polymers on Siglec-7 and -9 proteins was revealed by addition of TMB (Interchim) at RT in darkness, and the reaction was stopped by addition of H2S04. The absorbance was read at 450 nm.

Figure 9:
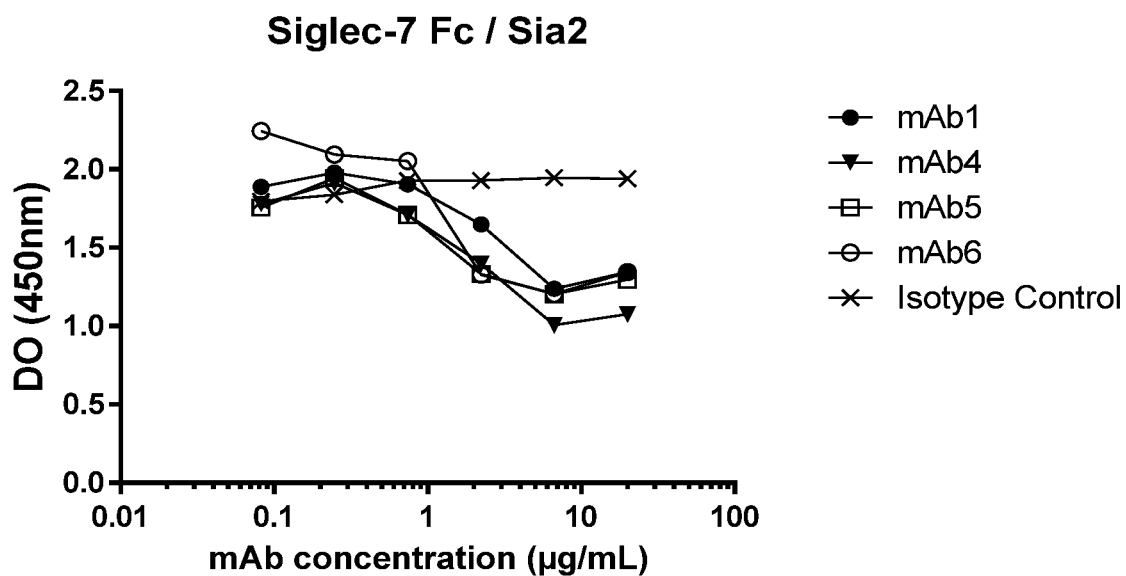
FIGS. 9 and 10 show testing of blocking of the interaction between Siglec-7 and -9 and sialylated ligands by anti Siglec-7/9 antibodies using ELISA assays.
Figure 9:
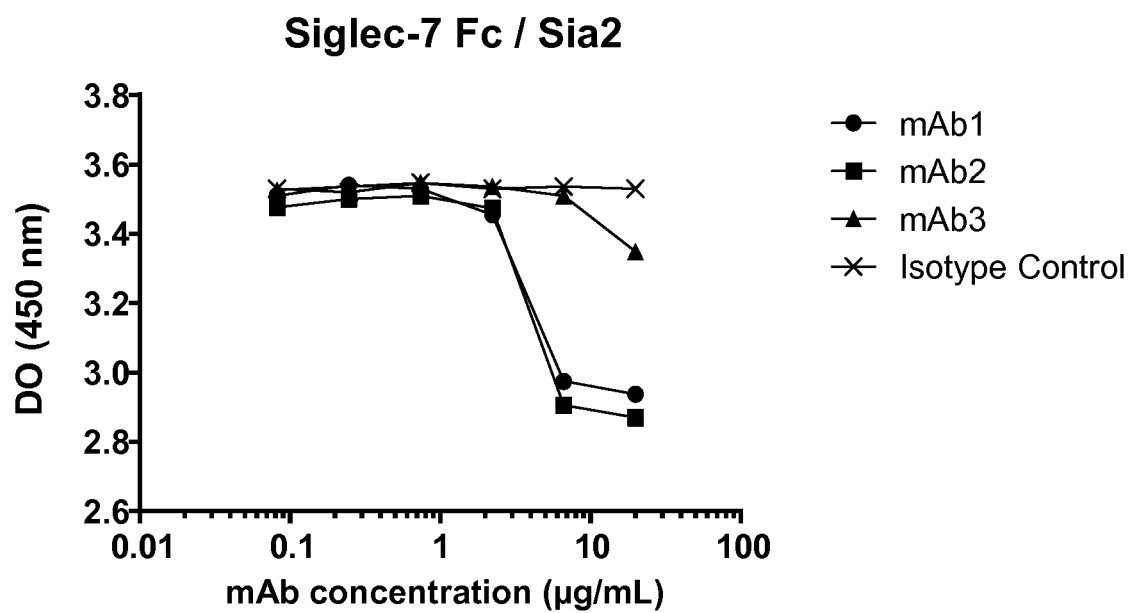
Figure 10:
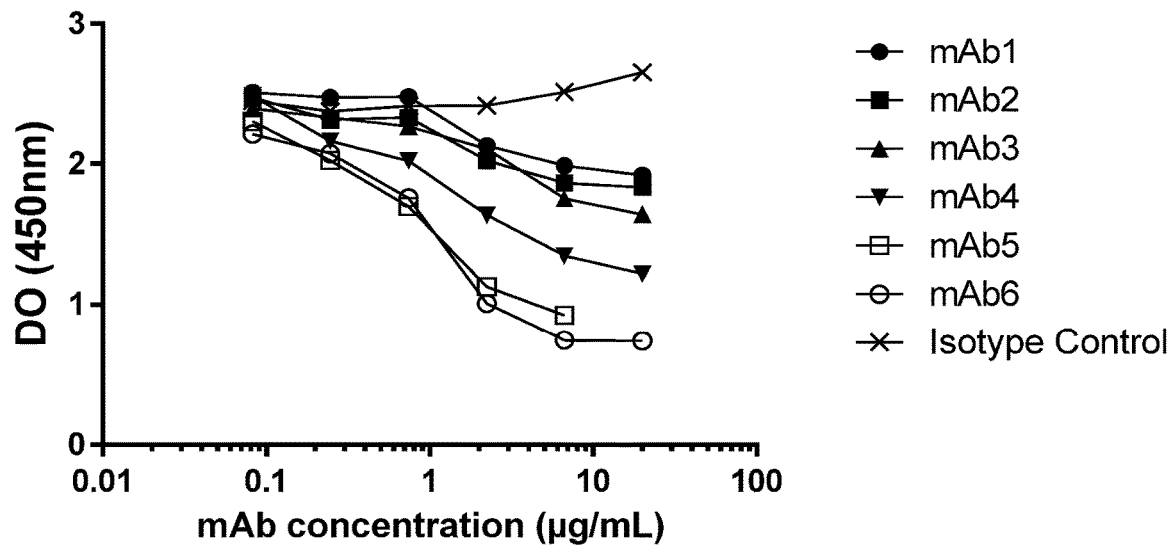
Figure 10:
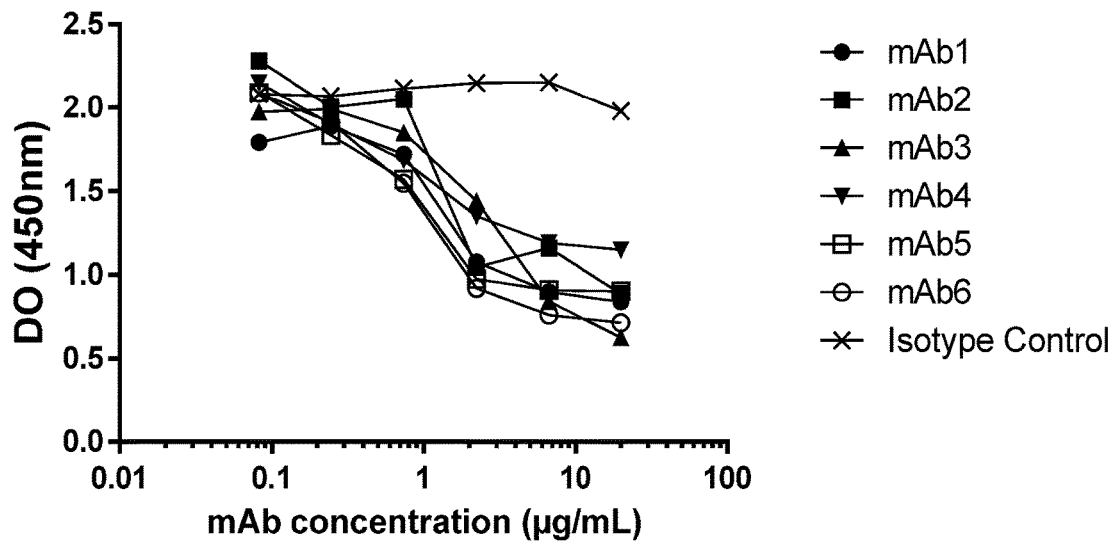

Results are shown in FIGS. 9 and 10. mAbs 1, 2, 4, 5 and 6 block Siglec-7 interaction with Sia2, but mAb3 did not (FIG. 9). All mAbs blocked the Siglec-9 interaction with Sia2 (FIG. 10), however mAb1, mAb2 and mAb3 showed low ability to inhibit the Siglec-9 interaction with Sia1 (FIG. 10), and thus did not substantially block the Sia1 interaction.

mAb5 and mAb6 blocked the Siglec-9 interaction with Sia1, and mAb4 had intermediate ability to block the Siglec-9 interaction with Sia1. The blocking effect on Siglec-9 is dependent on sialic acid type. On the overall, the most complete inhibition was observed with anti-Siglec-9 antibodies mAbA, mAbB, mAbC and mAbD which achieved substantially full inhibition of the Siglec-9 interaction with sialic acids.

Example 11: Epitopes of Anti-Siglec Antibodies Using Point Mutants

In order to define the epitopes of anti-Siglec-9 antibodies, we first identified the binding domain of our antibodies by expressing each single Siglec-9 domain (V-set Ig-like domain, Ig-like C2-type domain 1, and Ig-like 02-type domain 2) with the tag V5 in HEK293T cells and testing binding of the antibodies to each protein.

We then designed Siglec-9 mutants defined by substitutions of amino acids exposed at the molecular surface over the surface of the N-terminal V-set Ig-like domain. The structure of Siglec-9 has not been resolved yet, and among available Siglec structures, Siglec-7 is the closest member (more than 80% of identity with Siglec-9 amino acid sequence). Consequently, we used the Siglec-7 structure to design Siglec-9 mutants. The native Siglec-9 peptide leader of the polypeptide of SEQ ID NO: 2 was replaced by a substitute leader sequence and V5 tag (shown in the Siglec-9 domain proteins V-set Ig-like domain, Ig-like C2-type domain 1, and Ig-like C2-type domain 2 in Table 1), followed by the Siglec-9 amino acid sequence of Table 1, into which were incorporated amino acid substitutions listed in Table 3. Proteins were expressed in the HEK293T cell line.

All figures (FIGS. 11-14) correspond to the N-terminal V-set Ig-like domain of SIGLEC-7 structure 107V, described by Alphey et al (2003), supra. The figures show in light shading the ligand binding area, including arginine 124, which is a key residue conserved in all Siglecs for the interaction with the carboxyl group on the terminal sialic acid sugar, and surrounding residues W132, K131, K135 and N133 which are conserved between Siglec-7 and Siglec-9 and are also described as essential for sialic acid binding. W132 provides a hydrophobic interaction with the glycerol moiety of sialic acid. The targeted amino acid mutations in the Table 3 are residues present in both Siglec-7 and -9, and are shown using numbering of SEQ ID NO: 1 for Siglec-7 or SEQ ID NO: 2 for Siglec-9 (residue in wild type Siglec-9/position of residue/residue in mutant).

TABLE 3

| Ref. | Mutations with Reference to Siglec-7 of SEQ ID NO: 1 | Mutations with Reference to Siglec-9 of SEQ ID NO: 2 |
| --- | --- | --- |
| M1 | Q19A-T20A-S21N-K22A | Q18A-T19A-S20N-K21A |
| M2 | L27T-T29A-S47A-S49A-K104N | L22T-T24A-S42A-S44A-K100N |
| M3 | Q31E-S33K-T35V | Q26E-S28K-T30V |
| M5 | H43L-P45A-H96F-L98S-N105D-T107A-S109A | H38L-P40A-H92F-L94S-N101D-T103A-S105A |
| M6 | S52L-H53T-G54D-W55S-I56A-Y57A-P58A-G59S | S47L-H48T-G49D-W50S-I51A-Y52A-P53A-G54S |
| M7 | P60S-H62A-E126A-G128S-S129K-K131A | P55S-H58A-E122A-G124S-S125K-K127A |
| M8 | R67A-A70T-N71A-T72R-D73R-Q74K-D75A | R63A-A66T-N67A-T68R-D69R-Q70K-D71A |
| M9 | N82A-P83S-A84S-R85S-A86K-V87S | N78A-P79S-A80S-R81S-A82K-V83S |

TABLE 3-continued

| Ref. | Mutations with Reference to Siglec-7 of SEQ ID NO: 1 | Mutations with Reference to Siglec-9 of SEQ ID NO: 2 |
| --- | --- | --- |
| M10 | N81A-D100A-H102W-T103R | N77A-D96A-H98W-T99R |
| M11 | W88V-E89K-E90A-R92A | W84V-E85K-E86A-R88A |
| M12 | D93A-R94A-R111S-D112A-R114A | D89A-R90A-R107S-D108A-R110A |
| M13 | E38A-R115A-S116K-N142V-T144A-A118S | E33A-R111A-S112K-N138V-T140A-A114S |
| M14 | R124A-W132Y-N133A | R120A-W128Y-N129A |
| M15 | H137D-R138A-R120S-S32R | H133D-R134A-R116S-S27R |
| M16 | K135M-H136W | K131M-H132W |

Generation of Mutants

Siglec-9 mutants were generated by PCR. The sequences amplified were run on agarose gel and purified using the Macherey Nagel PCR Clean-Up Gel Extraction kit. The purified PCR products generated for each mutant were then ligated into an expression vector, with the ClonTech InFusion™ system. The vectors containing the mutated sequences were prepared as Miniprep and sequenced. After sequencing, the vectors containing the mutated sequences were prepared as Midiprep™ using the Promega PureYield™ Plasmid Midiprep System. HEK293T cells were grown in DMEM medium (Invitrogen), transfected with vectors using Invitrogen's Lipofectamine™ 2000 and incubated at 37° C. in a $CO^2$ incubator for 24 or 48 hours prior to testing for transgene expression.

Flow Cytometry Analysis of Anti-Siglec-9 Binding to the HEK293T Transfected Cells Antibodies mAb4, mAb5 and mAb6 bound the Ig-like C2-type domain 1 whereas mAbA, mAbB, mAbC, mAbD, mAbE mAbF, mAb1, mAb2 and mAb3 bound the N-terminal V-set Ig-like domain. The V-set Ig-like domain binding antibodies were tested for their binding to each of mutants 1-16 by flow cytometry. A first experiment was performed to determine antibodies that lose their binding to one or several mutants at one concentration. To confirm a loss of binding, titration of antibodies was done on antibodies for which binding seemed to be affected by the Siglec-9 mutations. Results are shown in Table 4, below.

No antibodies lost binding to mutant M2 which include a substation at residue K100 (with reference to Siglec-9 of SEQ ID NO: 2) or K104 (with reference to Siglec-7 of SEQ ID NO: 1) that varies in the population; thus the antibodies will bind to the Siglec-9 allele shown in Table 1 (SEQ ID NO: 160).

Figure 11:
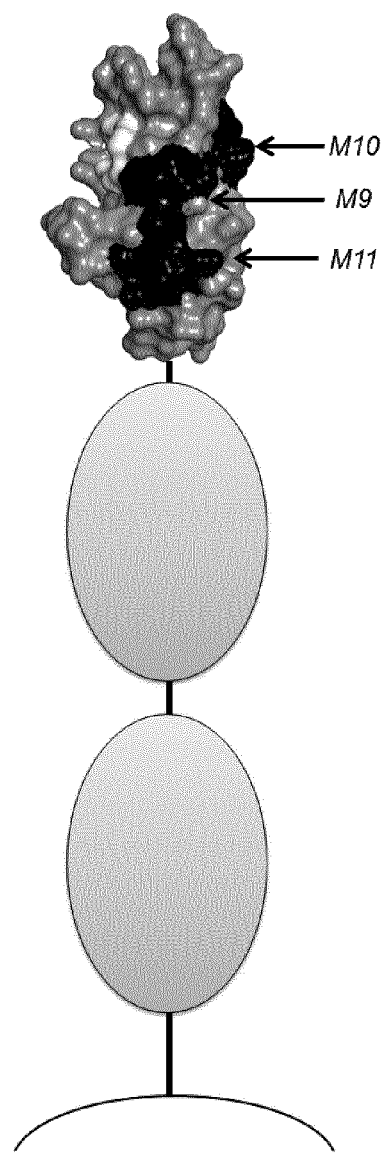
FIGS. 11-14 show the human Siglec-9 protein.

The anti-Siglec-7 and -9 specific antibodies mAb1, mAb2 and mAb3, and the Siglec-9 specific antibodies mAbE and mAbF all lost binding to mutants M9, M10 and M11 of Siglec-9, but not to any other mutant. Mutant 9 contains amino acid substitutions at residues N78, P79, A80, R81, A82 and V83 (reference to Siglec-9), indicating that one or more, or all of, the residues of the mutant are important to the core epitope of these antibodies. Mutant 10 contains amino acid substitutions at residues N77, D96, H98 and T99, indicating that one or more, or all of, the residues of the mutant are important to the core epitope of these antibodies. Mutant 11 contains amino acid substitutions at residues W84, E85, E86 and R88, indicating that one or more, or all of, the residues of the mutant are important to the core epitope of these antibodies. As shown in FIG. 11, the residues substituted in M9, M10 and M11 are found on the side of the N-terminal V-set Ig-like domain (dark shading), away from the face that contains the sialic acid binding sites (light shading). Notably, the antibodies did not lose binding to M8 which has mutations in the C-C' loop domain which defines the sialic ligand specificity of Siglecs (see, e.g., Alphey et al., 2003 J. Biol. Chem. 278(5):3372-3377), nor to M15 of M16 which cover in part a ligand binding region. The antibodies therefore achieve high potency in blocking Siglec-9, without binding to a sialic acid contact region or binding site, or to the C-C' loop.

Figure 12:
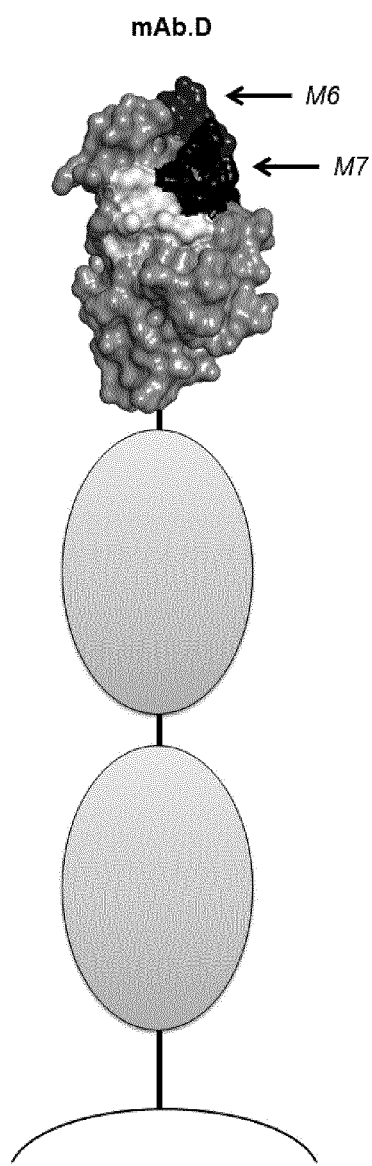
Figure 13:
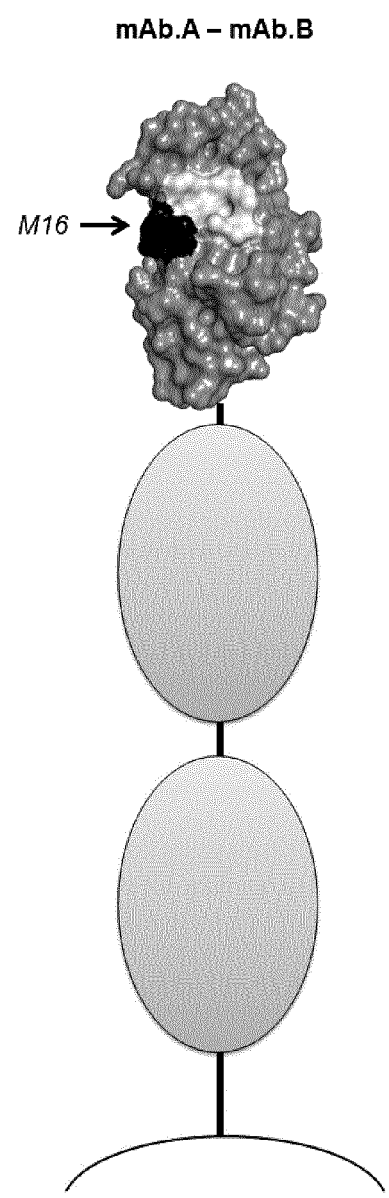

The anti-Siglec-9 specific antibody mAbD lost binding to mutant M6, but not to any other mutant. Mutant 6 contains amino acid substitutions at residues S47, H48, G49, W50, I51, Y52, P53 and G54 (reference to Siglec-9), indicating that one or more, or all of, the residues of the mutant are important to the core epitope of the antibody. As shown in FIG. 12, the residues substituted in M6 (dark shading) are found on the top of the N-terminal V-set Ig-like domain face that contains the sialic acid binding sites, but outside the ligand binding site (light shading). mAbD did not lose binding to M7, but did show partial decrease in binding to this mutant M7; M7 contains residues that may partially overlap into the ligand binding region (in light shading). M7 included amino acid substitutions at residues P55, H58, E122, G124, S125 and K127 (reference to Siglec-9). Thus, while the residues of M7 are not important to the core epitope of the antibody. The antibodies did not lose binding to M8 which has mutations in the C-C' loop domain or to M15 of M16 which cover in part a ligand binding region. The antibodies therefore achieve high potency in blocking Siglec-9, without binding to a sialic acid contact region or binding site, or to the C-C' loop.

The anti-Siglec-9 specific antibodies mAbA and mAbB both lost binding to mutant M16 of Siglec-9, but not to any other mutant. Mutant 16 contains amino acid substitutions at residues K131 and H136 (reference to Siglec-9), indicating that one or more, or all of, the residues of the mutant are important to the core epitope of these antibodies. Interestingly, while M16 is proximal or within a sialic acid ligand contact site of Siglec-9 (see FIG. 13), the antibodies did not lose binding to M8 (C-C' loop domain mutant, nor to M15. The antibodies therefore achieve high potency in blocking Siglec-9, and moreover within a sialic acid contact region, yet without binding to the C-C' loop.

Figure 14:
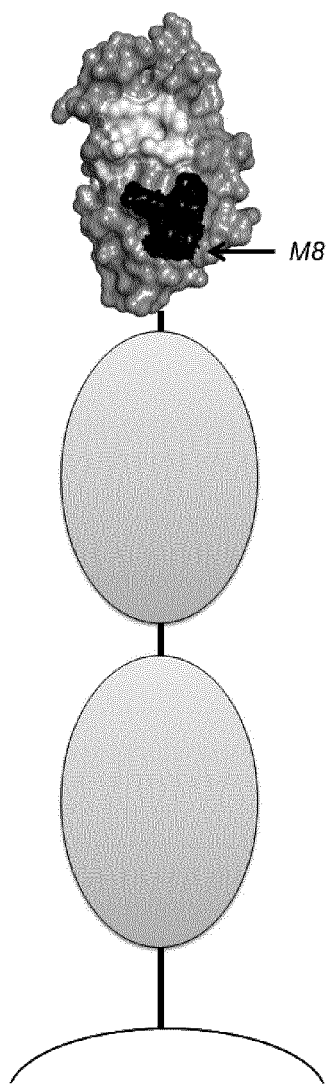

Antibody mAbC on the other hand lost binding to mutant M8 of Siglec-9 (i.e. within the C-C' loop) but did not lose binding to M15 or M16, nor to M6, M7 or M8, nor to M9, M10 or M11 (nor to any other mutant), although a partial decrease in binding to M15 and M16. The residues mutated in M8 are shown in FIG. 14. Mutant 8 contains amino acid substitutions at residues R63, A66, N67, T68, D69, Q70 and D71 (reference to Siglec-9), indicating that one or more, or all of, the residues of the mutant are important to the core epitope of these antibodies. The antibody thus binds to residues in the C-C' loop domain that defines the sialic acid specificity of Siglecs.

Example 12: Anti-Siglec Antibodies Enhance the Activity of NKG2A Blockade in Human Donor Purified NK Cells The anti-Siglec antibodies disclosed herein that were found to restore the cytotoxic activity of primary human NK cells were studied to evaluate whether the Siglec at the surface of the NKG2A+ NK cell subset is restricting the cytotoxic activity of these NKG2A+ cells. The anti-Siglec antibodies were thus tested to evaluate whether they display the ability to enhance the activity of primary NK cells from human donors in the presence of the NKG2A blocking antibody monalizumab (also referred to as IPH2201).

CD137 Expression

Increase of CD137 expression in 24 hours is correlated with the activation of several lymphocytes including NK cells (Kohrt et al. (2011) Blood 117(8):2423-2432). Effect of anti-Siglec-7/9 and anti-Siglec-9 antibodies on NK cells activation was determined by analysis of CD137 expression on Siglec-9 positive NK cells by flow cytometry. Effector cells (fresh NK cells purified from donors, incubation overnight at 37° C. before use) and K562 E6 tumor target cells (K562 cells made to express HLA-E) were mixed at a ratio 1:1. The CD137 assay was carried out in 96 U well plates in completed RPMI, 200 µL final/well. Antibodies were pre-incubated 30 minutes at 37° C. with effector cells and then target cells were co-incubated overnight at 37° C. The following steps were: spin 3 min at 500 g; wash twice with Staining Buffer (SB); addition of 50 µL of staining Ab mix (anti CD3 Pacific blue—BD Pharmingen #558124; anti CD56-PE-Vio770—Milteny #130 100 676; anti CD137-APC—Milteny #130 094 821—anti Siglec-9 K8 PE-Biolegend #351504); incubation 30 min at 4° C.; wash twice with SB; resuspended pellet with SB; and fluorescence revealed with Canto II (HTS).

Negative controls were NK cell vs K562 E6 (K562 cells made to express HLA-E) alone and in presence of isotype control.

Experiments were reproduced on 10 human donors. In absence of antibody ("medium" condition), the % of NK expressing CD137 varied among donors between 5% and 24%. Data were normalized to be a relative change compared to the control medium value from each experiment: ((X−Xmedium))/Xmedium) (%).

Figure 15:
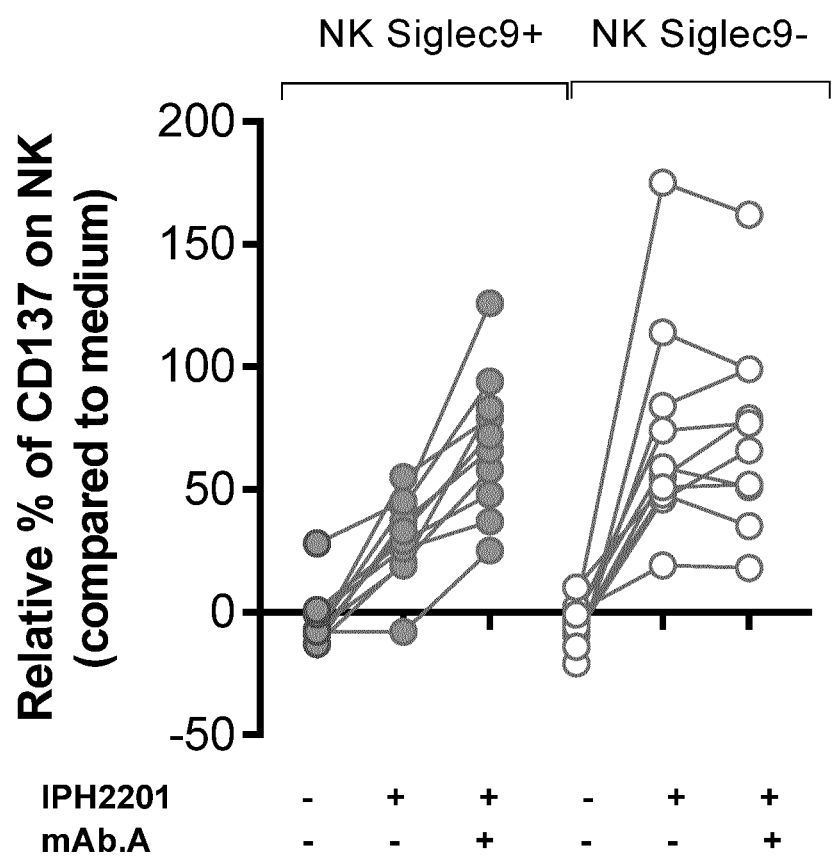
FIG. 15 shows that anti-Siglec antibodies (mAbA) induced an increase of CD137 positive cells among Siglec-9+ NK cells, but did not induce an increase in CD137 positive cells in Siglec-9− NK cells, and that anti-NKG2A antibody enhanced the cytotoxicity (as assessed by increase in CD137 expression) of both Siglec-9− and Siglec-9+ NK cells toward HLA-E-positive tumor target cells, the increase in CD137 expression was greater in the Siglec-9− (negative) cells, suggesting that Siglec-9 is restricting the cytotoxicity of the NKG2A-expressing NK cells in the presence of NKG2A blockade. Addition of anti-Siglec antibodies restored CD137 expression/cytotoxicity in the NKG2A-expressing NK cells.

As shown in FIG. 15, anti-Siglec-9 antibody (mAbA) induced an increase of CD137 positive cells among Siglec-9+ NK cells, but did not induce an increase in CD137 positive cells among Siglec-9− NK cells. Although anti-NKG2A antibody (IPH2201, also known as monalizumab; antibody having VH of SEQ ID NO: 172 and VL of SEQ ID NO: 176) enhanced the cytotoxicity (as assessed by increase in CD137 expression) of both Siglec-9− and Siglec-9+ NK cells toward K562 E6 target cells, the increase in CD137 expression was greater in the Siglec-9− (negative) cells, suggesting that Siglec-9 is restricting the cytotoxicity of these NKG2A expressing NK cells in the presence of NKG2A blockade. Addition of anti-Siglec antibodies restored CD137 expression/cytotoxicity in the NKG2A-expressing NK cells. The results show that the anti-siglec antibodies potentiate the cytotoxicity-enhancing effect of the neutralizing anti-NKG2A antibodies.

$^{51}$Cr Assay

The cytotoxicity assay measured the cytotoxicity of NK cell line KHYG-1 Siglec-9* (NK cell line transduced with Siglec-9) by directly quantifying the lysis of $^{51}$Cr-loaded target cells K562-HLA-E* (K562 transduced with HLA-E). Briefly, target cells were first labelled with radioactive $^{51}$Cr isotope and then co-incubated for 4 h at 37° C. with effector cells. During this time, target cells that are sensitive to KHYG-1 Siglec-9* cells were lysed releasing $^{51}$Cr into the medium. The $^{51}$Cr in the recovered supernatant were measured by liquid scintillation counting. The results obtained allow the evaluation the percent lysis of target cells by NK cells. The assay was carried out in 96 U well plates in completed RPMI, 200 µL final/well, with an E:T ratio 5/1. A dose-range of anti-Siglec-9, cross-reactive anti-Siglec-7/9 antibodies and isotype control were added in combination with a fixed dose of neutralizing anti-NKG2A antibody (10 µg/ml).

Each of the anti-Siglec9 antibodies mAbA, mAbB, mAbC, mAbD, mAbE, and mAbF and anti-Siglec7/9 antibodies mAb1, mAb2, mAb3, mAb4, mAb5 and mAb6 induced an increase of NK cells cytotoxicity in combination with the anti-NKG2A antibody.

TABLE 4

| ANTIBODY | MUTANT | | | | | | | | | | | | |
|---|---|---|---|---|---|---|---|---|---|---|---|---|---|
|  | M1 | M2 | M3 | M5 | M6 | M7 | M8 | M9 | M10 | M11 | M14 | M15 | M16 |
| mAb1 | + | + | + | + | + | + | + | − | − | − | + | + | + |
| mAb2 | + | + | + | + | + | + | + | − | − | − | + | + | + |
| mAb3 | + | + | + | + | + | + | + | − | − | − | + | + | + |
| mAb.A | + | + | + | + | + | + | + | + | + | + | + | + | − |
| mAb.B | + | + | + | + | + | + | + | + | + | + | + | + | − |
| mAb.C | + | + | + | + | + | + | − | + | + | + | + | +/− | +/− |
| mAb.D | + | + | + | + | − | +/− | + | + | + | + | + | + | + |
| mAb.E | + | + | + | + | + | + | + | − | − | − | + | + | + |
| mAb.F | + | + | + | + | + | + | + | − | − | − | + | + | + |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A pharmaceutical composition comprising an antibody that neutralizes the inhibitory activity of NKG2A, and an antibody that neutralizes the inhibitory activity of Siglec-9, wherein the antibody that neutralizes the inhibitory activity of Siglec-9 is selected from the group consisting of:

(a) a monoclonal antibody comprising (i) a heavy chain comprising CDR 1, 2 and 3 of the heavy chain variable region of SEQ ID NO: 15 and (ii) a light chain comprising CDR 1, 2 and 3 of the light chain variable region of SEQ ID NO: 16;

(b) a monoclonal antibody comprising (i) a heavy chain comprising CDR 1, 2 and 3 of the heavy chain variable region of SEQ ID NO: 17 and (ii) a light chain comprising CDR 1, 2 and 3 of the light chain variable region of SEQ ID NO: 18;

(c) a monoclonal antibody comprising (i) a heavy chain comprising CDR 1, 2 and 3 of the heavy chain variable region of SEQ ID NO: 19 and (ii) a light chain comprising CDR 1, 2 and 3 of the light chain variable region of SEQ ID NO: 20;

(d) a monoclonal antibody comprising (i) a heavy chain comprising CDR 1, 2 and 3 of the heavy chain variable region of SEQ ID NO: 21 and (ii) a light chain comprising CDR 1, 2 and 3 of the light chain variable region of SEQ ID NO: 22;

(e) a monoclonal antibody comprising (i) a heavy chain comprising CDR 1, 2 and 3 of the heavy chain variable region of SEQ ID NO: 23 and (ii) a light chain comprising CDR 1, 2 and 3 of the light chain variable region of SEQ ID NO: 24;

(f) a monoclonal antibody comprising (i) a heavy chain comprising CDR 1, 2 and 3 of the heavy chain variable region of SEQ ID NO: 25 and (ii) a light chain comprising CDR 1, 2 and 3 of the light chain variable region of SEQ ID NO: 26;
(g) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;
(h) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;
(i) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;
(j) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;
(k) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and
(l) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

2. A kit comprising: (a) a dose of an antibody, that neutralizes the inhibitory activity of NKG2A, and (b) a dose of an antibody, that neutralizes the inhibitory activity of Siglec-9, wherein the antibody that neutralizes the inhibitory activity of Siglec-9 is selected from the group consisting of:
(a) a monoclonal antibody comprising (i) a heavy chain comprising CDR 1, 2 and 3 of the heavy chain variable region of SEQ ID NO: 15 and (ii) a light chain comprising CDR 1, 2 and 3 of the light chain variable region of SEQ ID NO: 16;
(b) a monoclonal antibody comprising (i) a heavy chain comprising CDR 1, 2 and 3 of the heavy chain variable region of SEQ ID NO: 17 and (ii) a light chain comprising CDR 1, 2 and 3 of the light chain variable region of SEQ ID NO: 18;
(c) a monoclonal antibody comprising (i) a heavy chain comprising CDR 1, 2 and 3 of the heavy chain variable region of SEQ ID NO: 19 and (ii) a light chain comprising CDR 1, 2 and 3 of the light chain variable region of SEQ ID NO: 20;
(d) a monoclonal antibody comprising (i) a heavy chain comprising CDR 1, 2 and 3 of the heavy chain variable region of SEQ ID NO: 21 and (ii) a light chain comprising CDR 1, 2 and 3 of the light chain variable region of SEQ ID NO: 22;
(e) a monoclonal antibody comprising (i) a heavy chain comprising CDR 1, 2 and 3 of the heavy chain variable region of SEQ ID NO: 23 and (ii) a light chain comprising CDR 1, 2 and 3 of the light chain variable region of SEQ ID NO: 24;
(f) a monoclonal antibody comprising (i) a heavy chain comprising CDR 1, 2 and 3 of the heavy chain variable region of SEQ ID NO: 25 and (ii) a light chain comprising CDR 1, 2 and 3 of the light chain variable region of SEQ ID NO: 26;
(g) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;
(h) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;
(i) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;
(j) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;
(k) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and
(l) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

3. A method for modulating NKG2A+ Siglec+ lymphocytes, optionally NK cells, optionally CD8+ T cells, in an individual, the method comprising administering to said individual an effective amount of a pharmaceutical composition according to claim 1.

4. An in vitro method for modulating the activity of NKG2A+ Siglec+ lymphocytes, optionally NK cells, optionally CD8+ T cells, comprising bringing lymphocytes expressing at their surface NKG2A and Siglec-9 into contact with an antibody that neutralizes the inhibitory activity of NKG2A and an antibody that neutralizes the inhibitory activity of Siglec-9, wherein the antibody that neutralizes the inhibitory activity of Siglec-9 is selected from the group consisting of:
(a) a monoclonal antibody comprising (i) a heavy chain comprising CDR 1, 2 and 3 of the heavy chain variable region of SEQ ID NO: 15 and (ii) a light chain comprising CDR 1, 2 and 3 of the light chain variable region of SEQ ID NO: 16;
(b) a monoclonal antibody comprising (i) a heavy chain comprising CDR 1, 2 and 3 of the heavy chain variable region of SEQ ID NO: 17 and (ii) a light chain comprising CDR 1, 2 and 3 of the light chain variable region of SEQ ID NO: 18;
(c) a monoclonal antibody comprising (i) a heavy chain comprising CDR 1, 2 and 3 of the heavy chain variable region of SEQ ID NO: 19 and (ii) a light chain comprising CDR 1, 2 and 3 of the light chain variable region of SEQ ID NO: 20;
(d) a monoclonal antibody comprising (i) a heavy chain comprising CDR 1, 2 and 3 of the heavy chain variable region of SEQ ID NO: 21 and (ii) a light chain comprising CDR 1, 2 and 3 of the light chain variable region of SEQ ID NO: 22;

(e) a monoclonal antibody comprising (i) a heavy chain comprising CDR 1, 2 and 3 of the heavy chain variable region of SEQ ID NO: 23 and (ii) a light chain comprising CDR 1, 2 and 3 of the light chain variable region of SEQ ID NO: 24;

(f) a monoclonal antibody comprising (i) a heavy chain comprising CDR 1, 2 and 3 of the heavy chain variable region of SEQ ID NO: 25 and (ii) a light chain comprising CDR 1, 2 and 3 of the light chain variable region of SEQ ID NO: 26;

(g) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(h) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(i) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(j) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(k) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (l) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

5. A method of treating cancer comprising administering a pharmaceutical composition according to claim 1 to an individual expressing HLA-E polypeptides on malignant cells of said cancer.

6. A method of treating cancer comprising administering a pharmaceutical composition according to claim 1 to an individual having cancer.

7. The method according to claim 6, wherein the cancer is a solid tumor.

8. The method according to claim 6, wherein the cancer is hematological tumor.

9. The method according to claim 6, wherein the cancer is characterized by malignant cells bearing at their surface sialic acid ligands of Siglec-7 and/or Siglec-9.

10. The kit according to claim 2, wherein the antibody that neutralizes the inhibitory activity of Siglec-9 is selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

11. The method according to claim 3, wherein the pharmaceutical composition comprises an antibody that neutralizes the inhibitory activity of Siglec-9 selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

12. The in vitro method according to claim 4, wherein the antibody that neutralizes the inhibitory activity of Siglec-9 is selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

13. The method according to claim 5, wherein the antibody that neutralizes the inhibitory activity of Siglec-9 is selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

14. The method according to claim 6, wherein the antibody that neutralizes the inhibitory activity of Siglec-9 is selected from the group consisting of:

(a) a monoclonal antibody comprising (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;

(b) a monoclonal antibody comprising (i) a heavy chain comprising CDR 1, 2 and 3 of the heavy chain variable region of SEQ ID NO: 5 and (ii) a light chain comprising CDR 1, 2 and 3 of the light chain variable region of SEQ ID NO: 6;

(c) a monoclonal antibody comprising (i) a heavy chain comprising CDR 1, 2 and 3 of the heavy chain variable region of SEQ ID NO: 7 and (ii) a light chain comprising CDR 1, 2 and 3 of the light chain variable region of SEQ ID NO: 8;

(d) a monoclonal antibody comprising (i) a heavy chain comprising CDR 1, 2 and 3 of the heavy chain variable region of SEQ ID NO: 9 and (ii) a light chain comprising CDR 1, 2 and 3 of the light chain variable region of SEQ ID NO: 10;

(e) a monoclonal antibody comprising (i) a heavy chain comprising CDR 1, 2 and 3 of the heavy chain variable region of SEQ ID NO: 11 and (ii) a light chain comprising CDR 1, 2 and 3 of the light chain variable region of SEQ ID NO: 12; and (f) a monoclonal antibody comprising (i) a heavy chain comprising CDR 1, 2 and 3 of the heavy chain variable region of SEQ ID NO: 13 and (ii) a light chain comprising CDR 1, 2 and 3 of the light chain variable region of SEQ ID NO: 14.

* * * * *

UNITED STATES PATENT AND TRADEMARK OFFICE
CERTIFICATE OF CORRECTION

| | | |
|---|---|---|
| PATENT NO. | : 11,447,545 B2 | Page 1 of 1 |
| APPLICATION NO. | : 16/629585 | |
| DATED | : September 20, 2022 | |
| INVENTOR(S) | : Stéphanie Cornen, Benjamin Rossi and Nicolai Wagtmann | |

It is certified that error appears in the above-identified patent and that said Letters Patent is hereby corrected as shown below:

In the Specification

Column 10,
Line 38, "antibodies arc can" should read --antibodies can--.

Column 12,
Line 42, "FOR" should read --FcγR--.

Column 20,
Line 60, "IYPGPWHGY" should read --IYPGPVVHGY--.

Column 49,
Line 14, "SEQ ID should read --SEQ ID
          38"                    44--.

Column 56,
Line 46, "HTETGEP" should read --IITETGEP--.

Column 82,
Line 26, "(pg/ml)" should read --(μg/ml)--.

Column 88,
Line 16, "and Ig-like O2-type" should read --and Ig-like C2-type--.

Signed and Sealed this
Eighteenth Day of April, 2023

Katherine Kelly Vidal
*Director of the United States Patent and Trademark Office*